US012331085B2

(12) United States Patent
Picking et al.

(10) Patent No.: US 12,331,085 B2
(45) Date of Patent: *Jun. 17, 2025

(54) METHODS AND COMPOSITIONS RELATED TO THE NEXT GENERATION VACCINE

(71) Applicant: UNIVERSITY OF KANSAS, Lawrence, KS (US)

(72) Inventors: Wendy L. Picking, Lawrence, KS (US); William D. Picking, Lawrence, KS (US)

(73) Assignee: University of Kansas, Lawrence, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/931,356

(22) Filed: Sep. 12, 2022

(65) Prior Publication Data

US 2023/0112697 A1    Apr. 13, 2023

Related U.S. Application Data

(63) Continuation of application No. 17/053,544, filed as application No. PCT/US2019/030694 on May 3, 2019, now Pat. No. 11,439,700.

(60) Provisional application No. 62/667,599, filed on May 6, 2018.

(51) Int. Cl.
| | | |
|---|---|---|
| *A61K 39/104* | (2006.01) | |
| *A61K 39/02* | (2006.01) | |
| *C07K 14/21* | (2006.01) | |
| *C07K 14/235* | (2006.01) | |
| *C07K 14/245* | (2006.01) | |
| *C07K 14/28* | (2006.01) | |

(52) U.S. Cl.
CPC ............ *C07K 14/28* (2013.01); *A61K 39/104* (2013.01); *A61K 39/107* (2013.01); *C07K 14/21* (2013.01); *C07K 14/235* (2013.01); *C07K 14/245* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 9,492,523 B2 | 11/2016 | Picking et al. | |
| 11,439,700 B2* | 9/2022 | Picking | C07K 14/28 |
| 2008/0044438 A1 | 2/2008 | Ostroff et al. | |
| 2009/0324638 A1 | 12/2009 | Dattwyler et al. | |
| 2013/0149329 A1 | 6/2013 | Picking et al. | |
| 2014/0206016 A1* | 7/2014 | Lozano | C12Q 1/045 435/7.1 |
| 2016/0220655 A1 | 8/2016 | Picking et al. | |

FOREIGN PATENT DOCUMENTS

WO    2016193161 A1    12/2016

OTHER PUBLICATIONS

Heine et al. J. Immunol. 192: 1630-1640, 2014.*
Huang, "Characterization of the A Subunit Epitopes in Immunogenicity and Enterotoxicity of Enterotoxigenic *Escherichia coli* (ETEC) Heat-Labile Toxin," Thesis, Huazhong Agricultural University, College of Veterinary Medicine, Aug. 1, 2017, pp. 1-52.
Heine et al. "AA Combined YopB and LcrV Subunit Vaccine Elicits Protective Immunity against Yersinia Infection in Adult and Infant Mice," The Journal of Immunology, Feb. 20, 2019, vol. 203, Iss. 3, pp. 2005-2016.
Huang et al. "Significance of Enterotoxigenic *Escherichia coli* (ETEC) HeatLabile Toxin (LT) Enzymatic Subunit Epitopes in LT Enterotoxicity and Immunogenicity," Appl Environ Microbiol, May 25, 2018, vol. 84, Iss. 15, pp. 1-13.
International Search Report and Written Opinion for International Application No. PCT/US2019/030694 dated Aug. 20, 2019.
Communication Pursuant to Rule 164(1) EPC, issued for European Application No. 19800219.8, dated Jan. 20, 2022.
Martinez-Becerra, Francisco J., et al. "Characterization and protective efficacy of type III secretion proteins as a broadly protective subunit vaccine against *Salmonella enterica* serotypes." Infection and immunity 86.3 (2018): e00473-17.
Martinez-Becerra, Francisco J., et al. "Characterization of a novel fusion protein from IpaB and IpaD of *Shigella* spp. and its potential as a pan-*Shigella* vaccine." Infection and immunity 81.12 (2013): 4470-4477.
Nandre, Rahul M., et al. "Passive antibodies derived from intramuscularly immunized toxoid fusion 3xSTaN12S-dmLT protect against STa+ enterotoxigenic *Escherichia coli* (ETEC) diarrhea in a pig model." Vaccine 35.4 (2017): 552-556.
Müller, Simone, Mario F. Feldman, and Guy R. Cornelis. "The Type III secretion system of Gram-negative bacteria: a potential therapeutic target?." Expert opinion on therapeutic targets 5.3 (2001): 327-339.
Romano, Fabian B., et al. "Type 3 secretion translocators spontaneously assemble a hexadecameric transmembrane complex." Journal of Biological Chemistry 291.12 (2016): 6304-6315.
Ruan, Xiaosai, et al. "Characterization of heat-stable (STa) toxoids of enterotoxigenic *Escherichia coli* fused to double mutant heat-labile toxin peptide in inducing neutralizing anti-STa antibodies." Infection and immunity 82.5 (2014): 1823-1832.
Greenspan, Neil S., and Enrico Di Cera. "Defining epitopes: It's not as easy as it seems." Nature biotechnology 17.10 (1999): 936-937.
Rudinger, J. "Characteristics of the amino acids as components of a peptide hormone sequence." Peptide Hormones. Palgrave, London, 1976. 1-7.

(Continued)

*Primary Examiner* — S. Devi
(74) *Attorney, Agent, or Firm* — Meunier Carlin & Curfman LLC

(57) ABSTRACT

Disclosed are compositions comprising a Gram negative needle tip protein and a translocator protein and methods of their use.

11 Claims, 17 Drawing Sheets

Specification includes a Sequence Listing.

(56) References Cited

OTHER PUBLICATIONS

Skolnick, Jeffrey, and Jacquelyn S. Fetrow. "From genes to protein structure and function: novel applications of computational approaches in the genomic era." Trends in biotechnology 18.1 (2000): 34-39.

* cited by examiner (a)
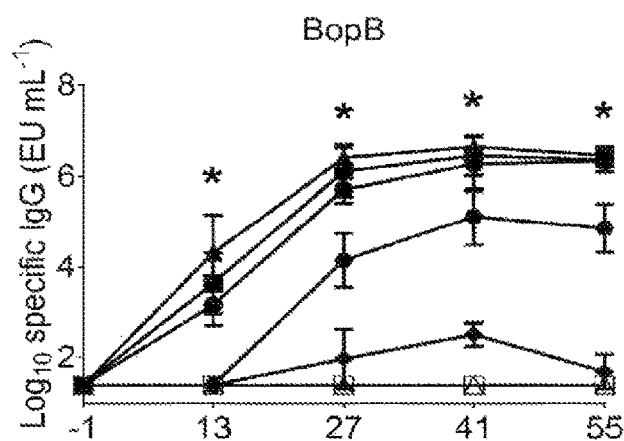
(b)
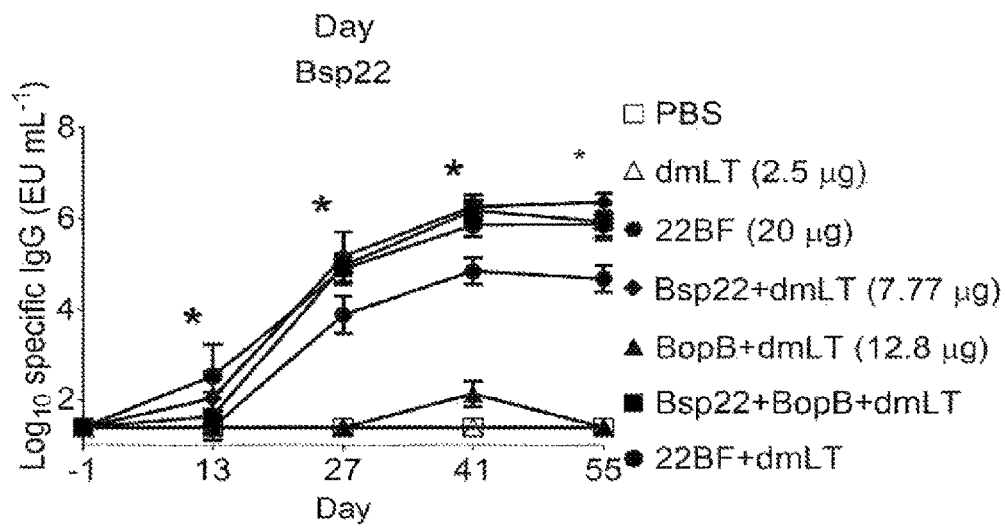
(c)
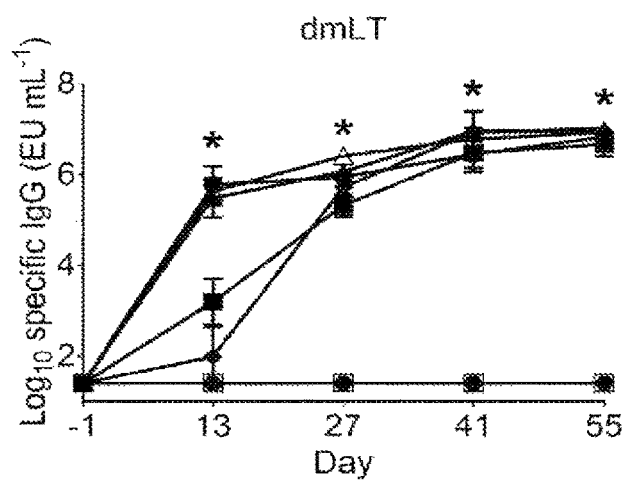
FIG. 4A, FIG. 4B, and FIG. 4C

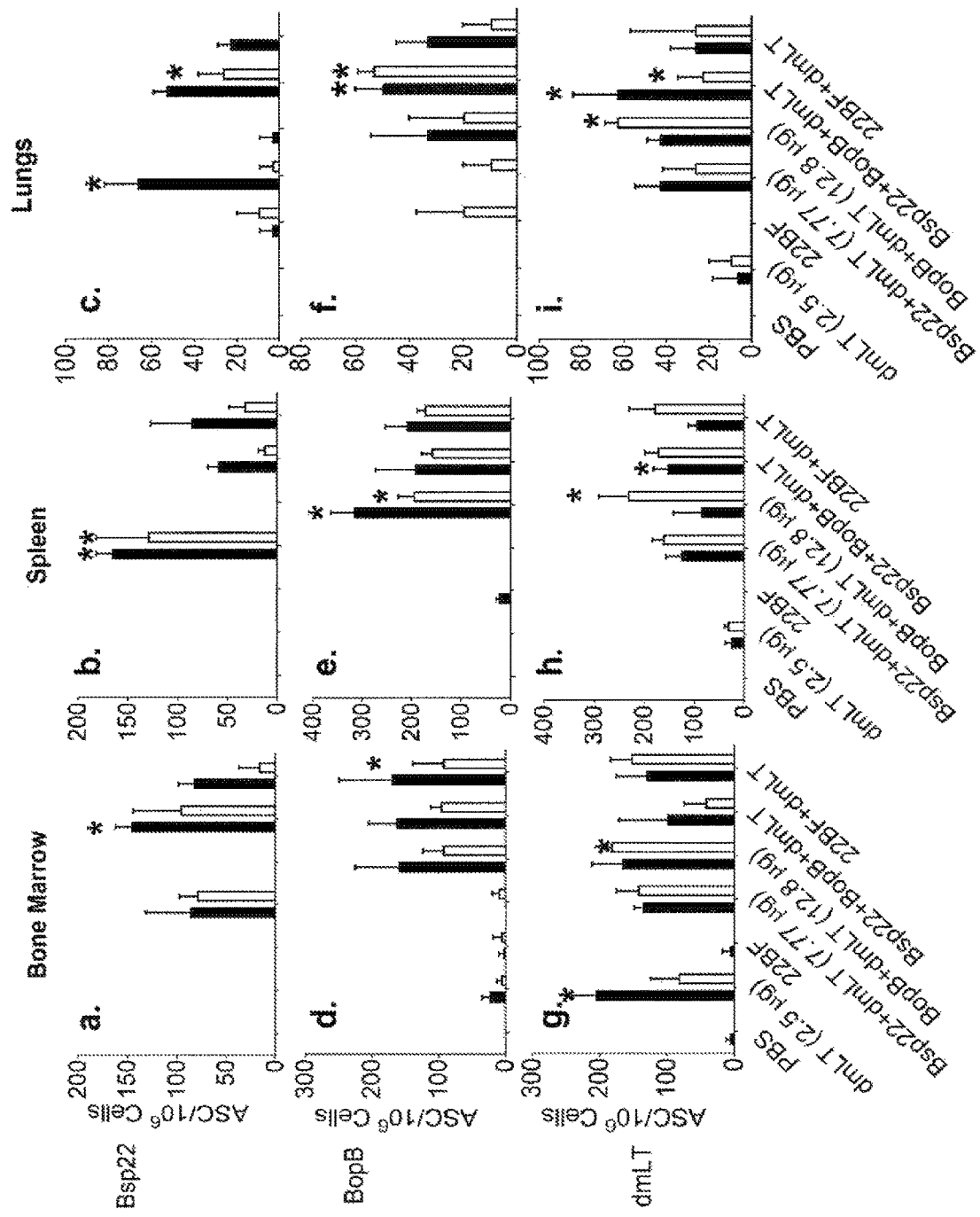
FIG. 5A, FIG. 5B, FIG. 5C, FIG. 5D, FIG. 5E, FIG. 5F, FIG. 5G, FIG. 5H, and FIG. 5I

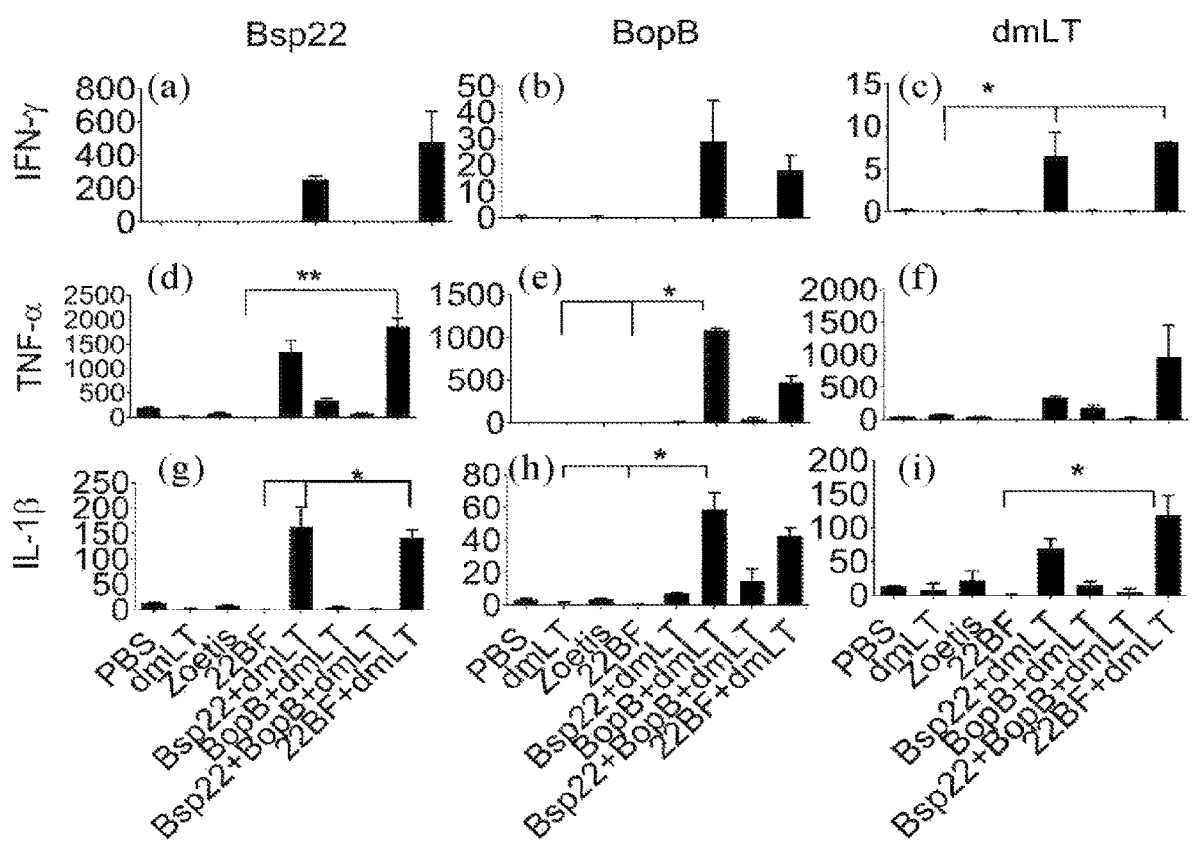
FIG. 6A, FIG. 6B, FIG. 6C, FIG. 6D, FIG. 6E, FIG. 6F, FIG. 6G, FIG. 6H, and FIG. 6I

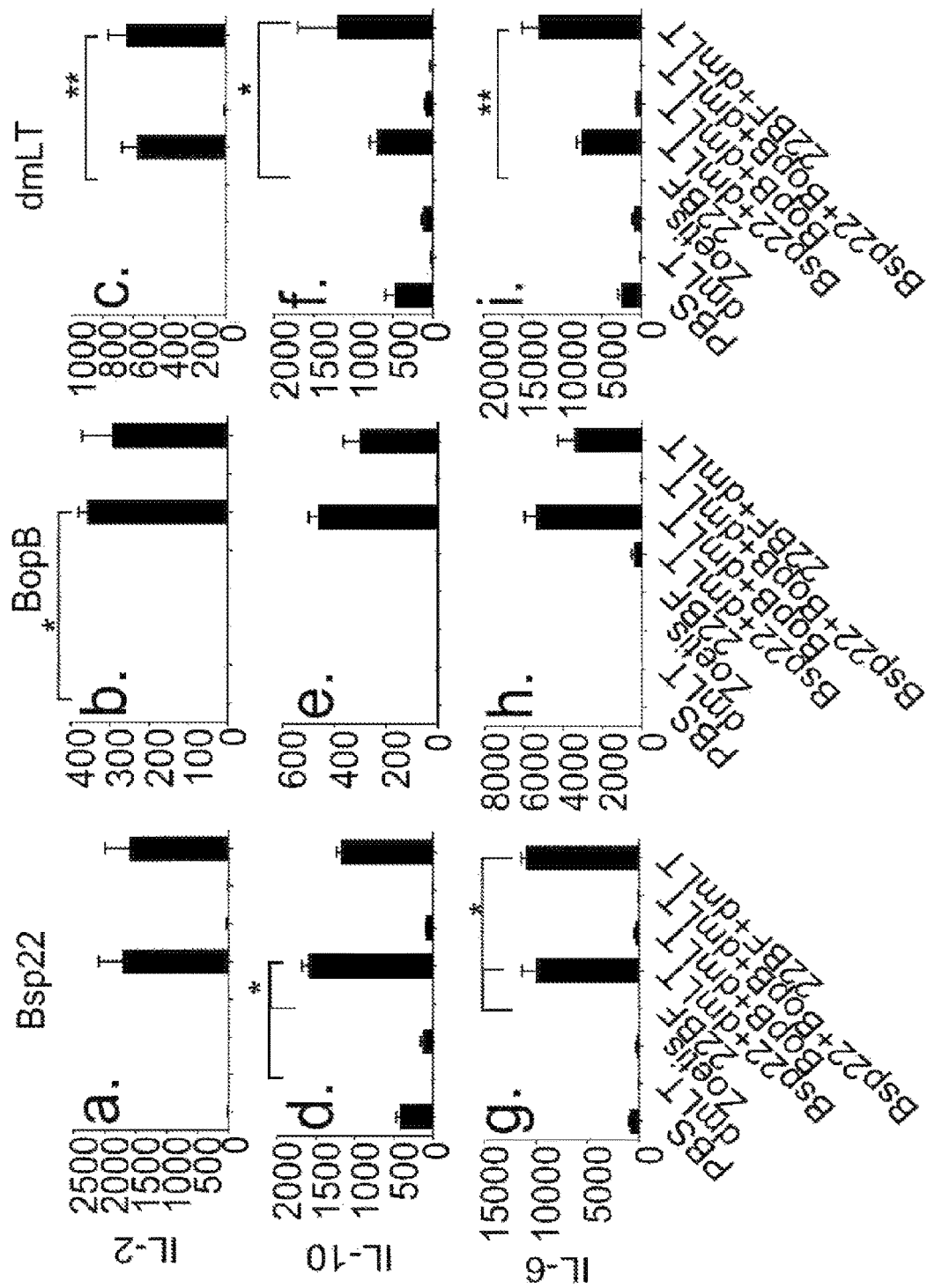
FIG. 7A, FIG. 7B, FIG. 7C, FIG. 7D, FIG. 7E, FIG. 7F, FIG. 7G, FIG. 7H, and FIG. 7I

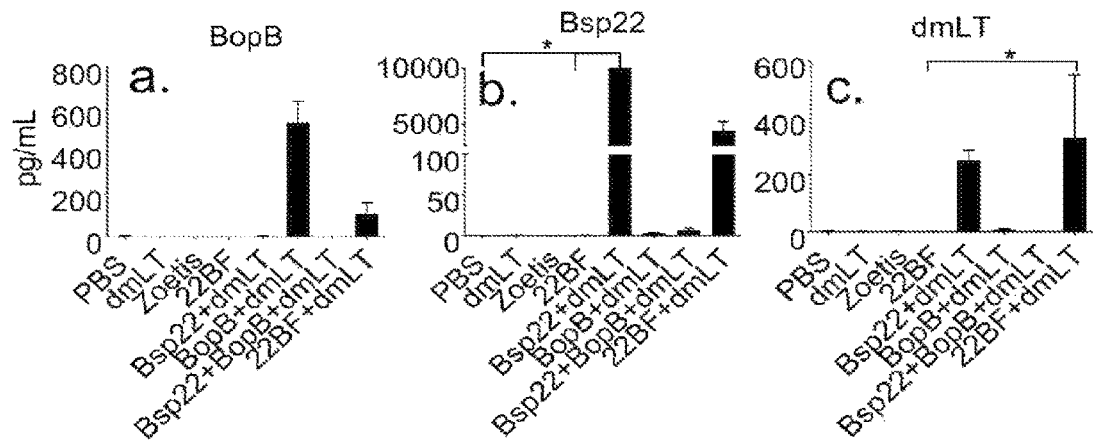
FIG. 8A, FIG. 8B, and FIG. 8C
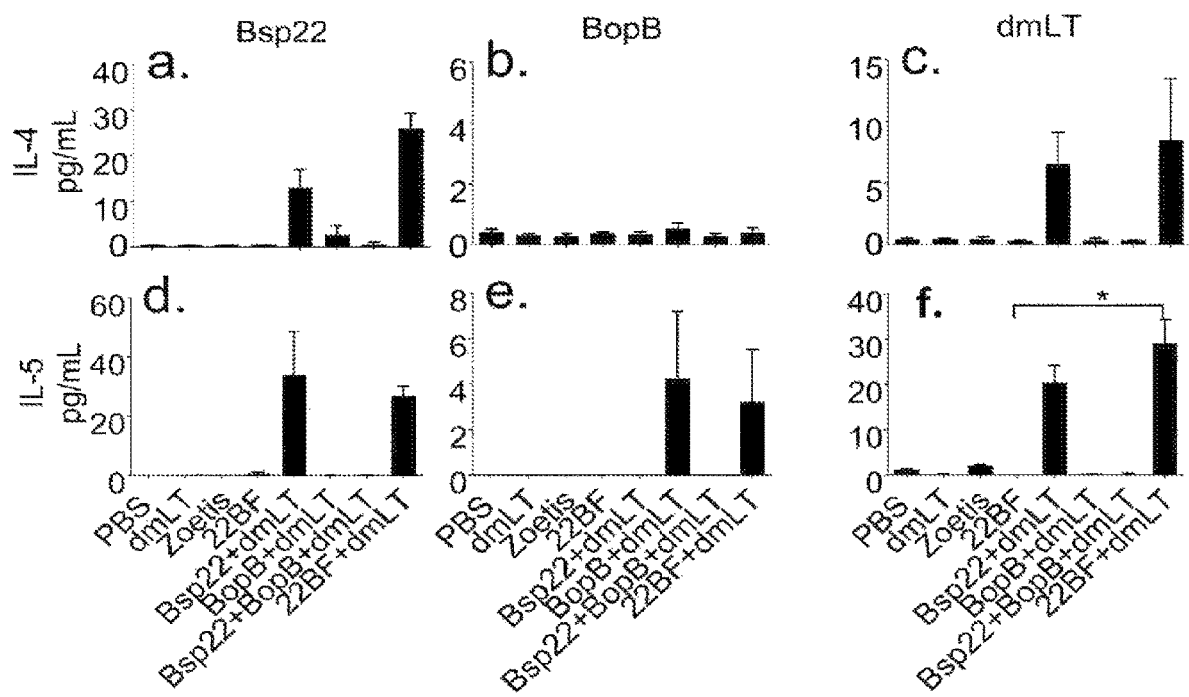
FIG. 9A, FIG. 9B, FIG. 9C, FIG. 9D, FIG. 9E, and FIG. 9F FIG. 11A, FIG. 11B, FIG. 11C, and FIG. 11D

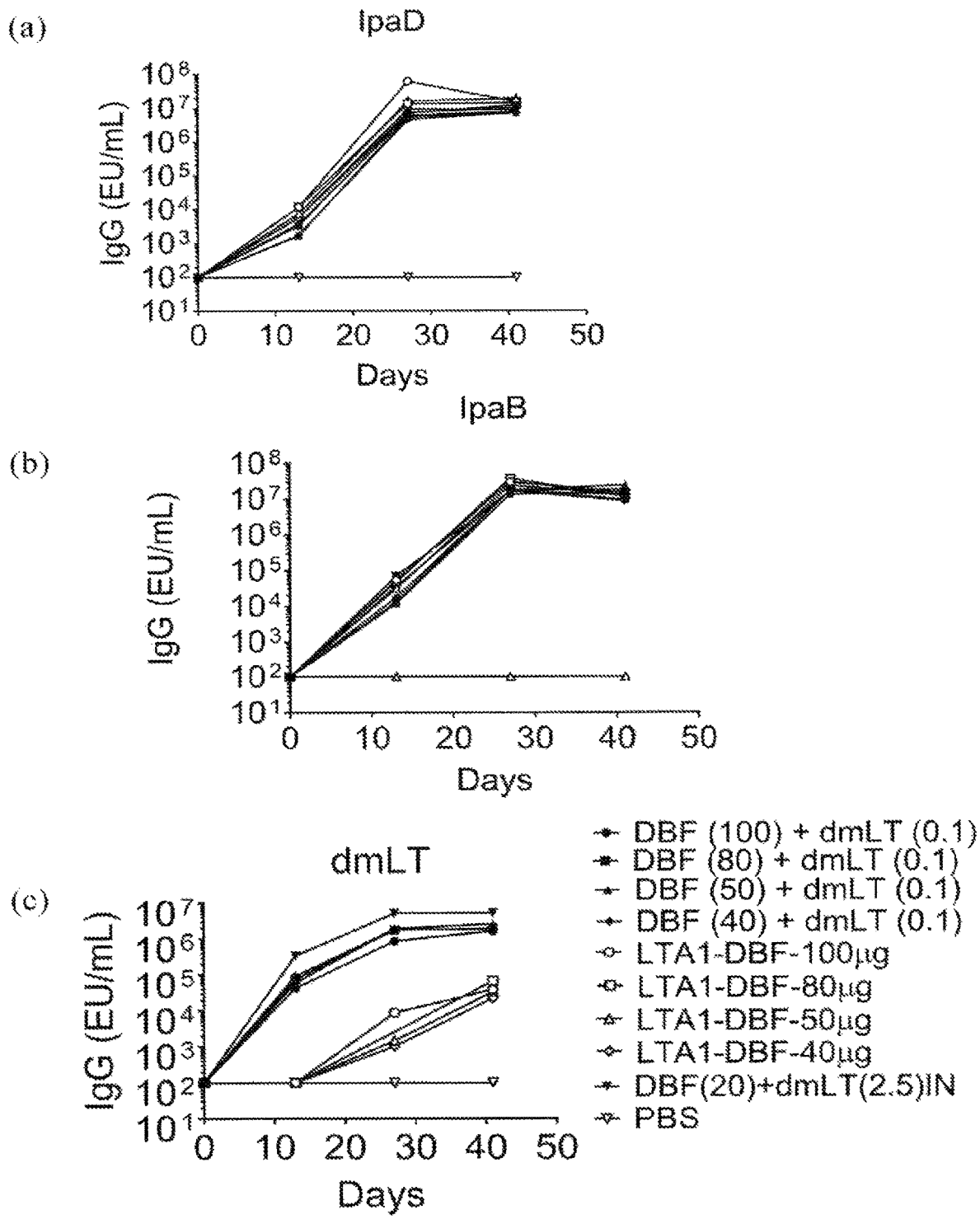
FIG. 15A, FIG. 15B, and FIG. 15C

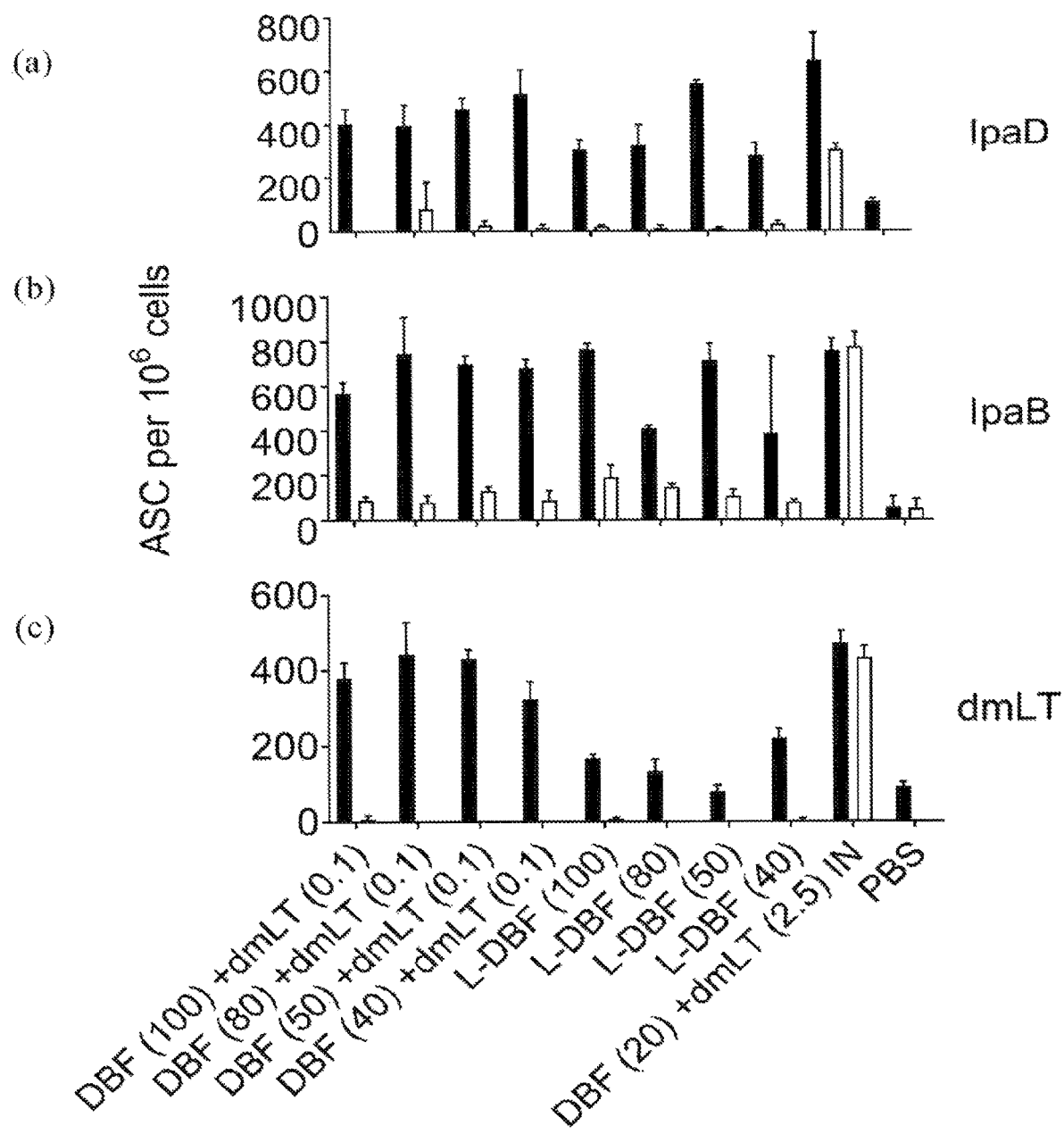
FIG. 16A, FIG. 16B, and FIG. 16C

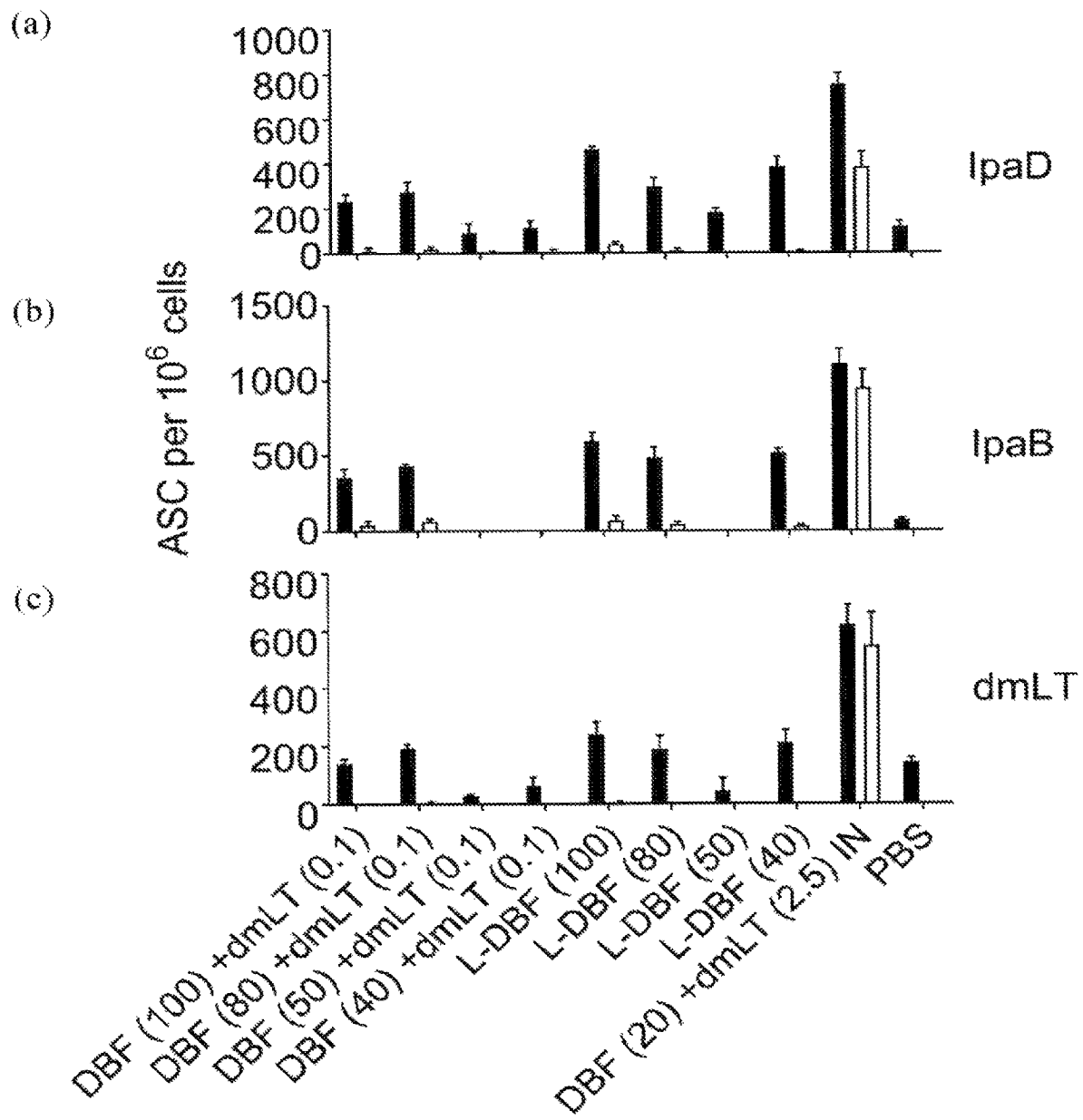
FIG. 17A, FIG. 17B, and FIG. 17C

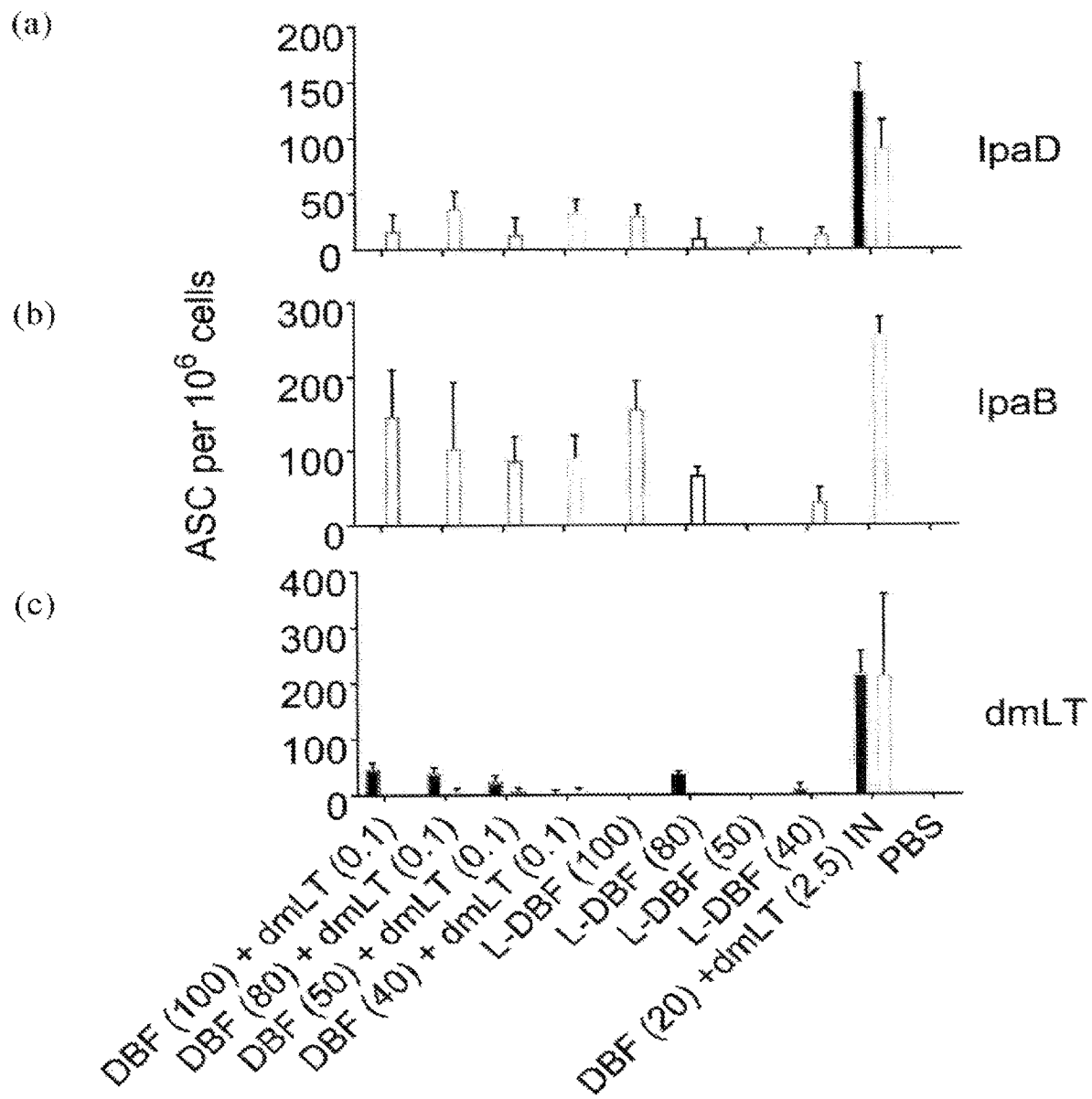
FIG. 18A, FIG. 18B, and FIG. 18C

METHODS AND COMPOSITIONS RELATED TO THE NEXT GENERATION VACCINE

CROSS REFERENCE TO RELATED APPLICATIONS

This application is a continuation of U.S. application Ser. No. 17/053,544, filed on Nov. 6, 2020, now U.S. Pat. No. 11,439,700, which is a national stage application filed under 35 U.S.C. § 371 of PCT/US2019/030694 filed on May 3, 2019, which-claims the benefit of U.S. Provisional Patent Application Ser. No. 62/667,599, filed May 6, 2018, which is incorporated by reference in its entity herein.

SEQUENCE LISTING

A Sequence Listing was filed in electronic format on Sep. 12, 2022. The Sequence Listing was provided as a file entitled "10776_006US2.xml", created Sep. 12, 2022, which is 245,448 bytes in size. The information in the electronic format of the Sequence Listing is incorporated herein by reference in its entirety.

BACKGROUND

*Bordetella pertussis* is a Gram-negative bacterial pathogen that causes pertussis, or whooping cough, a highly contagious, severe respiratory disease that is life threatening for infants and young children. This pathogen colonizes the trachea and secretes toxins that paralyze the cilia, which prevents clearance of mucous. Severe (paroxysmal), non-productive coughing fits are a result and attempts to acquire oxygen are manifested by the characteristic "whoop" upon gasps for air. The majority of deaths associated with pertussis are actually caused by secondary respiratory infections resulting from the inability to clear pulmonary secretions. In the 1940s a whole-cell pertussis (wP) vaccine was introduced that dramatically reduced the mortality caused by pertussis. Due to side effects attributed to the wP vaccine, a new acellular pertussis (aP) vaccine was developed and introduced in the US and other parts of the world in the 1990s. Although the aP vaccine has few side effects, its protective efficacy is lower than that of the wP vaccine. In 2012, which is considered the most recent major epidemic, 48,277 cases of pertussis were reported and, in 2015, 20,762 cases were reported. During the last 15 years, in addition to a greater overall incidence of pertussis, there is growing concern over the increase in the peak number of reported cases for each ensuing epidemic. In 2015, 45% of the 0.5 to 6-year-old children that contracted pertussis had been vaccinated with DTaP at least three times (with five vaccinations being optimal: 2, 4, 6, 15 months and one at 4-6 years). Additionally, there is evidence that selective pressure is causing *B. pertussis* to eliminate virulence factors that are components of the aP vaccine, further compromising the vaccine's efficacy. Taken together, a better vaccine is needed.

SUMMARY

Disclosed are methods and compositions related to polypeptides comprising a fusion of the needle tip protein and translocator protein of a type III secretion apparatus (T3SA) from a type III secretion system (T3SS) of a Gram negative bacteria. 5. Disclosed herein are fusion polypeptides comprising a fusion of a needle tip protein (such as, for example, Bsp22, LcrV, BipD, PcrV, CT053, or CT668) or an antigenic fragment thereof and a translocator protein (such as, for example, BopB, YopB, BipB, PopB, CopB, or CopB2) or an antigenic fragment thereof from a Type III secretion system (T3SS) of a Gram negative bacteria (such as, for example, *Bordetella* spp., *Burkholderia* spp., *Chlamydia* spp., *Pseudomonas* spp., *Vibrio* spp. or *Yersinia* spp.); wherein the gram negative bacteria is not a *Salmonella enterica* or *Shigella* spp.

In one aspect, disclosed herein are fusion polypeptides, wherein the fusion polypeptide is arranged such that the needle tip protein is 5' of the translocator protein.

Also disclosed herein are fusion polypeptides of any preceding aspect, wherein the fusion further comprises an adjuvant such as, for example, Cholera Toxin or antigenic fragment thereof (such as, for example, CTA1) or double mutant labile toxin (dmLT) or an antigenic fragment thereof labile toxin (such as, for example, LTA1) from Enterotoxigenic *Escherichia coli*. In some aspect, the dmLT or fragment thereof can also be fused to the needle tip protein-translocator protein fusion at the 5' end.

In one aspect, disclosed herein are fusion polypeptides of any preceding aspect, wherein the fusion polypeptide further comprises pertussis toxoid (PTd).

Also disclosed herein are compositions comprising a T3SA needle tip protein (such as, for example, Bsp22, LcrV, BipD, PcrV, or CdsF) or an antigenic fragment thereof from a Gram negative bacteria (such as, for example, *Bordetella* spp., *Burkholderia* spp., *Chlamydia* spp., *Pseudomonas* spp., *Vibrio* spp., or *Yersinia* spp.) and a T3SA first translocator protein (such as, for example, BopB, YopB, BipB, PopB, or CopB/CopB2) or an antigenic fragment thereof from a Gram negative bacteria; wherein the gram negative bacteria is not a *Salmonella enterica* or *Shigella* spp. In one aspect, the composition can comprise the needle tip protein or fragment thereof and the translocator protein or fragment thereof as separate components or as a fusion polypeptide. Also disclosed herein are compositions of any preceding aspect, wherein the composition comprises an adjuvant (such as, for example, dmLT, LTA1, cholera toxin, or CTA1) and/or bacterial toxin protein such as a pertussis toxoid (PTd).

In one aspect, disclosed herein are vaccines comprising the fusion polypeptides or compositions of any preceding aspect. In some embodiments, the vaccine can further comprise an acellular gram negative vaccine or active components thereof. In one aspect, the vaccine can comprise pertussis toxoid (PTd).

Also disclosed herein are methods of treating, inhibiting, or preventing an infection of a Gram negative bacteria (such as, for example, *Bordetella* spp., *Burkholderia* spp., *Chlamydia* spp., *Pseudomonas* spp., *Vibrio* spp., or *Yersinia* spp.) in a subject comprising administering to the subject the fusion polypeptide, composition, or vaccine of any preceding aspect.

In one aspect, disclosed herein are methods of treating, inhibiting, or preventing an infection of a Gram negative bacteria of any preceding aspect, wherein the method further inhibits or prevents colony formation of the bacteria and/or transmission of the bacteria to another subject.

Also disclosed herein are methods of eliciting an immune response in a subject to a Gram negative bacteria (such as, for example, *Bordetella* spp., *Burkholderia* spp., *Chlamydia* spp., *Pseudomonas* spp., *Vibrio* spp., or *Yersinia* spp.) comprising administering to the subject the fusion polypeptide, composition, or vaccine of any preceding aspect. For example, disclosed herein are methods of eliciting an immune response against at least one Gram negative bacteria serovar in a subject in need thereof, comprising administering to the subject a composition comprising at least one needle tip protein or an antigenic fragment thereof and/or at least one translocator protein or an antigenic fragment thereof; wherein said composition is administered in an amount sufficient to elicit an immune response to said at least one Gram negative bacteria serovar in said subject; and wherein the Gram negative bacteria is not a *Shigella* spp. or *Salmonella enterica*.

In one aspect, disclosed herein are methods of eliciting an immune response in a subject to a Gram negative bacteria of any preceding aspect, wherein the immune response provides sterilizing immunity.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 3A shows that on day 7 of the challenge, the CFU/lung were determined. *=P<0.05, **=P<0.01 when compared to dmLT. FIG. 3B shows the decrease in CFU compared to the 22BF average. *=P<0.05, **=P<0.01 when compared to 22BF.

FIGS. 4A, 4B, and 4C show the kinetics of IgG response. Blood was collected on days −1, 13, 27, 41, and 55. The kinetics of anti-Bsp22, -BopB and -dmLT IgG were assessed in all sera and shown in (4A) BopB, (4B) Bsp22, and (4C) dmLT. Typical logarithmic increases were seen. *=P value of <0.05 when comparing to PBS controls.

FIGS. 5A, 5B, 5C, 5D, 5E, 5F, 5G, 5H, and 5I show stimulation of antibody secreting cells from bone marrow, spleen and lungs. Bone marrow, spleens and lungs were collected on day 56. Single cell suspensions from 5 mice per group were stimulated in vitro Bsp22, BopB or dmLT. IgG (black) and IgA (white) ASC were measured by ELISpot. Bars represent mean ASC per $10^6$ cells+SD from replicate wells. Data for bone marrow is shown in (4A), (5D), and (5G) for Bsp22, BopB, and dmLT, respectively. Data for spleen is shown in (5B), (5E), and (5H) for Bsp22, BopB, and dmLT, respectively. Data for lungs is shown in (5C), (5F), and (5I) for Bsp22, BopB, and dmLT, respectively.

FIGS. 6A, 6B, 6C, 6D, 6E, 6F, 6G, 6H, and 6I show Th1 cytokine secretion. Splenocytes were extracted from 5 mice of each group and incubated with Bsp22, BopB or dmLT. After 48 h, supernatants were collected and levels of cytokine secretion in response to specified antigen were then measured (in pg/ml) using an MSD cytokine detection plate. Each bar represents mean of triplicate wells±S.D. Asterisk specified a P<0.05 when comparing specified groups. Data for IFN-γ is shown in (6A), (6B), and (6C) for Bsp22, BopB, and dmLT, respectively. Data for TNF-α is shown in (6D), (6E), and (6F) for Bsp22, BopB, and dmLT, respectively. Data for IL-1β is shown in (6G), (6H), and (6I) for Bsp22, BopB, and dmLT, respectively.

FIGS. 7A, 7B, 7C, 7D, 7E, 7F, 7G, 7H, and 7I show Th1 cytokine secretion. Splenocytes were extracted from 5 mice of each group and incubated with Bsp22, BopB or dmLT. After 48 h, supernatants were collected and levels of cytokine secretion in response to specified antigen were then measured (in pg/ml) using an MSD cytokine detection plate. Each bar represents mean of triplicate wells±S.D. Asterisk specified a P<0.05 when comparing specified groups. Data for IL-2 is shown in (7A), (7B), and (7C) for Bsp22, BopB, and dmLT, respectively. Data for IL-10 is shown in (7D), (7E), and (7F) for Bsp22, BopB, and dmLT, respectively. Data for IL-6 is shown in (7G), (7H), and (7I) for Bsp22, BopB, and dmLT, respectively.

FIGS. 8A, 8B, and 8C shows IL-17 secretion. Splenocytes were extracted from 5 mice of each group and incubated with Bsp22, BopB or dmLT. After 48 h, supernatants were collected and levels of IL-17 secretion in response to labeled antigen were then measured by the MSD® U-Plex Platform Multiplex Assay and the data is shown in (8A) BopB, (8B) Bsp22, and (8C) dmLT. Each bar represents the mean of triplicate wells±S.D. Significance (Asterisk=P<0.05) was calculated for the comparison between labeled groups.

FIGS. 9A, 9B, 9C, 9D, 9E, and 9F show Th2 cytokine secretion. Splenocytes were extracted from 5 mice of each group and incubated with Bsp22, BopB or dmLT. After 48 h, supernatants were collected and levels of cytokine secretion in response to specified antigen were then measured (in pg/ml) using an MSD cytokine detection plate. Each bar represents mean of triplicate wells±S.D. Asterisk specified a P<0.05 when comparing specified groups. Data for IL-4 is shown in (9A), (9B), and (9C) for Bsp22, BopB, and dmLT, respectively. Data for IL-5 is shown in (9D), (9E), and (9F) for Bsp22, BopB, and dmLT, respectively.

FIG. 14 indicates the percent survival of mice post infection with Shigella flexneri.

FIGS. 15A, 15B, and 15C show the kinetics of IgG response. Mice from FIG. 14 were bled prior to vaccination and on day 42. Sera were assessed for anti-IpaD, -IpaB and -dmLT IgG, and the data is shown in (15A) IpaD, (15Bb) IpaB, and (15C) dmLT. Differences in the IgG levels in mice vaccinated with dmLT vs. LTA1 are attributed to the recognition of the entire dmLT on the well.

FIGS. 16A, 16B, and 16C show the stimulation of antibody secreting cells from bone marrow. Bone marrow was collected on day 56. Single cell suspensions from 5 mice per group were stimulated in vitro IpaD, IpaB or dmLT. IgG (black) and IgA (white) ASC were measured by ELISpot, and the data is shown in (16A) IpaD, (16B) IpaB, and (16C) dmLT. Bars represent mean ASC per $10^6$ cells+SD from replicate wells.

FIGS. 17A, 17B, and 17C show the stimulation of antibody secreting cells from spleen. Spleens were collected on day 56. Single cell suspensions from 5 mice per group were stimulated in vitro IpaD, IpaB or dmLT. IgG (black) and IgA (white) ASC were measured by ELISpot. Bars represent mean ASC per $10^6$ cells+SD from replicate wells.

FIGS. 18A, 18B, and 18C show the stimulation of antibody secreting cells from lungs. Lungs were collected on day 56. Single cell suspensions from 5 mice per group were stimulated in vitro IpaD, IpaB or dmLT. IgG (black) and IgA (white) ASC were measured by ELISpot, and the data is shown in (18A) IpaD, (18B) IpaB, and (18C) dmLT. Bars represent mean ASC per $10^6$ cells+SD from replicate wells.

FIG. 19A shows the CFU/lung while FIG. 19B shows the decrease in CFU compared to the PBS average. *=P<0.05 when compared to PBS. FIGS. 19C and 19D how the kinetics of the response of the anti-Bsp22 and anti-BopB IgG, respectively. No difference is seen between the mice vaccinated with 22BF+ dmLT and LTA1-22BF.

DETAILED DESCRIPTION

Figure 1:
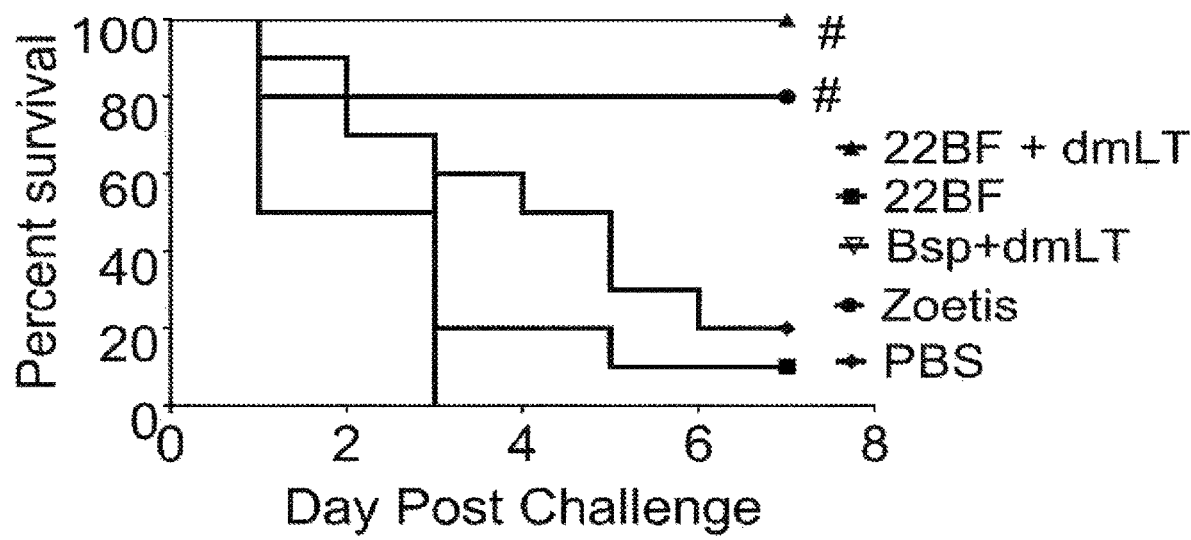
FIG. 1 shows the protective efficacy of intranasally administered 22BF against *B. bronchiseptica* challenge. Mice (n=10) were vaccinated intranasally biweekly three times with the indicated formulation which contained 10 μg protein±dmLT. ZOETIS® vaccine was delivered subcutaneously on day 1 and 21 as per manufacturer's directions. Mice were challenged with $1.3 \times 10^7$ *B. bronchiseptica* on day 56. BopB was not available at day 0. #P<0.05 compared to survival of mice vaccinated with PBS.
Figure 2:
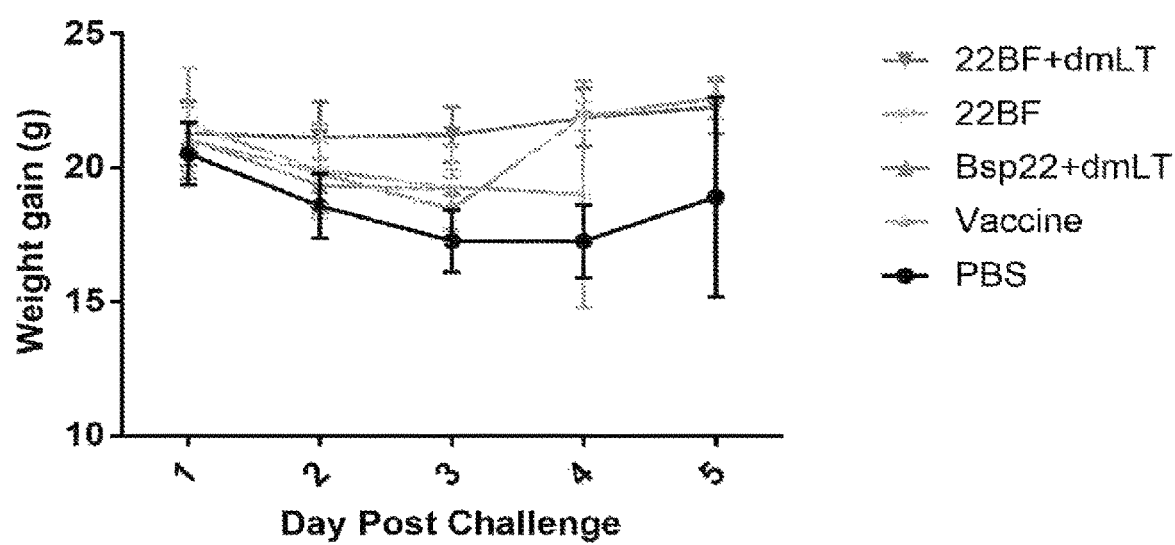
FIG. 2 shows the weight gain/loss of vaccinated mice during *B. bronchiseptica* challenge. Mice (same as above) were weighed daily in p.m. Note that the 22BF+dmLT mice gain weight and have small error bars.
Figures 3A, 3B:
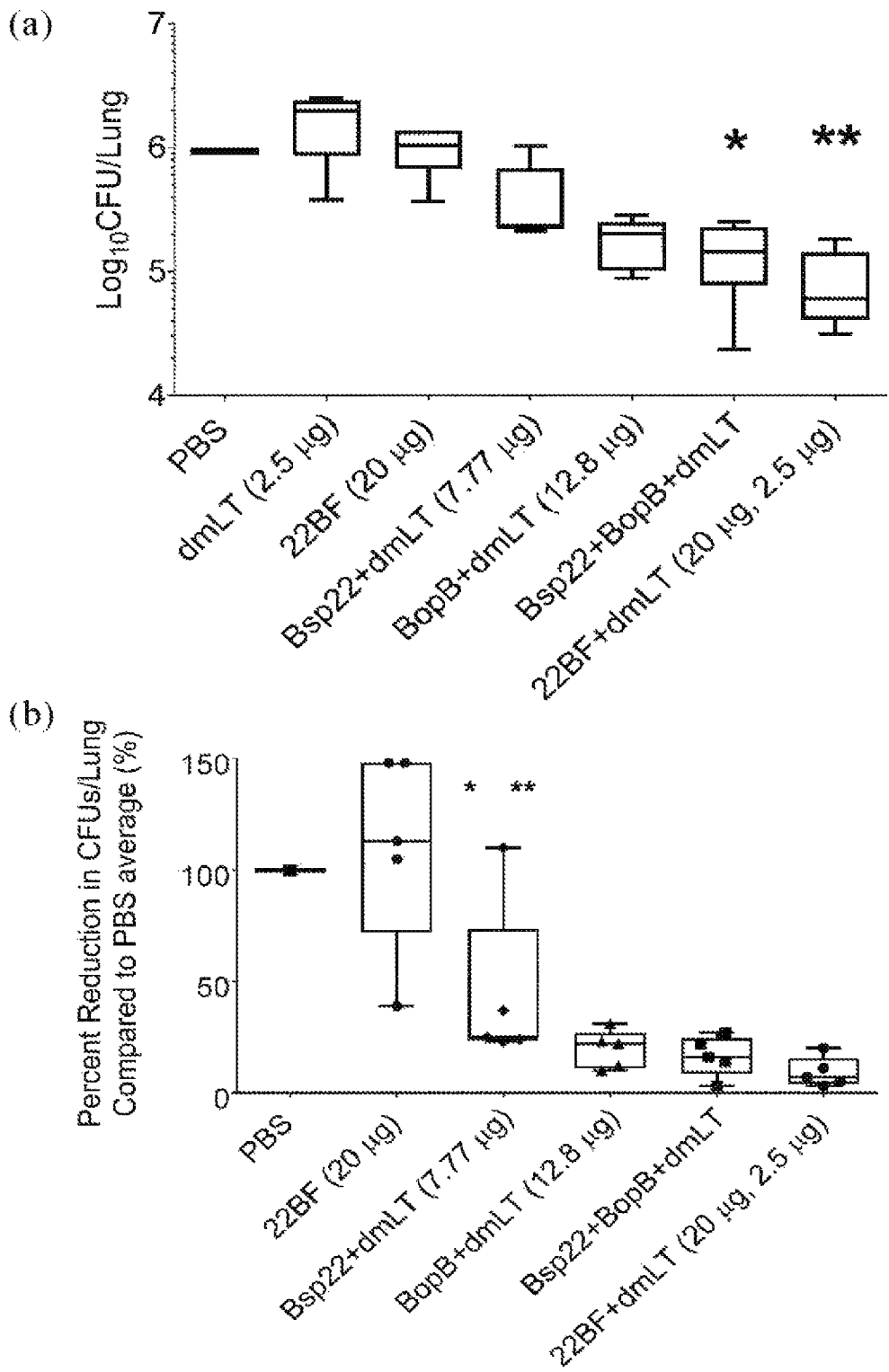
FIG. 3A and FIG. 3B show the protective efficacy of 22BF+dmLT. Mice were vaccinated on days 0, 14, 28 and challenged on day 56 with a sublethal dose of *B. bronchiseptica*.
Figure 10:
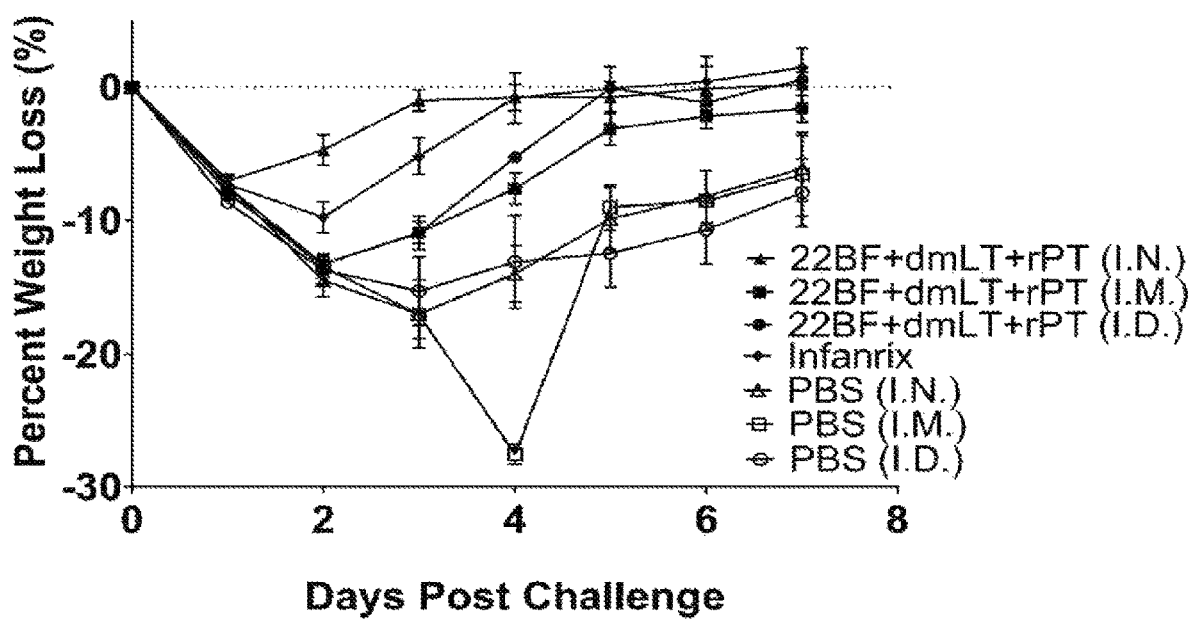
FIG. 10 shows the change in weight in percentage after infection with sublethal dosage of *B. pertussis* intranasally. There was an observable difference in weight loss between mice vaccinated with the 22BF+dmLT+PTd formulation and those that only received PBS. By Day 7 all mice aside from PBS treated mice had recovered to within 3% of pre-infection weight.
Figure 11:
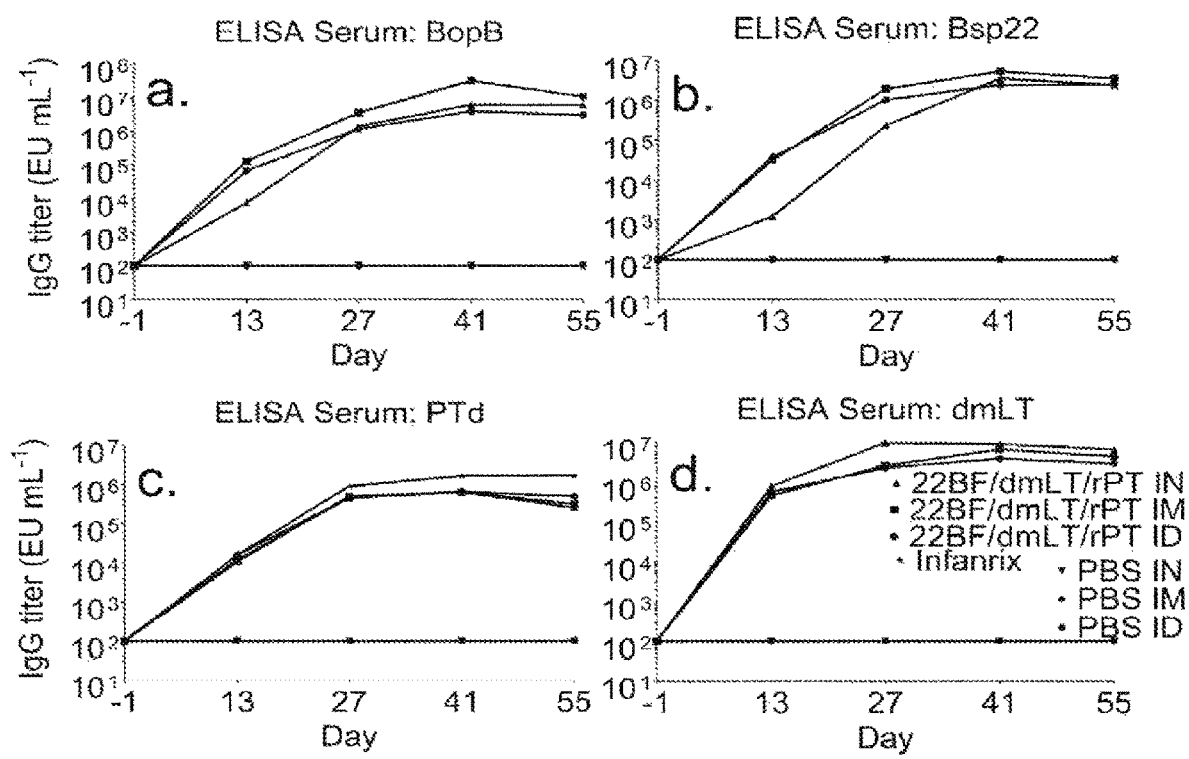
FIGS. 11A, 11B, 11C, and 11D show serum antibody responses to BopB, Bsp22, Pertussis Toxin Mutant, and dmLT. Mice were immunized on days 0, 14, and 28 with 22BF+PTd admixed with dmLT. Serum IgG antibodies specific for BopB, Bsp22, PTd, and dmLT were measured by ELISA and the data is shown in (11A) BopB, (11B) Bsp22, (11C) PTd, and (11D) dmLT. Data are the mean titers (EU ml-1) from group pools of animal samples. An asterisk indicates a P value of 0.05 when comparing vaccinated mice and the PBS controls. No responses were seen in the control mice that received PBS. Mice vaccinated with INFANRIX® only displayed a response against pertussis toxin mutant, which is part of its formulation.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

The needle tip protein and/or translocator proteins or antigenic portions thereof disclosed herein are used to elicit an immune response in subjects to whom they are administered. By "elicit an immune response", "induces or enhances an immune response", or "stimulates an immune response" which are used interchangeably herein, is meant that the subject mounts one or both of an innate and/or an adaptive immune reaction against antigenic determinants of the proteins or antigenic portions thereof that are administered. Preferably a statistically measurable induction or increase in an immune response over a control sample to which the needle tip protein and/or translocator proteins or antigenic portions thereof disclosed herein has not been administered. Preferably the induction or enhancement of the immune response results in a prophylactic or therapeutic response in a subject. In particular, the adaptive immune reaction entails production of e.g. B and T cell lymphocytes and antibodies specific for binding and forming complexes with the antigenic determinants. In some embodiments, the proteins and/or antigenic fragments thereof elicit a protective immune response in the subject, i.e. administration of one or more of the proteins and/or antigenic portions thereof results in an immune response that is protective against later challenge by the disease causing organism itself, either preventing infection altogether, or lessening the impact of infection by decreasing disease symptoms that would otherwise occur, had the subject not been vaccinated as described herein.

"Vaccine" as used herein is a preparation that stimulates an immune response that produces immunity against particular antigens, e.g. Gram negative bacteria. Vaccines may be administered prophylactically (for example, to prevent or inhibit the establishment of an infection) or therapeutically to inhibit, reduce, or treat an established infection, or to ameliorate the effects or symptoms of an infection. Vaccines may contain, but are not limited to, live, attenuated infectious material such as viruses or bacteria, and dead or inactivated organisms or purified products derived therefrom. A vaccine can be administered by injection, orally, or by inhalation. Injections may be, but are not limited to, subcutaneous (sc), intramuscular (im), intraperitoneal (ip), intradermal (id) or intravenous (iv).

"Optional" or "optionally" means that the subsequently described event or circumstance may or may not occur, and that the description includes instances where said event or circumstance occurs and instances where it does not.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient. The term "patient" refers to a subject under the treatment of a clinician, e.g., physician or veterinarian.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a particular needle tip protein (such as, for example, IpaD, SipD, SseB, Bsp22, LcrV, BipD, PcrV, CT053, or CT668), translocator protein (such as, for example, IpaB, SipB, SseC, BopB, YopB, BipB, PopB, CopB, or CopB2), or fusion polypeptide thereof (such as, for example, 22BF, BurkF, PaF, YerF, CT053-CopB, CT053-CopB2, CT668-CopB, or CT668-CopB2) is disclosed and discussed and a number of modifications that can be made to a number of molecules including the needle tip protein (such as, for example, IpaD, SipD, SseB, Bsp22, LcrV, BipD, PcrV, CT053, or CT668), translocator protein (such as, for example, IpaB, SipB, SseC, BopB, YopB, BipB, PopB, CopB, or CopB2), or fusion polypeptide thereof (such as, for example, 22BF, BurkF, PaF, YerF, CT053-CopB, CT053-CopB2, CT668-CopB, or CT668-CopB2) are discussed, specifically contemplated is each and every combination and permutation of needle tip protein such as, for example, IpaD, SipD, SseB, Bsp22, LcrV, BipD, PcrV, CT053, or CT668), translocator protein (such as, for example, IpaB, SipB, SseC, BopB, YopB, BipB, PopB, CopB, or CopB2), or fusion polypeptide thereof (such as, for example, DBF, S1, S2, 22BF, BurkF, PaF, YerF, CT053-CopB, CT053-CopB2, CT668-CopB, or CT668-CopB2) and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

To infect a host, *B. pertussis* uses an arsenal of well-characterized virulence factors. These factors include pertussis toxin (PT), adenylate cyclase toxin (ACT), the type III secretion system (T3SS), tracheal cytotoxin (TCT), dermonecrotic toxin (DNT), filamentous hemagglutinin (FHA), pertactin (PRN), and lipooligosaccharide (LOS). Current aP vaccines are comprised of PT, FHA, PRN, and the fimbrial proteins in varying proportions, but not necessarily all four proteins. Though the aP vaccine causes fewer adverse reactions than the wP vaccine, it is not as efficacious. This same situation exists for other pathogenic Gram negative bacteria. Accordingly, disclosed herein are fusion polypeptides from a Type III secretion system (T3SS) of a Gram negative bacteria (such as, for example, *Shigella* spp., *Salmonella enterica, Bordetella* spp. (such as, for example *B. pertussis* and/or *B. bronchiseptica*), *Burkholderia* spp. (such as, for example, *B. cepacian, B. mallei*, and/or *B. pseudomallei*), *Chlamydia* spp. (such as, for example, *C. trachomatis*), *Pseudomonas* spp., *Vibrio* spp. or *Yersinia* spp.) comprising a polypeptide of needle tip protein (such as, for example, IpaD, SipD, SseB, Bsp22, LcrV, BipD, PcrV, CT053, or CT668) or an antigenic fragment thereof and polypeptides of a translocator protein (such as, for example, IpaB, SipB, SseC, BopB, YopB, BipB, PopB, CopB, or CopB2) or an antigenic fragment thereof. In some aspect, the fusion polypeptide does not comprise a needle tip protein polypeptide or translocator polypeptide from a *Shigella* spp. (IpaD and IpaB) or a *Salmonella* spp. (such as, for example, *S. enterica*) (SipD, SseB, SipB, and SseC). It is recognized and herein contemplated that the disclosed polypeptides can be separate components of a composition or more preferably a fusion construct. By a "fusion polypeptide" is meant a peptide, polypeptide, or protein that is translated from a single, contiguous nucleic acid molecule, and which comprises sequences from at least two different proteins or antigenic regions thereof. Typically, the individual sequences are joined via a linker or spacer sequence of e.g. from about 2 to about 20 amino acids, usually from about 2 to about 10 amino acids. The amino acids in linking sequences are typically uncharged and the linker sequence usually does not exhibit secondary or tertiary structure, but does allow the fused protein/peptide segments to adopt functional secondary, tertiary, etc. conformations. One such exemplary fusion polypeptide includes Bsp22 (as set forth in SEQ ID NO: 4 and encoded by the nucleic acid sequence as set forth in SEQ ID NO: 3) and BopB (as set forth in SEQ ID NO: 6 and encoded by the nucleic acid sequence as set forth in SEQ ID NO: 5). The amino acid sequence of this chimera (i.e., 22BF) is set forth in SEQ ID NO: 2. The chimera may be encoded by any suitable nucleic acid sequence, e.g. the exemplary nucleic acid sequence depicted in SEQ ID NO: 1.

Thus, in one aspect, disclosed herein are fusion polypeptides comprising a fusion of a needle tip protein (such as, for example, IpaD, SipD, SseB, Bsp22, LcrV, BipD, PcrV, CT053, or CT668) or an antigenic fragment thereof and a translocator protein (such as, for example, IpaB, SipB, SseC, BopB, YopB, BipB, PopB, CopB, or CopB2) or an antigenic fragment thereof from a Type III secretion system (T3SS) of a Gram negative bacteria (such as, for example, *Bordetella* spp., *Burkholderia* spp., *Chlamydia* spp., *Pseudomonas* spp., *Vibrio* spp. or *Yersinia* spp. For example, the fusion polypeptide can comprise a fusion of the *Shigella* spp. needle tip protein (IpaD) and first translocator protein (IpaB) or fragments thereof (the fusion referred to as DBF), *Salmonella* spp. (such as, for example, *S. enterica*) SPI-1 needle tip protein (SipD) (as set forth in SEQ ID NO: 52 and encoded by the nucleic acid sequence as set forth in SEQ ID NO: 51) and translocator protein (SipB) (as set forth in SEQ ID NO: 54 and encoded by the nucleic acid sequence as set forth in SEQ ID NO: 53) or fragments thereof (the fusion referred to as 51) (as set forth in SEQ ID NO: 56 and encoded by the nucleic acid sequence as set forth in SEQ ID NO: 55), *Salmonella* spp. (such as, for example, *S. enterica*) SPI-2 needle tip protein (SseB) (as set forth in SEQ ID NO: 62 and encoded by the nucleic acid sequence as set forth in SEQ ID NO: 61) and translocator protein (SseC) (as set forth in SEQ ID NO: 64 and encoded by the nucleic acid sequence as set forth in SEQ ID NO: 63) or fragments thereof (the fusion referred to as S2) (as set forth in SEQ ID NO: 66 and encoded by the nucleic acid sequence as set forth in SEQ ID NO: 65), *Bordetella* spp. needle-tip protein (Bsp22) and translocator protein (BopB), or fragments thereof (the fusion referred to as 22BF); a fusion of the *Yersinia* spp. needle-tip protein (LcrV) (as set forth in SEQ ID NO: 42 and encoded by the nucleic acid sequence as set forth in SEQ ID NO: 41) and translocator protein (YopB) (as set forth in SEQ ID NO: 44 and encoded by the nucleic acid sequence as set forth in SEQ ID NO: 43), or fragments thereof (the fusion referred to as YerF) (as set forth in SEQ ID NO: 46 and encoded by the nucleic acid sequence as set forth in SEQ ID NO: 45); a fusion of the *Burkholderia* spp. needle-tip protein (BipD) (as set forth in SEQ ID NO: 22 and encoded by the nucleic acid sequence as set forth in SEQ ID NO: 21) and translocator protein (BipB) (as set forth in SEQ ID NO: 24 and encoded by the nucleic acid sequence as set forth in SEQ ID NO: 23), or fragments thereof (the fusion referred to as BurkF) (as set forth in SEQ ID NO: 26 and encoded by the nucleic acid sequence as set forth in SEQ ID NO: 25); a fusion of the *Pseudomonas* spp. needle-tip protein (PcrV) (as set forth in SEQ ID NO: 32 and encoded by the nucleic acid sequence as set forth in SEQ ID NO: 31) and translocator protein (PopB) (as set forth in SEQ ID NO: 34 and encoded by the nucleic acid sequence as set forth in SEQ ID NO: 33), or fragments thereof (the fusion referred to as PaF) (as set forth in SEQ ID NO: 36 and encoded by the nucleic acid sequence as set forth in SEQ ID NO: 35); and/or a fusion of the *Chlamydia* spp. needle-tip protein CT053 (as set forth in SEQ ID NO: 74 and encoded by the nucleic acid sequence as set forth in SEQ ID NO: 73) or CT668 (as set forth in SEQ ID NO: 84 and encoded by the nucleic acid sequence as set forth in SEQ ID NO: 83) and translocator protein (CopB (as set forth in SEQ ID NO: 76 and encoded by the nucleic acid sequence as set forth in SEQ ID NO: 75) or CopB2 (as set forth in SEQ ID NO: 92 and encoded by the nucleic acid sequence as set forth in SEQ ID NO: 91)), or fragments thereof such fusions including but not limited to CT053-CopB (the CT053-CopB fusion as set forth in SEQ ID NO: 78 and encoded by the nucleic acid sequence as set forth in SEQ ID NO: 77), CT668-CopB (the CT668-CopB fusion as set forth in SEQ ID NO: 86 and encoded by the nucleic acid sequence as set forth in SEQ ID NO: 85), CT053-CopB2 (the CT053-CopB2 fusion as set forth in SEQ ID NO: 94 and encoded by the nucleic acid sequence as set forth in SEQ ID NO: 93), and CT053-CopB2 (the CT668-CopB2 fusion as set forth in SEQ ID NO: 100 and encoded by the nucleic acid sequence as set forth in SEQ ID NO: 99) and collectively each fusion being referred to as ChlamF. In one aspect, the fusion polypeptide does not comprise any needle tip protein or translocator protein or fragment thereof from a *Salmonella* spp. or a *Shigella* spp. Accordingly, disclosed herein are fusion polypeptides comprising a fusion of a needle tip protein (such as, for example, Bsp22, LcrV, BipD, PcrV, CT053, or CT668) or an antigenic fragment thereof and a translocator protein (such as, for example, BopB, YopB, BipB, PopB, CopB, or CopB2) or an antigenic fragment thereof from a Type III secretion system (T3SS) of a Gram negative bacteria (such as, for example, *Bordetella* spp., *Burkholderia* spp., *Chlamydia* spp., *Pseudomonas* spp., *Vibrio* spp. or *Yersinia* spp. wherein the gram negative bacteria is not a *Salmonella enterica* or *Shigella* spp.

It is understood and herein contemplated that the arrangement of the polypeptides in a fusion construct can have significant impact on the antigenicity of the fusion construct. Accordingly, in one aspect, disclosed herein are fusion polypeptides, wherein the fusion polypeptide is arranged such that the needle tip protein is 5' of the translocator protein.

The present invention provides compositions for use in eliciting an immune response and/or vaccinating an individual against Gram negative bacterial infection, and/or against disease symptoms caused by Gram negative bacterial infection. The compositions include one or more substantially purified proteins, polypeptides or antigenic regions thereof as described herein, or substantially purified nucleic acid sequences (e.g. DNA cDNA, RNA, etc.) encoding such proteins, polypeptides or antigenic regions thereof, and a pharmacologically suitable/compatible carrier. By "substantially purified" is meant that the molecule is largely free of other organic molecules, cellular debris, solvents, etc. when tested using standard techniques known to those of skill in the art (e.g. gel electrophoresis, column chromatography, sequencing, mass spectroscopy, etc.). For example, the molecule is generally at least about 50, 55, 60, 65, 70, or 75% pure by wt %, and preferably is at least about 80, 85, 90, 95% or more preferably pure (e.g. 96, 97, 98, 99 or even 100% pure). The preparation of proteins, polypeptides, and peptides as described herein is well-known to those in the art, and includes, for example, recombinant preparation; isolation from a natural source; chemical synthesis; etc. The purification of proteinaceous materials is also known. However, specific exemplary methods for preparing the vaccinating agents utilized in the practice of the invention are described in detail in the Examples section below.

In addition, the composition may contain adjuvants, many of which are known in the art. For example, adjuvants suitable for use in the invention include but are not limited to: bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof. Non-toxic derivatives of LPS include monophosphoryl lipid A (MPL) and 3-O-deacylated MPL (3dMPL). 3dMPL is a mixture of three de-O-acylated monophosphoryl lipid A with 4, 5 or 6 acylated chains. A preferred non-toxic derivative of LPS is 3 De-O-acylated monophosphoryl lipid nostimulatory. The CpG's can include nucleotide modifications/analogs such as phosphorothioate modifications and can be double-stranded or single-stranded, e.g. replacement of guanosine with 2'-deoxy-7-deazaguanosine. The CpG sequence may include, for example, the motif GTCGTT or TTCGTT. The CpG sequence may be specific for inducing a Th1 immune response, such as a CpG-A ODN, or it may be more specific for inducing a B cell response, such a CpG-B ODN, CpG-A and CpG-B ODNs. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers".

Bacterial ADP-ribosylating toxins and detoxified derivatives thereof may be used as adjuvants in the invention. Preferably, the protein is derived from *E. coli* (e.g. *E. coli* heat labile enterotoxin "LT"), cholera ("CT")(Table 1), or pertussis ("PT").

TABLE 1

Cholera Toxin (CTA1) subunits and sequences

| Subunit | DNA sequence | AA sequence |
|---|---|---|
| Subunit A | ATGGTAAAGATAATATTTGTGTTTTTTATTTTCTT<br>ATCATCATTTTCATATGCAAATGATGATAAGTTAT<br>ATCGGGCAGATTCTAGACCTCCTGATGAAATAAA<br>GCAGTCAGGTGGTCTTATGCCAAGAGGACAGAGT<br>GAGTACTTTGACCGAGGTACTCAAATGAATATCA<br>ACCTTTATGATCATGCAAGAGGAACTCAGACGGG<br>ATTTGTTAGGCACGATGATGGATATGTTTCCACCT<br>CAATTAGTTTGAGAAGTGCCCACTTAGTGGGTCA<br>AACTATATTGTCTGGTCATTCTACTTATTATATAT<br>ATGTTATAGCCACTGCACCCAACATGTTTAACGTT<br>AATGATGTATTAGGGGCATACAGTCCTCATCCAG<br>ATGAACAAGAAGTTTCTGCTTTAGGTGGGATTCC<br>ATACTCCCAAATATATGGATGGTATCGAGTTCAT<br>TTTGGGGTGCTTGATGAACAATTACATCGTAATA<br>GGGGCTACAGAGATAGATATTACAGTAACTTAGA<br>TATTGCTCCAGCAGCAGATGGTTATGGATTGGCA<br>GGTTTCCCTCCGGAGCATAGAGCTTGGAGGGAAG<br>AGCCGTGGATTCATCATGCACCGCCGGGTTGTGG<br>GAATGCTCCAAGATCATCGATCAGTAATACTTGC<br>GATGAAAAAACCCAAAGTCTAGGTGTAAAATTCC<br>TTGACGAATACCAATCTAAAGTTAAAAGACAAAT<br>ATTTTCAGGCTATCAATCTGATATTGATACACATA<br>ATAGAATTAAGGATGAATTATGA<br>(SEQ ID NO: 115) | MVKIIFVFFIFLSSFSYAND<br>DKLYRADSRPPDEIKQSGG<br>LMPRGQSEYFDRGTQMNI<br>NLYDHARGTQTGFVRHDD<br>GYVSTSISLRSAHLVGQTIL<br>SGHSTYYIYVIATAPNMFN<br>VNDVLGAYSPHPDEQEVS<br>ALGGIPYSQIYGWYRVHFG<br>VLDEQLHRNRGYRDRYYS<br>NLDIAPAADGYGLAGFPPE<br>HRAWREEPWIHHAPPGCG<br>NAPRSSMSNTCDEKTQSLG<br>VKFLDEYQSKVKRQIFSGY<br>QSDIDTHNRIKDEL<br>(SEQ ID NO: 116) |
| Subunit B | ATGATTAAATTAAAATTTGGTGTTTTTTTACAGT<br>TTTACTATCTTCAGCATATGCACATGGAACACCTC<br>AAAATATTACTGATTTGTGTGCAGAATACCACAA<br>CACACAAATATATACGCTAAATGATAAGATATTT<br>TCGTATACAGAATCTCTAGCTGGAAAAAGAGAGA<br>TGGCTATCATTACTTTTAAGAATGGTGCAATTTTT<br>CAAGTAGAAGTACCAGGTAGTCAACATATAGATT<br>CACAAAAAAAAGCGATTGAAAGGATGAAGGATA<br>CCCTGAGGATTGCATATCTTACTGAAGCTAAAGT<br>CGAAAAGTTATGTGTATGGAATAATAAAACGCCT<br>CATGCGATTGCCGCAATTAGTATGGCAAATTAA<br>(SEQ ID NO: 117) | MIKLKFGVFFTVLLSSAYA<br>HGTPQNITDLCAEYHNTQI<br>YTLNDKIFSYTESLAGKRE<br>MAIITFKNGAIFQVEVPGS<br>QHIDSQKKAIERMKDTLRI<br>AYLTEAKVEKLCVWNNKT<br>PHAIAAISMAN<br>(SEQ ID NO: 118) |

A. Other non-toxic LPS derivatives include monophosphoryl lipid A mimics, such as aminoalkyl glucosaminide phosphate derivatives, e.g. RC-529.

Lipid A derivatives include derivatives of lipid A from *Escherichia coli* such as OM-174. Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immu- The toxin or toxoid is preferably in the form of a holotoxin, comprising both A and B subunits. Preferably, the A subunit contains a detoxifying mutation; preferably the B subunit is not mutated. More preferably, the adjuvant is a detoxified LT mutant such as LT-K63, LT-R72, and LT-G192. The use of ADP-ribosylating toxins and detoxified derivatives thereof, particularly LT-K63 and LT-R72, is known. Such adjuvants are described, for example, in issued U.S. Pat. No. 8,039,007 (the complete contents of which is hereby incorporated by reference in entirety). Various interleukins may also be used as adjuvants to increase the immune response in a subject. In preferred embodiments, the adjuvant is a mucosal adjuvant such as, for example, the double mutant heat-labile toxin (dmLT) as set forth in SEQ ID NOs: 113 and 114) from enterotoxigenic *E. coli* or the active moiety thereof known as LTA1 (as set forth in SEQ ID NO: 13 and encoded by the nucleic acid sequence as set forth in SEQ ID NO: 12) and encoded by nor cholera toxin or the active moiety thereof known as CTA1. Accordingly, disclosed herein are fusion polypeptides of any preceding aspect, wherein the fusion further comprises an adjuvant such as, for example, double mutant labile toxin (dmLT) or an antigenic fragment thereof (such as, for example, LTA1 or CTA1) from Enterotoxigenic *Escherichia coli*. In some aspect, the dmLT or fragment thereof can also be fused to the needle tip protein-translocator protein fusion at the 5' end. For example, specifically disclosed herein are LTA1-DBF, LTA1-S1 (as set forth in SEQ ID NO: 57 and encoded by the nucleic acid sequence as set forth in SEQ ID NO: 58), LTA1-52 (as set forth in SEQ ID NO: 68 and encoded by the nucleic acid sequence as set forth in SEQ ID NO: 67), LTA1-SseB (as set forth in SEQ ID NO: 70 and encoded by the nucleic acid sequence as set forth in SEQ ID NO: 69), LTA1-22BF (as set forth in SEQ ID NO: 18 and encoded by the nucleic acid sequence as set forth in SEQ ID NO: 17), LTA1-BurkF (as set forth in SEQ ID NO: 28 and encoded by the nucleic acid sequence as set forth in SEQ ID NO: 27), LTA1-CT668-CopB (as set forth in SEQ ID NO: 88 and encoded by the nucleic acid sequence as set forth in SEQ ID NO: 87), LTA1-CT668-CopB2 (as set forth in SEQ ID NO: 102 and encoded by the nucleic acid sequence as set forth in SEQ ID NO: 101), LTA1-CT053-CopB (as set forth in SEQ ID NO: 80 and encoded by the nucleic acid sequence as set forth in SEQ ID NO: 79), LTA1-CT053-CopB2 (as set forth in SEQ ID NO: 96 and encoded by the nucleic acid sequence as set forth in SEQ ID NO: 95), LTA1-PaF (as set forth in SEQ ID NO: 38 and encoded by the nucleic acid sequence as set forth in SEQ ID NO: 37), and LTA1-YerF (as set forth in SEQ ID NO: 48 and encoded by the nucleic acid sequence as set forth in SEQ ID NO: 47).

Whooping cough still causes significant mortality and morbidity in children all over the world. It also continues to be a problem in adults whose immunity has waned. Herein is disclosed a strong candidate for a new protective vaccine based on research on the T3SS proteins and resulting subunit vaccines, including the vaccine against shigellosis. It is demonstrated herein that the vaccine has 100% protective efficacy against *B. bronchiseptica* using 22BF+dmLT. While this is a remarkable step forward, examined herein is the immune response and the protective efficacy of 22BF+ dmLT±PTd against *B. pertussis*. The vaccine can also be taken a step further by eliciting sterilizing immunity so that the *B. pertussis* transmission chain can be broken.

Originally, the mechanism of protection against *B. pertussis*, an extracellular organism, was thought to be the humoral immune response, however, cell-mediated immunity has been found to also be important for protection with bacterial clearance mediated by Th1 and Th17 cells. By measuring cytokines corresponding to specific immune pathways, Ross et al. concluded that the wP vaccine promotes Th1 and Th17 responses while the aP vaccine elicits a mix of Th1 and Th2 responses. These differences likely account for the increased protection seen for the wP vaccine. A study in a baboon model compared wP vaccines with an aP vaccine and confirmed that the wP elicits a Th1/Th17 response while the aP vaccine elicits a Th1/Th2 response. Moreover, these studies found that aP does not prevent colonization or transmission of *B. pertussis*, even in asymptomatic subjects. Thus, the current pertussis resurgence could be due, in part, to the ability of the aP vaccine to protect the host against the overt symptoms of the disease while not preventing colonization and the resulting transmission of *B. pertussis* to susceptible children. Furthermore, protection of newborns against pertussis via aP or wP is problematic due not only to possible side effects but also because newborns lack the ability to mount a vaccine-induced Th1 response elicited through the requisite antigen presentation and T-cell activation. Although it has been shown, in some cases, that neonatal immunization can prime the immune system for subsequent booster vaccinations, the development of a protective pertussis vaccine for infants remains a need.

As noted above, the current aP vaccine does not provide sterilizing immunity. That is, the aP vaccine protects the immunized host, but does not stop colonization and transmission of the *Bordetella* spp. In one aspect, disclosed herein are fusion polypeptides of any preceding aspect, wherein the composition or fusion polypeptide further comprises an acellular Gram negative vaccine component (such as, for example, the acellular pertussis vaccine (aP) component pertussis toxoid (PTd)).

Pertussis toxin (PTX) is produced by *Bordetella pertussis*, the bacterium responsible for whooping cough. Pertussis toxin is a multi-component protein composed of six non-covalently bound subunits ranging in molecular weight from approximately about 9 kDa to about 28 kDa. These subunits are designated as S1, S2, S3, S4 and S5 and occur in native pertussis toxin in a ratio of 1:1:1:2:1, where the subunit S4 is present in two copies The largest subunit S1, also called the A protomer, is responsible for the ADP-ribosyltransferase activity. List Labs produces Pertussis Toxin Mutant R9K, E129A (both in the S1 subunit), a genetically inactivated mutant of pertussis toxin, which has a modified sequence encoding the enzyme subunit (Table 2). Virulence of this pertussis mutant is reduced relative to that found with the wild type.

TABLE 2

| Pertussis Toxic Mutant R9K, E129A | | |
|---|---|---|
| Subunit | DNA sequence | AA sequence |
| Subunit 1 | ATGCGTTGCACTCGGGCAATTCGCCAAACCGC | MRCTRAIRQTARTGWLTWL |
|  | AAGAACAGGCTGGCTGACGTGGCTGGCGATT | AILAVTAPVTSPAWADDPPA |
|  | CTTGCCGTCACGGCGCCCGTGACTTCGCCGGC | TVYRYDSRPPEDVFQNGFTA |
|  | ATGGGCCGACGATCCTCCCGCCACCGTATACC | WGNNDNVLDHLTGRSCQV |
|  | GCTATGACTCCCGCCCGCCGGAGGACGTTTTC | GSSNSAFVSTSSSRRYTEVYL |
|  | CAGAACGGATTCACGGCGTGGGGAAACAACG | EHRMQEAVEAERAGRGTGH |
|  | ACAATGTGCTCGACCATCTGACCGGACGTTCC | FIGYIYEVRADNNFYGAASS |
|  | TGCCAGGTCGGCAGCAGCAACAGCGCTTTCGT | YFEYVDTYGDNAGRILAGA |
|  | CTCCACCAGCAGCAGCCGGCGCTATACCGAG | LATYQSEYLAHRRIPPENIRR |

TABLE 2-continued

Pertussis Toxic Mutant R9K, E129A

| Subunit | DNA sequence | AA sequence |
|---|---|---|
| | GTCTATCTCGAACATCGCATGCAGGAAGCGGT<br>CGAGGCCGAACGCGCCGGCAGGGGCACCGGC<br>CACTTCATCGGCTACATCTACGAAGTCCGCGC<br>CGACAACAATTTCTACGGCGCCGCCAGCTCGT<br>ACTTCGAATACGTCGACACTTATGGCGACAAT<br>GCCGGCCGTATCCTCGCCGGCGCGCTGCCAC<br>CTACCAGAGCGAATATCTGGCACACCGGCGC<br>ATTCCGCCCGAAAACATCCGCAGGGTAACGC<br>GGGTCTATCACAACGGCATCACCGGCGAGAC<br>CACGACCACGGAGTATTCCAACGCTCGCTACG<br>TCAGCCAGCAGACTCGCGCCAATCCCAACCCC<br>TACACATCGCGAAGGTCCGTAGCGTCGATCGT<br>CGGCACATTGGTGCGCATGGCGCCGGTGATA<br>GGCGCTTGCATGGCGCGGCAGGCCGAAAGCT<br>CCGAGGCCATGGCAGCCTGGTCCGAACGCGC<br>CGGCGAGGCGATGGTTCTCGTGTACTACGAA<br>AGCATCGCGTATTCGTTCTAG<br>(SEQ ID NO: 103) | VTRVYHNGITGETTTTEYSN<br>ARYVSQQTRANPNPYTSRRS<br>VASIVGTLVRMAPVIGACM<br>ARQAESSEAMAAWSERAGE<br>AMVLVYYESIAYSF<br>(SEQ ID NO: 104) |
| Subunit 2 | ATGCCGATCGACCGCAAGACGCTCTGCCATCT<br>CCTGTCCGTTCTGCCGTTGGCCCTCCTCGGAT<br>CTCACGTGGCGCGGGCCTCCACGCCAGGCATC<br>GTCATTCCGCCGCAGGAACAGATTACCCAGC<br>ATGGCAGCCCCTATGGAGCGTGCGCGAACAA<br>GACCCGTGCCCTGACCGTGGCGGAATTGCGC<br>GGCAGCGGCGATCTGCAGGAGTACCTGCGTC<br>ATGTGACGCGCGGCTGGTCAATATTTGCGCTC<br>TACGATGGCACCTATCTCGGCGGCGAATATGG<br>CGGCGTGATCAAGGACGGAACACCCGGCGGC<br>GCATTCGACCTGAAAACGACGTTCTGCATCAT<br>GACCACGCGCAATACGGGTCAACCCGCAACG<br>GATCACTACTACAGCAACGTCACCGCCACTCG<br>CCTGCTCTCCAGCACCAACAGCAGGCTATGCG<br>CGGTCTTCGTCAGAAGCGGGCAACCGGTCATT<br>GGCGCCTGCACCAGCCCGTATGACGGCAAGT<br>ACTGGAGCATGTACAGCCGGCTGCGGAAAAT<br>GCTTTACCTGATCTACGTGGCCGGCATCTCCG<br>TACGCGTCCATGTCAGCAAGGAAGAACAGTA<br>TTACGACTATGAGGACGCAACGTTCGAGACTT<br>ACGCCCTTACCGGCATCTCCATCTGCAATCCT<br>GGATCATCCTTATGCTGA<br>(SEQ ID NO: 105) | MPIDRKTLCHLLSVLPLALL<br>GSHVARASTPGIVIPPQEQIT<br>QHGGPYGRCANKTRALTVA<br>ELRGSGDLQEYLRHVTRGW<br>SIFALYDGTYLGGEYGGVIK<br>DGTPGGAFDLKTTFCIMTTR<br>NTGQPATDHYYSNVTATRL<br>LSSTNSRLCAVFVRSGQPVIG<br>ACTSPYDGKYWSMYSRLRK<br>MLYLIYVAGISVRVHVSKEE<br>QYYDYEDATFETYALTGISI<br>CNPGSSLC<br>(SEQ ID NO: 106) |
| Subunit 3 | ATGCTGATCAACAACAAGAAGCTGCTTCATCA<br>CATTCTGCCCATCCTGGTGCTCGCCCTGCTGG<br>GCATGCGCACGGCCCAGGCCGTTGCGCCAGG<br>CATCGTCATCCCGCCAAGGCACTGTTCACCC<br>AACAGGGCGGCGCCTATGGACGCTGCCCGAA<br>CGGAACCCGCGCCTTGACCGTGGCCGAACTG<br>CGCGGCAACGCCGAATTGCAGACGTATTTGC<br>GCCAGATAACGCCCGGCTGGTCCATATACGGT<br>CTCTATGACGGTACGTACCTGGGCCAGGCGTA<br>CGGCGGCATCATCAAGGACGCGCCGCCAGGC<br>GCGGGGTTCATTTATCGCGAAACTTTCTGCAT<br>CACGACCATATACAAGACCGGGCAACCGGCT<br>GCGGATCACTACTACAGCAAGGTCACGGCCA<br>CGCGCCTGCTCGCCAGCACCAACAGCAGGCT<br>GTGCGCGGTATTCGTCAGGGACGGGCAATCG<br>GTCATCGGAGCCTGCCGCCAGCCCGTATGAAG<br>GCAGGTACAGAGACATGTACGACGCGCTGCG<br>GCGCCTGCTGTACATGATCTATATGTCCGGCC<br>TTGCCGTACGCGTCCACGTCAGCAAGGAAGA<br>GCAGTATTACGACTACGAGGACGCCACATTCC<br>AGACCTATGCCCTCACCGGCATTTCCCTCTGC<br>AACCCGGCAGCGTCGATATGCTGA<br>(SEQ ID NO: 107) | MLINNKKLLHHILPILVLALL<br>GMRTAQAVAPGIVIPPKALF<br>TQQGGAYGRCPNGTRALTV<br>AELRGNAELQTYLRQITPGW<br>SIYGLYDGTYLGQAYGGIIK<br>DAPPGAGFIYRETFCITTIYK<br>TGQPAADHYYSKVTATRLL<br>ASTNSRLCAVFVRDGQSVIG<br>ACASPYEGRYRDMYDALRR<br>LLYMIYMSGLAVRVHVSKE<br>EQYYDYEDATFQTYALTGIS<br>LCNPAASIC<br>(SEQ ID NO: 108) |
| Subunit 4 | ATGCTGAGACGCTTCCCCACTCGAACCACCGC<br>CCCGGGACAGGGCGGCGCCCGGCGGTCGCGC<br>GTGCGCGCCCTGGCGTGGTTGCTGGCATCCGG<br>CGCGATGACGCATCTTTCCCCCGCCTGGCCG<br>GTGGTCACCAGCGTAGCCATGAAGCCGTATG<br>AAGTCACCCCGACGCGCATGCTGGTCTGCGGC<br>ATCGCCGCAAACTGGGCGCCGCGGCCAGCA<br>GCCCGGACGCGCACGTGCCGTTCTGCTTCGGC | MLRRFPTRTTAPGQGGARRS<br>RVRALAWLLASGAMTHLSP<br>ALADVPYVLVKTNMVVTSV<br>AMKPYEVTPTRMLVCGIAA<br>KLGAAASSPDAHVPFCFGKD<br>LKRPGSSPMEVMLRAVFMQ<br>QRPLRMFLGPKQLTFEGKPA<br>LELIRMVECSGKQDCP<br>(SEQ ID NO: 110) |

TABLE 2-continued

| Pertussis Toxic Mutant R9K, E129A | | |
|---|---|---|
| Subunit | DNA sequence | AA sequence |
| | AAGGATCTCAAGCGTCCCGGCAGCAGTCCCA TGGAAGTCATGTTGCGCGCCGTCTTCATGCAA CAACGGCCGCTGCGCATGTTTCTGGGTCCCAA GCAACTCACTTTCGAAGGCAAGCCCGCGCTCG AACTGATCCGGATGGTCGAATGCAGCGGCAA GCAGGATTGCCCCTGA (SEQ ID NO: 109) | |
| Subunit 5 | ATGCAGCGGCAAGCAGGATTGCCCCTGAAGG CGAACCCCATGCATACCATCGCATCCATCCTG TTGTCCGTGCTCGGCATATACAGCCCGGCTGA CGTCGCCGGCTTGCCGACCCATCTGTACAAGA ACTTCACTGTCCAGGAGCTGGCCTTGAAACTG AAGGGCAAGAATCAGGAGTTCTGCCTGACCG CCTTCATGTCGGGCAGAAGCCTGGTCCGGGCG TGCCTGTCCGACGCGGGACACGAGCACGACA CGTGGTTCGACACCATGCTTGGCTTTGCCATA TCCGCGTATGCGCTCAAGAGCCGGATCGCGCT GACGGTGGAAGACTCGCCGTATCCGGGCACT CCCGGCGATCTGCTCGAACTGCAGATCTGCCC GCTCAACGGATATTGCGAATGA (SEQ ID NO: 111) | MQRQAGLPLKANPMHTIASI LLSVLGIYSPADVAGLPTHL YKNFTVQELALKLKGKNQE FCLTAFMSGRSLVRACLSDA GHEHDTWFDTMLGFAISAY ALKSRIALTVEDSPYPGTPG DLLELQICPLNGYCE (SEQ ID NO: 112) |

It is understood and herein contemplated that the disclosed polypeptides, adjuvants, and acellular vaccine components for use in eliciting an immune response or for treating, inhibiting, or preventing a Gram negative bacterial infection can be administered in compositions such as vaccines as individual polypeptides or as a fusion construct or a combination thereof. Thus, in one aspect, disclosed herein are compositions comprising a T3SA needle tip protein (such as, for example, Bsp22, LcrV, BipD, PcrV, CT053, or CT668) or an antigenic fragment thereof from a Gram negative bacteria (such as, for example, *Bordetella* spp., *Burkholderia* spp., *Chlamydia* spp., *Pseudomonas* spp., *Vibrio* spp. or *Yersinia* spp.) and a T3SA translocator protein (such as, for example, BopB, YopB, BipB, PopB, CopB, or CopB2) or an antigenic fragment thereof from a Gram negative bacteria; wherein the gram negative bacteria is not a *Salmonella enterica* or *Shigella* spp. In one aspect, the composition can comprise the needle tip protein or fragment thereof and the translocator protein or fragment thereof as separate components or as a fusion polypeptide. Also disclosed herein are compositions of any preceding aspect, wherein the composition comprises an adjuvant (such as, for example, cholera toxin, CTA1, dmLT, or LTA1) and/or bacterial toxin protein, such as a pertussis toxoid (PTd). Thus, in one aspect, disclosed herein are vaccines comprising any of the peptides, polypeptides, proteins, fusion peptides, fusion polypeptides, fusion proteins, or compositions disclosed herein. In some embodiments, the vaccine can further comprise an acellular gram negative vaccine or active components thereof.

1. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed (such as, for example, Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2) typically have at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

2. Nucleic Acids

There are a variety of molecules disclosed herein that are nucleic acid based, including for example the nucleic acids that encode, for example Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2 or antigenic fragments thereof, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine, as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., *Proc. Natl. Acad. Sci. USA*, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the protein molecules involved in the signaling pathways disclosed herein, for example Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2, or any of the nucleic acids disclosed herein for making Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2, all of which are encoded by nucleic acids or are nucleic acids. The sequences for the human analogs of these genes, as well as other analogs, and alleles of these genes, and splice variants and other types of variants, are available in a variety of protein and gene databases, including GENBANK®. Those of skill in the art understand how to resolve sequence discrepancies and differences and to adjust the compositions and methods relating to a particular sequence to other related sequences. Primers and/or probes can be designed for any given sequence given the information disclosed herein and known in the art.

3. Nucleic Acid Delivery

In the methods described above which include the administration and uptake of exogenous DNA into the cells of a subject (i.e., gene transduction or transfection), the disclosed nucleic acids can be in the form of naked DNA or RNA, or the nucleic acids can be in a vector for delivering the nucleic acids to the cells, whereby the antibody-encoding DNA fragment is under the transcriptional regulation of a promoter, as would be well understood by one of ordinary skill in the art. The vector can be a commercially available preparation, such as an adenovirus vector (Quantum Biotechnologies, Inc. (Laval, Quebec, Canada). Delivery of the nucleic acid or vector to cells can be via a variety of mechanisms. As one example, delivery can be via a liposome, using commercially available liposome preparations such as LIPOFECTIN, LIPOFECTAMINE (GIBCO-BRL, Inc., Gaithersburg, MD), SUPERFECT (Qiagen, Inc. Hilden, Germany) and TRANSFECTAM (Promega Biotec, Inc., Madison, WI), as well as other liposomes developed according to procedures standard in the art. In addition, the disclosed nucleic acid or vector can be delivered in vivo by electroporation, the technology for which is available from Genetronics, Inc. (San Diego, CA) as well as by means of a SONOPORATION machine (ImaRx Pharmaceutical Corp., Tucson, AZ). 72. As one example, vector delivery can be via a viral system, such as a retroviral vector system which can package a recombinant retroviral genome (see e.g., Pastan et al., *Proc. Natl. Acad. Sci. U.S.A.* 85:4486, 1988; Miller et al., *Mol. Cell. Biol.* 6:2895, 1986). The recombinant retrovirus can then be used to infect and thereby deliver to the infected cells nucleic acid encoding a broadly neutralizing antibody (or active fragment thereof). The exact method of introducing the altered nucleic acid into mammalian cells is, of course, not limited to the use of retroviral vectors. Other techniques are widely available for this procedure including the use of adenoviral vectors (Mitani et al., *Hum. Gene Ther.* 5:941-948, 1994), adeno-associated viral (AAV) vectors (Goodman et al., *Blood* 84:1492-1500, 1994), lentiviral vectors (Naidini et al., *Science* 272:263-267, 1996), pseudotyped retroviral vectors (Agrawal et al., *Exper. Hematol.* 24:738-747, 1996). Physical transduction techniques can also be used, such as liposome delivery and receptor-mediated and other endocytosis mechanisms (see, for example, Schwartzenberger et al., *Blood* 87:472-478, 1996). This disclosed compositions and methods can be used in conjunction with any of these or other commonly used gene transfer methods. 73. As one example, if the antibody-encoding nucleic acid is delivered to the cells of a subject in an adenovirus vector, the dosage for administration of adenovirus to humans can range from about $10^7$ to about $10^9$ plaque forming units (pfu) per injection but can be as high as about $10^{12}$ pfu per injection (Crystal, *Hum. Gene Ther.* 8:985-1001, 1997; Alvarez and Curiel, *Hum. Gene Ther.* 8:597-613, 1997). A subject can receive a single injection, or, if additional injections are necessary, they can be repeated at six month intervals (or other appropriate time intervals, as determined by the skilled practitioner) for an indefinite period and/or until the efficacy of the treatment has been established.

Parenteral administration of the nucleic acid or vector, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. For additional discussion of suitable formulations and various routes of administration of therapeutic compounds, see, e.g., *Remington: The Science and Practice of Pharmacy* (19th ed.) ed. A. R. Gennaro, Mack Publishing Company, Easton, PA 1995.

4. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., *Science,* 247, 1465-1468, (1990); and Wolff, J. A. *Nature,* 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as 22BF into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, *Eur. J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

5. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, CA, which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Large Payload Viral Vectors

Molecular genetic experiments with large human herpes-viruses have provided a means whereby large heterologous DNA fragments can be cloned, propagated and established in cells permissive for infection with herpesviruses (Sun et al., *Nature genetics* 8: 33-41, 1994; Cotter and Robertson, *Curr Opin Mol Ther* 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed needle tip protein-translocator protein fusion (such as, for example, 22BF) or vectors for example, lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci USA* 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, MD), SUPERFECT (Qiagen, Inc. Hilden, Germany) and TRANSFECTAM (Promega Biotec, Inc., Madison, WI), as well as other liposomes developed according to procedures standard in the art. In addition, the disclosed nucleic acid or vector can be delivered in vivo by electroporation, the technology for which is available from Genetronics, Inc. (San Diego, CA) as well as by means of a SONOPORATION machine (ImaRx Pharmaceutical Corp., Tucson, AZ).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral integration systems can also be incorporated into nucleic acids which are to be delivered using a non-nucleic acid based system of deliver, such as a liposome, so that the nucleic acid contained in the delivery system can become integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

6. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puromycin.

7. Peptides a) Protein Variants

As discussed herein there are numerous variants of the needle tip protein-translocator protein fusion (such as, for example, Bsp22, LcrV, BipD, PcrV, CT053, CT668, BopB, YopB, BipB, PopB, CopB, CopB2, 22BF, BurkF, PaF, YerF, CT053-CopB, CT053-CopB2, CT668-CopB, or CT668-CopB2) that are known and herein contemplated. In addition, to the known functional strain variants there are derivatives of the needle tip protein and translocator protein which also function in the disclosed methods and compositions. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than from about 2 to about 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of from about 1 to about 10 amino acid residues; and deletions will range from about 1 to about 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 3 and 4 and are referred to as conservative substitutions.

TABLE 3

Amino Acid Abbreviations

| Amino Acid | Abbreviations | |
|---|---|---|
| Alanine | Ala | A |
| Allosoleucine | AIle | |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isolelucine | Ile | I |
| Leucine | Leu | L |
| Lysine | Lys | K |
| Phenylalanine | Phe | F |
| Proline | Pro | P |
| Pyroglutamic acid | pGlu | |
| Serine | Ser | S |
| Threonine | Thr | T |
| Tyrosine | Tyr | Y |
| Tryptophan | Trp | W |
| Valine | Val | V |

TABLE 4

Amino Acid Substitutions

| Original Residue | Exemplary Conservative Substitutions, others are known in the art. |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 4, i.e., selecting residues that differ more significantly in their effect on maintaining (a) the structure of the polypeptide backbone in the area of the substitution, for example as a sheet or helical conformation, (b) the charge or hydrophobicity of the molecule at the target site, or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; (d) a residue having a bulky side chain, e.g., phenylalanine, is substituted for (or by) one not having a side chain, e.g., glycine, in this case, or (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO: 1 sets forth a particular sequence of *Bordetella* needle tip protein-translocator protein fusion (22BF) and SEQ ID NO: 2 sets forth a particular sequence of a 22BF fusion protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman *Adv. Appl. Math.* 2: 482 (1981), by the homology alignment algorithm of Needleman and Wunsch, *J. MoL Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, WI), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO: 2 is set forth in SEQ ID NO: 1. It is understood that for this mutation all of the nucleic acid sequences that encode this particular derivative of the 22BF are also disclosed. It is also understood that while no amino acid sequence indicates what particular DNA sequence encodes that protein within an organism, where particular variants of a disclosed protein are disclosed herein, the known nucleic acid sequence that encodes that protein in the particular needle tip protein-translocator protein fusion (such as, for example, 22BF) from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 3 and Table 4. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way.

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH— (cis and trans), —$COCH_2$—, —$CH(OH)$ $CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, Peptide Backbone Modifications (general review); Morley, *Trends Pharm Sci* (1980) pp. 463-468; Hudson, D. et al., *Int J Pept Prot Res* 14:177-185 (1979) (—$CH_2NH$—, —$CH_2CH_2$—); Spatola et al. *Life Sci* 38:1243-1249 (1986) (—$CH_2$—S); Hann *J. Chem. Soc Perkin Trans.* I 307-314 (1982) (—CH=CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. *European Appln*, EP 45665 CA (1982): 97:39405 (1982) (—$CH(OH)$ $CH_2$—); Holladay et al. *Tetrahedron. Lett* 24:4401-4404 (1983) (—$C(OH)CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as β-alanine, γ-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations.

8. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, more preferably from about 7 to about 7.6, and most preferably about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, tri-alkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

In a preferred embodiment, the amount of protein that is administered per dose of vaccine is in the range of from about 0.0001 to about 1000 µg/kg. In one embodiment, the amount is in the range of from about 0.001 to about 1000 µg/kg of body weight of the recipient. In one embodiment, the amount is in the range of from about 0.01 to about 1000 µg/kg of body weight of the recipient. In one embodiment, the amount is in the range of from about 0.01 to about 100 µg/kg of body weight of the recipient. Those of skill in the art will recognize that the precise dosage may vary from situation to situation and from patient to patient, depending on e.g. age, gender, overall health, various genetic factors, and other variables known to those of skill in the art. Dosages are typically determined e.g. in the course of animal and/or human clinical trials as conducted by skilled medical personnel, e.g. physicians or veterinarians.

C. METHODS OF USING THE COMPOSITIONS

Herein, the protective efficacy of the *Bordetella* spp. tip/translocator fusion, 22BF, is examined against lethal lung challenge and with complete (sterilizing) clearance of colonizing bacteria. Unlike some components of the current aP vaccine, Bsp22 and BopB are required for infection and are not mutable since they must be retained structurally and functionally within the context of a large nanomachine residing within the *Bordetella* cell envelope. Furthermore, targeting the *Bordetella* T3SA renders the pathogen less able to fight off the host innate and adaptive immune responses. Regardless of whether 22BF is protective alone or when used with components of the current aP vaccine, the innovation of this high risk, high reward investigation lies in whether this subunit vaccine can elicit sterilizing immunity and thereby prevent the colonization that results in host to host transmission. It has been reported that Bsp22 (a component of the 22BF fusion vaccine) does not elicit a serum antibody response in humans during the course of natural infection and is not a protective antigen in mice. Nevertheless, as shown herein, protective and sterilizing immunity can be obtained with the compositions disclosed herein.

Thus, in one aspect, disclosed herein are methods of eliciting an immune response in a subject to a Gram negative bacteria (such as, for example, *Bordetella* spp., *Burkholderia* spp., *Chlamydia* spp., *Pseudomonas* spp., *Vibrio* spp. Enteropathogenic or Enterohemorrhagic *E. coli* or *Yersinia* spp.) comprising administering to the subject the fusion polypeptides, compositions, or vaccines disclosed herein. Accordingly, in one aspect, disclosed herein are methods of eliciting an immune response against at least one Gram negative bacteria serovar in a subject in need thereof, comprising administering to the subject a composition comprising at least one needle tip protein or a fragment thereof and/or at least one translocator protein or a fragment thereof; wherein said composition is administered in an amount sufficient to elicit an immune response to said at least one Gram negative bacteria serovar in said subject; and wherein the Gram negative bacteria is not a *Shigella* spp. or *Salmonella* spp. In one aspect, the immune response elicited provides sterilizing immunity to the infectious bacterium.

As can be appreciated by the skilled artisan, the methods of eliciting an immune response can be used for the purpose of treating, inhibiting, or preventing an infection of a Gram negative bacteria (such as, for example, *Bordetella* spp., *Burkholderia* spp., *Chlamydia* spp., *Pseudomonas* spp., *Vibrio* spp. Enteropathogenic or Enterohemorrhagic *E. coli* or *Yersinia* spp). Thus, in one aspect, disclosed herein are methods of treating, inhibiting, or preventing an infection of a Gram negative bacteria in a subject comprising administering to the subject a therapeutic amount of any of the fusion polypeptides, compositions, or vaccines disclosed herein. As one goal of any vaccine is not only to prevent infection or reducing the severity of disease in the individual receiving the vaccine, but also to prevent further transmission of the infectious agent (sterilizing immunity), it is understood and herein contemplated that the disclosed methods of treatment, inhibition, or preventing an infection can further comprise inhibiting and/or preventing colony formation of the bacteria and/or transmission of the bacteria to another subject.

The term "therapeutically effective" refers to the amount of the composition used that is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "inhibit" refers to a decrease in an activity, response, condition, disease, or other biological parameter. This can include, but is not limited to, the complete ablation of the activity, response, condition, or disease. This can also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 a) Use of a T3SS Needle Tip/Translocator Protein Fusion as a Protective Antigen Against *B. pertussis*:

The dominant antigen eliciting protection against Gram-negative pathogens is LPS, which confers O-antigen serotype specificity. The initial project focused on *Shigella*, however, there are at least 58 distinct *Shigella* serotypes. This reduces broad-spectrum efficacy for live, attenuated and whole, killed vaccines, which tend to be somatic antigen driven. IpaD and IpaB are the surface-localized needle tip and first translocator proteins of the T3SA, respectively. They are essential for virulence in all *Shigella*, are >98% conserved across all *Shigella* species, and provide serotype-independent protection. When IpaD+IpaB+dmLT was given IN to mice, the formulation was about 80-90% protective against lethal challenge by homologous and heterologous *Shigella* spp. (Table 5). To reduce the production cost, IpaD and IpaB were genetically fused to make DBF. Not only did the DBF provide protection against lethal challenge, it also unexpectedly increased the cell-mediated immunity, most notably the IL-17 and IFN-γ responses. When the *Salmonella enterica* tip and first translocator proteins of the T3SSs of SPI-1 and SPI-2 (*Salmonella* Pathogenicity Islands 1 and 2) were fused, about 70% protection against lethal challenge by two *S. enterica* serovars was observed when both fusion proteins were administered simultaneously (Table 5).

TABLE 5

Protective efficacy of tip/translocator fusions against challenge by appropriate pathogen.

| Vaccine | Protection (%) | Pathogen |
|---|---|---|
| DBF + dmLT | 80-90 | *S. flexneri, S. sonnei* |
| S1S2 + MPL (IM) | 70 | *S. Typhimurium, S. Enteritidis* |
| 22BF + dmLT | 100 | *B. bronchiseptica* |

Mice (n = 10) were vaccinated 3 times biweekly with the vaccine and then challenged with indicated pathogen at day 56. Protection is indicated as percent survival after 21 days.

*B. bronchiseptica* and *B. pertussis* infections have been shown to also require a T3SS for virulence. To determine if a subunit of the T3SS could be used to confer protection, *B. pertussis* Bsp22 and BopB, the T3SS needle tip and first translocator proteins, which are 98% conserved with those of *B. bronchiseptica* were genetically fused. Mice were vaccinated biweekly, three times with 22BF, 22BF+dmLT, Bsp22+dmLT, or PBS. One group was also vaccinated twice with the ZOETIS® canine vaccine that is a killed cellular extract of *B. bronchiseptica*. The 22BF+dmLT exhibited 100% protection against *B. bronchiseptica* in a mouse lethal pulmonary model, while the commercial vaccine provided 80% protection (FIG. 1). Moreover, the mice vaccinated with 22BF+dmLT did not show signs of illness and they actually gained weight throughout the challenge (FIG. 2). In contrast, the mice vaccinated with the Zeetis ZOETIS® vaccine lost weight and then regained it, however, they continued to display lower health scores than the mice vaccinated with 22BF+dmLT for the remainder of the experiment (FIG. 2).

Next, the protective efficacy of the 22BF fusion with and without dmLT and in comparison to the needle tip protein Bsp22 and translocator protein BopB and the effect of fusion of dmLT relative to concurrent administration was examined. Mice were vaccinated IN on days 0, 14, 28 and challenged with *Bordetella bronchiseptica* on day 56. On day 7 mice were sacrificed and the colony forming units (CFU)/lung were determined (FIG. 3). 22BF+dmLT reduced the *B. bronchiseptica* CFU lung burden by 96.5%. Blood and fecal samples were collected on days −1, 13, 27, 41, and 55. The kinetics of IgG were assessed. Typical logarithmic increases were seen (FIG. 4) regardless of the antigen on the well. No IgA was detected in fecal samples of any of the mice. Antibody secreting cells in the bone marrow, spleen, and lungs (FIG. 5) were stimulated with Bsp22, BopB and dmLT. All organs from mice that had been vaccinated with the single proteins or double proteins or fusion, as long as the dmLT was present, exhibited some level of IgG or IgA ASCs While protection is important, the key to a next generation subunit vaccine against *Bordetella* spp. must be that it exhibits sterilizing immunity (to prevent carriage). The lungs of the mice that survived the challenge of FIG. 2 were examined to look for sterilizing immunity. All of the remaining 22BF and PBS vaccinated mice exhibited CFU/lung. In contrast, the 22BF+dmLT vaccinated mice demonstrated 38% sterilizing immunity while only 12% of the mice vaccinated with the ZOETIS® vaccine demonstrated sterilizing immunity. Thus, the 22BF represents an innovative new antigen to protect against *B. bronchiseptica* and *B. pertussis* due to the conservation of these antigens.

It is shown herein that the use of a broad, serotype-independent subunit vaccine against *Shigella* spp. and *S. enterica* serotypes. These vaccines are based on the fusion of the T3SA tip and first translocator proteins, which are highly conserved within a given bacterial genus. The DBF has also been shown to protect monkeys from severe diarrhea and *S. enterica* S1S2 fusions are protective in a bovine calf model. A genetic fusion of the *B. pertussis* T3SA tip/translocator system, 22BF, was generated which protects 100% of the mice challenged with a lethal dose of the heterologous *B. bronchiseptica*. Furthermore, 22BF elicited 38% sterilizing immunity while the commercial vaccine provided 12%. Herein, not only was the *B. bronchiseptica* experiment repeated, but also it demonstrated that the 22BF+dmLT protects against *B. pertussis*. *B. bronchiseptica* was chosen as the first challenge pathogen since it lacks pertussis toxin (PT), which could conceivably compromise adequate assessment of the 22BF. PT is an especially important toxin secreted by *B. pertussis* that can significantly affect the health of the host. Shiga toxin was also considered when DBF vaccinated mice were challenged with *S. dysenteriae*, however, DBF protected 40% of those vaccinated mice while the individual proteins did not. Furthermore, due to the disease progression of *S. dysenteriae*, mice killed by the Shiga toxin versus those succumbing to the bacterial infection (based on health score immediately preceding death) were distinguished. 22BF provides some level of protection against *B. pertussis*, which can be boosted by the addition of pertussis toxoid (PTd). At the end of this study, it was demonstrated that 22BF protects against both *B. bronchiseptica* and *B. pertussis*. Results for two vaccination routes and doses are obtained. PTd is required in the protection against *B. pertussis* was shown herein. Finally, it is demonstrated that 22BF+dmLT elicits>90, if not 100%, sterilizing immunity.

b) Cytokine Assay

Cytokines were collected from splenocytes collected on Day 55. 100 μL of homogenized splenocytes were seeded at a concentration of $5\times10^6$ cells/mL onto a flat-bottom 96-well plate. 100 μL of BopB, Bsp22, or dmLT at a concentration of 20 μg/mL was added onto cells (bringing final protein concentration to 10 μg/mL). Plates were incubated at 37° C. and 5% $CO_2$ for 48 hours. After incubation, plates were centrifuged at 1600 rpm at 4° C. for seven minutes. Supernatants were collected and stored at −20° C. until analysis. Cytokines were analyzed using the MSD® U-Plex Platform Multiplex Assay for the following cytokines for the following immune responses: Th1: IFN-γ, TNF-α, IL-1β, IL-2, IL-6, IL-10; (FIGS. 6 and 7) Th17: IL-17A; (FIG. 8) Th2: IL-4, IL-5 (FIG. 9).

2. Example 2: Assess the Respective Humoral and Cell-Mediated Immune Responses Elicited by 22BF+dmLT Delivered IN and IM IN delivery of 20 μg 22BF+2.5 μg dmLT protects 100% of vaccinated mice from death and provide 38% sterilizing immunity in the lungs following *B. bronchiseptica* challenge. 50 μg or 15 μg 22BF IN is delivered and then in parallel deliver 100 μg or 20 μg 22BF IM or ID to assess the humoral and cell mediated responses in each case. Based on previous work, it is known that some of these dose/route combinations do not protect mice while others offer protection.

First the effect of the route of administration of 22BF following challenge was assessed. Group 1 is a 22BF+2.5 μg dmLT IN, group 2 is 22BF+2.5 μg dmLT IM, and group 3 is a 22BF+2.5 μg dmLT IN. For each administrative route, PBS vaccinated controls were included (Groups 4, 5, and 6). Group 7 (n=10) is vaccinated subcutaneously on day 1 and 21 with the ZOETIS® vaccine. After day 56 following initial vaccination, mice were challenged with a sublethal dosage of *B. pertussis* intranasally. There was an observable difference in weight loss between mice vaccinated with the 22BF+dmLT+PTd formulation and those that only received PBS. By Day 7 all mice aside from PBS treated mice had recovered to within 3% of pre infection weight.

The immune responses can be compared with the protective efficacy and potentially define a protective correlate in the mouse model. The correlate is useful in the development of the 22BF vaccine, making the necessary adjustments when it is translated to humans. The systemic immune response can be assessed by measuring serum IgG against BopB, Bsp22, and dmLT, as well as the mucosal immune response by assessing IgA in fecal pellets. Cytokine secretion is assessed in splenocytes from vaccinated mice.

This experiment can be performed in two parts. The IN route can use a high dose of 50 µg and low dose of 15 µg. The IM route uses a high dose of 100 µg and a low dose of 40 µg. For each route, three groups of female C57BL/6 mice (10/group) are vaccinated on days 0, 14 and 28. Group 1 is a 22BF+2.5 µg dmLT IN, group 2 is 22BF+2.5 µg dmLT IM, and group 3 is a 22BF+2.5 µg dmLT IN. For each administrative route, PBS vaccinated controls were included (Groups 4, 5, and 6). Group 7 (n=10) is vaccinated subcutaneously on day 1 and 21 with the ZOETIS® vaccine. Blood and fecal pellets are collected on days-1, 13, 27, 41 and 55 to assess mucosal and systemic humoral responses. Individual samples are tested for the presence of anti-Bsp22, -BopB, -dmLT, -PTd IgG and IgA antibodies by ELISA. Mice were immunized on days 0, 14, and 28 with 22BF+PTd admixed with dmLT. Serum IgG antibodies specific for BopB, Bsp22, PTd, and dmLT were measured by ELISA. and IFN-γ/IL-17A secreting cells by ELISpot and cytokine secretion using Multi array assays. BAL is collected to measure IgG and IgA responses. GraphPad Prism 5.04 can be used for graphics and statistical comparisons. Differences were analyzed using t test or ANOVA where appropriate. A P value of less than 0.05 is considered significant for all comparisons.

For these experiments, serum IgG levels are >$10^5$ EU/ml, antibody secreting cells at >50 IgG ASC/$10^6$ cells or >20 IgA ASC/$10^6$ cells, and cytokine secreting cells at >50 IFN-γ/$10^6$ cells and IL-17/$10^6$ cells. There can also be unique systemic and mucosal humoral immune responses from mice immunized via the IN and IM routes. 50 µg IN was chosen to facilitate an increase in sterilizing immunity. The 100 µg IM dose was based on prior findings. Antibody secreting cells specific for both proteins are detected in both mucosal and memory compartments. Finally, the full profile of cytokine secretion elicited by the vaccine can demonstrate a dose and administration route dependence. Thus, these two routes (each with a high and low dose) are expected to give rise to unique immune response profiles.

3. Example 3: Determine the Protective Efficacy of 22BF+dmLT Against *B. bronchiseptica* and *B. pertussis* Challenge As discussed above, it is demonstrated herein that initial protective efficacy of 22BF+dmLT against *B. bronchiseptica* challenge. Insight is gained into the immune responses elicited by two doses of 22BF delivered IN and IM. Here, mice can be vaccinated and challenged with *B. bronchiseptica* and *B. pertussis*. In addition to assessing protective efficacy and sterilizing immunity of the 22BF+dmLT as well as the requirement for PTd, a protective correlate can be established for use. This method was used to identify a protective correlate associated with DBF protection of mice against *Shigella*. This, however, prior to the present disclosure has never been determined for such a vaccine type against an extracellular pathogen.

a) Assess Protective Efficacy of the 22BF+dmLT Delivered IN and IM Against B. Bronshiseptica Challenge Using the Mouse Lung Model with Two Challenge Doses—a Lethal Dose to Assess Survival and a Sublethal Dose to Assess Sterilizing Immunity.

Protective efficacy of 22BF+dmLT delivered IN, IM, and ID against a *B. bronchiseptica* challenge can be assessed in the mouse lung model. A high dose of *B. bronchiseptica* can be administered initially to assess protection via the lethal dose. In a second trial, a lower dose can be used to assess sterilizing immunity.

Experimental Details: Mice (20/group) are vaccinated IN on days 0, 14 and 28. Serum, and stool samples are collected as described above to measure specific antibody responses to confirm that immune responses are comparable to those obtained above. For bacterial challenges, 10 mice are challenged on day 56 with 1×10' *B. bronchiseptica* (lethal dose) and 10 animals are challenged with 1×$10^6$ *B. bronchiseptica* (sub-lethal dose). The mouse experiment can be repeated with vaccination occurring by the IM route. Survival can be plotted and a Log-rank test used to evaluate the differences. A P value of less than 0.05 is considered significant for all comparisons. Association of protective efficacy and markers of humoral and cellular immunity can be assessed with logistic regression models (see FIG. 1).

With respect to the IN vaccinated mice, at both doses, some level of protection is shown in the lethal lung model. The mice vaccinated with 50 µg are protected with complete sterilizing immunity. The 15 µg dose gives>90% protection with a moderate level of sterilizing immunity. Similarly, 100 µg 22BF+dmLT delivered IM has a high level of protection as well as sterilizing immunity, but perhaps not 100%, but greater than 70% protection. The 40 µg dose shows minimal protection. With these results, a protective correlate for *B. bronchiseptica* can be predicted, as long as the immune responses were above the levels anticipated.

b) Assess Protective Efficacy of the 22BF+dmLT f PTd Delivered IN, IM, and ID Against *B. pertussis* Challenge Using the Mouse Lung Model with Two Challenge Doses—a Lethal Dose to Assess Survival and a Sublethal Dose to Assess Sterilizing Immunity.

The ultimate test of the 22BF formulation is the protective efficacy against *B. pertussis*. Here, the protective efficacy of 22BF+dmLT is tested with a focus on a *B. pertussis* challenge using the mouse lung model. Vaccinations occur IN with PTd. Furthermore, a high dose of *B. pertussis* is used initially to assess protection via the lethal lung model.

Mice (10/group) are vaccinated IN on days 0, 14 and 28. Serum, and stool samples are collected. as described above to measure specific antibody responses to confirm a comparable immune response. For bacterial challenges, all mice can be challenged on day 56 with 1×$10^7$ *B. pertussis* (lethal dose). The experiment can be repeated using IM route and ID route again with the most protective vaccine and challenge with a lethal dose and a sub-lethal dose to assess protection and sterilizing immunity. Survival can be plotted and a Log-rank test used to evaluate the differences. A P value of less than 0.05 is considered significant for all comparisons.

Figure 12:
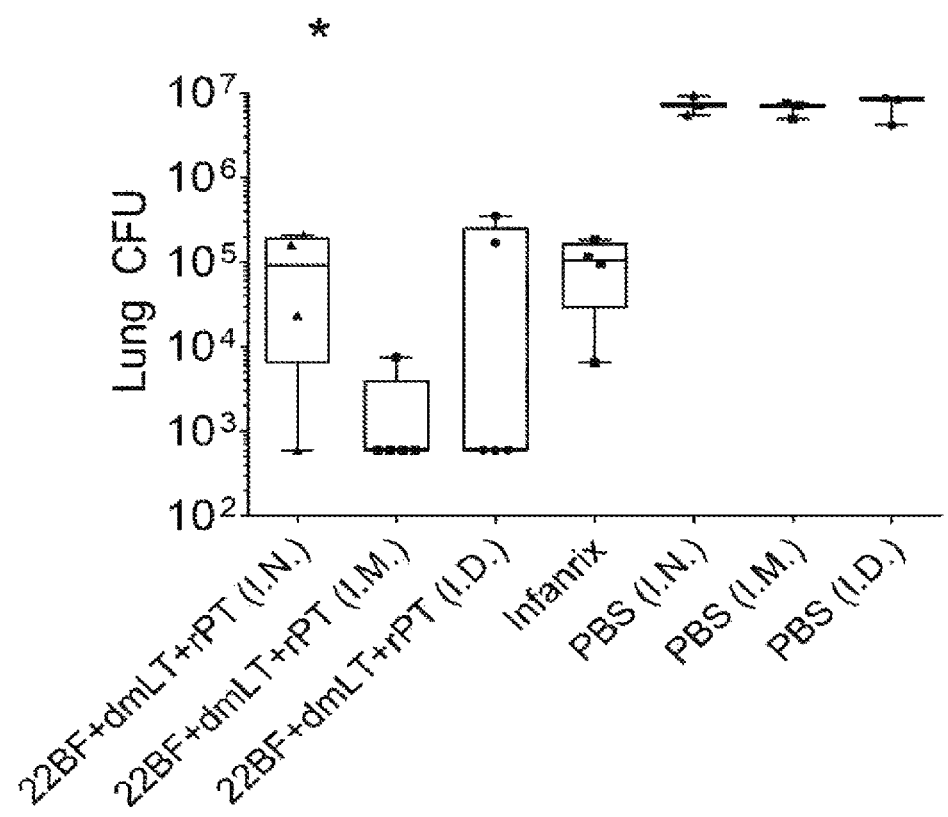
FIG. 12 shows the Lung Colony forming units (CFU) from mice 3 days post intranasal infection. Mice vaccinated intranasally with 22BF+PTd and dmLT showed statistical (P<0.05) decreases in lung CFUs when compared to PBS treated mice. The mice vaccinated intradermally and mice vaccinated intramuscularly with 22BF+PTd and dmLT either showed sterilizing immunity, or no statistical decrease in lung CFUs. INFANRIX® appeared to show a decrease in lung CFU, but this was not statistically significant (P>0.05). (*=P<0.05, KW p-value=0.0003).
Figure 13:
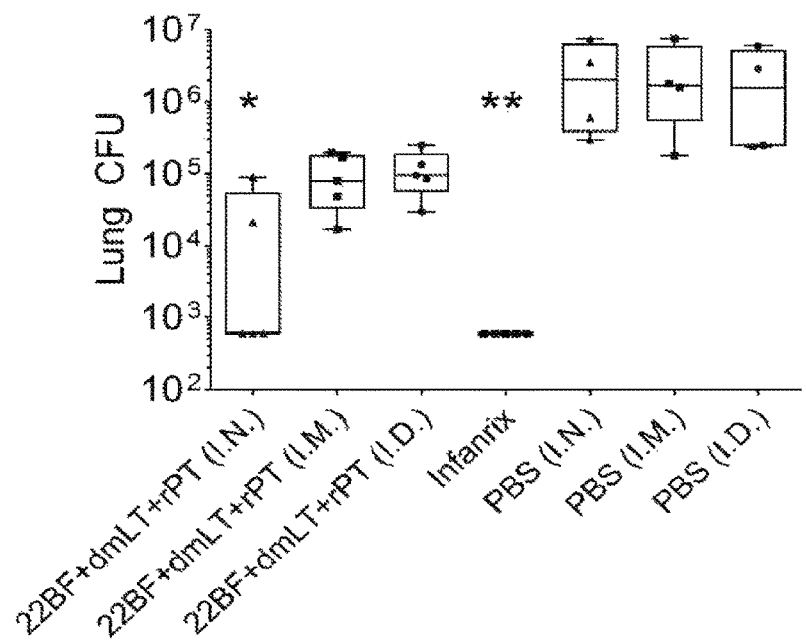
FIG. 13 shows the Lung Colony forming units (CFU) from mice 7 days post intranasal infection. Mice vaccinated intranasally with 22BF+PTd and dmLT showed statistical (P<0.05) decreases in lung CFUs when compared to PBS treated mice, with 60% of the mice showing sterilizing immunity. The mice vaccinated intramuscularly or intradermally with 22BF+PTd and dmLT showed no statistical decrease in lung CFUs. INFANRIX® appeared to display sterilizing immunity with CFU measuring below the limit of detection. (*=P<0.05, ** P<0.01, KW p-value=0.0001).
Figure 14:
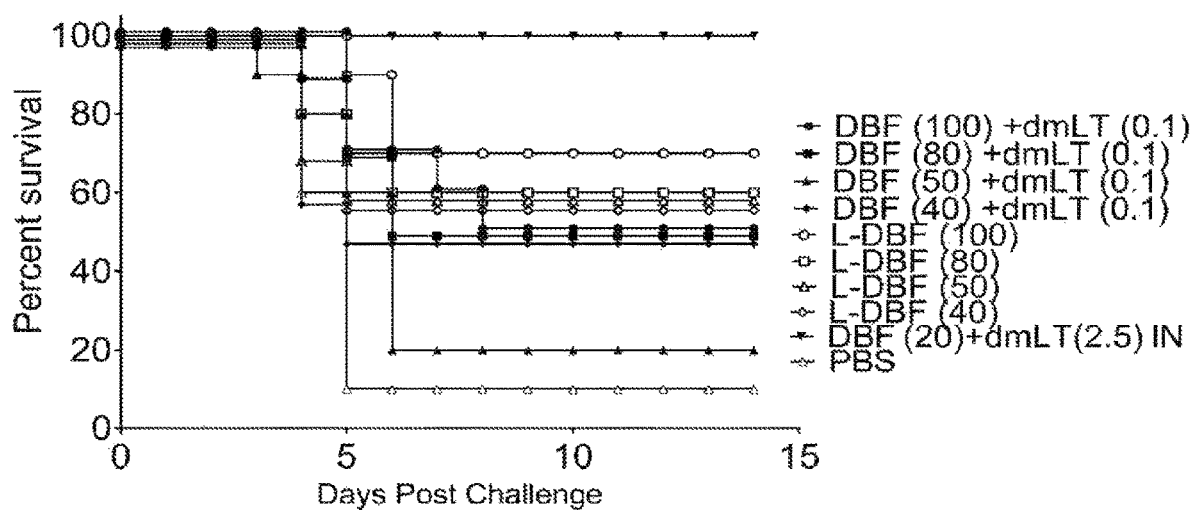
FIG. 14 shows the protective efficacy of LTA1-DBF vs DBF+dmLT. Mice were vaccinated intramuscularly on days 0, 14 and 28 with the indicated µg of DBF+ 0.1 µg dmLT or DBF equivalent of LTA1-DBF. The positive control was DBF+dmLT delivered intranasally. On day 56 the mice were challenged with Shigella flexneri.

PTd can additionally be administered for protection against *B. pertussis* and to prevent the cellular damage associated with PT as well as increase sterilizing immunity. Mice can be vaccinated IN, IM, or ID with 22BF+PTd and dmLT and challenged with *B. pertussis*. Lung CFU were measured at day 3 (FIG. 12) and day 7 (FIG. 13) post challenge. As with the predicted *B. bronchiseptica* results, 100% protection and sterilizing immunity is obtained with 50 µg 22BF+dmLT+PTd delivered IN with reduced protection for the 15 µg dose delivered IN. Similarly, the 100 µg 22BF+dmLT+PTd delivered IM and ID achieves some significant level of protection, but sterilizing immunity is limited though could be greater at higher dosage by day 7 post challenge. Antibodies are important, but the impact of cytokines cannot be ignored.

4. Example 4: LTA-1 Fusion

Figures 19A, 19B, 19C, 19D:
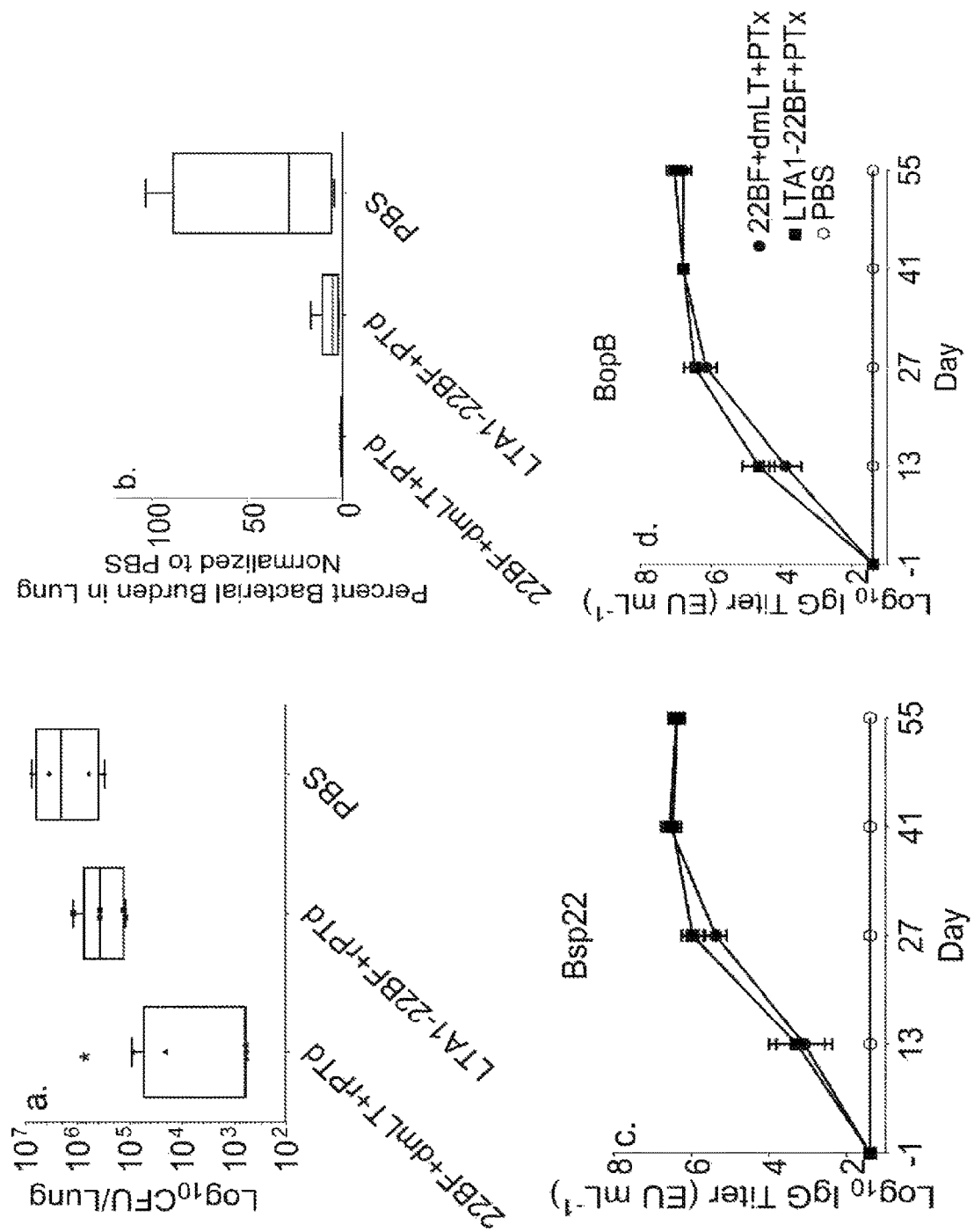
FIGS. 19A, 19B, 19C, and 19D show the protective efficacy and IgG response kinetics of LTA1-22BF. Mice were vaccinated on days 0, 14, 28 and challenged on day 56 with a sublethal dose of B. pertussis. On day 7 of the challenge, the CFU/lung were determined.
Figure 20:
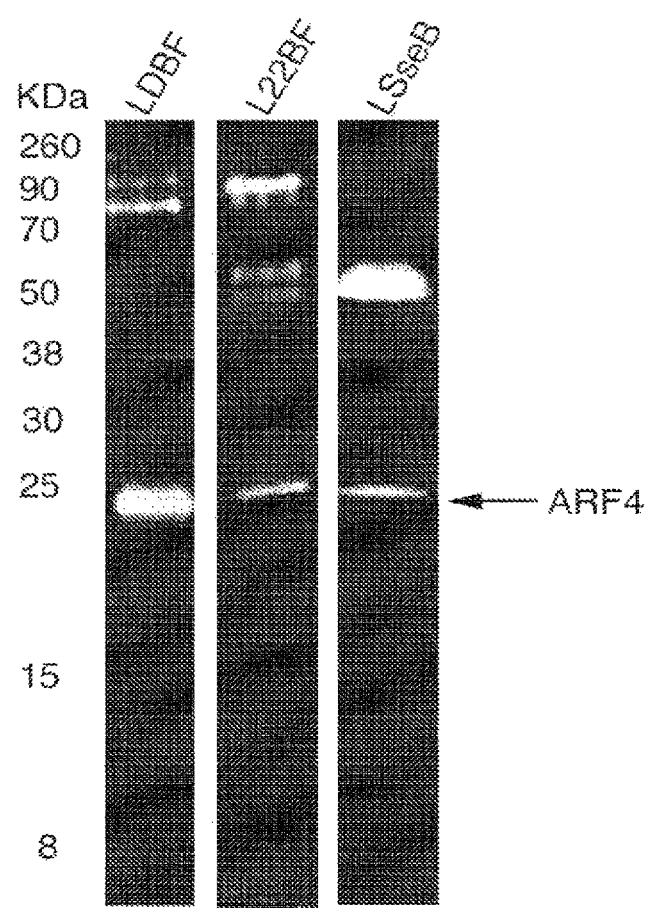
FIG. 20 shows the ADPr activity of L-antigens. LTA1 was fused to DBF, 22BF or SseB. LTA1, however, must retain its ADP-ribosylation activity to maintain adjuvant activity. The ADPr of NAD+ was biotin conjugated and LTA1 transferred the biotin-ADPr moiety to ARF4. The biotin was then detected with Streptavidin-IR800. Lane 1: LTA1-DBF; 2: LTA1-22BF; 3: LTA1-SseB.

LTA1 is the active moiety of lethal toxin from Enterotoxigenic *E. coli* (ETEC). The activity of the LTA1 is required for the adjuvant activity of dmLT. The double mutants are in the region usually targeted by a protease to allow A1 to traffic to the cytoplasm of intestinal cells to cause the secretory diarrhea. Without the protease the LT still has some activation of cAMP. Likewise, LTA1 remains active.

a) LTA1-Fusions:

The LTA1-fusions were expressed in a manner similar to the fusion alone. The LTA1 sequence was inserted 5' to the start of the each fusion. Some of the LTA1-fusions required a small linker between the LTA1 and fusion in order for protein production to occur. LTA1-DBF, LTA1-S1, LTA1-52, LTA1-SseB, LTA1-22BF, LTA1-BurkF, and LTA1-PaF were produced. One of the assays that appear to be required for adjuvant activity is the ability to ADP ribosylate ARF4. The ADP ribosylation assay was performed with the LTA1-fusions. In the assay, ADPr was biotin conjugated and when mixed with LTA1 and rARF4, the LTA1 transferred the biot-ADPr to rARF4. The biotin was then detected with Streptavidin-IR800 (FIG. 20).

b) LTA1-Fusion Protective Efficacy:

Mice were vaccinated parenterally with LTA1-DBF or DBF+dmLT (FIG. 14). Although the DBF+dmLT delivered IN elicited complete protection, this formulation cannot be given to humans since the dmLT can travel the olfactory nerve to the brain causing Bell's palsy. Thus, parenteral routes or other mucosal routes are required. DBF (100 μg)+dmLT (0.1 μg) delivered IM was only 50% protective while LTA1-DBF at a concentration of 100 μg DBF equivalent was 70% protective. The lower dilutions, regardless of formulation, exhibited less protective efficacy. Similarly, LTA1-22BF+PTd elicited significant protective efficacy at a concentration of 80 μg of 22BF equivalents (FIG. 19A-D)

c) LTA1-DBF Immune Response:

When the kinetics of the IgG titer was examined, responses against IpaD and IpaB were essentially the same. Mice from FIG. 14 were bled prior to vaccination and on day 42. Sera were assessed for anti-IpaD, -IpaB and -dmLT IgG. The lower IgG titers of the LTA1 samples can be attributed to the lower recognition of the dmLT on the well for the LTA1 samples vs the samples from mice vaccinated with dmLT (FIG. 15). No IgA was detected in the fecal samples of the mice vaccinated IM, but was detectable in mice vaccinated IN with DBF+dmLT. Antibody-secreting cells (ASCs) present in the bone marrow (FIG. 16), spleen (FIG. 17), and lungs (FIG. 18) were also stimulated with IpaD, IpaB and dmLT. In each compartment, anti-IpaD, anti-IpaB, and anti-dmLT IgG ASCs could be detected. Interestingly, IgA ASCs could also be detected in the bone marrow against all dilutions of LTA1-DBF and resemble a curve similar to the dose escalation. A similar phenomenon was seen in the IgA ASCs from the lungs, but less pronounced.

d) LTA1-DBF Purification.

The yield of LTA1-DBF was very low. Therefore, a linker was inserted in the DNA sequence between LTA1 and DBF to encode GSAAS (Seq. ID No. 14). The mother plasmid was Novagen's pACYCDuet-1. The translocator for each fusion cannot be made without its cognate chaperone. Therefore, the complex of LTA1-DBF/Histag-IpgC (IPG chaperone comprises the nucleic acid sequence as set forth in SEQ ID NO: 10 which encodes the amino acid sequence as set forth in SEQ ID NO: 11) was produced from the plasmid pACYC-His-IpgC-LTA1-GSAAS-DBF where the ipgC gene was inserted into the BamHI/HindIII sites allowing for expression of His-tag IpgC and LTA1-GSAAS-DBF (nucleic acid sequence as set forth in SEQ ID NO: 15 and amino acid sequence as set forth in SEQ ID NO: 16)) was inserted at the NdeI-XhoI site. The DBF sequence had a 3' stop codon prior to the XhoI restriction site.

pACYC-His-IpgC-LTA1-GSAAS-DBF was transformed into Tuner cells. A small overnight culture of LB+ Chloramphenicol (Cm) that had been inoculated with the freezer stock of the cells was transferred to 8 L TB, and grown at 37° C. until OD=1-1.5, add 0.5 mM IPTG with 20 ug/liter AEBSF, 16 C overnight, harvested at 4000 rpm for 15 min at 4° C., and resuspended in IMAC binding buffer. The cells were frozen at −80° C. until ready for purification. After thawing the suspension was sonicated at 70% amplitude for 3-4 min, 15 s on, 30 s off, clarified by centrifugation at 13000 rpm for 30 min at 4° C. and decanted to obtain supernatant.

IMAC purification with 5 ml NiNTA FF crude column on AKTA was as follows: (1) equilibrate column with 5 CV binding buffer (20 mM Tris, 500 mM NaCl, 5 mM Imidazole pH 7.9), (2) load supernatant on column, collect FT in outlet1, (3) wash with binding buffer for 30 CV, (4) elute with linear 0-60% elution buffer (20 mM Tris, 500 mM NaCl, 500 mM Imidazole pH 7.9) for 10 CV, (5) elute with 60% elution buffer for 2 CV, (6) wash column with 100% elution buffer for 3 CV, (7) re-equilibrate column with 5 CV binding buffer for 5 CV.

HIC purification of the protein was as follows: Dilute pooled fraction into equal volume of 2×HIC binding buffer (50 mM Sodium Phosphate (dibasic), 1M Ammonium Sulfate, pH 7.0). Purify with 5 ml HIC Phenyl HP column: (1) equilibrate column with 5 CV binding buffer, (2) load diluted sample on column, collect FT in outlet1, (3) wash with binding buffer for 5 CV, (4) elute with linear 0-100% elution buffer (5 mM Sodium Phosphate (dibasic), pH 7.0) for 40 CV, (6) elute with 100% elution buffer for 6 CV, (7) wash column with 100% elution buffer for 3 CV, (8) reequilibrate column with binding buffer for 5 CV.

Pooled fractions were dialyzed in 4 L Q binding buffer for 2 hrs, exchanged buffer, and then dialyzed overnight.

Purification using a 5 mL Q FF columns on AKTA was as follows: (1) equilibrate column with 5 CV binding buffer (50 mM Tris, pH 8.0), (2) load dialyzed sample on column, collect FT in outlet1, (3) wash with binding buffer for 5 CV, (4) elute with linear 0-30% elution buffer (50 mM Tris, 1M NaCl, pH 8.0) for 20 CV, (6) elute with 100% elution buffer for 5 CV, (7) wash column with 100% elution buffer for 3 CV, (8) re-equilibrate column with binding buffer for 5 CV.

To facilitate final IMAC purification 8×IMAC binding buffer (NO Imidazole) was added to pooled fractions to obtain 1× and then LDAO to 0.05% was added Purification by LDAO IMAC using 5 ml NiNTA FF was as follows: (1) equilibrate column with 5 CV LDAO (20 mM Tris, 500 mM NaCl, 0.05% LDAO pH 7.9) binding buffer, (2) load supernatant on column, fractionate FT, (3) wash with binding buffer for 5 CV, fractionate, (4) wash with 3% LDAO elution buffer (20 mM Tris, 500 mM NaCl, 500 mM Imidazole, 0.005% LDAO pH 7.9) for 5 CV, fractionate (5) elute with 6% LDAO elution buffer for 6.65 CV, fractionate (6) elute with 100% LDAO elution buffer for 5 CV, (8) re-equilibrate column with 5 CV binding buffer for 5 CV.

Pooled samples were dialyzed in 4 L PBS+0.005% LDAO, exchanged buffer after 2 hrs, and then dialyzed overnight.

e) Protective Efficacy of LTA1-22BF The initial assessment of the protective efficacy of the LTA1-22BF is presented here and demonstrated that LTA1-22BF+rPT reduced the CFU lung burden by 99.8% while the 22BF+dmLT+rPT reduced it to 99.98% (FIG. 19 (a)). Non-toxic pertussis toxin was added to the groups that prior to challenge by B. pertussis to offset the damage that pertussis toxin would cause and negatively impact the challenge. The kinetics of the IgG response is also shown where no differences are seen between the two groups (FIG. 19 (b))

f) LTA1-22BF Purification

The mother plasmid was Novagen's pACYCDuet-1. The translocator for each fusion cannot be made without its cognate chaperone. Therefore, the complex of LTA1-22BF/Histag-BcrHI is produced from the plasmid pACYC-His-BcrH1-LTA1-22BF where the brcHI gene (as set forth in SEQ ID NO: 7 with a histidine tag and encodes the amino acid sequence as set forth in SEQ ID NO: 8, the sequence minus the his-tag set forth in SEQ ID NO: 9) is inserted into the BamHI/HindIII sites allowing for expression of His-tag BcrHI and 22BF is inserted at the NdeI-XhoI site. The 22BF sequence has a 3' stop codon prior to the XhoI restriction site.

pACYC-His-BcrHI-22BF was transformed into Tuner cells. A small overnight culture of LB+ Chloramphenicol (Cm) that had been inoculated with the freezer stock of the cells was transferred to 8 L TB, grown at 37° C. until OD=1-1.5, added 0.5 mM IPTG with 20 ug/liter AEBSF, 16° C. overnight, harvested at 4000 rpm for 15 min at 4 C, and resuspended in IMAC binding buffer. The cells were frozen at −80 until ready for purification. After thawing, the suspension was sonicated at 70% amplitude for 3-4 min, 15 s on, 30 s off, clarified by centrifugation at 13000 rpm for 30 min at 4° C., and decanted to obtain supernatant.

IMAC purification with 5 ml NiNTA FF crude column on AKTA was as follows: (1) equilibrate column with 5 CV binding buffer (IMAC elution buffer: 20 mM Tris, 500 mM NaCl, 500 mM Imidazole pH 7.9), (2) load supernatant on column, collect FT in outlet1, (3) wash with binding buffer for 30 CV, (4) elute with linear 0-60% elution buffer for 10 CV, (5) elute with 60% elution buffer for 2 CV, (6) wash column with 100% elution buffer for 3 CV, (7) re-equilibrate column with 5 CV binding buffer (IMAC binding buffer: 20 mM Tris, 500 mM NaCl, 5 mM Imidazole pH 7.9) for 5 CV.

Diluted pooled fractions 20× into Q binding buffer Q binding buffer: 50 mM Tris, pH 8.0). Purification with 3×5 mL Q FF columns on AKTA was as follows: (1) equilibrate column with 6 CV binding buffer, (2) load dialyzed sample on column, collect FT in outlet1, (3) wash with binding buffer for 12 CV, (4) elute with 15% elution buffer (Q elution buffer: 50 mM Tris, 1M NaCl, pH 8.0) for 6 CV, (5) elute with linear 15-40% elution buffer for 34 CV, (6) elute with 100% elution buffer for 6 CV, (7) wash column with 100% elution buffer for 3 CV, (8) re-equilibrate column with binding buffer for 6 CV.

To facilitate final IMAC purification 8×IMAC binding buffer (NO Imidazole) was added to pooled fractions to obtain 1× and then LDAO to 0.05% was added. Purification by LDAO IMAC using 5 ml NiNTA FF was as follows: (1) equilibrate column with 5 CV LDAO binding buffer (LDAO IMAC binding buffer: 20 mM Tris, 500 mM NaCl, 0.05% LDAO pH 7.9), (2) load supernatant on column, fractionate FT, (3) wash with binding buffer for 5 CV, fractionate, (4) wash with 3% LDAO elution buffer (LDAO IMAC elution buffer: 20 mM Tris, 500 mM NaCl, 500 mM Imidazole, 0.005% LDAO pH 7.9) for 5 CV, fractionate (5) elute with 6% LDAO elution buffer for 6.65 CV, fractionate (6) elute with 100% LDAO elution buffer for 5 CV, (8) re-equilibrate column with 5 CV binding buffer for 5 CV.

Pooled samples were dialyzed in 4 L PBS+0.005% LDAO, exchanged buffer after 2 hrs, and then dialyzed overnight.

g) LTA1-BurkF Purification

The mother plasmid was Novagen's pACYCDuet-1. The translocator for each fusion cannot be made without its cognate chaperone. Therefore, the complex of LTA1-BurkF/Histag-BicA (SEQ ID NOs: 28 and 20) was produced from the plasmid pACYC-His-BicA-LTA1-BurkF (as set forth in SEQ ID NO: 20 and encoded by the nucleic acid sequence as set forth in SEQ ID NO: 19) wherein the bicA gene was inserted into the BamHI/HindIII sites allowing for expression of His-tag BicA and LTA1-BurkF was inserted at the NdeI-XhoI site. The BurkF sequence had a 3' stop codon prior to the XhoI restriction site.

pACYC-His-BicA-LTA1-BurkF was transformed into Tuner cells. A small overnight culture of LB+ Chloramphenicol (Cm) that had been inoculated with the freezer stock of the cells was transferred to 8 L TB, grown at 37° C. until OD=1-1.5, added 0.5 mM IPTG with 20 ug/liter AEBSF, 16° C. overnight, harvested at 4000 rpm for 15 min at 4 C, and resuspended in IMAC binding buffer. The cells were frozen at −80 until ready for purification. After thawing the suspension was sonicated at 70% amplitude for 3-4 min, 15 s on, 30 s off, Clarified by centrifugation at 13000 rpm for 30 min at 4° C., and decanted to obtain supernatant.

IMAC purification with 5 ml NiNTA FF crude column on AKTA was as follows: (1) equilibrate column with 5 CV binding buffer (20 mM Tris, 500 mM NaCl, 5 mM Imidazole pH 7.9), (2) load supernatant on column, collect FT in outlet1, (3) wash with binding buffer for 30 CV, (4) elute with linear 0-60% elution buffer (20 mM Tris, 500 mM NaCl, 500 mM Imidazole pH 7.9) for 10 CV, (5) elute with 60% elution buffer for 2 CV, (6) wash column with 100% elution buffer for 3 CV, (7) re-equilibrate column with 5 CV binding buffer for 5 CV.

The pooled fractions were diluted 20× into Q binding buffer (50 mM Tris, pH 8.0). Purification using 3×5 mL Q FF columns on AKTA was as follows: (1) equilibrate column with 6 CV binding buffer, (2) load dialyzed sample on column, collect FT in outlet1, (3) wash with binding buffer for 12 CV, (4) elute with 15% elution buffer (50 mM Tris, 1M NaCl, pH 8.0) for 6 CV, (5) elute with linear 15-40% elution buffer for 34 CV, (6) elute with 100% elution buffer for 6 CV, (7) wash column with 100% elution buffer for 3 CV, (8) re-equilibrate column with binding buffer for 6 CV.

To facilitate final IMAC purification add 8×IMAC binding buffer (NO Imidazole) to pooled fractions to obtain 1× and then LDAO to 0.05% was added:

Purification by LDAO IMAC using 5 ml NiNTA FF was as follows: (1) equilibrate column with 5 CV LDAO binding buffer (20 mM Tris, 500 mM NaCl, 0.05% LDAO pH 7.9), (2) load supernatant on column, fractionate FT, (3) wash with binding buffer for 5 CV, fractionate, (4) wash with 3% LDAO elution buffer (20 mM Tris, 500 mM NaCl, 500 mM Imidazole, 0.005% LDAO pH 7.9) for 5 CV, fractionate (5) elute with 6% LDAO elution buffer for 6.65 CV, fractionate (6) elute with 100% LDAO elution buffer for 5 CV, (8) re-equilibrate column with 5 CV binding buffer for 5 CV. 191. Pooled samples were dialyzed in 4 L PBS+0.005% LDAO, exchanged buffer after 2 hrs, and then dialyzed overnight.

h) LTA1-PaF

The PaF+dmLT vaccinated mice exhibited 100% survival with 44% sterilizing immunity against Pa challenge in a mouse lethal pulmonary model, while the PBS vaccinated mice exhibited 60% survival but all had >10" CFU/lung.

i) LTA1-PaF Purification

The mother plasmid is Novagen's pACYCDuet-1. The translocator for each fusion cannot be made without its cognate chaperone. Therefore, the complex of LTA1-PaF/Histag-PcrHI was produced from the plasmid pACYC-His-PcrH1-LTA1-PaF where the brcHI gene was inserted into the BamHI/HindIII sites allowing for expression of His-tag PcrHI (as set forth in SEQ ID NO: 30 and encoded by the nucleic acid sequence as set forth in SEQ ID NO: 29) and LTA1-PaF (as set forth in SEQ ID NO: 38 and encoded by the nucleic acid sequence as set forth in SEQ ID NO: 37) which was inserted at the NdeI-XhoI site. The PaF sequence had a 3' stop codon prior to the XhoI restriction site. The purification of LTA1-PaF was the same of for LTA1-22BF.

E. REFERENCES

Amuguni J H, Lee S, Kerstein K O, Brown D W, Belitsky B R, Herrmann J E, Keusch G T, Sonenshein A L, Tzipori S. Sublingually administered *Bacillus subtilis* cells expressing tetanus toxin C fragment induce protective systemic and mucosal antibodies against tetanus toxin in mice. Vaccine. 2011; 29(29-30):4778-84. Epub 2011/05/14. doi: S0264-410X(11)00638-4 [pii]

Bulir D C, Liang S, Lee A, Chong S, Simms E, Stone C, Kaushic C, Ashkar A, Mahony J B. Immunization with chlamydial type III secretion antigens reduces vaginal shedding and prevents fallopian tube pathology following live *C. muridarum* challenge. Vaccine. 2016; 34(34): 3979-85. doi: 10.1016/j.vaccine.2016.06.046. PubMed PMID: 27325352.

Chen X, Choudhari S P, Martinez-Becerra F J, Kim J H, Dickenson N E, Toth R T t, Joshi S B, Greenwood J C, 2nd, Clements J D, Picking W D, Middaugh C R, Picking W L. Impact of Detergent on Biophysical Properties and Immune Response of the IpaDB Fusion Protein, a Candidate Subunit Vaccine against *Shigella* Species. Infect Immun. 2015; 83(1):292-9. doi: 10.1128/IAI.02457-14. PubMed PMID: 25368115.

Fennelly N K, Sisti F, Higgins S C, Ross P J, van der Heide H, Mooi F R, Boyd A, Mills K H. *Bordetella pertussis* expresses a functional type III secretion system that subverts protective innate and adaptive immune responses. Infect Immun. 2008; 76(3):1257-66. doi: 10.1128/IAI.00836-07. PubMed PMID: 18195025; PMCID: PMC2258832.

Galan J E, Wolf-Watz H. Protein delivery into eukaryotic cells by type III secretion machines. Nature. 2006; 444 (7119):567-73. PubMed PMID: 17136086.

Higgs R, Higgins S C, Ross P J, Mills K H. Immunity to the respiratory pathogen *Bordetella pertussis*. Mucosal Immunol. 2012; 5(5):485-500. doi: 10.1038/mi.2012.54. PubMed PMID: 22718262.

Kilgore P E, Salim A M, Zervos M J, Schmitt H J. Pertussis: Microbiology, Disease, Treatment, and Prevention. Clin Microbiol Rev. 2016; 29(3):449-86. doi: 10.1128/CMR.00083-15. PubMed PMID: 27029594; PMCID: PMC4861987.

Martin S W, Pawloski L, Williams M, Weening K, DeBolt C, Qin X, Reynolds L, Kenyon C, Giambrone G, Kudish K, Miller L, Selvage D, Lee A, Skoff T H, Kamiya H, Cassiday P K, Tondella M L, Clark T A. Pertactin-negative *Bordetella pertussis* strains: evidence for a possible selective advantage. Clin Infect Dis. 2015; 60(2): 223-7. doi: 10.1093/cid/ciu788. PubMed PMID: 25301209.

Martinez-Becerra F J, Chen X, Dickenson N E, Choudhari S P, Harrison K, Clements J D, Picking W D, Van De Verg L L, Walker R I, Picking W L. Characterization of a novel fusion protein from IpaB and IpaD of *Shigella* spp. and its potential as a pan-*Shigella* vaccine. Infect Immun. 2013; 81(12):4470-7. doi: 10.1128/IAI.00859-13. PubMed PMID: 24060976; PMCID: 3837967.

Martinez-Becerra F J, Kissmann J M, Diaz-McNair J, Choudhari S P, Quick A M, Mellado-Sanchez G, Clements J D, Pasetti M F, Picking W L. Broadly protective *Shigella* vaccine based on type III secretion apparatus proteins. Infect Immun. 2012; 80(3):1222-31. doi: 10.1128/IAI.06174-11. PubMed PMID: 22202122; PMCID: 3294653.

Mattoo S, Cherry J D. Molecular pathogenesis, epidemiology, and clinical manifestations of respiratory infections due to *Bordetella pertussis* and other *Bordetella* subspecies. Clin Microbiol Rev. 2005; 18(2):326-82. doi: 10.1128/CMR.18.2.326-382.2005. PubMed PMID: 15831828; PMCID: PMC1082800.

Medhekar B, Shrivastava R, Mattoo S, Gingery M, Miller J F. *Bordetella* Bsp22 forms a filamentous type III secretion system tip complex and is immunoprotective in vitro and in vivo. Molecular microbiology. 2009; 71(2):492-504. PubMed PMID: 19040642. National Center for Immunization and Respiratory Diseases DoBD, CDC. 2015 Final Pertussis Surveillance Report 2017.

Nogawa H, A. Kuwae, T. Matsuzawa, and A. Abe. The type III secretion protein BopD in *Bordetella bronchiseptica* is complexed with BopB for pore formation on the host plasma membrane. J Bacteriol. 2004; 186(12):3806-13.

Norton E B, Lawson L B, Freytag L C, Clements J D. Characterization of a mutant *Escherichia coli* heat-labile toxin, L T(R192G/L211A), as a safe and effective oral adjuvant. Clinical and vaccine immunology: CVI. 2011; 18(4):546-51. doi: 10.1128/CVI.00538-10. PubMed PMID: 21288994; PMCID: 3122563.

Norton E B, Lawson L B, Mandi Z, Freytag L C, Clements J D. The A subunit of *Escherichia coli* heat-labile enterotoxin functions as a mucosal adjuvant and promotes IgG2a, IgA, and Th17 responses to vaccine antigens. Infect Immun. 2012; 80(7):2426-35. doi: 10.1128/IAI.00181-12. PubMed PMID: 22526674; PMCID: 3416479.

Qin L, Gilbert P B, Corey L, McElrath M J, Self S G. A framework for assessing immunological correlates of protection in vaccine trials. J Infect Dis. 2007; 196(9): 1304-12. doi: 10.1086/522428. PubMed PMID: 17922394.

Ross P J, Sutton C E, Higgins S, Allen A C, Walsh K, Misiak A, Lavelle E C, McLoughlin R M, Mills K H. Relative contribution of Th1 and Th17 cells in adaptive immunity to *Bordetella pertussis*: towards the rational design of an improved acellular pertussis vaccine. PLoS Pathog. 2013; 9(4):e1003264. doi: 10.1371/journal.ppat.1003264. PubMed PMID: 23592988; PMCID: PMC3617212.

Sealey K L, Belcher T, Preston A. *Bordetella pertussis* epidemiology and evolution in the light of pertussis resurgence. Infect Genet Evol. 2016; 40:136-43. doi: 10.1016/j.meegid.2016.02.032. PubMed PMID: 26932577.

Siegrist C A. Neonatal and early life vaccinology. Vaccine. 2001; 19(25-26):3331-46. PubMed PMID: 11348697.

Villarino Romero R, Bibova I, Cerny O, Vecerek B, Wald T, Benada O, Zavadilova J, Osicka R, Sebo P. The *Bordetella pertussis* type III secretion system tip complex protein Bsp22 is not a protective antigen and fails to elicit serum antibody responses during infection of humans and mice. Infect Immun. 2013; 81(8):2761-7. doi: 10.1128/IAI.00353-13. PubMed PMID: 23690400; PMCID: PMC3719584.

Warfel J M, Zimmerman L I, Merkel T J. Acellular pertussis vaccines protect against disease but fail to prevent infection and transmission in a nonhuman primate model. Proc Natl Acad Sci USA. 2014; 111(2):787-92. doi: 10.1073/pnas.1314688110. PubMed PMID: 24277828; PMCID: PMC3896208.

Warfel J M, Zimmerman L I, Merkel T J. Comparison of Three Whole-Cell Pertussis Vaccines in the Baboon Model of Pertussis. Clin Vaccine Immunol. 2015; 23(1): 47-54. doi: 10.1128/CVI.00449-15. PubMed PMID: 26561389; PMCID: PMC4711092.

F. SEQUENCES

22BF Nucleotide Sequence

SEQ ID NO: 1

```
CATatgaccattgatctcggagtttcactcacgtcgcaggccggcggcctgcaaggcatcgacctcaagagcatggata
tccagactctcatggtgtatgtgcagggtcgtcgcgccgaactcctcacggctcaaatgcagacccaggccgaagtggtgcagaagg
ccaatgaacgcatggcgcagctcaacgaggtcctgtccgcgctgtcccgggcaaggccgagtttccgcccaatccgaagccggg
cgacaccatcccgggctgggacaaccagaaggtcagccggatcgaggttcctctcaatgatgcgctgcgcgctgccggcctgacg
ggcatgttcgaagcgcgcgatggccaagtgaccgcccccggcggccggggtacgcaggtcgtgaacggcacgggcgtcatggcc
ggttccacgacctataaggaactcgaaagtgcctacaccaccgtaaaggggatgctggatacggcgtccaatacgcaacagatggac
atgatcaggctgcaggccgccagcaacaagcgcaacgaggctttcgaggtcatgaccaacaccgagaagcggcgcagcgacctg
aacagttccatcaccaacaacatgcgcaagcttatgaccgtcatgagtacgaccatatccacagccccgagcggcgccgcgcttgcg
ccgtctcgcatagatatgcgggcaccggagcccgggagtgccggcgaaggcgccggcatcctggcgccggtgacgacgctggct
ctggcggcgggccggccggcttttccagcgtcaccgtcgctgcgcaccgcgcccgtcctggatccgccagtgcgcgatctcagccc
cgccgacttggccgacctgctgcgcgtcttgcgatccagggcggtggacgggcagttggccacggcgcgcgagaacctgcagga
cgcgcaagtcaaggcgaagcagaacacccaggcccagctcgacaagctggacgcatggtttcggaaggccgaagaggccgaga
gcaagggatggctgagcaaggtgttcggctggatcggcaaggtgctggcggtcgtggcatcggccctggcggtgggctttgccgcc
gtcgccagcgtggccaccggcgcggcggccacacccatgctgctgctcagcggcatggcactggtcagcgccgtgacatcgctgg
ccgaccagatatcgcaagaggcgggaggcccgcctatcagcctgggcgggtttctctccgggctggccgacgtctgctgacagc
gttggggtggatcagtcgcaggccgaccaaattgccaagatcgtcgccggcctggccgtgcccgtcgtcttgctgatcgaacccca
gatgctgggcgaaatggcgcaaggcgtggccaggctggctggcgccagcgatgccaccgcggggtacatagccatggcgatgtc
catcgtggcggcgatcgcggtcgccgcgatcaatgccgccggtacagccggcgcgggtagcgcttcggcgatcaaggggggcctg
ggatcgggccgccgcggtagccacccaggtccttcaaggggggtacggcagtggcgcaaggcggcgtcggcgtgtcgatggcagt
cgatcgcaaacaggccgatctcctggtcgccgacaaggcggatctggcggcgagcctgacaaaactgcgggcggccatggagcg
tgaggcggacgatatcaagaagatcctggctcaattcgacgaggcctatcacatgatcgcgaagatgatcagcgatatggcgagtac
gcacagccaggtcagcgccaacctcgggcggcgccaggcggtgtagCTCGAG
```

22BF Amino Acid Sequence

SEQ ID NO: 2

```
MTIDLGVSLTSQAGGLQGIDLKSMDIQTLMVYVQGRRAELLTAQMQTQAEV
VQKANERMAQLNEVLSALSRAKAEFPPNPKPGDTIPGWDNQKVSRIEVPLNDALRA
AGLTGMFEARDGQVTAPGGRGTQVVNGTGVMAGSTTYKELESAYTTVKGMLDTA
SNTQQMDMIRLQAASNKRNEAFEVMTNTEKRRSDLNSSITNNMRKLMTVMSTTIST
APSGAALAPSRIDMRAPEPGSAGEGAGILAPVTTLALAAGRPAFPASPSLRTAPVLDP
PVRDLSPADLADLLRVLRSRAVDGQLATARENLQDAQVKAKQNTQAQLDKLDAWF
RKAEEAESKGWLSKVFGWIGKVLAVVASALAVGFAAVASVATGAAATPMLLLSGM
ALVSAVTSLADQISQEAGGPPISLGGFLSGLAGRLLTALGVDQSQADQIAKIVAGLAV
PVVLLIEPQMLGEMAQGVARLAGASDATAGYIAMAMSIVAAIAVAAINAAGTAGAG
```

SASAIKGAWDRAAAVATQVLQGGTAVAQGGVGVSMAVDRKQADLLVADKADLA

ASLTKLRAAMEREADDIKKILAQFDEAYHMIAKMISDMASTHSQVSANLGRRQAV

Bsp22 Nucleotide Sequence SEQ ID NO: 3

CATatgaccattgatctcggagtttcactcacgtcgcaggccggcggcctgcaaggcatcgacctcaagagcatggata tccagactctcatggtgtatgtgcagggtcgtcgcgccgaactcctcacggctcaaatgcagacccaggccgaagtggtgcagaagg ccaatgaacgcatggcgcagctcaacgaggtcctgtccgcgctgtcccgggccaaggccgagtttccgcccaatccgaagccggg cgacaccatcccgggctgggacaaccagaaggtcagccggatcgaggttcctctcaatgatgcgctgcgcgctgccggcctgacg ggcatgttcgaagcgcgcgatggccaagtgaccgcccccggcggccggggtacgcaggtcgtgaacggcacgggcgtcatggcc ggttccacgacctataaggaactcgaaagtgcctacaccaccgtaaaggggatgctggatacggcgtccaatacgcaacagatggac atgatcaggctgcaggccgccagcaacaagcgcaacgaggcttcgaggtcatgaccaacaccgagaagcggcgcagcgacctg aacagttccatcaccaacaacatgcgc Bsp22 Amino Acid Sequence SEQ ID NO: 4

MTIDLGVSLTSQAGGLQGIDLKSMDIQTLMVYVQGRRAELLTAQMQTQAEV

VQKANERMAQLNEVLSALSRAKAEFPPNPKPGDTIPGWDNQKVSRIEVPLNDALRA

AGLTGMFEARDGQVTAPGGRGTQVVNGTGVMAGSTTYKELESAYTTVKGMLDTA

SNTQQMDMIRLQAASNKRNEAFEVMTNTEKRRSDLNSSITNNMR

BopB Nucleotide Sequence SEQ ID NO: 5

Atgaccgtcatgagtacgaccatatccacagccccgagcggcgccgcgcttgcgccgtctcgcatagatatgcgggcac cggagcccggggagtgccggcgaaggcgccggcatcctggcgccggtgacgacgctggctctggcggcggggccggccggcttttc cagcgtcaccgtcgctgcgcaccgcgcccgtcctggatccgccagtgcgcgatctcagccccgccgacttggccgacctgctgcgc gtcttgcgatccagggcggtggacgggcagttggccacggcgcgcgagaacctgcaggacgcgcaagtcaaggcgaagcagaa cacccaggcccagctcgacaagctggacgcatggtttcggaaggccgaagaggccgagagcaagggatggctgagcaaggtgtt cggctggatcggcaaggtgctggcggtcgtggcatcggccctggcggtgggctttgccgccgtcgccagcgtggccaccggcgcg gcggccacacccatgctgctgctcagcggcatggcactggtcagcgccgtgacatcgctggccgaccagatatcgcaagaggcgg gaggcccgcctatcagcctgggcgggtttctctccgggctggccggacgtctgctgacagcgttgggggtggatcagtcgcaggcc gaccaaattgccaagatcgtcgccggcctggccgtgcccgtcgtcttgctgatcgaaccccagatgctgggcgaaatggcgcaagg cgtggccaggctggctggcgccagcgatgccaccgcggggtacatagccatggcgatgtccatcgtggcggccgatcgcggtcgcc gcgatcaatgccgccggtacagccggcgcgggtagcgcttcggcgatcaaggggcctgggatcgggccgccgcggtagccacc caggtccttcaaggggtacggcagtggcgcaaggcggcgtcggcgtgtcgatggcagtcgatcgcaaacaggccgatctcctggt cgccgacaaggcggatctggcggcgagcctgacaaaactgcgggcggccatggagcgtgaggcggacgatatcaagaagatcct ggctcaattcgacgaggcctatcacatgatcgcgaagatgatcagcgatatggcgagtacgcacagccaggtcagcgccaacctcg gcggcgccaggcggtgtagCTCGAG BopB Amino Acid Sequence SEQ ID NO: 6

MTVMSTTISTAPSGAALAPSRIDMRAPEPGSAGEGAGILAPVTTLALAAGRPA

FPASPSLRTAPVLDPPVRDLSPADLADLLRVLRSRAVDGQLATARENLQDAQVKAK

QNTQAQLDKLDAWFRKAEEAESKGWLSKVFGWIGKVLAVVASALAVGFAAVASV

ATGAAATPMLLLSGMALVSAVTSLADQISQEAGGPPISLGGFLSGLAGRLLTALGVD

QSQADQIAKIVAGLAVPVVLLIEPQMLGEMAQGVARLAGASDATAGYIAMAMSIVA

AIAVAAINAAGTAGAGSASAIKGAWDRAAAVATQVLQGGTAVAQGGVGVSMAVD

RKQADLLVADKADLAASLTKLRAAMEREADDIKKILAQFDEAYHMIAKMISDMAST

HSQVSANLGRRQAV

His-BcrH1 chaperone with histidine tag nucleotide sequence
SEQ ID NO: 7

ATGGGCAGCAGCCATCACCATCATCACCACAGCCAGGATCCGATGCCAAA

GTCAGCCGAGCAGGGCGGCTCCCCGGCGTCAGCTTCGCATGAGGCGTTGCGCCA

TATTCTCGACGCAGGCGCTTCGATGGGCAGCTTGCAGGGGTTGGACGAGGTGCA

ACAGCAGGCGTTGTACGCGATCGCTCATGGCGCCTACGAACAGGGCCGCTATGC

CGACGCGTTGAAAATGTTCTGCCTGCTGGTCGCGTGCGATCCGCTGGAAGCCCGT

TATCTGCTGGCCCTGGGCGCCGCGGCCCAGGAGCTGGGGCTGTACGAGCATGCC

TTGCAGCAATACGCGGCCGCGGCGGCTTTGCAGTTGGACTCCCCCAGGCCCCTGT

TGCATGGCGCCGAGTGCCTGTATGCGTTGGGTCGTCGCCGCGACGCCCTGGATAC

GCTCGACATGGTGCTTGAGTTGTGCGGGTCGCCGGAGCATGCGGCCCTGCGCGA

ACGGGCCGAGTCGCTGCGCAGGAGCTATGCACGTGCCGACTGAAAGCTT

His-BcrH1 with histidine tag chaperone amino acid sequence
SEQ ID NO: 8

MGSSHHHHHHSQDPMPKSAEQGGSPASASHEALRHILDAGASMGSLQGLDE

VQQQALYAIAHGAYEQGRYADALKMFCLLVACDPLEARYLLALGAAAQELGLYEH

ALQQYAAAAALQLDSPRPLLHGAECLYALGRRRDALDTLDMVLELCGSPEHAALRE

RAESLRRSYARAD

BcrH1 amino acid sequence
SEQ ID NO: 9

MPKSAEQGGSPASASHEALRHILDAGASMGSLQGLDEVQQQALYAIAHGAY

EQGRYADALKMFCLLVACDPLEARYLLALGAAAQELGLYEHALQQYAAAAALQLD

SPRPLLHGAECLYALGRRRDALDTLDMVLELCGSPEHAALRERAESLRRSYARAD

IpgC Chaperone of DBF nucleic acid sequence
SEQ ID NO: 10

CCatgggcagcagccatcatcatcatcatcacagcagcggcctggtgccgcgcggcagccatatgctcgagatgtcttta aatatcaccgaaaatgaaagcatctctactgcagtaattgatgcaattaactctggcgctacactgaaagatattaatgcaattcctgatga tatgatggatgacatttattcatatgcttatgacttttacaacaaaggaagaatagaggaagctgaagttttcttcaggtttttatgtatatacg acttttacaatatagactacattatgggactcgcagctatttatcagataaaagaacagttccaacaagcagcagacctttatgctgtcgct tttgcattaggaaaaaatgactatacaccagtattccatactggacaatgccagcttcggttgaaagccccctaaaagctaaagagtgct tcgaactcgtaattcaacacagcaatgatgaaaaattaaaaataaaagcacaatcatacttggacgcaattcaggatatcaaggagtag

GATCC

IpgC Chaperone of DBF Amino Acid sequence
SEQ ID NO: 11

MSLNITENESISTAVIDAINSGATLKDINAIPDDMMDDIYSYAYDFYNKGRIEE

AEVFFRFLCIYDFYNVDYIMGLAAIYQIKEQFQQAADLYAVAFALGKNDYTPVFHTG

QCQLRLKAPLKAKECFELVIQHSNDEKLKIKAQSYLDAIQDIKE

LTA1 nucleic acid sequence
SEQ ID NO: 12

CATAtggacaatggcgatcgtttataccgtgccgactcgcgtcccccagatgagattaaacgtagcggtgggttaatgc cacgtgggcacaatgagtattttgaccgtggaacacagatgaacattaacctttacgatcatgcccgtgggacccagaccgggtttgtc cgttatgatgacgggtatgttagtacgagtttgtccttacgctccgcacaccttgcgggacaaagtattttatcaggctacagcacatatta catttatgtgatcgccactgccccaaacatgttcaatgtgaacgatgtgttgggggtttacagcccccatccatatgaacaagaagtctcg -continued gcccttggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgc LTA1 amino acid sequence

SEQ ID NO: 13

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSR

GSAAS Linker amino acid sequence
SEQ ID NO: 14

*GSAAS*

LTA1-GSAAS-DBF (IpaD-LE-IpaB) nucleic acid sequence

SEQ ID NO: 15

CATAtggacaatggcgatcgtttataccgtgccgactcgcgtcccccagatgagattaaacgtagcggtgggttaatgc cacgtgggcacaatgagtattttgaccgtggaacacagatgaacattaacctttacgatcatgcccgtgggacccagaccgggtttgtc cgttatgatgacgggtatgttagtacgagtttgtccttacgctccgcacaccttgcgggacaaagtattttatcaggctacagcacatatta catttatgtgatcgccactgccccaaacatgttcaatgtgaacgatgtgttggggggtttacagccccccatccatatgaacaagaagtctcg gcccttggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcgggtccgcggcatccatgaatat aacaactctg actaatagta tttccacctc atcattcagt ccaaacaata ccaacggttc atcaaccgaa acagttaatt ctgatataaa aacaacgacc agttctcatc ctgtaagttc ccttactatg ctcaacgaca cccttcataa tatcagaaca acaaatcagg cattaaagaa agagctttca caaaaaacgt tgactaaaac atcgctagaa gaaatagcat tacattcatc tcagattagc atggatgtaa ataaatccgc tcaactattg gatattcttt ccaggaacga atatccaatt aataaagacg caagagaatt attacattca gccccgaaag aagccgagct tgatggagat caaatgatat ctcatagaga actgtgggct aaaattgcaa actccatcaa tgatattaat gaacagtatc tgaaagtata tgaacatgcc gttagttcat atactcaaat gtatcaagat tttagcgctg ttctttccag tcttgccggc tggatctctc ccggaggtaa cgacggaaac tccgtgaaat tacaagtcaa ctcgcttaaa aaggcattgg aagaactcaa ggaaaaatat aaagataaac cgctatatcc agcaaataat actgttagtc aggaacaagc aaataaatgg cttacagaat taggtggaac aatcggcaag gtatctcaaa aaaacggggg atatgttgtc agtataaaca tgaccccaat agacaatatg ttaaaaagct tagataatct aggtggaaat ggcgaggttg tgctagataa tgcaaaatat caggcatgga atgccggatt ctctgccgaa gatgaaacaa tgaaaaataa tcttcaaact ttagttcaaa aatacagtaa tgccaatagt atttttgata atttagtaaa ggttttgagt agtacaataa gctcatgtac agatacagat aaactttttc tccatttc CTCGAG atgcataatgta agcaccacaa ccactggttt tcctcttgcc aaaatattga cttccactgagcttggagac aatactatcc aagctgcaaa tgatgcagct aacaaattat tttctcttacaattgctgat cttactgcta accaaaatat taatacaact aatgcacact caacttcaaatatattaatc cctgaactta aagcaccaaa gtcattaaat gcaagttccc aactaacgcttttaattgga aaccttattc aaatactcgg tgaaaaatct ttaactgcat taacaaataaaattactgct tggaagtccc agcaacaggc aagacagcaa aaaaacctag aattctccgataaaattaac actcttctat ctgaaactga aggactaacc agagactatg aaaaacaaattaataaacta aaaaacgcag attctaaaat aaaagaccta gaaaataaaa ttaaccaaattcaaacaaga ttatcgaacc tcgatccaga gtcaccagaa aagaaaaaat taagccgggaagaaatacaa ctcactatca aaaaagacgc agcagttaaa gacaggacat tgattgagcagaaaaccctg tcaattcata gcaaacttac agataaatca atgcaactcg aaaaagaaatagactctttt tctgcatttt caaacacagc atctgctgaa cagctatcaa cccagcagaaatcattaacc ggacttgcca gtgttactca attgatggca acctttattc aactagttggaaaaaataat gaagaatctt taaaaaatga tctggctcta ttccagtctc tccaagaatcaagaaaaact -continued

```
gaaatggaga gaaatctga tgagtatgct gctgaagtac gtaaagcagaagaactcaac agagtaatgg gttgtgttgg gaaaatactt ggggcactttt taactatcgttagtgttgtt gcagcagctt tttctggagg agcctctcta gcactggcag ctgttggtttagctcttatg gttacggatg ctatagtaca agcagcgacc ggcaattcct tcatggaacaagccctgaat ccgatcatga aagcagtcat tgaacccttaatcaaactcc tttcagatgcatttacaaaaatgctcgaaggcttgggcgt cgactcgaaaaaagccaaaa tgattggctctattctgggg gcaatcgcaggcgctcttgtcctagttgcagcagtcgttc tcgtagccactgttggtaaacaggcagcagcaaaacttgcagaaaatattggcaaaataataggtaaaaccctcacagac cttataccaaagtttctcaagaatttttcttctcaactggacgatttaatcactaatgctgttgccagattaaataaatt tcttggtgcagcgggtgatgaagtaatatccaaacaaattatttccaccc atttaaaccaagcagttttattaggagaaa gtgttaactctgccacacaagcgggaggaagtgtcgcttctgctgttttc cagaacagcgcgtcgacaaatctagcagac ctgacattatcgaaatatca agttgaacaactgtcaaaat atatcagtgaagcaatagaaaaattcggccaattgcagga agtaattgcagatctattagcctcaatgtccaactctcaggctaatgaaactgatgttgcaaaagcaatttgcaacaaa ctactgcttga GGATCC
```

LTA1-GSAAS-IpaD-LE-IpaB (DBF) Amino Acid sequence

SEQ

-continued aggccggcggcctgcaaggcatcgacctcaagagcatggatatccagactctcatggtgtatgtgcagggtcgtcgcgccgaactcc tcacggctcaaatgcagacccaggccgaagtggtgcagaaggccaatgaacgcatggcgcagctcaacgaggtcctgtccgcgct gtcccgggccaaggccgagtttccgcccaatccgaagccgggcgacaccatcccgggctgggacaaccagaaggtcagccggat cgaggttcctctcaatgatgcgctgcgcgctgccggcctgacgggcatgttcgaagcgcgcgatggccaagtgaccgcccccggcg gccggggtacgcaggtcgtgaacggcacgggcgtcatggccggttccacgacctataaggaactcgaaagtgcctacaccaccgta aaggggatgctggatacggcgtccaatacgcaacagatggacatgatcaggctgcaggccgccagcaacaagcgcaacgaggctt tcgaggtcatgaccaacaccgagaagcggcgcagcgacctgaacagttccatcaccaacaacatgcgcaagcttatgaccgtcatga gtacgaccatatccacagccccgagcggcgccgcgcttgcgccgtctcgcatagatatgcgggcaccggagcccgggagtgccgg cgaaggcgccggcatcctggcgccggtgacgacgctggctctggcggcgggccggccggcttttccagcgtcaccgtcgctgcgc accgcgcccgtcctggatccgccagtgcgcgatctcagccccgccgacttggccgacctgctgcgcgtcttgcgatccagggcggt ggacgggcagttggccacggcgcgcgagaacctgcaggacgcgcaagtcaaggcgaagcagaacacccaggcccagctcgac aagctggacgcatggtttcggaaggccgaagaggccgagagcaagggatggctgagcaaggtgttcggctggatcggcaaggtg ctggcggtcgtggcatcggccctggcggtgggctttgccgccgtcgccagcgtggccaccggcgcggcggccacacccatgctgc tgctcagcggcatggcactggtcagcgccgtgacatcgctggccgaccagatatcgcaagaggcgggaggcccgcctatcagcct gggcgggtttctctccgggctggccgacgtctgctgacagcgttggggtggatcagtcgcaggccgaccaaattgccaagatcgt cgccggcctggccgtgcccgtcgtcttgctgatcgaacccagatgctgggcgaaatggcgcaaggcgtggccaggctggctggc gccagcgatgccaccgcggggtacatagccatggcgatgtccatcgtggcggcgatcgcggtcgccgcgatcaatgccgccggta cagccggcgcgggtagcgcttcggcgatcaaggggcctgggatcgggccgccgcggtagccacccaggtccttcaaggggta cggcagtggcgcaaggcggcgtcggcgtgtcgatggcagtcgatcgcaaacaggccgatctcctggtcgccgacaaggcggatct ggcggcgagcctgacaaaactgcgggcggccatggagcgtgaggcggacgatatcaagaagatcctggctcaattcgacgaggc ctatcacatgatcgcgaagatgatcagcgatatggcgagtacgcacagccaggtcagcgccaacctcgggcggcgccaggcggtg tagCTCGAG LTA1-22BF Amino acid sequence

SEQ ID NO: 18

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMTIDLGVSLTSQAGGLQGIDLKSMDIQT

LMVYVQGRRAELLTAQMQTQAEVVQKANERMAQLNEVLSALSRAKAEFPPNPKPG

DTIPGWDNQKVSRIEVPLNDALRAAGLTGMFEARDGQVTAPGGRGTQVVNGTGVM

AGSTTYKELESAYTTVKGMLDTASNTQQMDMIRLQAASNKRNEAFEVMTNTEKRR

SDLNSSITNNMRKLMTVMSTTISTAPSGAALAPSRIDMRAPEPGSAGEGAGILAPVTT

LALAAGRPAFPASPSLRTAPVLDPPVRDLSPADLADLLRVLRSRAVDGQLATARENL

QDAQVKAKQNTQAQLDKLDAWFRKAEEEAESKGWLSKVFGWIGKVLAVVASALAV

GFAAVASVATGAAATPMLLLSGMALVSAVTSLADQISQEAGGPPISLGGFLSGLAGR

LLTALGVDQSQADQIAKIVAGLAVPVVLLIEPQMLGEMAQGVARLAGASDATAGYI

AMAMSIVAAIAVAAINAAGTAGAGSASAIKGAWDRAAAVATQVLQGGTAVAQGG

VGVSMAVDRKQADLLVADKADLAASLTKLRAAMEREADDIKKILAQFDEAYHMIA

KMISDMASTHSQVSANLGRRQAV\*

His-BicA (Chaperone of BurkF) nucleic acid sequence

SEQ ID NO: 19

ATGGGCAGCAGCCATCACCATCATCACCACAGCCAGGATCCGATGACGCA

ACGCGACGTGAACATAGACGACATCGAGGCGCAGGAAATGGCGGCGGCGCTGCT

```
GGACGCGGTCCAGAACGGCGCGACGCTGAAGGACCTGCATCAGGTGCCGCAGGA

CCTGATGGACGGCATCTATGCGTTCGCGTACCGCTTCTACCAGCAGGGGCGGCTC

GACGACGCGGAGGTGTTCTTCCGCTTTCTGCGCATCTACGACTTCTACAACGCCG

AATACGCGATGGGGCTCGCGGCGGTGTGCCAGTTGAAGAAGGAGTACGCGCGGG

CGATCGATCTGTATGCACTCGCGTATTCGCTGTCGAAGGACGACCACCGGCCGAT

GTTCCACACCGGCCAATGCCATCTGCTGATGGGCAAGGCGGCGCTCGCGCGGCG

CTGCTTCGGCATCGTCGTCGAGCGCTCGCGCGACGAGCGCCTCGCGCAGAAGGC

GCAGTCCTATCTCGACGGGCTCGACGAAGTGGGCGCCGACGCGGCGCCCGCATC

CGCCGGGAACGACCACTGAGCGGCCGC
```

His-BicA (Chaperone of BurkF) Amino acid sequence  SEQ ID NO: 20

```
MGSSHHHHHHSQDPMTQRDVNIDDIEAQEMAAALLDAVQNGATLKDLHQV

PQDLMDGIYAFAYRFYQQGRLDDAEVFFRFLRIYDFYNAEYAMGLAAVCQLKKEY

ARAIDLYALAYSLSKDDHRPMFHTGQCHLLMGKAALARRCFGIVVERSRDERLAQK

AQSYLDGLDEVGADAAPASAGNDH-
```

BipD nucleic acid sequence  SEQ ID NO: 21

```
CATATGAACATGCACGTGGACATGGGTCGTGCGCTGACCGTTCGTGATTG

GCCGGCGCTGGAGGCGCTGGCGAAAACCATGCCGGCGGATGCGGGTGCGCGTGC

GATGACCGATGATGACCTGCGTGCGGCGGGTGTGGACCGTCGTGTTCCGGAGCA

GAAGCTGGGTGCGGCGATTGATGAATTCGCGAGCCTGCGTCTGCCGGATCGTATC

GACGGTCGTTTCGTGGATGGCCGTCGTGCGAACCTGACCGTTTTTGATGATGCGC

GTGTTGCGGTTCGTGGTCATGCGCGTGCGCAACGTAACCTGCTGGAGCGTCTGGA

GACCGAACTGCTGGGTGGCACCCTGGATACCGCGGGTGACGAAGGTGGCATTCA

GCCGGACCCGATCCTGCAAGGCCTGGTGGATGTTATCGGTCAGGGCAAAAGCGA

TATTGACGCGTACGCGACCATCGTGGAAGGTCTGACCAAGTATTTTCAAAGCGTG

GCGGACGTTATGAGCAAACTGCAGGATTACATTAGCGCGAAGGATGACAAAAAC

ATGAAGATCGACGGTGGCAAGATCAAAGCGCTGATTCAGCAAGTGATCGACCAC

CTGCCGACCATGCAGCTGCCGAAGGGTGCGGATATTGCGCGTTGGCGTAAAGAG

CTGGGCGACGCGGTTAGCATCAGCGATAGCGGTGTGGTTACCATTAACCCGGAC

AAACTGATCAAGATGCGTGATAGCCTGCCGCCGGATGGCACCGTTTGGGATACC

GCGCGTTACCAAGCGTGGAACACCGCGTTCAGCGGTCAGAAAGGCCAGCATCCG

GAACGTCGTGCGGATGCGCGTCGTAAATATAGCCACCAGAACAGCAACTTTGAT

AACCTGGTGAAGGTTCTGAGCGGTGCGATTAGCACCCTGACCGACACCCAGAGC

TATCTGCAAATC
```

BipD amino acid sequence  SEQ ID NO: 22

```
MNMHVDMGRALTVRDWPALEALAKTMPADAGARAMTDDDLRAAGVDRR

VPEQKLGAAIDEFASLRLPDRIDGRFVDGRRANLTVFDDARVAVRGHARAQRNLLE

RLETELLGGTLDTAGDEGGIQPDPILQGLVDVIGQGKSDIDAYATIVEGLTKYFQSVA
```

DVMSKLQDYISAKDDKNMKIDGGKIKALIQQVIDHLPTMQLPKGADIARWRKELGD

AVSISDSGVVTINPDKLIKMRDSLPPDGTVWDTARYQAWNTAFSGQKGQHPERRAD

ARRKYSHQNSNFDNLVKVLSGAISTLTDTQSYLQI

BipB nucleic acid sequence

SEQ ID NO: 23

ATGAGCAGCGGTGTTCAAGGTGGCCCGGCGGCGAACGCGAACGCGTACC

AGACCCACCCGCTGCGTGATGCGGCGAGCGCGCTGGGCACCCTGAGCCCGCAGG

CGTATGTGGATGTGGTTAGCGCGGCGCAACGTAACTTCCTGGAGCGTATGAGCC

AACTGGCGAGCGAACAGTGCGATGCGCAACCGGCGGCGCATGATGCGCGTCTGG

ATGATCGTCCGGCGCTGCGTGCGCCGCAGGAACGTGACGCGCCGCCGCTGGGTG

CGAGCGATACCGGTAGCCGTGCGAGCGGTGCGGCGAAACTGACCGAGCTGCTGG

GTGTGCTGATGAGCGTTATTAGCGCGAGCAGCCTGGACGAACTGAAGCAACGTA

GCGATATCTGGAACCAGATGAGCAAAGCGGCGCAAGACAACCTGAGCCGTCTGA

GCGATGCGTTTCAGCGTGCGACCGACGAGGCGAAAGCGGCGGCGGATGCGGCGG

AACAGGCGGCGGCGGCGGCGAAGCAAGCGGGTGCGGACGCGAAAGCGGCGGAT

GCGGCGGTGGATGCGGCGCAAAAACGTTACGATGACGCGGTTAAGCAGGGCCTG

CCGGATGACCGTCTGCAAAGCCTGAAAGCGGCGCTGGAGCAGGCGCGTCAGCAA

GCGGGTGATGCGCATGGTCGTGCGGATGCGCTGCAGGCGGATGCGACCAAGAAA

CTGGACGCGGCGAGCGCGCTGGCGACCCAAGCGCGTGCGTGCGAACAGCAAGTG

GATGACGCGGTTAACCAGGCGACCCAGCAATATGGTGCGAGCGCGAGCCTGCGT

ACCCCGCAAAGCCCGCGTCTGAGCGGTGCGGCGGAGCTGACCGCGGTGCTGGGC

AAGCTGCAGGAACTGATTAGCAGCGGCAACGTTAAAGAGCTGGAAAGCAAGCA

GAAACTGTTCACCGAGATGCAAGCGAAGCGTGAGGCGGAACTGCAAAAGAAAA

GCGACGAATATCAGGCGCAAGTGAAGAAAGCGGAGGAAATGCAGAAAACGATG

GGTTGCATCGGCAAGATTGTGGGTTGGGTTATTACCGCGGTTAGCTTTGCGGCGG

CGGCGTTTACCGGTGGCGCGAGCCTGGCGCTGGCGGCGGTGGGCCTGGCGCTGG

CGGTTGGTGACGAGATTAGCCGTGCGACCACCGGTGTGAGCTTCATGGACAAGC

TGATGCAGCCGGTTATGGATGCGATCCTGAAACCGCTGATGGAGATGATTAGCA

GCCTGATCACCAAGGCGCTGGTTGCGTGCGGCGTTGATCAGCAAAAAGCGGAAC

TGGCGGGTGCGATTCTGGGTGCGGTTGTTACCGGTGTGGCGCTGGTTGCGGCGGC

GTTTGTTGGTGCGAGCGCGGTGAAAGCGGTTGCGAGCAAGGTTATCGACGCGAT

GGCGGGTCAGCTGACCAAGCTGATGGATAGCGCGATTGGCAAAATGCTGGTGCA

ACTGATCGAGAAATTCAGCGAAAGAGCGGTCTGCAGGCGCTGGGTAGCCGTAC

CGCGACCGCGATGACCCGTATGCGTCGTGCGATTGGCGTTGAGGCGAAGGAAGA

CGGTATGCTGCTGGCGAACCGTTTTGAAAAAGCGGGCACCGTGATGAACGTTGG

TAACCAAGTGAGCCAAGCGGCGGGTGGCATTGTGGTTGGCGTTGAGCGTGCGAA

AGCGATGGGTCTGCTGGCGGATGTGAAAGAAGCGATGTATGACATCAAGCTGCT

```
GGGTGATCTGCTGAAACAGGCGGTGGACGCGTTTGCGGAGCACAACCGTGTTCT

GGCGCAACTGATGCAGCAAATGAGCGATGCGGGCGAAATGCAGACCAGCACCG

GCAAGCTGATCCTGCGTAACGCGCGTGCGGTTTAAGGATCC
```

BipB amino acid sequence                                    SEQ ID NO: 24

```
MSSGVQGGPAANANAYQTHPLRDAASALGTLSPQAYVDVVSAAQRNFLER

MSQLASEQCDAQPAAHDARLDDRPALRAPQERDAPPLGASDTGSRASGAAKLTELL

GVLMSVISASSLDELKQRSDIWNQMSKAAQDNLSRLSDAFQRATDEAKAAADAAEQ

AAAAAKQAGADAKAADAAVDAAQKRYDDAVKQGLPDDRLQSLKAALEQARQQA

GDAHGRADALQADATKKLDAASALATQARACEQQVDDAVNQATQQYGASASLRT

PQSPRLSGAAELTAVLGKLQELISSGNVKELESKQKLFTEMQAKREAELQKKSDEYQ

AQVKKAEEMQKTMGCIGKIVGWVITAVSFAAAAFTGGASLALAAVGLALAVGDEIS

RATTGVSFMDKLMQPVMDAILKPLMEMISSLITKALVACGVDQQKAELAGAILGAV

VTGVALVAAAFVGASAVKAVASKVIDAMAGQLTKLMDSAIGKMLVQLIEKFSEKS

GLQALGSRTATAMTRMRRAIGVEAKEDGMLLANRFEKAGTVMNVGNQVSQAAGG

IVVGVERAKAMGLLADVKEAMYDIKLLGDLLKQAVDAFAEHNRVLAQLMQQMSD

AGEMQTSTGKLILRNARAV
```

BurkF nucleic acid sequence                                 SEQ ID NO: 25

```
CATATGAACATGCACGTGGACATGGGTCGTGCGCTGACCGTTCGTGATTG

GCCGGCGCTGGAGGCGCTGGCGAAAACCATGCCGGCGGATGCGGGTGCGCGTGC

GATGACCGATGATGACCTGCGTGCGGCGGGTGTGGACCGTCGTGTTCCGGAGCA

GAAGCTGGGTGCGGCGATTGATGAATTCGCGAGCCTGCGTCTGCCGGATCGTATC

GACGGTCGTTTCGTGGATGGCCGTCGTGCGAACCTGACCGTTTTTGATGATGCGC

GTGTTGCGGTTCGTGGTCATGCGCGTGCGCAACGTAACCTGCTGGAGCGTCTGGA

GACCGAACTGCTGGGTGGCACCCTGGATACCGCGGGTGACGAAGGTGGCATTCA

GCCGGACCCGATCCTGCAAGGCCTGGTGGATGTTATCGGTCAGGGCAAAAGCGA

TATTGACGCGTACGCGACCATCGTGGAAGGTCTGACCAAGTATTTTCAAAGCGTG

GCGGACGTTATGAGCAAACTGCAGGATTACATTAGCGCGAAGGATGACAAAAAC

ATGAAGATCGACGGTGGCAAGATCAAAGCGCTGATTCAGCAAGTGATCGACCAC

CTGCCGACCATGCAGCTGCCGAAGGGTGCGGATATTGCGCGTTGGCGTAAAGAG

CTGGGCGACGCGGTTAGCATCAGCGATAGCGGTGTGGTTACCATTAACCCGGAC

AAACTGATCAAGATGCGTGATAGCCTGCCGCCGGATGGCACCGTTTGGGATACC

GCGCGTTACCAAGCGTGGAACACCGCGTTCAGCGGTCAGAAAGGCCAGCATCCG

GAACGTCGTGCGGATGCGCGTCGTAAATATAGCCACCAGAACAGCAACTTTGAT

AACCTGGTGAAGGTTCTGAGCGGTGCGATTAGCACCCTGACCGACACCCAGAGC

TATCTGCAAATCAAGCTTATGAGCAGCGGTGTTCAAGGTGGCCCGGCGGCGAAC

GCGAACGCGTACCAGACCCACCCGCTGCGTGATGCGGCGAGCGCGCTGGGCACC

CTGAGCCCGCAGGCGTATGTGGATGTGGTTAGCGCGGCGCAACGTAACTTCCTG

GAGCGTATGAGCCAACTGGCGAGCGAACAGTGCGATGCGCAACCGGCGGCGCAT

GATGCGCGTCTGGATGATCGTCCGGCGCTGCGTGCGCCGCAGGAACGTGACGCG

CCGCCGCTGGGTGCGAGCGATACCGGTAGCCGTGCGAGCGGTGCGGCGAAACTG
```

-continued

ACCGAGCTGCTGGGTGTGCTGATGAGCGTTATTAGCGCGAGCAGCCTGGACGAA
CTGAAGCAACGTAGCGATATCTGGAACCAGATGAGCAAAGCGGCGCAAGACAA
CCTGAGCCGTCTGAGCGATGCGTTTCAGCGTGCGACCGACGAGGCGAAAGCGGC

GGCGGATGCGGCGGAACAGGCGGCGGCGGCGGCGAAGCAAGCGGGTGCGGACG

CGAAAGCGGCGGATGCGGCGGTGGATGCGGCGCAAAAACGTTACGATGACGCG
GTTAAGCAGGGCCTGCCGGATGACCGTCTGCAAAGCCTGAAAGCGGCGCTGGAG
CAGGCGCGTCAGCAAGCGGGTGATGCGCATGGTCGTGCGGATGCGCTGCAGGCG
GATGCGACCAAGAAACTGGACGCGGCGAGCGCGCTGGCGACCCAAGCGCGTGC
GTGCGAACAGCAAGTGGATGACGCGGTTAACCAGGCGACCCAGCAATATGGTGC
GAGCGCGAGCCTGCGTACCCCGCAAAGCCCGCGTCTGAGCGGTGCGGCGGAGCT
GACCGCGGTGCTGGGCAAGCTGCAGGAACTGATTAGCAGCGGCAACGTTAAAGA
GCTGGAAAGCAAGCAGAAACTGTTCACCGAGATGCAAGCGAAGCGTGAGGCGG

AACTGCAAAAGAAAAGCGACGAATATCAGGCGCAAGTGAAGAAAGCGGAGGAA

ATGCAGAAAACGATGGGTTGCATCGGCAAGATTGTGGGTTGGGTTATTACCGCG

GTTAGCTTTGCGGCGGCGGCGTTTACCGGTGGCGCGAGCCTGGCGCTGGCGGCG

GTGGGCCTGGCGCTGGCGGTTGGTGACGAGATTAGCCGTGCGACCACCGGTGTG
AGCTTCATGGACAAGCTGATGCAGCCGGTTATGGATGCGATCCTGAAACCGCTG
ATGGAGATGATTAGCAGCCTGATCACCAAGGCGCTGGTTGCGTGCGGCGTTGAT
CAGCAAAAAGCGGAACTGGCGGGTGCGATTCTGGGTGCGGTTGTTACCGGTGTG
GCGCTGGTTGCGGCGGCGTTTGTTGGTGCGAGCGCGGTGAAAGCGGTTGCGAGC
AAGGTTATCGACGCGATGGCGGGTCAGCTGACCAAGCTGATGGATAGCGCGATT
GGCAAAATGCTGGTGCAACTGATCGAGAAATTCAGCGAAAAGAGCGGTCTGCAG
GCGCTGGGTAGCCGTACCGCGACCGCGATGACCCGTATGCGTCGTGCGATTGGC
GTTGAGGCGAAGGAAGACGGTATGCTGCTGGCGAACCGTTTTGAAAAAGCGGGC
ACCGTGATGAACGTTGGTAACCAAGTGAGCCAAGCGGCGGGTGGCATTGTGGTT
GGCGTTGAGCGTGCGAAAGCGATGGGTCTGCTGGCGGATGTGAAAGAAGCGATG
TATGACATCAAGCTGCTGGGTGATCTGCTGAAACAGGCGGTGGACGCGTTTGCG
GAGCACAACCGTGTTCTGGCGCAACTGATGCAGCAAATGAGCGATGCGGGCGAA
ATGCAGACCAGCACCGGCAAGCTGATCCTGCGTAACGCGCGTGCGGTTTAAGGA
TCC

BurkF amino acid sequence

SEQ ID NO: 26

MNMHVDMGRALTVRDWPALEALAKTMPADAGARAMTDDDLRAAGVDRR

VPEQKLGAAIDEFASLRLPDRIDGRFVDGRRANLTVFDDARVAVRGHARAQRNLLE

RLETELLGGTLDTAGDEGGIQPDPILQGLVDVIGQGKSDIDAYATIVEGLTKYFQSVA

DVMSKLQDYISAKDDKNMKIDGGKIKALIQQVIDHLPTMQLPKGADIARWRKELGD

AVSISDSGVVTINPDKLIKMRDSLPPDGTVWDTARYQAWNTAFSGQKGQHPERRAD

ARRKYSHQNSNFDNLVKVLSGAISTLTDTQSYLQIKLMSSGVQGGPAANANAYQTH

PLRDAASALGTLSPQAYVDVVSAAQRNFLERMSQLASEQCDAQPAAHDARLDDRP

ALRAPQERDAPPLGASDTGSRASGAAKLTELLGVLMSVISASSLDELKQRSDIWNQM

SKAAQDNLSRLSDAFQRATDEAKAAADAAEQAAAAAKQAGADAKAADAAVDAA

QKRYDDAVKQGLPDDRLQSLKAALEQARQQAGDAHGRADALQADATKKLDAASA

LATQARACEQQVDDAVNQATQQYGASASLRTPQSPRLSGAAELTAVLGKLQELISS
GNVKELESKQKLFTEMQAKREAELQKKSDEYQAQVKKAEEMQKTMGCIGKIVGW
VITAVSFAAAAFTGGASLALAAVGLALAVGDEISRATTGVSFMDKLMQPVMDAILK
PLMEMISSLITKALVACGVDQQKAELAGAILGAVVTGVALVAAAFVGASAVKAVAS
KVIDAMAGQLTKLMDSAIGKMLVQLIEKFSEKSGLQALGSRTATAMTRMRRAIGVE
AKEDGMLLANRFEKAGTVMNVGNQVSQAAGGIVVGVERAKAMGLLADVKEAMY
DIKLLGDLLKQAVDAFAEHNRVLAQLMQQMSDAGEMQTSTGKLILRNARAV

LTA1-BurkF nucleic acid sequence

SEQ ID NO: 27

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATATGAACATGCACGTGGA

CATGGGTCGTGCGCTGACCGTTCGTGATTGGCCGGCGCTGGAGGCGCTGGCGAA

AACCATGCCGGCGGATGCGGGTGCGCGTGCGATGACCGATGATGACCTGCGTGC

GGCGGGTGTGGACCGTCGTGTTCCGGAGCAGAAGCTGGGTGCGGCGATTGATGA

ATTCGCGAGCCTGCGTCTGCCGGATCGTATCGACGGTCGTTTCGTGGATGGCCGT

CGTGCGAACCTGACCGTTTTTGATGATGCGCGTGTTGCGGTTCGTGGTCATGCGC

GTGCGCAACGTAACCTGCTGGAGCGTCTGGAGACCGAACTGCTGGGTGGCACCC

TGGATACCGCGGGTGACGAAGGTGGCATTCAGCCGGACCCGATCCTGCAAGGCC

TGGTGGATGTTATCGGTCAGGGCAAAAGCGATATTGACGCGTACGCGACCATCG

TGGAAGGTCTGACCAAGTATTTTCAAAGCGTGGCGGACGTTATGAGCAAACTGC

AGGATTACATTAGCGCGAAGGATGACAAAAACATGAAGATCGACGGTGGCAAG

ATCAAAGCGCTGATTCAGCAAGTGATCGACCACCTGCCGACCATGCAGCTGCCG

AAGGGTGCGGATATTGCGCGTTGGCGTAAAGAGCTGGGCGACGCGGTTAGCATC

AGCGATAGCGGTGTGGTTACCATTAACCCGGACAAACTGATCAAGATGCGTGAT

AGCCTGCCGCCGGATGGCACCGTTTGGGATACCGCGCGTTACCAAGCGTGGAAC

ACCGCGTTCAGCGGTCAGAAAGGCCAGCATCCGGAACGTCGTGCGGATGCGCGT

CGTAAATATAGCCACCAGAACAGCAACTTTGATAACCTGGTGAAGGTTCTGAGC

GGTGCGATTAGCACCCTGACCGACACCCAGAGCTATCTGCAAATCAAGCTTATG

AGCAGCGGTGTTCAAGGTGGCCCGGCGGCGAACGCGAACGCGTACCAGACCCAC

CCGCTGCGTGATGCGGCGAGCGCGCTGGGCACCCTGAGCCCGCAGGCGTATGTG

GATGTGGTTAGCGCGGCGCAACGTAACTTCCTGGAGCGTATGAGCCAACTGGCG

AGCGAACAGTGCGATGCGCAACCGGCGGCGCATGATGCGCGTCTGGATGATCGT

CCGGCGCTGCGTGCGCCGCAGGAACGTGACGCGCCGCCGCTGGGTGCGAGCGAT

ACCGGTAGCCGTGCGAGCGGTGCGGCGAAACTGACCGAGCTGCTGGGTGTGCTG

ATGAGCGTTATTAGCGCGAGCAGCCTGGACGAACTGAAGCAACGTAGCGATATC

TGGAACCAGATGAGCAAAGCGGCGCAAGACAACCTGAGCCGTCTGAGCGATGCG

-continued

TTTCAGCGTGCGACCGACGAGGCGAAAGCGGCGGCGGATGCGGCGGAACAGGC

GGCGGCGGCGGCGAAGCAAGCGGGTGCGGACGCGAAAGCGGCGGATGCGGCGG

TGGATGCGGCGCAAAAACGTTACGATGACGCGGTTAAGCAGGGCCTGCCGGATG

ACCGTCTGCAAAGCCTGAAAGCGGCGCTGGAGCAGGCGCGTCAGCAAGCGGGTG

ATGCGCATGGTCGTGCGGATGCGCTGCAGGCGGATGCGACCAAGAAACTGGACG

CGGCGAGCGCGCTGGCGACCCAAGCGCGTGCGTGCGAACAGCAAGTGGATGACG

CGGTTAACCAGGCGACCCAGCAATATGGTGCGAGCGCGAGCCTGCGTACCCCGC

AAAGCCCGCGTCTGAGCGGTGCGGCGGAGCTGACCGCGGTGCTGGGCAAGCTGC

AGGAACTGATTAGCAGCGGCAACGTTAAAGAGCTGGAAAGCAAGCAGAAACTG

TTCACCGAGATGCAAGCGAAGCGTGAGGCGGAACTGCAAAAGAAAAGCGACGA

ATATCAGGCGCAAGTGAAGAAAGCGGAGGAAATGCAGAAAACGATGGGTTGCA

TCGGCAAGATTGTGGGTTGGGTTATTACCGCGGTTAGCTTTGCGGCGGCGGCGTT

TACCGGTGGCGCGAGCCTGGCGCTGGCGGCGGTGGGCCTGGCGCTGGCGGTTGG

TGACGAGATTAGCCGTGCGACCACCGGTGTGAGCTTCATGGACAAGCTGATGCA

GCCGGTTATGGATGCGATCCTGAAACCGCTGATGGAGATGATTAGCAGCCTGAT

CACCAAGGCGCTGGTTGCGTGCGGCGTTGATCAGCAAAAAGCGGAACTGGCGGG

TGCGATTCTGGGTGCGGTTGTTACCGGTGTGGCGCTGGTTGCGGCGGCGTTTGTT

GGTGCGAGCGCGGTGAAAGCGGTTGCGAGCAAGGTTATCGACGCGATGGCGGGT

CAGCTGACCAAGCTGATGGATAGCGCGATTGGCAAAATGCTGGTGCAACTGATC

GAGAAATTCAGCGAAAAGAGCGGTCTGCAGGCGCTGGGTAGCCGTACCGCGACC

GCGATGACCCGTATGCGTCGTGCGATTGGCGTTGAGGCGAAGGAAGACGGTATG

CTGCTGGCGAACCGTTTTGAAAAAGCGGGCACCGTGATGAACGTTGGTAACCAA

GTGAGCCAAGCGGCGGGTGGCATTGTGGTTGGCGTTGAGCGTGCGAAAGCGATG

GGTCTGCTGGCGGATGTGAAAGAAGCGATGTATGACATCAAGCTGCTGGGTGAT

CTGCTGAAACAGGCGGTGGACGCGTTTGCGGAGCACAACCGTGTTCTGGCGCAA

CTGATGCAGCAAATGAGCGATGCGGGCGAAATGCAGACCAGCACCGGCAAGCTG

ATCCTGCGTAACGCGCGTGCGGTTTAAGGATCC

LTA1-BurkF Amino acid sequence

SEQ ID NO: 28

MDNGDRLYRADSRPPDEIKRSGGLMPRGHNEYFDRGTQMNINLYDHARGTQ
TGFVRYDDGYVSTSLSLRSAHLAGQSILSGYSTYYIYVIATAPNMFNVNDVLGVYSP
HPYEQEVSALGGIPYSQIYGWYRVNFGVIDERLHRNREYRDRYYRNLNIAPAEDGYR
LAGFPPDHQAWREEPWIHHAPQGCGNSSRMNMHVDMGRALTVRDWPALEALAKT
MPADAGARAMTDDDLRAAGVDRRVPEQKLGAAIDEFASLRLPDRIDGRFVDGRRA
NLTVFDDARVAVRGHARAQRNLLERLETELLGGTLDTAGDEGGIQPDPILQGLVDVI
GQGKSDIDAYATIVEGLTKYFQSVADVMSKLQDYISAKDDKNMKIDGGKIKALIQQ
VIDHLPTMQLPKGADIARWRKELGDAVSISDSGVVTINPDKLIKMRDSLPPDGTVWD
TARYQAWNTAFSGQKGQHPERRADARRKYSHQNSNFDNLVKVLSGAISTLTDTQSY
LQIKLMSSGVQGGPAANANAYQTHPLRDAASALGTLSPQAYVDVVSAAQRNFLER
MSQLASEQCDAQPAAHDARLDDRPALRAPQERDAPPLGASDTGSRASGAAKLTELL
GVLMSVISASSLDELKQRSDIWNQMSKAAQDNLSRLSDAFQRATDEAKAAADAAEQ
AAAAAKQAGADAKAADAAVDAAQKRYDDAVKQGLPDDRLQSLKAALEQARQQA

-continued

```
GDAHGRADALQADATKKLDAASALATQARACEQQVDDAVNQATQQYGASASLRT
PQSPRLSGAAELTAVLGKLQELISSGNVKELESKQKLFTEMQAKREAELQKKSDEYQ
AQVKKAEEMQKTMGCIGKIVGWVITAVSFAAAAFTGGASLALAAVGLALAVGDEIS
RATTGVSFMDKLMQPVMDAILKPLMEMISSLITKALVACGVDQQKAELAGAILGAV
VTGVALVAAAFVGASAVKAVASKVIDAMAGQLTKLMDSAIGKMLVQLIEKFSEKS
GLQALGSRTATAMTRMRRAIGVEAKEDGMLLANRFEKAGTVMNVGNQVSQAAGG
IVVGVERAKAMGLLADVKEAMYDIKLLGDLLKQAVDAFAEHNRVLAQLMQQMSD
AGEMQTSTGKLILRNARAV-
```

His-PcrH (Chaperone of PaF) nucleic acid sequence SEQ ID NO: 29

```
ATGGGCAGCAGCCATCACCATCATCACCACAGCCAGGATCCGATGAACCA
GCCGACCCCTTCCGACACCGACCAGCAACAGGCGCTGGAGGCCTTCCTGCGCGA
CGGCGGCACCCTGGCGATGCTTCGCGGACTCAGCGAGGACACCCTGGAGCAGCT
CTATGCGCTGGGCTTCAACCAGTACCAGGCGGGCAAGTGGGACGACGCGCAGAA
GATCTTCCAGGCACTGTGCATGCTCGACCACTACGACGCCCGCTACTTTCTCGGC
CTGGGCGCCTGCCGCCAGTCCCTCGGTCTCTATGAACAGGCCCTGCAGAGCTACA
GCTACGGCGCGCTGATGGACATCAACGAGCCGCGCTTTCCCTTCCATGCCGCCGA
GTGCCACCTGCAACTGGGTGATCTCGACGGAGCCGAGAGTGGCTTCTACTCGGCC
CGGGCCCTGGCCGCGGCACAGCCGGCGCACGAGGCCCTGGCCGCGCGTGCCGGC
GCCATGTTGGAAGCCGTAACCGCGAGAAAGGATCGAGCCTATGAATCCGATAAC
GCTTGAAAGCTT
```

His-PcrH (Chaperone of PaF) Amino acid sequence SEQ ID NO: 30

```
MGSSHHHHHHSQDPMNQPTPSDTDQQQALEAFLRDGGTLAMLRGLSEDTLE
QLYALGFNQYQAGKWDDAQKIFQALCMLDHYDARYFLGLGACRQSLGLYEQALQS
YSYGALMDINEPRFPFHAAECHLQLGDLDGAESGFYSARALAAAQPAHEALAARAG
AMLEAVTARKDRAYESDNA-
```

PcrV nucleic acid sequence SEQ ID NO: 31

```
CATATGGAAGTCAGAAACCTTAATGCCGCTCGCGAGCTGTTCCTGGACGA
GCTCCTGGCCGCGTCGGCGGCGCCTGCCAGTGCCGAGCAGGAGGAACTGCTGGC
CCTGTTGCGCAGCGAGCGGATCGTGCTGGCCCACGCCGGCCAGCCGCTGAGCGA
GGCGCAAGTGCTCAAGGCGCTCGCCTGGTTGCTCGCGGCCAATCCGTCCGCGCCT
CCGGGGCAGGGCCTCGAGGTACTCCGCGAAGTCCTGCAGGCACGTCGGCAGCCC
GGTGCGCAGTGGGATCTGCGTGAGTTCCTGGTGTCGGCCTATTTCAGCCTGCACG
GGCGTCTCGACGAGGATGTCATCGGTGTCTACAAGGATGTCCTGCAGACCCAGG
ACGGCAAGCGCAAGGCGCTGCTCGACGAGCTCAAGGCGCTGACCGCGGAGTTGA
AGGTCTACAGCGTGATCCAGTCGCAGATCAACGCCGCGCTGTCGGCCAGGCAGG
GCATCAGGATCGACGCTGGCGGTATCGATCTGGTCGACCCCACGCTATATGGCTA
TGCCGTCGGCGATCCCAGGTGGAAGGACAGCCCCGAGTATGCGCTGCTGAGCAA
TCTGGATACCTTCAGCGGCAAGCTGTCGATCAAGGATTTTCTCAGCGGCTCGCCG
AAGCAGAGCGGGGAACTCAAGGGCCTCAGCGATGAGTACCCCTTCGAGAAGGAC
AACAACCCGGTCGGCAATTTCGCCACCACGGTGAGCGACCGCTCGCGTCCGCTG
```

```
                                                         -continued
AACGACAAGGTCAACGAGAAGACCACCCTGCTCAACGACACCAGCTCCCGCTAC

AACTCGGCGGTCGAGGCGCTCAACCGCTTCATCCAGAAATACGACAGCGTCCTG

AGCGACATTCTCAGCGCGATC

PcrV amino acid sequence
                                                                            SEQ ID NO: 32
MEVRNLNAARELFLDELLAASAAPASAEQEELLALLRSERIVLAHAGQPLSEA

QVLKALAWLLAANPSAPPGQGLEVLREVLQARRQPGAQWDLREFLVSAYFSLHGRL

DEDVIGVYKDVLQTQDGKRKALLDELKALTAELKVYSVIQSQINAALSARQGIRIDA

GGIDLVDPTLYGYAVGDPRWKDSPEYALLSNLDTFSGKLSIKDFLSGSPKQSGELKG

LSDEYPFEKDNNPVGNFATTVSDRSRPLNDKVNEKTTLLNDTSSRYNSAVEALNRFI

QKYDSVLSDILSAI

PopB nucleic acid sequence
                                                                            SEQ ID NO: 33
ATGAACCCGATTACGCTGGAACGTGCTGGTCTGCCGTATGGTGTTGCCGA

TGCTGGTGACATCCCGGCTCTGGGTCGCCCGGTCGCACGTGATGTGGAAAGTCTG

CGTGTTGAACGTCTGGCAGCACCGGCAGCTGCAAGCGCATCTGGCACCGGTGTC

GCTCTGACGCCGCCGTCTGCAGCAAGTCAGCAACGTCTGGAAGTTGCTAACCGC

GCGGAAATTGCCTCACTGGTCCAGGCAGTGGGTGAAGACGTGGGTCTGGCACGT

CAAGTGGTTCTGGCAGGTGCATCGACCCTGCTGAGCGCAGGTCTGATGTCGCCGC

AGGCGTTCGAAATTGAACTGGCCAAAATCACCGGCGAAGTTGAAAATCAGCAGA

AAAAACTGAAACTGACGGAAATCGAACAGGCCCGTAAACAGAACCTGCAAAAA

ATGGAAGATAACCAGCAAAAAATCCGCGAATCGGAAGAAGCTGCGAAAGAAGC

GCAGAAAAGCGGCCTGGCCGCAAAAATTTTTGGTTGGATTTCTGCTATCGCGAGT

ATTATCGTGGGTGCAATCATGGTTGCAACCGGTGTCGGTGCTGCAGCAGGTGCAC

TGATGATTGCTGGCGGTGTCATGGGTGTCGTGAGTCAGTCCGTGCAGCAAGCAGC

TGCGGATGGTCTGATCTCAAAAGAAGTGATGGAAAAACTGGGCCCGGCCCTGAT

GGGTATTGAAATGGCCGTGGCACTGCTGGCCGCAGTTGTCTCCTTTGGTGGTTCA

GCAGTTGGTGGTCTGGCACGTCTGGGTGCAAAAATCGGCGGTAAAGCTGCGGAA

ATGACGGCATCCCTGGCTTCAAAAGTGGCAGACCTGGGCGGTAAATTCGGCTCTC

TGGCGGGCCAGTCACTGTCGCATAGCCTGAAACTGGGTGTGCAAGTTTCTGATCT

GACCCTGGACGTTGCAAACGGCGCCGCACAGGCTACGCACAGTGGTTTTCAAGC

GAAAGCTGCGAATCGTCAGGCCGATGTTCAAGAATCCCGTGCAGACCTGACCAC

GCTGCAGGGTGTCATTGAACGTCTGAAAGAAGAACTGAGCCGCATGCTGGAAGC

CTTTCAGGAAATTATGGAACGCATCTTCGCAATGCTGCAAGCGAAAGGCGAAAC

CCTGCACAATCTGTCTTCCCGTCCGGCGGCTATCTGAGGATCC

PopB amino acid sequence
                                                                            SEQ ID NO: 34
MNPITLERAGLPYGVADAGDIPALGRPVARDVESLRVERLAAPAAASASGTG

VALTPPSAASQQRLEVANRAEIASLVQAVGEDVGLARQVVLAGASTLLSAGLMSPQ

AFEIELAKITGEVENQQKKLKLTEIEQARKQNLQKMEDNQQKIRESEEAAKEAQKSG

LAAKIFGWISAIASIIVGAIMVATGVGAAAGALMIAGGVMGVVSQSVQQAADGLIS
```

KEVMEKLGPALMGIEMAVALLAAVVSFGGSAVGGLARLGAKIGGKAAEMTASLAS

KVADLGGKFGSLAGQSLSHSLKLGVQVSDLTLDVANGAAQATHSGFQAKAANRQA

DVQESRADLTTLQGVIERLKEELSRMLEAFQEIMERIFAMLQAKGETLHNLSSRPAAI

PaF nucleic acid sequence

SEQ ID NO: 35

CATATGGAAGTCAGAAACCTTAATGCCGCTCGCGAGCTGTTCCTGGACGA

GCTCCTGGCCGCGTCGGCGGCGCCTGCCAGTGCCGAGCAGGAGGAACTGCTGGC

CCTGTTGCGCAGCGAGCGGATCGTGCTGGCCCACGCCGGCCAGCCGCTGAGCGA

GGCGCAAGTGCTCAAGGCGCTCGCCTGGTTGCTCGCGGCCAATCCGTCCGCGCCT

CCGGGGCAGGGCCTCGAGGTACTCCGCGAAGTCCTGCAGGCACGTCGGCAGCCC

GGTGCGCAGTGGGATCTGCGTGAGTTCCTGGTGTCGGCCTATTTCAGCCTGCACG

GGCGTCTCGACGAGGATGTCATCGGTGTCTACAAGGATGTCCTGCAGACCCAGG

ACGGCAAGCGCAAGGCGCTGCTCGACGAGCTCAAGGCGCTGACCGCGGAGTTGA

AGGTCTACAGCGTGATCCAGTCGCAGATCAACGCCGCGCTGTCGGCCAGGCAGG

GCATCAGGATCGACGCTGGCGGTATCGATCTGGTCGACCCCACGCTATATGGCTA

TGCCGTCGGCGATCCCAGGTGGAAGGACAGCCCCGAGTATGCGCTGCTGAGCAA

TCTGGATACCTTCAGCGGCAAGCTGTCGATCAAGGATTTTCTCAGCGGCTCGCCG

AAGCAGAGCGGGGAACTCAAGGGCCTCAGCGATGAGTACCCCTTCGAGAAGGAC

AACAACCCGGTCGGCAATTTCGCCACCACGGTGAGCGACCGCTCGCGTCCGCTG

AACGACAAGGTCAACGAGAAGACCACCCTGCTCAACGACACCAGCTCCCGCTAC

AACTCGGCGGTCGAGGCGCTCAACCGCTTCATCCAGAAATACGACAGCGTCCTG

AGCGACATTCTCAGCGCGATCGGATCCATGAACCCGATTACGCTGGAACGTGCT

GGTCTGCCGTATGGTGTTGCCGATGCTGGTGACATCCCGGCTCTGGGTCGCCCGG

TCGCACGTGATGTGGAAAGTCTGCGTGTTAACGTCTGGCAGCACCGGCAGCTG

CAAGCGCATCTGGCACCGGTGTCGCTCTGACGCCGCCGTCTGCAGCAAGTCAGC

AACGTCTGGAAGTTGCTAACCGCGCGGAAATTGCCTCACTGGTCCAGGCAGTGG

GTGAAGACGTGGGTCTGGCACGTCAAGTGGTTCTGGCAGGTGCATCGACCCTGCT

GAGCGCAGGTCTGATGTCGCCGCAGGCGTTCGAAATTGAACTGGCCAAAATCAC

CGGCGAAGTTGAAAATCAGCAGAAAAAACTGAAACTGACGGAAATCGAACAGG

CCCGTAAACAGAACCTGCAAAAAATGGAAGATAACCAGCAAAAAATCCGCGAA

TCGGAAGAAGCTGCGAAAGAAGCGCAGAAAAGCGGCCTGGCCGCAAAAATTTTT

GGTTGGATTTCTGCTATCGCGAGTATTATCGTGGGTGCAATCATGGTTGCAACCG

GTGTCGGTGCTGCAGCAGGTGCACTGATGATTGCTGGCGGTGTCATGGGTGTCGT

GAGTCAGTCCGTGCAGCAAGCAGCTGCGGATGGTCTGATCTCAAAAGAAGTGAT

GGAAAAACTGGGCCCGGCCCTGATGGGTATTGAAATGGCCGTGGCACTGCTGGC

CGCAGTTGTCTCCTTTGGTGGTTCAGCAGTTGGTGGTCTGGCACGTCTGGGTGCA

AAAATCGGCGGTAAAGCTGCGGAAATGACGGCATCCCTGGCTTCAAAAGTGGCA

GACCTGGGCGGTAAATTCGGCTCTCTGGCGGGCCAGTCACTGTCGCATAGCCTGA

AACTGGGTGTGCAAGTTTCTGATCTGACCCTGGACGTTGCAAACGGCGCCGCACA

GGCTACGCACAGTGGTTTTCAAGCGAAAGCTGCGAATCGTCAGGCCGATGTTCA

AGAATCCCGTGCAGACCTGACCACGCTGCAGGGTGTCATTGAACGTCTGAAAGA

```
AGAACTGAGCCGCATGCTGGAAGCCTTTCAGGAAATTATGGAACGCATCTTCGC

AATGCTGCAAGCGAAAGGCGAAACCCTGCACAATCTGTCTTCCCGTCCGGCGGC

TATCTGAGGATCC
```

PaF amino acid sequence                                                                                   SEQ ID NO: 36

```
MEVRNLNAARELFLDELLAASAAPASAEQEELLALLRSERIVLAHAGQPLSEA

QVLKALAWLLAANPSAPPGQGLEVLREVLQARRQPGAQWDLREFLVSAYFSLHGRL

DEDVIGVYKDVLQTQDGKRKALLDELKALTAELKVYSVIQSQINAALSARQGIRIDA

GGIDLVDPTLYGYAVGDPRWKDSPEYALLSNLDTFSGKLSIKDFLSGSPKQSGELKG

LSDEYPFEKDNNPVGNFATTVSDRSRPLNDKVNEKTTLLNDTSSRYNSAVEALNRFI

QKYDSVLSDILSAIGSMNPITLERAGLPYGVADAGDIPALGRPVARDVESLRVERLAA

PAAASASGTGVALTPPSAASQQRLEVANRAEIASLVQAVGEDVGLARQVVLAGAST

LLSAGLMSPQAFEIELAKITGEVENQQKKLKLTEIEQARKQNLQKMEDNQQKIRESE

EAAKEAQKSGLAAKIFGWISAIASIIVGAIMVATGVGAAAGALMIAGGVMGVVSQS

VQQAAADGLISKEVMEKLGPALMGIEMAVALLAAVVSFGGSAVGGLARLGAKIGG

KAAEMTASLASKVADLGGKFGSLAGQSLSHSLKLGVQVSDLTLDVANGAAQATHS

GFQAKAANRQADVQESRADLTTLQGVIERLKEELSRMLEAFQEIMERIFAMLQAKG

ETLHNLSSRPAAI
```

LTA1-PaF nucleic acid sequence                                                                            SEQ ID NO: 37

```
CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgccccctcaggggtgcgggaacagtagtcgcCATATGGAAGTCAGAAACCT

TAATGCCGCTCGCGAGCTGTTCCTGGACGAGCTCCTGGCCGCGTCGGCGGCGCCT

GCCAGTGCCGAGCAGGAGGAACTGCTGGCCCTGTTGCGCAGCGAGCGGATCGTG

CTGGCCCACGCCGGCCAGCCGCTGAGCGAGGCGCAAGTGCTCAAGGCGCTCGCC

TGGTTGCTCGCGGCCAATCCGTCCGCGCCTCCGGGGCAGGGCCTCGAGGTACTCC

GCGAAGTCCTGCAGGCACGTCGGCAGCCCGGTGCGCAGTGGGATCTGCGTGAGT

TCCTGGTGTCGGCCTATTTCAGCCTGCACGGGCGTCTCGACGAGGATGTCATCGG

TGTCTACAAGGATGTCCTGCAGACCCAGGACGGCAAGCGCAAGGCGCTGCTCGA

CGAGCTCAAGGCGCTGACCGCGGAGTTGAAGGTCTACAGCGTGATCCAGTCGCA

GATCAACGCCGCGCTGTCGGCCAGGCAGGGCATCAGGATCGACGCTGGCGGTAT

CGATCTGGTCGACCCCACGCTATATGGCTATGCCGTCGGCGATCCCAGGTGGAAG

GACAGCCCCGAGTATGCGCTGCTGAGCAATCTGGATACCTTCAGCGGCAAGCTG

TCGATCAAGGATTTTCTCAGCGGCTCGCCGAAGCAGAGCGGGGAACTCAAGGGC

CTCAGCGATGAGTACCCCTTCGAGAAGGACAACAACCCGGTCGGCAATTTCGCC

ACCACGGTGAGCGACCGCTCGCGTCCGCTGAACGACAAGGTCAACGAGAAGACC

ACCCTGCTCAACGACACCAGCTCCCGCTACAACTCGGCGGTCGAGGCGCTCAAC

CGCTTCATCCAGAAATACGACAGCGTCCTGAGCGACATTCTCAGCGCGATCGGAT
```

-continued

CCATGAACCCGATTACGCTGGAACGTGCTGGTCTGCCGTATGGTGTTGCCGATGC

TGGTGACATCCCGGCTCTGGGTCGCCCGGTCGCACGTGATGTGGAAAGTCTGCGT

GTTGAACGTCTGGCAGCACCGGCAGCTGCAAGCGCATCTGGCACCGGTGTCGCT

CTGACGCCGCCGTCTGCAGCAAGTCAGCAACGTCTGGAAGTTGCTAACCGCGCG

GAAATTGCCTCACTGGTCCAGGCAGTGGGTGAAGACGTGGGTCTGGCACGTCAA

GTGGTTCTGGCAGGTGCATCGACCCTGCTGAGCGCAGGTCTGATGTCGCCGCAGG

CGTTCGAAATTGAACTGGCCAAAATCACCGGCGAAGTTGAAAATCAGCAGAAAA

AACTGAAACTGACGGAAATCGAACAGGCCCGTAAACAGAACCTGCAAAAAATG

GAAGATAACCAGCAAAAAATCCGCGAATCGGAAGAAGCTGCGAAAGAAGCGCA

GAAAAGCGGCCTGGCCGCAAAAATTTTTGGTTGGATTTCTGCTATCGCGAGTATT

ATCGTGGGTGCAATCATGGTTGCAACCGGTGTCGGTGCTGCAGCAGGTGCACTG

ATGATTGCTGGCGGTGTCATGGGTGTCGTGAGTCAGTCCGTGCAGCAAGCAGCTG

CGGATGGTCTGATCTCAAAAGAAGTGATGGAAAAACTGGGCCCGGCCCTGATGG

GTATTGAAATGGCCGTGGCACTGCTGGCCGCAGTTGTCTCCTTTGGTGGTTCAGC

AGTTGGTGGTCTGGCACGTCTGGGTGCAAAAATCGGCGGTAAAGCTGCGGAAAT

GACGGCATCCCTGGCTTCAAAAGTGGCAGACCTGGGCGGTAAATTCGGCTCTCTG

GCGGGCCAGTCACTGTCGCATAGCCTGAAACTGGGTGTGCAAGTTTCTGATCTGA

CCCTGGACGTTGCAAACGGCGCCGCACAGGCTACGCACAGTGGTTTTCAAGCGA

AAGCTGCGAATCGTCAGGCCGATGTTCAAGAATCCCGTGCAGACCTGACCACGC

TGCAGGGTGTCATTGAACGTCTGAAAGAAGAACTGAGCCGCATGCTGGAAGCCT

TTCAGGAAATTATGGAACGCATCTTCGCAATGCTGCAAGCGAAAGGCGAAACCC

TGCACAATCTGTCTTCCCGTCCGGCGGCTATCTGAGGATCC

LTA1-PaF Amino acid sequence

SEQ ID NO: 38

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMEVRNLNAARELFLDELLAASAAPASA

EQEELLALLRSERIVLAHAGQPLSEAQVLKALAWLLAANPSAPPGQGLEVLREVLQA

RRQPGAQWDLREFLVSAYFSLHGRLDEDVIGVYKDVLQTQDGKRKALLDELKALT

AELKVYSVIQSQINAALSARQGIRIDAGGIDLVDPTLYGYAVGDPRWKDSPEYALLS

NLDTFSGKLSIKDFLSGSPKQSGELKGLSDEYPFEKDNNPVGNFATTVSDRSRPLNDK

VNEKTTLLNDTSSRYNSAVEALNRFIQKYDSVLSDILSAIGSMNPITLERAGLPYGVA

DAGDIPALGRPVARDVESLRVERLAAPAAASASGTGVALTPPSAASQQRLEVANRAE

IASLVQAVGEDVGLARQVVLAGASTLLSAGLMSPQAFEIELAKITGEVENQQKKLKL

TEIEQARKQNLQKMEDNQQKIRESEEAAKEAQKSGLAAKIFGWISAIASIIVGAIMVA

TGVGAAAGALMIAGGVMGVVSQSVQQAAADGLISKEVMEKLGPALMGIEMAVAL

LAAVVSFGGSAVGGLARLGAKIGGKAAEMTASLASKVADLGGKFGSLAGQSLSHSL

KLGVQVSDLTLDVANGAAQATHSGFQAKAANRQADVQESRADLTTLQGVIERLKE

ELSRMLEAFQEIMERIFAMLQAKGETLHNLSSRPAAI

SycD (Chaperone for YerF) nucleic acid sequence     SEQ ID NO: 39

ATGGGCAGCAGCCATCACCATCATCACCACAGCCAGGATCCGatgcaacaagag acgacagacactcaagaataccagctggcaatggaatccttcctaaaaggaggggaactatcgccatgctcaacgaaatttcaagtg acactttagagcaactctactctcttgcgtttaaccaataccagtcaggaaaatacgaggatgctcacaaggtctttcaagctctctgtgtg ctagaccactatgattcacgtttctttttagggctaggcgcttgtcgtcaagccatgggcaatacgacttagcgattcatagctacagcta tggcgccataatggatataaaagaacctcgttttccgtttcatgctgccgaatgtttactgcaaaagggagagcttgctgaagcagaaag tggcttgttcttggctcaagagcttatcgcagacaaacctgagtttaaggagctttccacccgagttagctcaatgttagaagcaattaaat tgaaaaaggagatggaacatgagtgcgttgataacccatgaAAGCTT

SycD (Chaperone for YerF) Amino acid sequence     SEQ ID NO: 40

MGSSHHHHHHSSGLVPRGSHMQQETTDTQEYQLAMESFLKGGGTIAMLNEIS

SDTLEQLYSLAFNQYQSGKYEDAHKVFQALCVLDHYDSRFFLGLGACRQAMGQYD

LAIHSYSYGAIMDIKEPRFPFHAAECLLQKGELAEAESGLFLAQELIADKPEFKELSTR

VSSMLEAIKLKKEMEHECVDNP-

LcrV amino acid sequence     SEQ ID NO: 41

CATATGATTAGAGCCTACGAACAAAACCCACAACATTTTATTGAGGATCT

AGAAAAAGTTAGGGTGGAACAACTTACTGGTCATGGTTCTTCAGTTTTAGAAGA

ATTGGTTCAGTTAGTCAAAGATAAAAATATAGATATTTCCATTAAATATGATCCC

AGAAAAGATTCGGAGGTTTTTGCCAATAGAGTAATTACTGATGATATCGAATTGC

TCAAGAAAATCCTAGCTTATTTTCTACCCGAGGATGCCATTCTTAAAGGCGGTCA

TTATGACAACCAACTGCAAAATGGCATCAAGCGAGTAAAAGAGTTCCTTGAATC

ATCGCCGAATACACAATGGGAATTGCGGGCGTTCATGGCAGTAATGCATTTCTCT

TTAACCGCCGATCGTATCGATGATGATATTTTGAAAGTGATTGTTGATTCAATGA

ATCATCATGGTGATGCCCGTAGCAAGTTGCGTGAAGAATTAGCTGAGCTTACCGC

CGAATTAAAGATTTATTCAGTTATTCAAGCCGAAATTAATAAGCATCTGTCTAGT

AGTGGCACCATAAATATCCATGATAAATCCATTAATCTCATGGATAAAAATTTAT

ATGGTTATACAGATGAAGAGATTTTTAAAGCCAGCGCAGAGTACAAAATTCTCG

AGAAAATGCCTCAAACCACCATTCAGGTGGATGGGAGCGAGAAAAAAATAGTCT

CGATAAAGGACTTTCTTGGAAGTGAGAATAAAAGAACCGGGGCGTTGGGTAATC

TGAAAAACTCATACTCTTATAATAAAGATAATAATGAATTATCTCACTTTGCCAC

CACCTGCTCGGATAAGTCCAGGCCGCTCAACGACTTGGTTAGCCAAAAACAAC

TCAGCTGTCTGATATTACATCACGTTTTAATTCAGCTATTGAAGCACTGAACCGTT

TCATTCAGAAATATGATTCAGTGATGCAACGTCTGCTAGATGACACGTCTGGTAA

A

LcrV amino acid sequence     SEQ ID NO: 42

MIRAYEQNPQHFIEDLEKVRVEQLTGHGSSVLEELVQLVKDKNIDISIKYDPR

KDSEVFANRVITDDIELLKKILAYFLPEDAILKGGHYDNQLQNGIKRVKEFLESSPNT

QWELRAFMAVMHFSLTADRIDDDILKVIVDSMNHHGDARSKLREELAELTAELKIYS

```
VIQAEINKHLSSSGTINIHDKSINLMDKNLYGYTDEEIFKASAEYKILEKMPQTTIQVD
GSEKKIVSIKDFLGSENKRTGALGNLKNSYSYNKDNNELSHFATTCSDKSRPLNDLV
SQKTTQLSDITSRFNSAIEALNRFIQKYDSVMQRLLDDTSGK
```

YopB nucleic acid sequence  SEQ ID NO: 43

```
ATGAGTGCGTTGATAACCCATGATCGCTCAACGCCAGTAACTGGAAGTCT
ACTTCCCTACGTCGAGACACCAGCGCCCGCCCCCCTTCAGACTCAACAAGTCGCG
GGAGAACTGAAGGATAAAAATGGTGGGGTGAGTTCTCAGGGCGTACAGCTCCCT
GCACCACTAGCAGTGGTTGCCAGCCAAGTCACTGAAGGACAACAGCAAGAAATC
ACTAAATTATTGGAGTCGGTCACCCGCGGCACGGCAGGATCTCAACTGATATCA
AATTATGTTTCAGTGCTAACGAATTTTACGCTCGCTTCACCTGATACATTTGAGAT
TGAGTTAGGTAAGCTAGTTTCTAATTTAGAAGAAGTACGCAAAGACATAAAAAT
CGCTGATATTCAGCGTCTTCATGAACAAAACATGAAGAAAATTGAAGAGAATCA
AGAGAAAATCAAAGAAACAGAAGAGAATGCCAAGCAAGTCAAGAAATCCGGCA
TGGCATCAAAGATTTTTGGCTGGCTCAGCGCCATAGCCTCAGTGGTTATCGGTGC
CATCATGGTGGCCTCAGGGGTAGGAGCCGTTGCCGGTGCAATGATGATTGCCTCA
GGCGTAATTGGGATGGCGAATATGGCTGTGAAACAAGCGGCGGAAGATGGCCTG
ATATCCCAAGAGGCAATGCAAGTATTAGGGCCGATACTCACTGCGATTGAAGTC
GCATTGACTGTAGTTTCAACCGTAATGACCTTTGGCGGTTCGGCACTAAAATGCC
TGGCTGATATTGGCGCAAAACTCGGTGCTAACACCGCAAGTCTTGCTGCTAAAGG
AGCCGAGTTTTCGGCCAAAGTTGCCCAAATTTCGACAGGCATATCAAACACTGTC
GGGAATGCAGTGACTAAATTAGGGGGCAGTTTTGGTAGTTTAACAATGAGCCAT
GTAATCCGTACAGGATCACAGGCAACACAAGTCGCCGTTGGTGTGGGCAGCGGA
ATAACTCAGACCATCAATAATAAAAAACAAGCTGATTTACAACATAATAACGCT
GATTTGGCCTTGAACAAGGCAGACATGGCAGCGTTACAAAGTATTATTGACCGA
CTCAAAGAAGAGTTATCCCATTTGTCAGAGTCACATCAACAAGTGATGGAACTG
ATTTTCCAGATGATTAATGCAAAAGGTGACATGCTGCATAATTTGGCCGGCAGAC
CCCATACTGTTTAAGGTACC
```

YopB amino acid sequence  SEQ ID NO: 44

```
MSALITHDRSTPVTGSLLPYVETPAPAPLQTQQVAGELKDKNGGVSSQGVQL
PAPLAVVASQVTEGQQQEITKLLESVTRGTAGSQLISNYVSVLTNFTLASPDTFEIELG
KLVSNLEEVRKDIKIADIQRLHEQNMKKIEENQEKIKETEENAKQVKKSGMASKIFG
WLSAIASVVIGAIMVASGVGAVAGAMMIASGVIGMANMAVKQAAEDGLISQEAMQ
VLGPILTAIEVALTVVSTVMTFGGSALKCLADIGAKLGANTASLAAKGAEFSAKVAQ
ISTGISNTVGNAVTKLGGSFGSLTMSHVIRTGSQATQVAVGVGSGITQTINNKKQADL
QHNNADLALNKADMAALQSIIDRLKEELSHLSESHQQVMELIFQMINAKGDMLHNL
AGRPHTV
```

YerF nucleic acid sequence  SEQ ID NO: 45

```
CATATGATTAGAGCCTACGAACAAAACCCACAACATTTTATTGAGGATCT
AGAAAAAGTTAGGGTGGAACAACTTACTGGTCATGGTTCTTCAGTTTTAGAAGA
ATTGGTTCAGTTAGTCAAAGATAAAAATATAGATATTTCCATTAAATATGATCCC
AGAAAAGATTCGGAGGTTTTTGCCAATAGAGTAATTACTGATGATATCGAATTGC
```

-continued

```
TCAAGAAAATCCTAGCTTATTTTCTACCCGAGGATGCCATTCTTAAAGGCGGTCA
TTATGACAACCAACTGCAAAATGGCATCAAGCGAGTAAAAGAGTTCCTTGAATC
ATCGCCGAATACACAATGGGAATTGCGGGCGTTCATGGCAGTAATGCATTTCTCT
TTAACCGCCGATCGTATCGATGATGATATTTTGAAAGTGATTGTTGATTCAATGA
ATCATCATGGTGATGCCCGTAGCAAGTTGCGTGAAGAATTAGCTGAGCTTACCGC
CGAATTAAAGATTTATTCAGTTATTCAAGCCGAAATTAATAAGCATCTGTCTAGT
AGTGGCACCATAAATATCCATGATAAATCCATTAATCTCATGGATAAAAATTTAT
ATGGTTATACAGATGAAGAGATTTTTAAAGCCAGCGCAGAGTACAAAATTCTCG
AGAAAATGCCTCAAACCACCATTCAGGTGGATGGGAGCGAGAAAAAAATAGTCT
CGATAAAGGACTTTCTTGGAAGTGAGAATAAAAGAACCGGGGCGTTGGGTAATC
TGAAAAACTCATACTCTTATAATAAAGATAATAATGAATTATCTCACTTTGCCAC
CACCTGCTCGGATAAGTCCAGGCCGCTCAACGACTTGGTTAGCCAAAAAACAAC
TCAGCTGTCTGATATTACATCACGTTTTAATTCAGCTATTGAAGCACTGAACCGTT
TCATTCAGAAATATGATTCAGTGATGCAACGTCTGCTAGATGACACGTCTGGTAA
AGGATCCATGAGTGCGTTGATAACCCATGATCGCTCAACGCCAGTAACTGGAAG
TCTACTTCCCTACGTCGAGACACCAGCGCCCGCCCCCCTTCAGACTCAACAAGTC
GCGGGAGAACTGAAGGATAAAAATGGTGGGGTGAGTTCTCAGGGCGTACAGCTC
CCTGCACCACTAGCAGTGGTTGCCAGCCAAGTCACTGAAGGACAACAGCAAGAA
ATCACTAAATTATTGGAGTCGGTCACCCGCGGCACGGCAGGATCTCAACTGATAT
CAAATTATGTTTCAGTGCTAACGAATTTTACGCTCGCTTCACCTGATACATTTGAG
ATTGAGTTAGGTAAGCTAGTTTCTAATTTAGAAGAAGTACGCAAAGACATAAAA
ATCGCTGATATTCAGCGTCTTCATGAACAAAACATGAAGAAAATTGAAGAGAAT
CAAGAGAAAATCAAAGAAACAGAAGAGAATGCCAAGCAAGTCAAGAAATCCGG
CATGGCATCAAAGATTTTTGGCTGGCTCAGCGCCATAGCCTCAGTGGTTATCGGT
GCCATCATGGTGGCCTCAGGGGTAGGAGCCGTTGCCGGTGCAATGATGATTGCCT
CAGGCGTAATTGGGATGGCGAATATGGCTGTGAAACAAGCGGCGGAAGATGGCC
TGATATCCCAAGAGGCAATGCAAGTATTAGGGCCGATACTCACTGCGATTGAAG
TCGCATTGACTGTAGTTTCAACCGTAATGACCTTTGGCGGTTCGGCACTAAAATG
CCTGGCTGATATTGGCGCAAAACTCGGTGCTAACACCGCAAGTCTTGCTGCTAAA
GGAGCCGAGTTTTCGGCCAAAGTTGCCCAAATTTCGACAGGCATATCAAACACT
GTCGGGAATGCAGTGACTAAATTAGGGGGCAGTTTTGGTAGTTTAACAATGAGC
CATGTAATCCGTACAGGATCACAGGCAACACAAGTCGCCGTTGGTGTGGGCAGC
GGAATAACTCAGACCATCAATAATAAAAAACAAGCTGATTTACAACATAATAAC
GCTGATTTGGCCTTGAACAAGGCAGACATGGCAGCGTTACAAAGTATTATTGACC
GACTCAAAGAAGAGTTATCCCATTTGTCAGAGTCACATCAACAAGTGATGGAAC
TGATTTTCCAGATGATTAATGCAAAAGGTGACATGCTGCATAATTTGGCCGGCAG
ACCCCATACTGTTTAAGGTACC
```

YerF amino acid sequence

SEQ ID NO: 46

MIRAYEQNPQHFIEDLEKVRVEQLTGHGSSVLEELVQLVKDKNIDISIKYDPR

KDSEVFANRVITDDIELLKKILAYFLPEDAILKGGHYDNQLQNGIKRVKEFLESSPNT

QWELRAFMAVMHFSLTADRIDDDILKVIVDSMNHHGDARSKLREELAELTAELKIYS

VIQAEINKHLSSSGTINIHDKSINLMDKNLYGYTDEEIFKASAEYKILEKMPQTTIQVD

GSEKKIVSIKDFLGSENKRTGALGNLKNSYSYNKDNNELSHFATTCSDKSRPLNDLV

SQKTTQLSDITSRFNSAIEALNRFIQKYDSVMQRLLDDTSGKGSMSALITHDRSTPVT

GSLLPYVETPAPAPLQTQQVAGELKDKNGGVSSQGVQLPAPLAVVASQVTEGQQQE

ITKLLESVTRGTAGSQLISNYVSVLTNFTLASPDTFEIELGKLVSNLEEVRKDIKIADIQ

RLHEQNMKKIEENQEKIKETEENAKQVKKSGMASKIFGWLSAIASVVIGAIMVASGV

GAVAGAMMIASGVIGMANMAVKQAAEDGLISQEAMQVLGPILTAIEVALTVVSTV

MTFGGSALKCLADIGAKLGANTASLAAKGAEFSAKVAQISTGISNTVGNAVTKLGGS

FGSLTMSHVIRTGSQATQVAVGVGSGITQTINNKKQADLQHNNADLALNKADMAA

LQSIIDRLKEELSHLSESHQQVMELIFQMINAKGDMLHNLAGRPHTV

LTA1-YerF nucleic acid sequence

SEQ ID NO: 47

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATATGATTAGAGCCTACGA

ACAAAACCCACAACATTTTATTGAGGATCTAGAAAAAGTTAGGGTGGAACAACT

TACTGGTCATGGTTCTTCAGTTTTAGAAGAATTGGTTCAGTTAGTCAAAGATAAA

AATATAGATATTTCCATTAAATATGATCCCAGAAAAGATTCGGAGGTTTTTGCCA

ATAGAGTAATTACTGATGATATCGAATTGCTCAAGAAAATCCTAGCTTATTTTCT

ACCCGAGGATGCCATTCTTAAAGGCGGTCATTATGACAACCAACTGCAAAATGG

CATCAAGCGAGTAAAAGAGTTCCTTGAATCATCGCCGAATACACAATGGGAATT

GCGGGCGTTCATGGCAGTAATGCATTTCTCTTTAACCGCCGATCGTATCGATGAT

GATATTTTGAAAGTGATTGTTGATTCAATGAATCATCATGGTGATGCCCGTAGCA

AGTTGCGTGAAGAATTAGCTGAGCTTACCGCCGAATTAAAGATTTATTCAGTTAT

TCAAGCCGAAATTAATAAGCATCTGTCTAGTAGTGGCACCATAAATATCCATGAT

AAATCCATTAATCTCATGGATAAAAATTTATATGGTTATACAGATGAAGAGATTT

TTAAAGCCAGCGCAGAGTACAAAATTCTCGAGAAAATGCCTCAAACCACCATTC

AGGTGGATGGGAGCGAGAAAAAAATAGTCTCGATAAAGGACTTTCTTGGAAGTG

AGAATAAAAGAACCGGGGCGTTGGGTAATCTGAAAAACTCATACTCTTATAATA

AAGATAATAATGAATTATCTCACTTTGCCACCACCTGCTCGGATAAGTCCAGGCC

GCTCAACGACTTGGTTAGCCAAAAAACAACTCAGCTGTCTGATATTACATCACGT

TTTAATTCAGCTATTGAAGCACTGAACCGTTTCATTCAGAAATATGATTCAGTGA

TGCAACGTCTGCTAGATGACACGTCTGGTAAAGGATCCATGAGTGCGTTGATAAC

CCATGATCGCTCAACGCCAGTAACTGGAAGTCTACTTCCCTACGTCGAGACACCA

GCGCCCGCCCCCCTTCAGACTCAACAAGTCGCGGGAGAACTGAAGGATAAAAAT

GGTGGGGTGAGTTCTCAGGGCGTACAGCTCCCTGCACCACTAGCAGTGGTTGCCA

GCCAAGTCACTGAAGGACAACAGCAAGAAATCACTAAATTATTGGAGTCGGTCA

-continued

```
CCCGCGGCACGGCAGGATCTCAACTGATATCAAATTATGTTTCAGTGCTAACGAA

TTTTACGCTCGCTTCACCTGATACATTTGAGATTGAGTTAGGTAAGCTAGTTTCTA

ATTTAGAAGAAGTACGCAAAGACATAAAAATCGCTGATATTCAGCGTCTTCATG

AACAAAACATGAAGAAAATTGAAGAGAATCAAGAGAAAATCAAAGAAACAGAA

GAGAATGCCAAGCAAGTCAAGAAATCCGGCATGGCATCAAAGATTTTTGGCTGG

CTCAGCGCCATAGCCTCAGTGGTTATCGGTGCCATCATGGTGGCCTCAGGGGTAG

GAGCCGTTGCCGGTGCAATGATGATTGCCTCAGGCGTAATTGGGATGGCGAATA

TGGCTGTGAAACAAGCGGCGGAAGATGGCCTGATATCCCAAGAGGCAATGCAAG

TATTAGGGCCGATACTCACTGCGATTGAAGTCGCATTGACTGTAGTTTCAACCGT

AATGACCTTTGGCGGTTCGGCACTAAAATGCCTGGCTGATATTGGCGCAAAACTC

GGTGCTAACACCGCAAGTCTTGCTGCTAAAGGAGCCGAGTTTTCGGCCAAAGTTG

CCCAAATTTCGACAGGCATATCAAACACTGTCGGAATGCAGTGACTAAATTAG

GGGGCAGTTTTGGTAGTTTAACAATGAGCCATGTAATCCGTACAGGATCACAGG

CAACACAAGTCGCCGTTGGTGTGGGCAGCGGAATAACTCAGACCATCAATAATA

AAAAACAAGCTGATTTACAACATAATAACGCTGATTTGGCCTTGAACAAGGCAG

ACATGGCAGCGTTACAAAGTATTATTGACCGACTCAAAGAAGAGTTATCCCATTT

GTCAGAGTCACATCAACAAGTGATGGAACTGATTTTCCAGATGATTAATGCAAA

AGGTGACATGCTGCATAATTTGGCCGGCAGACCCCATACTGTTTAAGGTACC
```

LTA1-YerF Amino acid sequence                                                      SEQ ID NO: 48

```
MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMIRAYEQNPQHFIEDLEKVRVEQLTGH

GSSVLEELVQLVKDKNIDISIKYDPRKDSEVFANRVITDDIELLKKILAYFLPEDAILK

GGHYDNQLQNGIKRVKEFLESSPNTQWELRAFMAVMHFSLTADRIDDDILKVIVDS

MNHHGDARSKLREELAELTAELKIYSVIQAEINKHLSSSGTINIHDKSINLMDKNLYG

YTDEEIFKASAEYKILEKMPQTTIQVDGSEKKIVSIKDFLGSENKRTGALGNLKNSYS

YNKDNNELSHFATTCSDKSRPLNDLVSQKTTQLSDITSRFNSAIEALNRFIQKYDSVM

QRLLDDTSGKGSMSALITHDRSTPVTGSLLPYVETPAPAPLQTQQVAGELKDKNGGV

SSQGVQLPAPLAVVASQVTEGQQQEITKLLESVTRGTAGSQLISNYVSVLTNFTLASP

DTFEIELGKLVSNLEEVRKDIKIADIQRLHEQNMKKIEENQEKIKETEENAKQVKKSG

MASKIFGWLSAIASVVIGAIMVASGVGAVAGAMMIASGVIGMANMAVKQAAEDGL

ISQEAMQVLGPILTAIEVALTVVSTVMTFGGSALKCLADIGAKLGANTASLAAKGAE

FSAKVAQISTGISNTVGNAVTKLGGSFGSLTMSHVIRTGSQATQVAVGVGSGITQTIN

NKKQADLQHNNADLALNKADMAALQSIIDRLKEELSHLSESHQQVMELIFQMINAK

GDMLHNLAGRPHTV-
```

His-SicA chaperone for S1 nucleic sequence                                         SEQ ID NO: 49

```
ATGGGCAGCAGCCATCACCATCATCACC

```
tatgattttacaatcccgattacaccatgggactggcggcagtatgccaactgaaaaaacaatttcagaaagcatgtgacctttatgcag tagcgtttacgttacttaaaaatgattatcgccccgttttttttaccgggcagtgtcaattattaatgcgtaaggcagcaaaagccagacagt gttttgaacttgtcaatgaacgtactgaagatgagtctctgcgggcaaaagcgttggtctatctggaggcgctaaaaacggcggagaca gagcagcacagcgagcaggagaaggagtaaAAGCTT
```

His-SicA chaperone for S1 Amino acid sequence

SEQ ID NO: 50

```
MGSSHHHHHHSQDPMDYQNNVSEERVAEMIWDAVSEGATLKDVHGIPQDM

MDGLYAHAYEFYNQGRLDEAETFFRFLCIYDFYNPDYTMGLAAVCQLKKQFQKAC

DLYAVAFTLLKNDYRPVFFTGQCQLLMRKAAKARQCFELVNERTEDESLRAKALVY

LEALKTAETEQHSEQEKE*
```

SipD nucleic acid sequence

SEQ ID NO: 51

```
atgcttaatattcaaaattattccgcttctcctcatccggggatcgttgccgaacggccgcagactccctcggcgagcgagc acgtcgagactgccgtggtaccgtctaccacagaacatcgcggtacagatatcatttcattatcgcaggcggctactaaaatccaccag gcacagcagacgctgcagtcaacgccaccgatctctgaagagaataatgacgagcgcacgctggcgcgccagcagttgaccagca gcctgaatgcgctggcgaagtccggcgtgtcattatccgcagaacaaaatgagaacctgcggagcgcgttttctgcgccgacgtcgg ccttatttagcgcttcgcctatggcgcagccgagaacaaccatttctgatgctgagatttgggatatggtttcccaaaatatatcggcgata ggtgacagctatctgggcgtttatgaaaacgttgtcgcagtctataccgattttatcaggccttcagtgatattctttccaaaatgggagg ctggttattaccaggtaaggacggtaataccgttaagctagatgttacctcactcaaaaatgatttaaacagtttagtcaataaatataatca aataaacagtaataccgttttatttccagcgcagtcaggcagcggcgttaaagtagccactgaagcggaagcgagacagtggctcagt gaattgaatttaccgaatagctgcctgaaatcttatggatccggttatgtcgtcaccgttgatctgacgccattacaaaaaatggttcagga tattgatggtttaggcgcgccgggaaaagactcaaaactcgaaatggataacgccaaatatcaagcctggcagtcgggttttaaagcg caggaagaaaatatgaaaaccacattacagacgctgacgcaaaaatatagcaatgccaattcattgtacgacaacctggtaaaagtgct gagcagtacgataagtagcagcctggaaaccgccaaaagcttcctgcaagga
```

SipD amino acid sequence

SEQ ID NO: 52

```
MLNIQNYSASPHPGIVAERPQTPSASEHVETAVVPSTTEHRGTDIISLSQAATKI

HQAQQTLQSTPPISEENNDERTLARQQLTSSLNALAKSGVSLSAEQNENLRSAFSAPT

SALFSASPMAQPRTTISDAEIWDMVSQNISAIGDSYLGVYENVVAVYTDFYQAFSDIL

SKMGGWLLPGKDGNTVKLDVTSLKNDLNSLVNKYNQINSNTVLFPAQSGSGVKVA

TEAEARQWLSELNLPNSCLKSYGSGYVVTVDLTPLQKMVQDIDGLGAPGKDSKLEM

DNAKYQAWQSGFKAQEENMKTTLQTLTQKYSNANSLYDNLVKVLSSTISSSLETAK

SFLQG
```

SipB nucleic acid sequence

SEQ ID NO: 53

```
atggtaaatgacgcaagtagcattagccgtagcggatatacccaaaatccgcgcctcgctgaggcggcttttgaaggcgtt cgtaagaacacggacttttaaaagcggcggataaagcttttaaagatgtggtggcaacgaaagcgggcgacccttaaagccggaaca aagtccggcgagagcgctattaatacggtgggtctaaagccgcctacggacgccgcccgggaaaaactctccagcgaagggcaatt gacattactgcttggcaagttaatgaccctactgggcgatgtttcgctgtctcaactggagtctcgtctggcggtatggcaggcgatgatt gagtcacaaaaagagatggggattcaggtatcgaaagaattccagacggctctgggagaggctcaggaggcgacggatctctatga agccagtatcaaaaagacggataccgccaagagtgtttatgacgctgcgaccaaaaaactgacgcaggcgcaaataaattgcaatc gctgacccggctgaccccggctatgcacaagctgaagccgcggtagaacaggccggaaaagaagcgacagaggcgaaagagg ccttagataaggccacggatgcgacggttaaagcaggcacagacgccaaagcgaaagccgagaaagcggataacattctgaccaa attccagggaacggctaatgccgcctctcagaatcaggtttcccagggtgagcaggataatctgtcaaatgtcgcccgcctcactatgc tcatggccatgtttattgagattgtgggcaaaaatacggaagaaagcctgcaaaacgatcttgcgcttttcaacgccttgcaggaaggg
```

-continued

```
cgtcaggcggagatggaaaagaaatcggctgaattccaggaagagacgcgcaaagccgaggaaacgaaccgcattatgggatgta
tcgggaaagtcctcggcgcgctgctaaccattgtcagcgttgtggccgctgttttaccggtggggcgagtctggcgctggctgcggt
gggacttgcggtaatggtggccgatgaaattgtgaaggcggcgacgggagtgtcgtttattcagcaggcgctaaacccgattatgga
gcatgtgctgaagccgttaatggagctgattggcaaggcgattaccaaagcgctggaaggattaggcgtcgataagaaaacggcag
agatggccggcagcattgttggtgcgattgtcgccgctattgccatggtggcggtcattgtggtggtcgcagttgtcgggaaggcgc
ggcggcgaaactgggtaacgcgctgagcaaaatgatgggcgaaacgattaagaagttggtgcctaacgtgctgaaacagttggcgc
aaaacggcagcaaactctttacccaggggatgcaacgtattactagcggtctgggtaatgtgggtagcaagatgggcctgcaaacga
atgccttaagtaaagagctggtaggtaataccctaaataaagtggcgttgggcatggaagtcacgaataccgcagcccagtcagccg
gtggtgttgccgagggcgtatttattaaaaatgccagcgaggcgcttgctgattttatgctcgcccgttttgccatggatcagattcagca
gtggcttaaacaatccgtagaaatatttggtgaaaaccagaaggtaacggcggaactgcaaaaagccatgtcttctgcggtacagcaa
aatgcggatgcttcgcgttttattctgcgccagagtcgcgcataa
```

SipB amino acid sequence                          SEQ ID NO: 54

```
MVNDASSISRSGYTQNPRLAEAAFEGVRKNTDFLKAADKAFKDVVATKAGD
LKAGTKSGESAINTVGLKPPTDAAREKLSSEGQLTLLLGKLMTLLGDVSLSQLESRL
AVWQAMIESQKEMGIQVSKEFQTALGEAQEATDLYEASIKKTDTAKSVYDAATKKL
TQAQNKLQSLDPADPGYAQAEAAVEQAGKEATEAKEALDKATDATVKAGTDAKA
KAEKADNILTKFQGTANAASQNQVSQGEQDNLSNVARLTMLMAMFIEIVGKNTEES
LQNDLALFNALQEGRQAEMEKKSAEFQEETRKAEETNRIMGCIGKVLGALLTIVSVV
AAVFTGGASLALAAVGLAVMVADEIVKAATGVSFIQQALNPIMEHVLKPLMELIGK
AITKALEGLGVDKKTAEMAGSIVGAIVAAIAMVAVIVVVAVVGKGAAAKLGNALS
KMMGETIKKLVPNVLKQLAQNGSKLFTQGMQRITSGLGNVGSKMGLQTNALSKEL
VGNTLNKVALGMEVTNTAAQSAGGVAEGVFIKNASEALADFMLARFAMDQIQQWL
KQSVEIFGENQKVTAELQKAMSSAVQQNADASRFILRQSRA
```

S1 nucleic acid sequence                          SEQ ID NO: 55

```
atgcttaatattcaaaattattccgcttctcctcatccggggatcgttgccgaacggccgcagactccctcggcgagcgagc
acgtcgagactgccgtggtaccgtctaccacagaacatcgcggtacagatatcatttcattatcgcaggcggctactaaaatccaccag
gcacagcagacgctgcagtcaacgccaccgatctctgaagagaataatgacgagcgcacgctggcgcgccagcagttgaccagca
gcctgaatgcgctggcgaagtccggcgtgtcattatccgcagaacaaaatgagaacctgcggagcgcgttttctgcgccgacgtcgg
ccttatttagcgcttcgcctatggcgcagccgagaacaaccatttctgatgctgagatttgggatatggtttcccaaaatatatcggcgata
ggtgacagctatctgggcgtttatgaaaacgttgtcgcagtctataccgattttatcaggccttcagtgatattctttccaaaatgggagg
ctggttattaccaggtaaggacggtaataccgttaagctagatgttacctcactcaaaaatgatttaaacagtttagtcaataaatataatca
aataaacagtaataccgttttatttccagcgcagtcaggcagcggcgttaaagtagccactgaagcggaagcgagacagtggctcagt
gaattgaatttaccgaatagctgcctgaaatcttatggatccggttatgtcgtcaccgttgatctgacgccattacaaaaaatggttcagga
tattgatggtttaggcgcgccgggaaaagactcaaaactcgaaatggataacgccaaatatcaagcctggcagtcgggttttaaagcg
caggaagaaaatatgaaaaccacattacagacgctgacgcaaaaatatagcaatgccaattcattgtacgacaacctggtaaaagtgct
gagcagtacgataagtagcagcctggaaaccgccaaaagcttcctgcaaggagtcgacatggtaaatgacgcaagtagcattagcc
gtagcggatatacccaaaatccgcgcctcgctgaggcggcttttgaaggcgttcgtaagaacacggacttttaaaagcggcggataa
agcttttaaagatgtggtggcaacgaaagcgggcgaccttaaagccggaacaaagtccggcgagagcgctattaatacggtgggtct
aaagccgcctcacggacgccgcccgggaaaaactctccagcgaagggcaattgacattactgcttggcaagttaatgaccctactggg
cgatgtttcgctgtctcaactggagtctcgtctggcggtatggcaggcgatgattgagtcacaaaaagagatggggattcaggtatcga
```

-continued aagaattccagacggctctgggagaggctcaggaggcgacggatctctatgaagccagtatcaaaaagacggataccgccaagagt gtttatgacgctgcgaccaaaaaactgacgcaggcgcaaaataaattgcaatcgctggacccggctgaccccggctatgcacaagct gaagccgcggtagaacaggccggaaaagaagcgacagaggcgaaagaggccttagataaggccacggatgcgacggttaaagc aggcacagacgccaaagcgaaagccgagaaagcggataacattctgaccaaattccagggaacggctaatgccgcctctcagaatc aggtttcccagggtgagcaggataatctgtcaaatgtcgcccgcctcactatgctcatggccatgtttattgagattgtgggcaaaaatac ggaagaaagcctgcaaaacgatcttgcgcttttcaacgccttgcaggaagggcgtcaggcggagatggaaaagaaatcggctgaatt ccaggaagagacgcgcaaagccgaggaaacgaaccgcattatgggatgtatcgggaaagtcctcggcgcgctgctaaccattgtca gcgttgtggccgctgtttttaccggtggggcgagtctggcgctggctgcggtgggacttgcggtaatggtggccgatgaaattgtgaa ggcggcgacgggagtgtcgtttattcagcaggcgctaaacccgattatggagcatgtgctgaagccgttaatggagctgattggcaag gcgattaccaaagcgctggaaggattaggcgtcgataagaaaacggcagagatggccggcagcattgttggtgcgattgtcgccgct attgccatggtggcggtcattgtggtggtcgcagttgtcgggaaaggcgcggcggcgaaactgggtaacgcgctgagcaaaatgat gggcgaaacgattaagaagttggtgcctaacgtgctgaaacagttggcgcaaaacggcagcaaactctttacccaggggatgcaac gtattactagcggtctgggtaatgtgggtagcaagatgggcctgcaaacgaatgccttaagtaaagagctggtaggtaatacccctaaat aaagtggcgttgggcatggaagtcacgaataccgcagcccagtcagccggtggtgttgccgagggcgtatttattaaaaatgccagc gaggcgcttgctgattttatgctcgcccgttttgccatggatcagattcagcagtggcttaaacaatccgtagaaatatttggtgaaaacc agaaggtaacggcggaactgcaaaaagccatgtcttctgcggtacagcaaaatgcggatgcttcgcgttttattctgcgccagagtcg cgcataa S1 amino acid sequence

SEQ ID NO: 56

MLNIQNYSASPHPGIVAERPQTPSASEHVETAVVPSTTEHRGTDIISLSQAATKI

HQAQQTLQSTPPISEENNDERTLARQQLTSSLNALAKSGVSLSAEQNENLRSAFSAPT

SALFSASPMAQPRTTISDAEIWDMVSQNISAIGDSYLGVYENVVAVYTDFYQAFSDIL
SKMGGWLLPGKDGNTVKLDVTSLKNDLNSLVNKYNQINSNTVLFPAQSGSGVKVA
TEAEARQWLSELNLPNSCLKSYGSGYVVTVDLTPLQKMVQDIDGLGAPGKDSKLEM
DNAKYQAWQSGFKAQEENMKTTLQTLTQKYSNANSLYDNLVKVLSSTISSSLETAK
SFLQGVDMVNDASSISRSGYTQNPRLAEAAFEGVRKNTDFLKAADKAFKDVVATKA
GDLKAGTKSGESAINTVGLKPPTDAAREKLSSEGQLTLLLGKLMTLLGDVSLSQLES
RLAVWQAMIESQKEMGIQVSKEFQTALGEAQEATDLYEASIKKTDTAKSVYDAATK
KLTQAQNKLQSLDPADPGYAQAEAAVEQAGKEATEAKEALDKATDATVKAGTDA
KAKAEKADNILTKFQGTANAASQNQVSQGEQDNLSNVARLTMLMAMFIEIVGKNTE
ESLQNDLALFNALQEGRQAEMEKKSAEFQEETRKAEETNRIMGCIGKVLGALLTIVS
VVAAVFTGGASLALAAVGLAVMVADEIVKAATGVSFIQQALNPIMEHVLKPLMELI
GKAITKALEGLGVDKKTAEMAGSIVGAIVAAIAMVAVIVVVAVVGKGAAAKLGNA
LSKMMGETIKKLVPNVLKQLAQNGSKLFTQGMQRITSGLGNVGSKMGLQTNALSKE
LVGNTLNKVALGMEVTNTAAQSAGGVAEGVFIKNASEALADFMLARFAMDQIQQW
LKQSVEIFGENQKVTAELQKAMSSAVQQNADASRFILRQSRA

LTA1-GSAAS-S1 Nucleic acid sequence

SEQ ID NO: 57

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttggggggatcccatatagccagatttatggttggtaccgcgtaaattttggtgtgattgatgaacgtttgcatcgtaaccgtgaata

```
ccgcgatcgctactaccgtaacttgaacattgcacctgccgaggacggctatcgtttagcgggattcccacccgatcatcaggcgtgg
cgtgaggaaccgtggatccatcacgcccctcaggggtgcgggaacagtagtcgcgggtccgcggcatccatgcttaatattcaaaatt
attccgcttctcctcatccggggatcgttgccgaacggccgcagactccctcggcgagcgagcacgtcgagactgccgtggtaccgt
ctaccacagaacatcgcggtacagatatcatttcattatcgcaggcggctactaaaatccaccaggcacagcagacgctgcagtcaac
gccaccgatctctgaagagaataatgacgagcgcacgctggcgcgccagcagttgaccagcagcctgaatgcgctggcgaagtcc
ggcgtgtcattatccgcagaacaaaatgagaacctgcggagcgcgttttctgcgccgacgtcggccttatttagcgcttcgcctatggc
gcagccgagaacaaccatttctgatgctgagatttgggatatggtttcccaaaatatatcggcgataggtgacagctatctgggcgtttat
gaaaacgttgtcgcagtctataccgattttatcaggccttcagtgatattctttccaaaatgggaggctggttattaccaggtaaggacgg
taataccgttaagctagatgttacctcactcaaaaatgatttaaacagtttagtcaataaatataatcaaataaacagtaataccgttttatttc
cagcgcagtcaggcagcggcgttaaagtagccactgaagcggaagcgagacagtggctcagtgaattgaatttaccgaatagctgc
ctgaaatcttatggatccggttatgtcgtcaccgttgatctgacgccattacaaaaaatggttcaggatattgatggtttaggcgcgccgg
gaaaagactcaaaactcgaaatggataacgccaaatatcaagcctggcagtcgggttttaaagcgcaggaagaaaatatgaaaacca
cattacagacgctgacgcaaaaatatagcaatgccaattcattgtacgacaacctggtaaaagtgctgagcagtacgataagtagcagc
ctggaaaccgccaaaagcttcctgcaaggagtcgacatggtaaatgacgcaagtagcattagccgtagcggatatacccaaaatccg
cgcctcgctgaggcggcttttgaaggcgttcgtaagaacacggactttttaaaagcggcggataaagcttttaaagatgtggtggcaac
gaaagcgggcgaccttaaagccggaacaaagtccggcgagagcgctattaatacggtgggtctaaagccgcctacggacgccgcc
cgggaaaaactctccagcgaagggcaattgacattactgcttggcaagttaatgaccctactgggcgatgtttcgctgtctcaactgga
gtctcgtctggcggtatggcaggcgatgattgagtcacaaaaagagatggggattcaggtatcgaaagaattccagacggctctggg
agaggctcaggaggcgacggatctctatgaagccagtatcaaaaagacggataccgccaagagtgtttatgacgctgcgaccaaaa
aactgacgcaggcgcaaaataaattgcaatcgctggaccggctgaccccggctatgcacaagctgaagccgcggtagaacaggc
cggaaaagaagcgacagaggcgaaagaggccttagataaggccacggatgcgacggttaaagcaggcacagacgccaaagcga
aagccgagaaagcggataacattctgaccaaattccaggaacggctaatgccgcctctcagaatcaggtttcccagggtgagcagg
ataatctgtcaaatgtcgcccgcctcactatgctcatggccatgtttattgagattgtgggcaaaaatacggaagaaagcctgcaaaacg
atcttgcgcttttcaacgccttgcaggaagggcgtcaggcggagatggaaaagaaatcggctgaattccaggaagagacgcgcaaa
gccgaggaaacgaaccgcattatgggatgtatcgggaaagtcctcggcgcgctgctaaccattgtcagcgttgtggccgctgttttttac
cggtggggcgagtctggcgctggctgcggtgggacttgcggtaatggtggccgatgaaattgtgaaggcggcgacgggagtgtcgt
ttattcagcaggcgctaaacccgattatggagcatgtgctgaagccgttaatggagctgattggcaaggcgattaccaaagcgctgga
aggattaggcgtcgataagaaaacggcagagatggccggcagcattgttggtgcgattgtcgccgctattgccatggtggcggtcatt
gtggtggtcgcagttgtcgggaaaggcgcggcggcgaaactgggtaacgcgctgagcaaaatgatgggcgaaacgattaagaagt
tggtgcctaacgtgctgaaacagttggcgcaaaacggcagcaaactctttacccaggggatgcaacgtattactagcggtctgggtaa
tgtgggtagcaagatgggcctgcaaacgaatgccttaagtaaagagctggtaggtaatacccctaaataaagtggcgttgggcatggaa
gtcacgaataccgcagcccagtcagccggtggtgttgccgagggcgtatttattaaaaatgccagcgaggcgcttgctgattttatgct
cgcccgttttgccatggatcagattcagcagtggcttaaacaatccgtagaaatatttggtgaaaaccagaaggtaacggcggaactgc
aaaaagccatgtcttctgcggtacagcaaaatgcggatgcttcgcgttttattctgcgccagagtcgcgcataaCTCGAG
```

LTA1-GSAAS-S1 Amino acid sequence
SEQ ID NO: 58

MDNGDRLYRADSRPPDEIKRSGG

LTSSLNALAKSGVSLSAEQNENLRSAFSAPTSALFSASPMAQPRTTISDAEIWDMVSQ

NISAIGDSYLGVYENVVAVYTDFYQAFSDILSKMGGWLLPGKDGNTVKLDVTSLKN

DLNSLVNKYNQINSNTVLFPAQSGSGVKVATEAEARQWLSELNLPNSCLKSYGSGY

VVTVDLTPLQKMVQDIDGLGAPGKDSKLEMDNAKYQAWQSGFKAQEENMKTTLQ

TLTQKYSNANSLYDNLVKVLSSTISSSLETAKSFLQGVDMVNDASSISRSGYTQNPRL

AEAAFEGVRKNTDFLKAADKAFKDVVATKAGDLKAGTKSGESAINTVGLKPPTDA

AREKLSSEGQLTLLLGKLMTLLGDVSLSQLESRLAVWQAMIESQKEMGIQVSKEFQT

ALGEAQEATDLYEASIKKTDTAKSVYDAATKKLTQAQNKLQSLDPADPGYAQAEA

AVEQAGKEATEAKEALDKATDATVKAGTDAKAKAEKADNILTKFQGTANAASQNQ

VSQGEQDNLSNVARLTMLMAMFIEIVGKNTEESLQNDLALFNALQEGRQAEMEKKS

AEFQEETRKAEETNRIMGCIGKVLGALLTIVSVVAAVFTGGASLALAAVGLAVMVA

DEIVKAATGVSFIQQALNPIMEHVLKPLMELIGKAITKALEGLGVDKKTAEMAGSIV

GAIVAAIAMVAVIVVVAVVGKGAAAKLGNALSKMMGETIKKLVPNVLKQLAQNGS

KLFTQGMQRITSGLGNVGSKMGLQTNALSKELVGNTLNKVALGMEVTNTAAQSAG

GVAEGVFIKNASEALADFMLARFAMDQIQQWLKQSVEIFGENQKVTAELQKAMSSA

VQQNADASRFILRQSRA*

His-SscA chaperone for S2 nucleic acid sequence
SEQ ID NO: 59

ATGGGCAGCAGCCATCACCATCATCACCACAGCCAGGATCCGatgaaaaaagac ccgaccctacaacaggcacatgacacgatgcggttttccggcgtggcggctcgctgcgtatgttgttggatgacgatgttacacagcc gcttaatactctgtatcgctatgccacgcagcttatggaggtaaaagaattcgccggcgcagcgcgacttttcaattgctgacgatatat gatgcctggtcatttgactactggtttcggttaggggaatgctgccaggctcaaaaacattgggggaagcgatatacgcttatggacg cgcggcacaaattaagattgatgcgccgcaggcgccatgggccgcagcggaatgctatctcgcgtgtgataacgtctgttatgcaatc aaagcgttaaaggccgtggtgcgtatttgcggcgaggtcagtgaacatcaaattctccgacagcgtgcagaaaagatgttacagcaac tttctgacaggagctaaAAGCTT His-SscA chaperone for S2 Amino acid sequence
SEQ ID NO: 60

MGSSHHHHHHSQDPMKKDPTLQQAHDTMRFFRRGGSLRMLLDDDVTQPLN

TLYRYATQLMEVKEFAGAARLFQLLTIYDAWSFDYWFRLGECCQAQKHWGEAIYA

YGRAAQIKIDAPQAPWAAAECYLACDNVCYAIKALKAVVRICGEVSEHQILRQRAE

KMLQQLSDRS*

SseB nucleic acid sequence
SEQ ID NO: 61

Atgtcttcaggaaacatcttatggggaagtcaaaaccctattgtgtttaaaaatagcttcggcgtcagcaacgctgataccgg gagccaggatgacttatcccagcaaaatccgtttgccgaagggtatggtgttttgcttattctccttatggttattcaggctatcgcaaataa taaatttattgaagtccagaagaacgctgaacgtgccagaaatacccaggaaaagtcaaatgagatggatgaggtgattgctaaagca gccaaaggggatgctaaaaccaaagaggaggtgcctgaggatgtaattaaatacatgcgtgataatggtattctcatcgatggtatgac cattgatgattatatggctaaatatggcgatcatgggaagctggataaaggtggcctacaggcgatcaaagcggctttggataatgacg ccaaccggaataccgatcttatgagtcaggggcagataacaattcaaaaaatgtctcaggagcttaacgctgtccttacccaactgaca gggcttatcagtaagtgggggaaatttccagtatgatagcgcagaaaacgtactca SseB amino acid sequence

SEQ ID NO: 62

MSSGNILWGSQNPIVFKNSFGVSNADTGSQDDLSQQNPFAEGYGVLLILLMVI

QAIANNKFIEVQKNAERARNTQEKSNEMDEVIAKAAKGDAKTKEEVPEDVIKYMRD

NGILIDGMTIDDYMAKYGDHGKLDKGGLQAIKAALDNDANRNTDLMSQGQITIQK

MSQELNAVLTQLTGLISKWGEISSMIAQKTYS

SseC nucleic acid sequence

SEQ ID NO: 63 atgaatcgaattcacagtaatagcgacagcgccgcaggagtaaccgccttaacacatcatcacttaagcaatgtcagttgcg tttcctcgggttcgctgggaaagcgccagcatcgtgtgaattctacttttggcgatggcaacgccgcgtgtctgctatccgggaaaatta gtcttcaggaggcaagcaatgcgttgaagcaactgcttgatgccgtacccggaaatcataagcgtccatcattgcctgacttttttgcaga ccaatcccgcggttttatcaatgatgatgacgtcattaatactcaacgtctttggtaataacgctcaatcgttatgccaacagcttgagcgg gcaactgaggtgcaaaatgcattacgtaataagcaggtaaaggagtatcaggagcagatccagaaagcgatagagcaggaggataa agcgcgtaaagcgggtattttttggcgctattttttgactggattaccggcatatttgaaaccgtgattggcgccttaaaagttgtggaaggtt ttctgtccggaaatcccgcagaaatggctagcggcgtagcttatatggccgcaggttgtgcaggaatggttaaagccggagccgaaa cggcaatgatgtgcggtgctgaccacgatacctgtcaggcaattattgacgtgacaagtaagattcaatttggttgtgaagccgtcgcg ctggcactggatgttttccagattggccgtgcttttatggcgacgagaggtttatctggcgcagctgcaaaagtgcttgactccggttttg gcgaggaagtggttgagcgtatggtaggtgcaggggaagcagaaatagaggagttggctgaaaagtttggcgaagaagtgagcga aagttttccaaacaatttgagccgcttgaacgtgaaatggctatggcgaatgagatggcagaggaggctgccgagttttctcgtaacgt agaaaataatatgacgcgaagcgcgggaaaaagctttacgaaagaggggtgaaagcaatggcaaaagaagcggcaaaagaagc cctggaaaaatgtgtgcaagaaggtggaaagttcctgttaaaaaaattccgtaataaagttctcttcaatatgttcaaaaaaatcctgtatg ccttactgagggattgttcatttaaaggcttacaggctatcagatgtgcaaccgagggcgccagtcagatgaatactggcatggttaaca cagaaaaagcgaagatcgaaaagaaaatagagcaattaataactcagcaacggtttctggatttcataatgcaacaaacagaaaaccca gaaaagatagaacaaaaacgcttagaggagctttataaggggagcggtgccgcgcttagagatgtattagataccattgatcactata gtagcgttcaggcgagaatagctggctatcgcgcttaa SseC amino acid sequence

SEQ ID NO: 64

MNRIHSNSDSAAGVTALTHHHLSNVSCVSSGSLGKRQHRVNSTFGDGNAAC

LLSGKISLQEASNALKQLLDAVPGNHKRPSLPDFLQTNPAVLSMMMTSLILNVFGNN

AQSLCQQLERATEVQNALRNKQVKEYQEQIQKAIEQEDKARKAGIFGAIFDWITGIFE

TVIGALKVVEGFLSGNPAEMASGVAYMAAGCAGMVKAGAETAMMCGADHDTCQ

AIIDVTSKIQFGCEAVALALDVFQIGRAFMATRGLSGAAAKVLDSGFGEEVVERMVG

AGEAEIEELAEKFGEEVSESFSKQFEPLEREMAMANEMAEEAAEFSRNVENNMTRSA

GKSFTKEGVKAMAKEAAKEALEKCVQEGGKFLLKKFRNKVLFNMFKKILYALLRD

CSFKGLQAIRCATEGASQMNTGMVNTEKAKIEKKIEQLITQQRFLDFIMQQTENQKKI

EQKRLEELYKGSGAALRDVLDTIDHYSSVQARIAGYRA

S2 nucleic acid sequence

SEQ ID NO: 65 atgtcttcaggaaacatcttatggggaagtcaaaaccctattgtgtttaaaaatagcttcggcgtcagcaacgctgataccgg gagccaggatgacttatcccagcaaaatccgtttgccgaagggtatggtgttttgcttattctccttatggttattcaggctatcgcaaataa taaatttattgaagtccagaagaacgctgaacgtgccagaaatacccaggaaaagtcaaatgagatggatgaggtgattgctaaagca gccaaaggggatgctaaaaccaaagaggaggtgcctgaggatgtaattaaatacatgcgtgataatggtattctcatcgatggtatgac cattgatgattatatggctaaatatggcgatcatgggaagctggataaaggtggcctacaggcgatcaaagcggctttggataatgacg ccaaccggaataccgatcttatgagtcaggggcagataacaattcaaaaaatgtctcaggagcttaacgctgtccttacccaactgaca -continued

```
gggcttatcagtaagtgggggaaatttccagtatgatagcgcagaaaacgtactcaGAGCTCatgaatcgaattcacagtaata
gcgacagcgccgcaggagtaaccgccttaacacatcatcacttaagcaatgtcagttgcgtttcctcgggttcgctgggaaagcgcca
gcatcgtgtgaattctacttttggcgatggcaacgccgcgtgtctgctatccgggaaaattagtcttcaggaggcaagcaatgcgttgaa
gcaactgcttgatgccgtacccggaaatcataagcgtccatcattgcctgacttttttgcagaccaatcccgcggttttatcaatgatgatg
acgtcattaatactcaacgtctttggtaataacgctcaatcgttatgccaacagcttgagcgggcaactgaggtgcaaaatgcattacgta
ataagcaggtaaaggagtatcaggagcagatccagaaagcgatagagcaggaggataaagcgcgtaaagcgggtattttttggcgct
atttttgactggattaccggcatatttgaaaccgtgattggcgccttaaaagttgtggaaggttttctgtccggaaatcccgcagaaatggc
tagccggcgtagcttatatggccgcaggttgtgcaggaatggttaaagccggagccgaaacgcaatgatgtgcggtgctgaccacga
tacctgtcaggcaattattgacgtgacaagtaagattcaatttggttgtgaagccgtcgcgctggcactggatgttttccagattggccgt
gcttttatggcgacgagaggtttatctggcgcagctgcaaaagtgcttgactccggttttggcgaggaagtggttgagcgtatggtaggt
gcaggggaagcagaaatagaggagttggctgaaaagtttggcgaagaagtgagcgaaagttttttccaaacaatttgagccgcttgaa
cgtgaaatggctatggcgaatgagatggcagaggaggctgccgagttttctcgtaacgtagaaaataatatgacgcgaagcgcggga
aaaagctttacgaaagagggggtgaaagcaatggcaaaagaagcggcaaaagaagccctggaaaatgtgtgcaagaaggtgga
aagttcctgttaaaaaaattccgtaataaagttctcttcaatatgttcaaaaaaatcctgtatgccttactgagggattgttcatttaaaggctt
acaggctatcagatgtgcaaccgagggcgccagtcagatgaatactggcatggttaacacagaaaaagcgaagatcgaaaagaaaa
tagagcaattaataactcagcaacggtttctggatttcataatgcaacaaacagaaaaccagaaaaagatagaacaaaaacgcttagag
gagctttataaggggagcggtgccgcgcttagagatgtattagataccattgatcactatagtagcgttcaggcgagaatagctggctat
cgcgcttaa
```

S2 amino acid sequence
SEQ ID NO: 66

MSSGNILWGSQNPIVFKNSFGVSNADTGSQDDLSQQNPFAEGYGVLLILLMVI

QAIANNKFIEVQKNAERARNTQEKSNEMDEVIAKAAKGDAKTKEEVPEDVIKYMRD

NGILIDGMTIDDYMAKYGDHGKLDKGGLQAIKAALDNDANRNTDLMSQGQITIQK

MSQELNAVLTQLTGLISKWGEISSMIAQKTYSELMNRIHSNSDSAAGVTALTHHHLS

NVSCVSSGSLGKRQHRVNSTFGDGNAACLLSGKISLQEASNALKQLLDAVPGNHKR

PSLPDFLQTNPAVLSMMMTSLILNVFGNNAQSLCQQLERATEVQNALRNKQVKEYQ

EQIQKAIEQEDKARKAGIFGAIFDWITGIFETVIGALKVVEGFLSGNPAEMASGVAYM

AAGCAGMVKAGAETAMMCGADHDTCQAIIDVTSKIQFGCEAVALALDVFQIGRAF

MATRGLSGAAAKVLDSGFGEEVVERMVGAGEAEIEELAEKFGEEVSESFSKQFEPLE

REMAMANEMAEEAAEFSRNVENNMTRSAGKSFTKEGVKAMAKEAAKEALEKCVQ

EGGKFLLKKFRNKVLFNMFKKILYALLRDCSFKGLQAIRCATEGASQMNTGMVNTE

KAKIEKKIEQLITQQRFLDFIMQQTENQKKIEQKRLEELYKGSGAALRDVLDTIDHYS

SVQARIAGYRA

LTA1-GSAAS-S2 nucleic acid sequence
SEQ ID NO: 67

```
CATatggacaatggcgatcgtttataccgtgccgactcgcgtccccagatgagattaaacgt

```
aaaatccgtttgccgaagggtatggtgttttgcttattctccttatggttattcaggctatcgcaaataataaatttattgaagtccagaagaa cgctgaacgtgccagaaatacccaggaaaagtcaaatgagatggatgaggtgattgctaaagcagccaaggggatgctaaaacca aagaggaggtgcctgaggatgtaattaaatacatgcgtgataatggtattctcatcgatggtatgaccattgatgattatatggctaaatat ggcgatcatgggaagctggataaaggtggcctacaggcgatcaaagcggctttggataatgacgccaaccggaataccgatcttatg agtcaggggcagataacaattcaaaaaatgtctcaggagcttaacgctgtccttacccaactgacagggcttatcagtaagtgggggg aaatttccagtatgatagcgcagaaaacgtactcaGAGCTCatgaatcgaattcacagtaatagcgacagcgccgcaggagtaa ccgccttaacacatcatcacttaagcaatgtcagttgcgtttcctcgggttcgctgggaaagcgccagcatcgtgtgaattctacttttggc gatggcaacgccgcgtgtctgctatccgggaaaattagtcttcaggaggcaagcaatgcgttgaagcaactgcttgatgccgtacccg gaaatcataagcgtccatcattgcctgacttttttgcagaccaatcccgcggttttatcaatgatgatgacgtcattaatactcaacgtctttg gtaataacgctcaatcgttatgccaacagcttgagcgggcaactgaggtgcaaaatgcattacgtaataagcaggtaaaggagtatca ggagcagatccagaaagcgatagagcaggaggataaagcgcgtaaagcgggtattttttggcgctattttttgactggattaccggcata tttgaaaccgtgattggcgccttaaaagttgtggaaggttttctgtccggaaatcccgcagaaatggctagcggcgtagcttatatggcc gcaggttgtgcaggaatggttaaagccggagccgaaacggcaatgatgtgcggtgctgaccacgatacctgtcaggcaattattgac gtgacaagtaagattcaatttggttgtgaagccgtcgcgctggcactggatgttttccagattggccgtgcttttatggcgacgagaggtt tatctggcgcagctgcaaaagtgcttgactccggttttggcgaggaagtggttgagcgtatggtaggtgcaggggaagcagaaatag aggagttggctgaaaagtttggcgaagaagtgagcgaaagttttttccaaacaatttgagccgcttgaacgtgaaatggctatggcgaat gagatggcagaggaggctgccgagttttctcgtaacgtagaaaataatatgacgcgaagcgcgggaaaaagctttacgaaagaggg ggtgaaagcaatggcaaaagaagcggcaaaagaagccctggaaaaatgtgtgcaagaaggtggaaagttcctgttaaaaaaattcc gtaataaagttctcttcaatatgttcaaaaaaatcctgtatgccttactgagggattgttcatttaaaggcttacaggctatcagatgtgcaac cgagggcgccagtcagatgaatactggcatggttaacacagaaaagcgaagatcgaaagaaaatagagcaattaataactcagc aacggtttctggatttcataatgcaacaaacagaaaaccagaaaagatagaacaaaaacgcttagaggagctttataaggggagcgg tgccgcgcttagagatgtattagataccattgatcactatagtagcgttcaggcgagaatagctggctatcgcgcttaaCTCGAG
```

LTA1-GSAAS-S2 Amino acid sequence

SEQ ID NO: 68

MDNGDRLYRADSRPPDEIKRSGGLMPRGHN

LTA1-SseB Nucleic acid sequence

SEQ ID NO: 69

ATGGGCAGCAGCCATCATCATCATCATCACAGCAGCGGCCTGGTGCCGCG

CGGCAGCCATatggacaatggcgatcgtttataccgtgccgactcgcgtccccagatgagattaaacgtagcggtgggtta atgccacgtgggcacaatgagtattttgaccgtggaacacagatgaacattaacctttacgatcatgcccgtgggacccagaccggatt tgtccgttatgatgacgggtatgttagtacgagtttgtccttacgctccgcacaccttgcgggacaaagtattttatcaggctacagcacat attacatttatgtgatcgccactgccccaaacatgttcaatgtgaacgatgtgttgggggtttacagcccccatccatgaacaagaagt ctcggcccttgggggatcccatatagccagatttatggttggtaccgcgtaaattttggtgtgattgatgaacgtttgcatcgtaaccgtg aataccgcgatcgctactaccgtaacttgaacattgcacctgccgaggacggctatcgtttagcgggattcccacccgatcatcaggcg tggcgtgaggaaccgtggatccatcacgcccctcaggggtgcgggaacagtagtcgcgggtccgcggcatccatgtcttcaggaaa catcttatggggaagtcaaaacccctattgtgttaaaaatagcttcggcgtcagcaacgctgataccgggagccaggatgacttatccca gcaaaatccgtttgccgaagggtatggtgttttgcttattctccttatggttattcaggctatcgcaaataataaatttattgaagtccagaag aacgctgaacgtgccagaaatacccaggaaagtcaaatgagatggatgaggtgattgctaaagcagccaaaggggatgctaaaac caaagaggaggtgcctgaggatgtaattaaatacatgcgtgataatggtattctcatcgatggtatgaccattgatgattatatggctaaat atggcgatcatgggaagctggataaaggtggcctacaggcgatcaaagcggctttggataatgacgccaaccggaataccgatcttat gagtcaggggcagataacaattcaaaaaatgtctcaggagcttaacgctgtccttacccaactgacagggcttatcagtaagtgggggg gaaatttccagtatgatagcgcagaaaacgtactcataaGGATCC LTA1-SseB Amino acid sequence

SEQ ID NO: 70

MGSSHHHHHHSSGLVPRG

LMKLNQPEESQDFLDITIDMCKNKPEYKVLKDRCSIMKQSLDAVLKKEKSAKGSETQ

ASSPKNTKAKKAASNKKKAK*

CT053 nucleic acid sequence

SEQ ID NO: 73

Aaaagtgagcgtttaaaaaaattagaatcagagcttcatgatcttacccagtggatgcaacttggccttgttcctaaaaaga aatcgagagacaccaggaagaaatccgtctgctagaaagcaaaatccttgaagagaaagaacgtctacaacttctcaaagaaagcgg tgagatcaaagagtacgtaaccctcgaagaactccagctaaaaccatttacccagatggccccagcgtttcagacgttgagtttgtag aatcctcggatacagaagtggatctcgatgccggtgacacaattgagattgacctaggtgatgaggcaagagaagaaagcggaaac gaactcgactactctagtgaagacgatgaggatccttttcagcgatcgcaatcgttggcgccgaggaggcatcatagatcctgacgcga atgaatgg CT053 amino acid sequence

SEQ ID NO: 74

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEW

CopB nucleic acid sequence

SEQ ID NO: 75 atgagcttgtcatccagcagcagctcggatagttcgaatctgaaaaatgtgttatctcaggtcatcgcgtctacaccAcagg gggttcctaatgctgacaaattaaccgacaatcaggtaaaacaagtccagcagacccgtcaaaaccgtgatgatctgtccatggagag cgacgtcgcggtggcgggaacagccggaaaagatcgtgctgcgtcggcgtcccagatcgagggacaagagctgattgagcaaca gggacttgcggctgggaaagagacggcttctgctgatgctacatcattgacccagtcggcatccaaaggcgcttccagtcagcagtgt attgaggataccagtaagtccctggagcttttcttcgctttcgagcctgtcaagcgtagatgcgacacatttgcaggaaatccaatcgatc gtgtcttcagcaatgggcgccaccaacgaattgtcattgacgaacttagagacaccgggattaccaaagccgagtaccactccAcgc caggaagttatggagatcagccttgccttagcgaaggccatcactgcattgggtgagagcactcaggctgccttggaaaattttcagtc cactcagagtcagtccgcgaacatgaataagatgagtttggaatcccaaggcttgaaaatcgacaaggagcgtgaagaatttaagaaa atgcaggagattcagcaaaagagcggcacaaattcaaccatggatactgtgaataaagttatgattggcgtgacagtggcaattacagt aatctctgttgtttcagcattgtttacctgcggtttgggcttgattggcacagccgctgcgggtgccacagccgccaccgctggggcaac ggccgccgccacgaccgctacctctgtgacgaccacagtcgctacccaggtgacgatgcaagcggtggtccaagtcgttaagcagg ctattatccaagcagtaaaacgcgccatcgtccaagcgattaaacaggggattaagcaaggcattaaacaagcgatcaaacaggcag tcaaggcaagcgtgaagacacttgccaaaaatgtaggcaagattttcagcgcaggcaagaacgctgtgagtaagtccttcccAaaatt gtctaaggtgattaatacacttggttccaaatgggttactcttggcgtggggcccttacgcggtgccgcagttagtcagtggcattac ctcccttcaattgtctgatatgcaaaaagaacttgcacaaatccaaaaggaagtgggtgcacttacggcgcagagtgagatgatgaaa gcgtttacactgttctggcagcaagcttcgaaaatcgcggccaaacaaacggaatcaccttcagagacgcaacaacaggcagctaag accggcgcccagatcgctaaagcgttgtccgccatttcgggtgctttagctgctgctgctTAG CopB amino acid sequence

SEQ ID NO: 76

MSLSSSSSSDSSNLKNVLSQVIASTPQGVPNADKLTDNQVKQVQQTRQNRDD

LSMESDVAVAGTAGKDRAASASQIEGQELIEQQGLAAGKETASADATSLTQSASKG

ASSQQCIEDTSKSLELSSLSSLSSVDATHLQEIQSIVSSAMGATNELSLTNLETPGLPKP

STTPRQEVMEISLALAKAITALGESTQAALENFQSTQSQSANMNKMSLESQGLKIDK

EREEFKKMQEIQQKSGTNSTMDTVNKVMIGVTVAITVISVVSALFTCGLGLIGTAAA

GATAATAGATAAATTATSVTTTVATQVTMQAVVQVVKQAIIQAVKRAIVQAIKQGI

KQGIKQAIKQAVKASVKTLAKNVGKIFSAGKNAVSKSFPKLSKVINTLGSKWVTLGV

GALTAVPQLVSGITSLQLSDMQKELAQIQKEVGALTAQSEMMKAFTLFWQQASKIA

AKQTESPSETQQQAAKTGAQIAKALSAISGALAAAA

CT053-CopB nucleic acid sequence

SEQ ID NO: 77 aaaagtgagcgtttaaaaaaattagaatcagagcttcatgatcttacccagtggatgcaacttggccttgttcctaaaaaagaa atcgagagacaccaggaagaaatccgtctgctagaaagcaaaatccttgaagagaagaacgtctacaacttctcaaagaaagcggt gagatcaaagagtacgtaacccctcgaagaactccagctaaaaccatttacccagatggccccagcgtttcagacgttgagtttgtaga atcctcggatacagaagtggatctcgatgccggtgacacaattgagattgacctaggtgatgaggcaagagaagaaagcggaaacg aactcgactactctagtgaagacgatgaggatccttttcagcgatcgcaatcgttggcgccgaggaggcatcatagatcctgacgcgaa tgaatggGGTTCAGCTGCTTCAatgagcttgtcatccagcagcagctcggatagttcgaatctgaaaaatgtgttatctca ggtcatcgcgtctacaccAcaggggttcctaatgctgacaaattaaccgacaatcaggtaaaacaagtccagcagacccgtcaaaa ccgtgatgatctgtccatggagagcgacgtcgcggtggcgggaacagccggaaaagatcgtgctgcgtcggcgtcccagatcgag ggacaagagctgattgagcaacagggacttgcggctgggaaagagacggcttctgctgatgctacatcattgacccagtcggcatcc aaaggcgcttccagtcagcagtgtattgaggataccagtaagtccctggagctttcttcgctttcgagcctgtcaagcgtagatgcgaca catttgcaggaaatccaatcgatcgtgtcttcagcaatgggcgccaccaacgaattgtcattgacgaacttagagacaccgggattacc aaagccgagtaccactccAcgccaggaagttatggagatcagccttgccttagcgaaggccatcactgcattgggtgagagcactca ggctgccttggaaaattttcagtccactcagagtcagtccgcgaacatgaataagatgagtttggaatcccaaggcttgaaaatcgaca aggagcgtgaagaatttaagaaaatgcaggagattcagcaaaagagcggcacaaattcaaccatggatactgtgaataaagttatgat tggcgtgacagtggcaattacagtaatctctgttgtttcagcattgtttacctgcggtttgggcttgattggcacagccgctgcgggtgcc acagccgccaccgctggggcaacgccgccgccacgaccgctacctctgtgacgaccacagtcgctacccaggtgacgatgcaag cggtggtccaagtcgttaagcaggctattatccaagcagtaaaacgcgccatcgtccaagcgattaaacaggggattaagcaaggcat taaacaagcgatcaaacaggcagtcaaggcaagcgtgaagacacttgccaaaaatgtaggcaagattttcagcgcaggcaagaacg ctgtgagtaagtccttcccAaaattgtctaaggtgattaatacacttggttccaaatgggttactcttggcgtggggcccttacagcggt gccgcagttagtcagtggcattacctcccttcaattgtctgatatgcaaaaagaacttgcacaaatccaaaaggaagtgggtgcacttac ggcgcagagtgagatgatgaaagcgtttacactgttctggcagcaagcttcgaaaatcgcggccaaacaaacggaatcaccttcaga gacgcaacaacaggcagctaagaccggcgcccagatcgctaaagcgttgtccgccatttcgggtgctttagctgctgctgctTAG CT053-CopB amino acid sequence

SEQ ID NO: 78

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEWGSAASMSLSSSSSSDSSNLKN

VLSQVIASTPQGVPNADKLTDNQVKQVQQTRQNRDDLSMESDVAVAGTAGKDRAA

SASQIEGQELIEQQGLAAGKETASADATSLTQSASKGASSQQCIEDTSKSLELSSLSSL

SSVDATHLQEIQSIVSSAMGATNELSLTNLETPGLPKPSTTPRQEVMEISLALAKAITA

LGESTQAALENFQSTQSQSANMNKMSLESQGLKIDKEREEFKKMQEIQQKSGTNST

MDTVNKVMIGVTVAITVISVVSALFTCGLGLIGTAAAGATAATAGATAAATTATSVT

TTVATQVTMQAVVQVVKQAIIQAVKRAIVQAIKQGIKQGIKQAIKQAVKASVKTLA

KNVGKIFSAGKNAVSKSFPKLSKVINTLGSKWVTLGVGALTAVPQLVSGITSLQLSD

MQKELAQIQKEVGALTAQSEMMKAFTLFWQQASKIAAKQTESPSETQQQAAKTGA

QIAKALSAISGALAAAA

LTA1-CT053-CopB nucleic acid sequence     SEQ ID NO: 79

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtatttatcaggctacagcacatattac atttatgtgatcgccactgccccaaacatgttcaatgtgaacgatgtgttgggggtttacagcccccatccatatgaacaagaagtctcg gcccttgggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATatgaaaagtgagcgtttaaaaaaattag aatcagagcttcatgatcttacccagtggatgcaacttggccttgttcctaaaaaagaaatcgagagacaccaggaagaaatccgtctg ctagaaagcaaaatccttgaagagaaagaacgtctacaacttctcaaagaaagcggtgagatcaaagagtacgtaacccctcgaaga actccagctaaaaccatttacccagatggccccagcgtttcagacgttgagtttgtagaatcctcggatacagaagtggatctcgatgcc ggtgacacaattgagattgacctaggtgatgaggcaagagaagaaagcggaaacgaactcgactactctagtgaagacgatgagga tcctttcagcgatcgcaatcgttggcgccgaggaggcatcatagatcctgacgcgaatgaatggGGTTCAGCTGCTTCA atgagcttgtcatccagcagcagctcggatagttcgaatctgaaaaatgtgttatctcaggtcatcgcgtctacaccAcaggggttcct aatgctgacaaattaaccgacaatcaggtaaaacaagtccagcagacccgtcaaaaccgtgatgatctgtccatggagagcgacgtc gcggtggcgggaacagccggaaaagatcgtgctgcgtcggcgtcccagatcgagggacaagagctgattgagcaacagggactt gcggctgggaaagagacggcttctgctgatgctacatcattgacccagtcggcatccaaaggcgcttccagtcagcagtgtattgagg ataccagtaagtccctggagctttcttcgctttcgagcctgtcaagcgtagatgcgacacatttgcaggaaatccaatcgatcgtgtcttc agcaatgggcgccaccaacgaattgtcattgacgaacttagagacaccgggattaccaaagccgagtaccactccAcgccaggaa gttatggagatcagccttgccttagcgaaggccatcactgcattgggtgagagcactcaggctgccttggaaaattttcagtccactcag agtcagtccgcgaacatgaataagatgagtttggaatcccaaggcttgaaaatcgacaaggagcgtgaagaatttaagaaaatgcag gagattcagcaaaagagcggcacaaattcaaccatggatactgtgaataaagttatgattggcgtgacagtggcaattacagtaatctct gttgtttcagcattgtttacctgcggtttgggcttgattggcacagccgctgcgggtgccacagccgccaccgctggggcaacggccg ccgccacgaccgctacctctgtgacgaccacagtcgctacccaggtgacgatgcaagcggtggtccaagtcgttaagcaggctattat ccaagcagtaaaacgcgccatcgtccaagcgattaaacaggggattaagcaaggcattaaacaagcgatcaaacaggcagtcaagg caagcgtgaagacacttgccaaaaatgtaggcaagattttcagcgcaggcaagaacgctgtgagtaagtccttcccAaaattgtctaa ggtgattaatacacttggttccaaatgggttactcttggcgtgggggcccttacagcggtgccgcagttagtcagtggcattacctcccttc caattgtctgatatgcaaaaagaacttgcacaaatccaaaggaagtgggtgcacttacggcgcagagtgagatgatgaaagcgttta cactgttctggcagcaagcttcgaaaatcgcggccaaacaaacggaatcaccttcagagacgcaacaacaggcagctaagaccggc gcccagatcgctaaagcgttgtccgccatttcgggtgctttagctgctgctgctTAGCTCGAG LTA1-CT053-CopB Amino acid sequence     SEQ ID NO: 80

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDYYRNLNIAPAEDGYR

LAGFPPDHQAWREEPWIHHAPQGCGNSSRMKSERLKKLESELHDLTQWMQLGLVP

KKEIERHQEEIRLLESKILEEKERLQLLKESGEIKEYVTPRRTPAKTIYPDGPSVSDVEF

VESSDTEVDLDAGDTIEIDLGDEAREESGNELDYSSEDDEDPFSDRNRWRRGGIIDPD

-continued

ANEWGSAASMSLSSSSSSDSSNLKNVLSQVIASTPQGVPNADKLTDNQVKQVQQTR

QNRDDLSMESDVAVAGTAGKDRAASASQIEGQELIEQQGLAAGKETASADATSLTQ

SASKGASSQQCIEDTSKSLELSSLSSLSSVDATHLQEIQSIVSSAMGATNELSLTNLETP

GLPKPSTTPRQEVMEISLALAKAITALGESTQAALENFQSTQSQSANMNKMSLESQG

LKIDKEREEFKKMQEIQQKSGTNSTMDTVNKVMIGVTVAITVISVVSALFTCGLGLIG

TAAAGATAATAGATAAATTATSVTTTVATQVTMQAVVQVVKQAIIQAVKRAIVQAI

KQGIKQGIKQAIKQAVKASVKTLAKNVGKIFSAGKNAVSKSFPKLSKVINTLGSKWV

TLGVGALTAVPQLVSGITSLQLSDMQKELAQIQKEVGALTAQSEMMKAFTLFWQQA

SKIAAKQTESPSETQQQAAKTGAQIAKALSAISGALAAAA*

HisScc2 chaperone for LTA1-CT668-CopB nucleic acid sequence

SEQ ID NO: 81

ATGGGCAGCAGCCATCACCATCATCACCACAGCCAGGATCCGatgagcactccat cttctaataattctaaaaaccttcggcctcttttaataaaaaatcacgtagccgcttggccgagattgctgcacaaaaaaaagcaaaagc tgaggatttggaacaaaaatatcctgttcctacggaagaggagacaaaacaagttctcatggacatcctacaggggttaagcaacgga ttaactcttcagcaaatttaggtctctccgacgtcctccttgaagagatctacaccgtagcatataccttctactcccaagggaaatatcg ggaagctatcggtcttttccaaatcttaacagcctccaaacctcaatgctacaaatacatcttaggtcttagctcttgctatcaccagctaaa aatgtatgatgaagccgcttttggtttcttcctagctttcgatgctcaacccgaaaaccccatccctccttactacatcgccgatagcttgat gaagctaaaccaacccgaagaatctcaagacttcctcgatattacgatcgatatgtgtaagaacaagccggaatataaagttcttaaaga tcgctgcagcattatgaagcaatctttagatgccgtgctgaaaaaagagaaatctgcaaaaggctctgaaacacaagcctcctctcctaa aaacacaaaagctaaaaaagctgcttctaacaagaaaaaagcaaagtaaGCGGCCGC HisScc2 chaperone for LTA1-CT668-CopB Amino acid sequence

SEQ ID NO: 82

MGSSHHHHHHSQDPMSTPSSNNSKKPSASFNKKSRSRLAEIAAQKKAKAEDL

EQKYPVPTEEETKQVLMDILQGLSNGLTLQQILGLSDVLLEEIYTVAYTFYSQGKYRE

AIGLFQILTASKPQCYKYILGLSSCYHQLKMYDEAAFGFFLAFDAQPENPIPPYYIADS

LMKLNQPEESQDFLDITIDMCKNKPEYKVLKDRCSIMKQSLDAVLKKEKSAKGSETQ

ASSPKNTKAKKAASNKKKAK*

CT668 nucleic acid sequence

SEQ ID NO: 83

Atagatcctcttaagctttttccaaattttgatggggataaggagagtgctgcggtgaataaaccttcagcatctcctatgccc agcgaattaagtaaaaatgttgcctcattctctttagggggtggaggtgctgcgttggattcgacagtgtccacagaaaagctatcgttga tggctatgatgcaggataaaaattcgcagttgatcgatcctgagttggaggaagctctgaactctgaagagttacaagagcagatccatt tgttaaaaagtcgtttgtgggatgcacaaacgcagatgcaaatgcaagatcccgacaagttggcctctgagcatgtagatgctttagga gtcattgttgatttaatcaatggggattttcaagcgatagctgaacatacacaacagacggtcaagcagggtaatggtgacgaagaaaa atctgttacacgcaagatagtcgattgggtctcttcaggagaagaaattttgaatcgtgctttgttgtatttctccgatcgtaatggagaaag agaaacattagccgatttcttaaaagttcagtatgccgttcaaagagctacacaacgcgccgagttatttgccagtattctaggtgccacg gtgagtagtgtaaaaacgattatgacaacccagttaggt CT668 amino acid sequence

SEQ ID NO: 84

MIDPLKLFPNFDGDKESAAVNKPSASPMPSELSKNVASFSLGGGGAALDSTVS

TEKLSLMAMMQDKNSQLIDPELEEALNSEELQEQIHLLKSRLWDAQTQMQMQDPD

KLASEHVDALGVIVDLINGDFQAIAEHTQQTVKQGNGDEEKSVTRKIVDWVSSGEEI

LNRALLYFSDRNGERETLADFLKVQYAVQRATQRAELFASILGATVSSVKTIMTTQL

CT668-CopB nucleic acid sequence

SEQ ID NO: 85 atagatcctcttaagcttttttccaaattttgatggggataaggagagtgctgcggtgaataaaaccttcagcatctcctatgccca
gcgaattaagtaaaaatgttgcctcattctctttagggggtggaggtgctgcgttggattcgacagtgtccacagaaaagctatcgttgat
ggctatgatgcaggataaaaattcgcagttgatcgatcctgagttggaggaagctctgaactctgaagagttacaagagcagatccattt
gttaaaaagtcgtttgtgggatgcacaaacgcagatgcaaatgcaagatcccgacaagttggcctctgagcatgtagatgctttaggag
tcattgttgatttaatcaatggggattttcaagcgatagctgaacatacacaacagacggtcaagcagggtaatggtgacgaagaaaat
ctgttacacgcaagatagtcgattgggtctcttcaggagaagaaattttgaatcgtgctttgttgtatttctccgatcgtaatggagaaga
gaaacattagccgatttcttaaaagttcagtatgccgttcaaagagctacacaacgcgccgagttatttgccagtattctaggtgccacgg
tgagtagtgtaaaaacgattatgacaacccagttaggtGGTTCAGCTGCTTCAatgagcttgtcatccagcagcagctcg
gatagttcgaatctgaaaaatgtgttatctcaggtcatcgcgtctacaccAcagggggttcctaatgctgacaaattaaccgacaatcag
gtaaaacaagtccagcagacccgtcaaaaccgtgatgatctgtccatggagagcgacgtcgcggtggcgggaacagccggaaaag
atcgtgctgcgtcggcgtcccagatcgagggacaagagctgattgagcaacagggacttgccggctgggaaagagacggcttctgct
gatgctacatcattgacccagtcggcatccaaaggcgcttccagtcagcagtgtattgaggataccagtaagtccctggagctttcttcg
ctttcgagcctgtcaagcgtagatgcgacacatttgcaggaaatccaatcgatcgtgtcttcagcaatgggcgccaccaacgaattgtc
attgacgaacttagagacaccgggattaccaaagccgagtaccactccAcgccaggaagttatggagatcagccttgccttagcgaa
ggccatcactgcattgggtgagagcactcaggctgccttggaaaattttcagtccactcagagtcagtccgcgaacatgaataagatga
gtttggaatcccaaggcttgaaaatcgacaaggagcgtgaagaatttaagaaaatgcaggagattcagcaaaagagcggcacaaatt
caaccatggatactgtgaataaagttatgattggcgtgacagtggcaattacagtaatctctgttgtttcagcattgtttacctgcggtttgg
gcttgattggcacagccgctgcgggtgccacagccgccaccgctggggcaacggccgccgccacgaccgctacctctgtgacgac
cacagtcgctacccaggtgacgatgcaagcggtggtccaagtcgttaagcaggctattatccaagcagtaaaacgcgccatcgtcca
agcgattaaacaggggattaagcaaggcattaaacaagcgatcaaacaggcagtcaaggcaagcgtgaagacacttgccaaaaatg
taggcaagattttcagcgcaggcaagaacgctgtgagtaagtccttcccAaaattgtctaaggtgattaatacacttggttccaaatggg
ttactcttggcgtgggggccccttacagcggtgccgcagttagtcagtggcattacctcccttcaattgtctgatatgcaaaaagaacttgc
acaaatccaaaggaagtgggtgcacttacggcgcagagtgagatgatgaaagcgtttacactgttctggcagcaagcttcgaaaatc
gcggccaaacaaacggaatcaccttcagagacgcaacaacaggcagctaagaccggcgcccagatcgctaaagcgttgtccgcca
tttcgggtgctttagctgctgctgctTAG CT668-CopB amino acid sequence

SEQ ID NO: 86

MIDPLKLFPNFDGDKESAAVNKPSASPMPSELSKNVASFSLGGGGAALDSTVS
TEKLSLMAMMQDKNSQLIDPELEEALNSEELQEQIHLLKSRLWDAQTQMQMQDPD
KLASEHVDALGVIVDLINGDFQAIAEHTQQTVKQGNGDEEKSVTRKIVDWVSSGEEI
LNRALLYFSDRNGERETLADFLKVQYAVQRATQRAELFASILGATVSSVKTIMTTQL
GGSAASMSLSSSSSSDSSNLKNVLSQVIASTPQGVPNADKLTDNQVKQVQQTRQNRD
DLSMESDVAVAGTAGKDRAASASQIEGQELIEQQGLAAGKETASADATSLTQSASK
GASSQQCIEDTSKSLELSSLSSLSSVDATHLQEIQSIVSSAMGATNELSLTNLETPGLPK
PSTTPRQEVMEISLALAKAITALGESTQAALENFQSTQSQSANMNKMSLESQGLKIDK
EREEFKKMQEIQQKSGTNSTMDTVNKVMIGVTVAITVISVVSALFTCGLGLIGTAAA
GATAATAGATAAATTATSVTTTVATQVTMQAVVQVVKQAIIQAVKRAIVQAIKQGI
KQGIKQAIKQAVKASVKTLAKNVGKIFSAGKNAVSKSFPKLSKVINTLGSKWVTLGV
GALTAVPQLVSGITSLQLSDMQKELAQIQKEVGALTAQSEMMKAFTLFWQQASKIA
AKQTESPSETQQQAAKTGAQIAKALSAISGALAAAA

LTA1-CT668-CopB nucleic acid sequence

SEQ ID NO: 87

CATatggacaatggcgatcgtttataccgtgccgactcgcgtcccccagatgagattaaacgtagcggtgggttaatgcc
acgtgggcacaatgagtattttgaccgtggaacacagatgaacattaacctttacgatcatgcccgtgggacccagaccgggtttgtcc
gttatgatgacgggtatgttagtacgagtttgtcctacgctccgcacaccttgcgggacaaagtattttatcaggctacagcacatattac
atttatgtgatcgccactgccccaaacatgttcaatgtgaacgatgtgttgggggtttacagcccccatccatatgaacaagaagtctcg
gcccttgggggatcccatatagccagatttatggttggtaccgcgtaaattttggtgtgattgatgaacgtttgcatcgtaaccgtgaata
ccgcgatcgctactaccgtaacttgaacattgcacctgccgaggacggctatcgtttagcgggattcccacccgatcatcaggcgtgg
cgtgaggaaccgtggatccatcacgcccctcaggggtgcgggaacagtagtcgcCATatgatagatcctcttaagcttttttccaaatt
ttgatggggataaggagagtgctgcggtgaataaaccttcagcatctcctatgcccagcgaattaagtaaaaatgttgcctcattctcttta
ggggtggaggtgctgcgttggattcgacagtgtccacagaaaagctatcgttgatggctatgatgcaggataaaaattcgcagttgat
cgatcctgagttggaggaagctctgaactctgaagagttacaagagcagatccatttgttaaaaagtcgtttgtgggatgcacaaacgc
agatgcaaatgcaagatcccgacaagttggcctctgagcatgtagatgctttaggagtcattgttgatttaatcaatggggattttcaagc
gatagctgaacatacaacagacggtcaagcagggtaatggtgacgaagaaaaatctgttacacgcaagatagtcgattgggtctct
tcaggagaagaaattttgaatcgtgctttgttgtatttctccgatcgtaatggagaaagagaaacattagccgatttcttaaaagttcagtat
gccgttcaaagagctacacaacgcgccgagttatttgccagtattctaggtgccacggtgagtagtgtaaaaacgattatgacaaccca
gttaggtGGTTCAGCTGCTTCAatgagcttgtcatccagcagcagctcggatagttcgaatctgaaaaatgtgttatctcag
gtcatcgcgtctacaccAcaggggttcctaatgctgacaaattaaccgacaatcaggtaaaacaagtccagcagacccgtcaaaac
cgtgatgatctgtccatggagagcgacgtcgcggtggcgggaacagccggaaaagatcgtgctgcgtcggcgtcccagatcgagg
gacaagagctgattgagcaacaggacttgccggctgggaaagagacggcttctgctgatgctacatcattgacccagtcggcatcca
aaggcgcttccagtcagcagtgtattgaggataccagtaagtccctggagctttcttcgctttcgagcctgtcaagcgtagatgcgacac
atttgcaggaaatccaatcgatcgtgtcttcagcaatgggcgccaccaacgaattgtcattgacgaacttagagacaccgggattacca
aagccgagtaccactccAcgccaggaagttatggagatcagccttgccttagcgaaggccatcactgcattgggtgagagcactca
ggctgccttggaaaattttcagtccactcagagtcagtccgcgaacatgaataagatgagtttggaatcccaaggcttgaaaatcgaca
aggagcgtgaagaatttaagaaaatgcaggagattcagcaaaagagcggcacaaattcaaccatggatactgtgaataaagttatgat
tggcgtgacagtggcaattacagtaatctctgttgtttcagcattgtttacctgcggtttgggcttgattggcacagccgctgcgggtgcc
acagccgccaccgctggggcaacggccgccgccacgaccgctacctctgtgacgaccacagtcgctacccaggtgacgatgcaag
cggtggtccaagtcgttaagcaggctattatccaagcagtaaaacgcgccatcgtccaagcgattaaacaggggattaagcaaggcat
taaacaagcgatcaaacaggcagtcaaggcaagcgtgaagacacttgccaaaaatgtaggcaagattttcagcgcaggcaagaacg
ctgtgagtaagtccttcccAaaattgtctaaggtgattaatacacttggttccaaatgggttactcttggcgtgggggcccttacagcggt
gccgcagttagtcagtggcattacctcccttcaattgtctgatatgcaaaaagaacttgcacaaatccaaaaggaagtgggtgcacttac
ggcgcagagtgagatgatgaaagcgtttacactgttctggcagcaagcttcgaaaatcgcggccaaacaaacggaatcaccttcaga
gacgcaacaacaggcagctaagaccggcgcccagatcgctaaagcgttgtccgccatttcgggtgctttagctgctgctgctTAG
CTCGAG LTA1-CT668-CopB Amino acid sequence

SEQ ID NO: 88

MDNGDRLYRADSRPPDEIKRSGGLMPRGHNEYFDRGTQMNINLYDHARGTQ
TGFVRYDDGYVSTSLSLRSAHLAGQSILSGYSTYYIYVIATAPNMFNVNDVLGVYSP
HPYEQEVSALGGIPYSQIYGWYRVNFGVIDERLHRNREYRDYYRNLNIAPAEDGYR
LAGFPPDHQAWREEPWIHHAPQGCGNSSRMIDPLKLFPNFDGDKESAAVNKPSASP
MPSELSKNVASFSLGGGGAALDSTVSTEKLSLMAMMQDKNSQLIDPELEEALNSEEL
QEQIHLLKSRLWDAQTQMQMQDPDKLASEHVDALGVIVDLINGDFQAIAEHTQQTV
KQGNGDEEKSVTRKIVDWVSSGEEILNRALLYFSDRNGERETLADFLKVQYAVQRA

-continued

TQRAELFASILGATVSSVKTIMTTQLGGSAASMSLSSSSSSDSSNLKNVLSQVIASTPQ

GVPNADKLTDNQVKQVQQTRQNRDDLSMESDVAVAGTAGKDRAASASQIEGQELI

EQQGLAAGKETASADATSLTQSASKGASSQQCIEDTSKSLELSSLSSLSSVDATHLQEI

QSIVSSAMGATNELSLTNLETPGLPKPSTTPRQEVMEISLALAKAITALGESTQAALEN

FQSTQSQSANMNKMSLESQGLKIDKEREEFKKMQEIQQKSGTNSTMDTVNKVMIGV

TVAITVISVVSALFTCGLGLIGTAAAGATAATAGATAAATTATSVTTTVATQVTMQA

VVQVVKQAIIQAVKRAIVQAIKQGIKQGIKQAIKQAVKASVKTLAKNVGKIFSAGKN

AVSKSFPKLSKVINTLGSKWVTLGVGALTAVPQLVSGITSLQLSDMQKELAQIQKEV

GALTAQSEMMKAFTLFWQQASKIAAKQTESPSETQQQAAKTGAQIAKALSAISGAL

AAAA*

HisScc3 chaperone for CT053-CopB2 Nucleic acid sequence
SEQ ID NO: 89
ATGGGCAGCAGCCATCACCATCATCACCACAGCCAGGATCCGatgccaccaagc aagatccaatgtcttgaaacttttgaaagaacttatggacaccttttatctacaacatgcgtccctaatgcgtcatttagcctatctactcgata aaattgctcgctcttaccctcatatgtgtccgcttccgataatatggaagcgtactttgagaattatatccccaataaagatatccctctgg acacctatcaaaaaattttcaaactgtcctcagaagatcttgaacaagtctacaaggaaggatacaacgcctatttacaaggagactatg aggaaagttctaccgctttttactggttgattttctttaacccattttgtgtctaaattttggttttcattaggagcttcgctccatatgcgccaaaa atatcaacaagctcttcatgcttatggtgtagctgctttgctaagagaaaaagacccttatcctcattactatgcctacatctgctacaccct gctcaataatcctgaagaagctgaaaaagctcttgatcttgcttggcaaaaagtaaaaacaagctctgcctatagctcttttaaaagaaga aattttagcgatcaaatcgtacgcctaaGCGGCCGC HisScc3 chaperone for CT053-CopB2 amino acid sequence
SEQ ID NO: 90
MGSSHHHHHHSQDPMPPSKIQCLETFERTYGHLYLQHASLMRHLAYLLDKIA

RSYPHMCPLPDNMEAYFENYIPNKDIPLDTYQKIFKLSSEDLEQVYKEGYNAYLQGD

YEESSTAFYWLIFFNPFVSKFWFSLGASLHMRQKYQQALHAYGVAALLREKDPYPH

YYAYICYTLLNNPEEAEKALDLAWQKVKTSSAYSSLKEEILAIKSYA*

CopB2 nucleic acid sequence
SEQ ID NO: 91
atgagctcttggtttgcacaggcgacggacgtcgctttgagccagacccttgatctgcctgacgcttcattggcggttcaaac cgaaaaatttccAtacagctgttcaatctctaaggaatccgccccAtcatgtattcgtaaaatcttcgcccatttagcatctcagaaggaa agtgctccgctgtctttttctcgtttacaaccgactactccgaaagaacgcatcctgttttttcgggtcatcgccttcctcccaattgtcctcga ctgtccgcaccacaacctcttctccatggaatctttttagcaactcccaggcacgcaactcgacccgtaaattgtcggagaagcttcattt gagctcagagttatccgcccgtgactccactaagccttcgtcgagcgaaccggttaaaccatcggaaaatcttttgcacacccctgagc atcataaggaatccttctcaagtttgaaaaaggataacttatctcctatcatggaggagatcgactcattctctgcagagacagagtcccttt gaagagcgtttggtcacccagaaaaaggaggagacggtggcccaggagcaaaagcacccAttgctgcgtacatctactccgccat caaaggccagcggggaatcacaagattctagcgaacacagctcaaggaagatccttatagtcaacaaccgagccataaaatccaac gccgtaaagagcgtgctaagcgcgtcgtcccAattattactccgccaacggtgggtatctttagtttgagctaccttcttacaaaacagg ggatcttagcggatttcagcgcctattcggcatacaaggataatttagaaacaactcagcaagagctgaccatgttgcatcaagaacgta tcgagcaagtccaaaaGatcgtggataaaagtaagacaatgcgcttttgggattcattagcatccattgtggccacaatcattccatgga tcgaaatgggtgttgcagtaaccatcatcgcactgggaggtggaatcctttcctggtgctctcttttttgctgcgcttatcatgattgtaatttc attattggaagcattcgacgggtggcgtgcaatcgctaagcatttaccaggtaacgatcttgaaaagaagatgcgttatttaggttacgta aagttggccttaactgtgttctcgtgcttactgagttttaagcgccttgtatgtagcaaaattaggaatgagtccgcttttggaggggttgtg aagagtatcgcaccAgcattaagtggtatgctgggtttgactcaaggcgtagcactgtatttacaatcttcatcgcaaaagattcgtgcc -continued cgctgcactcagatcgacgcacgcattgaattgattaactgggaacgcgatgagtatttcttgcgtgctgaacaacttcttgattcaatgc
aaacgtccttcgaacaacttactgaaacattacagttacaacgtgaaattgatcagacatttacagacgctttgcgcTAG CopB2 amino acid sequence SEQ ID NO: 92

MSSWFAQATDVALSQTLDLPDASLAVQTEKFPYSCSISKESAPSCIRKIFAHLA
SQKESAPLSFSRLQPTTPKERILFFGSSPSSQLSSTVRTTTSSPWNLFSNSQARNSTRKL
SEKLHLSSELSARDSTKPSSSEPVKPSENLLHTPEHHKESFSSLKKDNLSPIMEEIDSFS
AETESLEERLVTQKKEETVAQEQKHPLLRTSTPPSKASGESQDSSEHSSKEDPYSQQP
SHKIQRRKERAKRVVPIITPPTVGIFSLSYLLTKQGILADFSAYSAYKDNLETTQQELT
MLHQERIEQVQKIVDKSKTMRFWDSLASIVATIIPWIEMGVAVTIIALGGGILSWCSLF
AALIMIVISLLEAFDGWRAIAKHLPGNDLEKKMRYLGYVKLALTVFSCLLSLSALYV
AKLGMSPLLEGVVKSIAPALSGMLGLTQGVALYLQSSSQKIRARCTQIDARIELINWE
RDEYFLRAEQLLDSMQTSFEQLTETLQLQREIDQTFTDALR

CT053-CopB2 nucleic acid sequence SEQ ID NO: 93 aaaagtgagcgtttaaaaaaattagaatcagagcttcatgatcttacccagtggatgcaacttggccttgttcctaaaaaagaa
atcgagagacaccaggaagaaatccgtctgctagaaagcaaaatccttgaagagaaagaacgtctacaacttctcaaagaaagcggt
gagatcaaagagtacgtaacccctcgaagaactccagctaaaaccatttacccagatggccccagcgtttcagacgttgagtttgtaga
atcctcggatacagaagtggatctcgatgccggtgacacaattgagattgacctaggtgatgaggcaagagaagaaagcggaaacg
aactcgactactctagtgaagacgatgaggatccttttcagcgatcgcaatcgttggcgccgaggaggcatcatagatcctgacgcgaa
tgaatggGGTTCAGCTGCTTCAatgagctcttggtttgcacaggcgacgacgtcgctttgagccagaccttgatctgc
ctgacgcttcattggcggttcaaaccgaaaaatttccAtacagctgttcaatctctaaggaatccgccccAtcatgtattcgtaaaatctt
cgcccatttagcatctcagaaggaaagtgctccgctgtcttttctcgtttacaaccgactactccgaaagaacgcatcctgttttcgggt
catcgccttcctcccaattgtcctcgactgtccgcaccacaacctcttctccatggaatcttttagcaactcccaggcacgcaactcgac
ccgtaaattgtcggagaagcttcatttgagctcagagttatccgcccgtgactccactaagccttcgtcgagcgaaccggttaaaccatc
ggaaaatctttttgcacacccctgagcatcataaggaatccttctcaagtttgaaaaaggataacttatctcctatcatggaggagatcgac
tcattctctgcagagacagagtcccttgaagagcgtttggtcacccagaaaaaggaggagacggtggcccaggagcaaaagcaccc
Attgctgcgtacatctactccgccatcaaaggccagcggggaatcacaagattctagcgaacacagctcaaaggaagatccttatagt
caacaaccgagccataaaatccaacgccgtaaagagcgtgctaagcgcgtcgtcccAattattactccgccaacggtgggtatcttta
gtttgagctaccttcttacaaaacaggggatcttagcggatttcagcgcctattcggcatacaaggataatttagaaacaactcagcaag
agctgaccatgttgcatcaagaacgtatcgagcaagtccaaaaaGatcgtggataaaagtaagacaatgcgcttttgggattcattagca
tccattgtggccacaatcattccatggatcgaaatgggtgttgcagtaaccatcatcgcactgggaggtggaatcctttcctggtgctctc
tttttgctgcgcttatcatgattgtaatttcattattggaagcattcgacgggtggcgtgcaatcgctaagcatttaccaggtaacgatcttga
aaagaagatgcgttatttaggttacgtaaagttggccttaactgtgttctcgtgcttactgagtttaagcgccttgtatgtagcaaaattagg
aatgagtccgcttttggaggggggttgtgaagagtatcgcaccAgcattaagtggtatgctgggtttgactcaaggcgtagcactgtatttt
acaatcttcatcgcaaaagattcgtgcccgctgcactcagatcgacgcacgcattgaattgattaactgggaacgcgatgagtatttcttg
cgtgctgaacaacttcttgattcaatgcaaacgtccttcgaacaacttactgaaacattacagttacaacgtgaaattgatcagacatttac
agacgctttgcgcTAG CT053-CopB2 amino acid sequence SEQ ID NO: 94

MKSERLKKLESELHDLTQWMQLGLVPKKEIERHQEEIRLLESKILEEKERLQL
LKESGEIKEYVTPRRTPAKTIYPDGPSVSDVEFVESSDTEVDLDAGDTIEIDLGDEARE
ESGNELDYSSEDDEDPFSDRNRWRRGGIIDPDANEWGSAASMSSWFAQATDVALSQ
TLDLPDASLAVQTEKFPYSCSISKESAPSCIRKIFAHLASQKESAPLSFSRLQPTTPKERI

LFFGSSPSSQLSSTVRTTTSSPWNLFSNSQARNSTRKLSEKLHLSSELSARDSTKPSSSE

PVKPSENLLHTPEHHKESFSSLKKDNLSPIMEEIDSFSAETESLEERLVTQKKEETVAQ

EQKHPLLRTSTPPSKASGESQDSSEHSSKEDPYSQQPSHKIQRRKERAKRVVPIITPPT

VGIFSLSYLLTKQGILADFSAYSAYKDNLETTQQELTMLHQERIEQVQKIVDKSKTM

RFWDSLASIVATIIPWIEMGVAVTIIALGGGILSWCSLFAALIMIVISLLEAFDGWRAIA

KHLPGNDLEKKMRYLGYVKLALTVFSCLLSLSALYVAKLGMSPLLEGVVKSIAPALS

GMLGLTQGVALYLQSSSQKIRARCTQIDARIELINWERDEYFLRAEQLLDSMQTSFE

QLTETLQLQREIDQTFTDALR

LTA1-CT053-CopB2 nucleic acid sequence

SEQ ID NO: 95

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATatgaaaagtgagcgtttaaaaaaattag aatcagagcttcatgatcttacccagtggatgcaacttggccttgttcctaaaaagaaatcgagagacaccaggaagaaatccgtctg ctagaaagcaaaatccttgaagagaaagaacgtctacaacttctcaaagaaagcggtgagatcaaagagtacgtaacccctcgaaga actccagctaaaaccatttacccagatggccccagcgtttcagacgttgagtttgtagaatcctcggatacagaagtggatctcgatgcc ggtgacacaattgagattgacctaggtgatgaggcaagagaagaaagcggaaacgaactcgactactctagtgaagacgatgagga tcctttcagcgatcgcaatcgttggcgccgaggaggcatcatagatcctgacgcgaatgaatggGGTTCAGCTGCTTCA atgagctcttggtttgcacaggcgacggacgtcgctttgagccagacccttgatctgcctgacgcttcattggcggttcaaaccgaaaa atttccAtacagctgttcaatctctaaggaatccgccccAtcatgtattcgtaaaatcttcgcccatttagcatctcagaaggaaagtgct ccgctgtctttttctcgtttacaaccgactactccgaaagaacgcatcctgtttttcgggtcatcgccttcctcccaattgtcctcgactgtcc gcaccacaacctcttctccatggaatctttttagcaactcccaggcacgcaactcgacccgtaaattgtcggagaagcttcatttgagctc agagttatccgcccgtgactccactaagccttcgtcgagcgaaccggttaaaccatcggaaaatcttttgcacacccctgagcatcataa ggaatccttctcaagtttgaaaaaggataacttatctcctatcatggaggagatcgactcattctctgcagagacagagtcccttgaagag cgtttggtcacccagaaaaaggaggagacggtggcccaggagcaaaagcacccAttgctgcgtacatctactccgccatcaaaggc cagcggggaatcacaagattctagcgaacacagctcaaaggaagatccttatagtcaacaaccgagccataaaatccaacgccgtaa agagcgtgctaagcgcgtcgtcccAattattactccgccaacggtgggtatctttagtttgagctaccttcttacaaaacaggggatctta gcggatttcagcgcctattcggcatacaaggataatttagaaacaactcagcaagagctgaccatgttgcatcaagaacgtatcgagca agtccaaaaGatcgtggataaaagtaagacaatgcgcttttgggattcattagcatccattgtggccacaatcattccatggatcgaaat gggtgttgcagtaaccatcatcgcactgggaggtggaatcctttcctggtgctctctttttgctgcgcttatcatgattgtaatttcattattgg aagcattcgacgggtggcgtgcaatcgctaagcatttaccaggtaacgatcttgaaaagaagatgcgttatttaggttacgtaaagttgg ccttaactgtgttctcgtgcttactgagtttaagcgccttgtatgtagcaaaattaggaatgagtccgcttttggagggggttgtgaagagt atcgcaccAgcattaagtggtatgctgggtttgactcaaggcgtagcactgtatttacaatcttcatcgcaaaagattcgtgcccgctgc actcagatcgacgcacgcattgaattgattaactgggaacgcgatgagtatttcttgcgtgctgaacaacttcttgattcaatgcaaacgt ccttcgaacaacttactgaaacattacagttacaacgtgaaattgatcagacatttacagacgctttgcgcTAGCTCGAG -continued

LTA1-CT053-CopB2 Amino acid sequence

SEQ ID NO: 96

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMKSERLKKLESELHDLTQWMQLGLVP

KKEIERHQEEIRLLESKILEEKERLQLLKESGEIKEYVTPRRTPAKTIYPDGPSVSDVEF

VESSDTEVDLDAGDTIEIDLGDEAREESGNELDYSSEDDEDPFSDRNRWRRGGIIDPD

ANEWGSAASMSSWFAQATDVALSQTLDLPDASLAVQTEKFPYSCSISKESAPSCIRKI

FAHLASQKESAPLSFSRLQPTTPKERILFFGSSPSSQLSSTVRTTTSSPWNLFSNSQARN

STRKLSEKLHLSSELSARDSTKPSSSEPVKPSENLLHTPEHHKESFSSLKKDNLSPIMEE

IDSFSAETESLEERLVTQKKEETVAQEQKHPLLRTSTPPSKASGESQDSSEHSSKEDPY

SQQPSHKIQRRKERAKRVVPIITPPTVGIFSLSYLLTKQGILADFSAYSAYKDNLETTQ

QELTMLHQERIEQVQKIVDKSKTMRFWDSLASIVATIIPWIEMGVAVTIIALGGGILS

WCSLFAALIMIVISLLEAFDGWRAIAKHLPGNDLEKKMRYLGYVKLALTVFSCLLSL

SALYVAKLGMSPLLEGVVKSIAPALSGMLGLTQGVALYLQSSSQKIRARCTQIDARIE

LINWERDEYFLRAEQLLDSMQTSFEQLTETLQLQREIDQTFTDALR*

HisScc3 chaperone for CT668-CopB2 nucleic acid sequence

SEQ ID NO: 97

ATGGGCAGCAGCCATCACCATCATCACCACAGCCAGGATCCGatgccaccaagc aagatccaatgtcttgaaacttttgaaagaacttatggacacctttatctacaacatgcgtccctaatgcgtcatttagcctatctactcgata aaattgctcgctcttaccctcatatgtgtccgcttcccgataatatggaagcgtactttgagaattatatcccaataaagatatccctctgg acacctatcaaaaaattttcaaactgtcctcagaagatcttgaacaagtctacaaggaaggatacaacgcctatttacaaggagactatg aggaaagttctaccgcttttttactggttgattttctttaacccatttgtgtctaaattttggttttcattaggagcttcgctccatatgcgccaaaa atatcaacaagctcttcatgcttatggtgtagctgctttgctaagagaaaaagacccttatcctcattactatgcctacatctgctacaccct gctcaataatcctgaagaagctgaaaaagctcttgatcttgcttggcaaaaagtaaaaacaagctctgcctatagctcttaaaagaaga aattttagcgatcaaatcgtacgcctaaGCGGCCGC HisScc3 chaperone for CT668-CopB2 Amino acid sequence

SEQ ID NO: 98

MGSSHHHHHHSQDPMPPSKIQCLETFERTYGHLYLQHASLMRHLAYLLDKIA

RSYPHMCPLPDNMEAYFENYIPNKDIPLDTYQKIFKLSSEDLEQVYKEGYNAYLQGD

YEESSTAFYWLIFFNPFVSKFWFSLGASLHMRQKYQQALHAYGVAALLREKDPYPH

YYAYICYTLLNNPEEAEKALDLAWQKVKTSSAYSSLKEEILAIKSYA*

CT668-CopB2 nucleic acid sequence

SEQ ID NO: 99 aaaagtgagcgtttaaaaaaattagaatcagagcttcatgatcttacccagtggatgcaacttggccttgttcctaaaaaagaa atcgagagacaccaggaagaaatccgtctgctagaaagcaaaatccttgaagagaagaacgtctacaacttctcaaagaaagcggt gagatcaaagagtacgtaaccctcgaagaactccagctaaaaccatttacccagatggccccagcgtttcagacgttgagtttgtaga atcctcggatacagaagtggatctcgatgccggtgacacaattgagattgacctaggtgatgaggcaagagaagaaagcggaaacg aactcgactactctagtgaagacgatgaggatccttttcagcgatcgcaatcgttggcgccgaggaggcatcatagatcctgacgcgaa tgaatggGGTTCAGCTGCTTCAatgagctcttggttttgcacaggcgacggacgtcgctttgagccagaccccttgatctgc ctgacgcttcattggcggttcaaaccgaaaaatttccAtacagctgttcaatctctaaggaatccgccccAtcatgtattcgtaaaatcttt cgcccatttagcatctcagaaggaaagtgctccgctgtctttttctcgtttacaaccgactactccgaaagaacgcatcctgttttcgggt catcgccttcctcccaattgtcctcgactgtccgcaccacaacctcttctccatggaatctttttagcaactcccaggcacgcaactcgac -continued ccgtaaattgtcggagaagcttcatttgagctcagagttatccgcccgtgactccactaagccttcgtcgagcgaaccggttaaaccatc ggaaaatcttttgcacaccccctgagcatcataaggaatccttctcaagtttgaaaaaggataacttatctcctatcatggaggagatcgac tcattctctgcagagacagagtcccttgaagagcgtttggtcacccagaaaaaggaggagacggtggcccaggagcaaaagcaccc Attgctgcgtacatctactccgccatcaaaggccagcggggaatcacaagattctagcgaacacagctcaaaggaagatccttatagt caacaaccgagccataaaatccaacgccgtaaagagcgtgctaagcgcgtcgtcccAattattactccgccaacggtgggtatcttta gtttgagctaccttcttacaaaacaggggatcttagcggatttcagcgcctattcggcatacaaggataatttagaaacaactcagcaag agctgaccatgttgcatcaagaacgtatcgagcaagtccaaaaGatcgtggataaaagtaagacaatgcgcttttgggattcattagca tccattgtggccacaatcattccatggatcgaaatgggtgttgcagtaaccatcatcgcactgggaggtggaatcctttcctggtgctctc tttttgctgcgcttatcatgattgtaatttcattattggaagcattcgacgggtggcgtgcaatcgctaagcatttaccaggtaacgatcttga aaagaagatgcgttatttaggttacgtaaagttggccttaactgtgttctcgtgcttactgagtttaagcgccttgtatgtagcaaaattagg aatgagtccgcttttggaggggttgtgaagagtatcgcaccAgcattaagtggtatgctgggtttgactcaaggcgtagcactgtattt acaatcttcatcgcaaaagattcgtgccgctgcactcagatcgacgcacgcattgaattgattaactgggaacgcgatgagtatttcttg cgtgctgaacaacttcttgattcaatgcaaacgtccttcgaacaacttactgaaacattacagttacaacgtgaaattgatcagacatttac agacgctttgcgcTAG CT668-CopB2 amino acid sequence SEQ ID NO: 100

MKSERLKKLESELHDLTQWMQLGLVPKKEIERHQEEIRLLESKILEEKERLQL

LKESGEIKEYVTPRRTPAKTIYPDGPSVSDVEFVESSDTEVDLDAGDTIEIDLGDEARE

ESGNELDYSSEDDEDPFSDRNRWRRGGIIDPDANEWGSAASMSSWFAQATDVALSQ

TLDLPDASLAVQTEKFPYSCSISKESAPSCIRKIFAHLASQKESAPLSFSRLQPTTPKERI

LFFGSSPSSQLSSTVRTTTSSPWNLFSNSQARNSTRKLSEKLHLSSELSARDSTKPSSSE

PVKPSENLLHTPEHHKESFSSLKKDNLSPIMEEIDSFSAETESLEERLVTQKKEETVAQ

EQKHPLLRTSTPPSKASGESQDSSEHSSKEDPYSQQPSHKIQRRKERAKRVVPIITPPT

VGIFSLSYLLTKQGILADFSAYSAYKDNLETTQQELTMLHQERIEQVQKIVDKSKTM

RFWDSLASIVATIIPWIEMGVAVTIIALGGGILSWCSLFAALIMIVISLLEAFDGWRAIA

KHLPGNDLEKKMRYLGYVKLALTVFSCLLSLSALYVAKLGMSPLLEGVVKSIAPALS

GMLGLTQGVALYLQSSSQKIRARCTQIDARIELINWERDEYFLRAEQLLDSMQTSFE

QLTETLQLQREIDQTFTDALR

LTA1-CT668-CopB2 nucleic acid sequence SEQ ID NO: 101

CATatggacaatggcgatcgtttataccgtgccgactcgcgtcccccagatgagattaaacgtagcggtgggttaatgcc acgtgggcacaatgagtattttgaccgtggaacacagatgaacattaacctttacgatcatgcccgtgggacccagaccgggtttgtcc gttatgatgacgggtatgttagtacgagtttgtccttacgctccgcacaccttgcgggacaaagtattttatcaggctacagcacatattac atttatgtgatcgccactgccccaaacatgttcaatgtgaacgatgtgttgggggtttacagcccccatccatatgaacaagaagtctcg gcccttgggggggatcccatatagccagatttatggttggtaccgcgtaaattttggtgtgattgatgaacgtttgcatcgtaaccgtgaata ccgcgatcgctactaccgtaacttgaacattgcacctgccgaggacggctatcgtttagcgggattcccacccgatcatcaggcgtgg cgtgaggaaccgtggatccatcacgcccctcaggggtgcgggaacagtagtcgcCATatgaaaagtgagcgtttaaaaaaattag aatcagagcttcatgatcttacccagtggatgcaacttggccttgttcctaaaaaagaaatcgagagacaccaggaagaaatccgtctg ctagaaagcaaaatccttgaagagaaagaacgtctacaacttctcaaagaaagcggtgagatcaaagagtacgtaacccctcgaaga actccagctaaaaccatttacccagatggccccagcgtttcagacgttgagtttgtagaatcctcggatacagaagtggatctcgatgcc ggtgacacaattgagattgacctaggtgatgaggcaagagaagaaagcggaaacgaactcgactactctagtgaagacgatgagga tcctttcagcgatcgcaatcgttggcgccgaggaggcatcatagatcctgacgcgaatgaatggGGTTCAGCTGCTTCA atgagctcttggtttgcacaggcgacggacgtcgctttgagccagacccttgatctgcctgacgcttcattggcggttcaaaccgaaaa -continued atttccAtacagctgttcaatctctaaggaatccgccccAtcatgtattcgtaaaatcttcgcccatttagcatctcagaaggaaagtgct ccgctgtctttttctcgtttacaaccgactactccgaaagaacgcatcctgttttttcgggtcatcgccttcctcccaattgtcctcgactgtcc gcaccacaacctcttctccatggaatcttttagcaactcccaggcacgcaactcgacccgtaaattgtcggagaagcttcatttgagctc agagttatccgcccgtgactccactaagccttcgtcgagcgaaccggttaaaccatcggaaaatcttttgcacacccctgagcatcataa ggaatccttctcaagtttgaaaaggataacttatctcctatcatggaggagatcgactcattctctgcagagacagagtcccttgaagag cgtttggtcacccagaaaaggaggagacggtggcccaggagcaaaagcacccAttgctgcgtacatctactccgccatcaaaggc cagcggggaatcacaagattctagcgaacacagctcaaaggaagatccttatagtcaacaaccgagccataaaatccaacgccgtaa agagcgtgctaagcgcgtcgtcccAattattactccgccaacggtgggtatctttagtttgagctaccttcttacaaaacaggggatctta gcggatttcagcgcctattcggcatacaaggataatttagaaacaactcagcaagagctgaccatgttgcatcaagaacgtatcgagca agtccaaaaGatcgtggataaaagtaagacaatgcgcttttgggattcattagcatccattgtggccacaatcattccatggatcgaaat gggtgttgcagtaaccatcatcgcactggaggtggaatcctttcctggtgctctcttttttgctgcgcttatcatgattgtaatttcattattgg aagcattcgacgggtggcgtgcaatcgctaagcatttaccaggtaacgatcttgaaaagaagatgcgttatttaggttacgtaaagttgg ccttaactgtgttctcgtgcttactgagtttaagcgccttgtatgtagcaaaattaggaatgagtccgcttttggagggggttgtgaagagt atcgcaccAgcattaagtggtatgctgggtttgactcaaggcgtagcactgtatttacaatcttcatcgcaaaagattcgtgcccgctgc actcagatcgacgcacgcattgaattgattaactgggaacgcgatgagtatttcttgcgtgctgaacaacttcttgattcaatgcaaacgt ccttcgaacaacttactgaaacattacagttacaacgtgaaattgatcagacatttacagacgctttgcgcTAGCTCGAG LTA1-CT668-CopB2Amino acid sequence

SEQ ID NO: 102

MDNGDRLYRADSRPPDEIKRSGGLMPRGHNEYFDRGTQMNINLYDHARGTQ

TGFVRYDDGYVSTSLSLRSAHLAGQSILSGYSTYYIYVIATAPNMFNVNDVLGVYSP

HPYEQEVSALGGIPYSQIYGWYRVNFGVIDERLHRNREYRDRYYRNLNIAPAEDGYR

LAGFPPDHQAWREEPWIHHAPQGCGNSSRMKSERLKKLESELHDLTQWMQLGLVP

KKEIERHQEEIRLLESKILEEKERLQLLKESGEIKEYVTPRRTPAKTIYPDGPSVSDVEF

VESSDTEVDLDAGDTIEIDLGDEAREESGNELDYSSEDDEDPFSDRNRWRRGGIIDPD

ANEWGSAASMSSWFAQATDVALSQTLDLPDASLAVQTEKFPYSCSISKESAPSCIRKI

FAHLASQKESAPLSFSRLQPTTPKERILFFGSSPSSQLSSTVRTTTSSPWNLFSNSQARN

STRKLSEKLHLSSELSARDSTKPSSSEPVKPSENLLHTPEHHKESFSSLKKDNLSPIMEE

IDSFSAETESLEERLVTQKKEETVAQEQKHPLLRTSTPPSKASGESQDSSEHSSKEDPY

SQQPSHKIQRRKERAKRVVPIITPPTVGIFSLSYLLTKQGILADFSAYSAYKDNLETTQ

QELTMLHQERIEQVQKIVDKSKTMRFWDSLASIVATIIPWIEMGVAVTIIALGGGILS

WCSLFAALIMIVISLLEAFDGWRAIAKHLPGNDLEKKMRYLGYVKLALTVFSCLLSL

SALYVAKLGMSPLLEGVVKSIAPALSGMLGLTQGVALYLQSSSQKIRARCTQIDARIE

LINWERDEYFLRAEQLLDSMQTSFEQLTETLQLQREIDQTFTDALR dmLT eltA (LTa) nucleic acid sequence

SEQ ID NO: 113 atgattgaca tcatgttgca tataggttag ataaaacaag tggttatctt ccggattgt cttcttgtat gatatataag ttttcctcga tgaaaaatat aactttcatt ttttttattt tattagcatc gccattatat gcaaatggcg acagattata ccgtgctgac tctagacccc cagatgaaat aaaacgtttc cggagtctta tgcccagagg taatgagtac ttcgatagag aactcaaat gaatattaat ctttatgatc acgcgagagg aacacaaacc ggctttgtca gatatgatga cggatatgtt tccacttctc ttagtttgag aagtgctcac ttagcaggac agtatatatt atcaggatat tcacttacta tatatatcgt tatagcaaat atgtttaatg ttaatgatgt aattagcgta tacagccctc acccatatga acaggaggtt tctgcgttag gtggaatacc atattctcag atatatggat ggtatcgtgt taattttggt gtgattgatg aacgattaca tcgtaacagg gaatatagag accggtatta cagaaatctg

```
                       -continued
aatatagctc cggcagagga tggttacaga ttagcaggtt tcccaccgga tcaccaagct tggagagaag aaccctggat tcatcatgca ccacaaggtt gtggagattc atcaGgaaca atcacaggtg atacttgtaa tgaggagacc cagaatctga gcacaatata tGCcagggaa tatcaatcaa aagttaagag gcagatattt tcagactatc agtcagaggt tgacatatat aacagaattc gggatgaatt atgaataaag taaaatgt eltB (LTb) nucleic acid sequence
                                                                                                SEQ ID NO: 114
gttgacatat ataacagaat tcgggatgaa ttatgaataa agtaaaatgt tatgttttat ttacgcgtt actatcctct ctatatgcac acggagctcc ccagactatt acagaactat gttcggaata tcgcaacaca caaatatata cgataaatga caagatacta tcatatacgg aatcgatggc aggcaaaaga gaaatggtta tcattacatt taagagcggc gaaacatttc aggtcgaagt cccgggcagt caacatatag actcccagaa aaaagccatt gaaaggatga aggacacatt aagaatcaca tatctgaccg agaccaaaat tgataaatta tgtgtatgga ataataaaac ccccaattca attgcggcaa tcagtatgaa aaactagttt gctttaaaag catgtctaat gctaggaacc tatataacaa ctactgtact tatactaatg agccttatgc tgcatttgaa aaggcggtag aggaggcaat accgatcctt aaactgtaac actataacag cttccactac agggagctgt tatagcacac agaaaaaact aagctaggct ggaggggcaa gctt
```

---

SEQUENCE LISTING

```
Sequence total quantity: 118
SEQ ID NO: 1           moltype = DNA   length = 1833
FEATURE                Location/Qualifiers
misc_feature           1..1833
                       note = synthetic construct
source                 1..1833
                       mol_type = other DNA
                       organism = synthetic construct
SEQUENCE: 1
catatgacca ttgatctcgg agtttcactc acgtcgcagg ccggcggcct gcaaggcatc  60
gacctcaaga gcatggatat ccagactctc atggtgtatg tgcagggtcg tcgcgccgaa  120
ctcctcacgg ctcaaatgca gaccaggcc gaagtggtgc agaaggccaa tgaacgcatg  180
gcgcagctca acgaggtcct gtccgcgctg tcccgggcca aggccgagtt tccgcccaat  240
ccgaagccgg gcgacaccat cccgggctgg gacaaccaga aggtcagccg gatcgaggtt  300
cctctcaatg atgcgctgcg cgctgccggc ctgacgggca tgttcgaagc gcgcgatggc  360
caagtgaccg ccccgcggcg ccggggtacg caggtcgtga acggcacggg cgtcatggcc  420
ggttccacga cctataagga actcgaaagt gcctacacca ccgtaaaggg gatgctggat  480
acggcgtcca atacgcaaca gatggacatg atcaggctgc aggccgccag caacaagcgc  540
aacgaggctt cgaggtcat gaccaacacc gagaagcggc gcagcgacct gaacagttcc  600
atcaccaaca acatgcgcaa gcttatgacc gtcatgagta cgaccatatc cacagcccg  660
agcggcgccg cgcttgcgcc gtctcgcata gatatgcggg caccggagcc cgggagtgcc  720
ggcgaaggcg ccggcatcct ggccgcggtg acgacgctgg ctctggccgg gggccggccg  780
gcttttccag cgtcaccgtc gctgcgcacc gcgcccgtcc tggatccgcc agtgcgcgat  840
ctcagccccg ccgacttggc cgacctgctg cgcgtcttgc gatccaggcc ggtggacggg  900
cagttggcca cggcgcgcga gaacctgcag gacgcgcaag tcaaggcgaa gcagaacacc  960
caggcccagc tcgacaagct ggacgcatgg tttcggaagg ccgaagaggc cgagagcaag  1020
ggatggctga gcaaggtgtt cggctggatc ggcaaggtgc tggcggtcgt ggcatcggcc  1080
ctggcggtgg gcttttgccgc cgtcgccagc gtggccaccg gcgcgccggc cacacccatg  1140
ctgctgctca gcggcatggc actggtcagc gccgtgacat cgctggccga ccagatatcg  1200
caagaggcgg gaggcccgcc tatcagcctg gcgggtttc tctccgggct ggccggacgt  1260
ctgctgacag cgttggggggt ggatcagtcg caggccgacc aaaattgccaa gatcgtcgcc  1320
ggcctggccg tgcccgtcgt cttgctgatc gaacccaga tgctggcga aatgcgcaa  1380
ggcgtggcca ggctgctgg cgccagcgat gccaccgcgg ggtacatagc catggcgatg  1440
tccatcgtgg cggcgatcgc ggtcgccgcg atcaatgccg ccgtacagc cggcgcgggt  1500
agcgcttcgg cgatcaaggg ggcctgggat cgggccgccg cggtagccac ccaggtcctt  1560
caaggggggta cggcagtggc gcaaggcggc gtcggcgtgt cgatggcagt cgatcgcaaa  1620
caggccgatc tcctggtcgc cgacaaggcg gatctggcgg cgagcctgac aaaactgcgg  1680
gcggccatga gcgtgaggc ggacgatatc aagaagatcc tggctcaatt cgacgaggcc  1740
tatcacatga tcgcgaagat gatcagcgat atggcgagta cgcacagcca ggtcagcgcc  1800
aacctcgggc ggcgccaggc ggtgtagctc gag                                1833

SEQ ID NO: 2           moltype = AA   length = 607
FEATURE                Location/Qualifiers
REGION                 1..607
                       note = synthetic construct
source                 1..607
                       mol_type = protein
                       organism = synthetic construct
SEQUENCE: 2
```

```
MTIDLGVSLT SQAGGLQGID LKSMDIQTLM VYVQGRRAEL LTAQMQTQAE VVQKANERMA    60
QLNEVLSALS RAKAEFPPNP KPGDTIPGWD NQKVSRIEVP LNDALRAAGL TGMFEARDGQ   120
VTAPGGRGTQ VVNGTGVMAG STTYKELESA YTTVKGMLDT ASNTQQMDMI RLQAASNKRN   180
EAFEVMTNTE KRRSDLNSSI TNNMRKLMTV MSTTISTAPS GAALAPSRID MRAPEPGSAG   240
EGAGILAPVT TLALAAGRPA FPASPSLRTA PVLDPPVRDL SPADLADLLR VLRSRAVDGQ   300
LATARENLQD AQVKAKQNTQ AQLDKLDAWF RKAEEAESKG WLSKVFGWIG KVLAVVASAL   360
AVGFAAVASV ATGAAATPML LLSGMALVSA VTSLADQISQ EAGGPPISLG GFLSGLAGRL   420
LTALGVDQSQ ADQIAKIVAG LAVPVVLLIE PQMLGEMAQG VARLAGASDA TAGYIAMAMS   480
IVAAIAVAAI NAAGTAGAGS ASAIKGAWDR AAAVATQVLQ GGTAVAQGGV GVSMAVDRKQ   540
ADLLVADKAD LAASLTKLRA AMEREADDIK KILAQFDEAY HMIAKMISDM ASTHSQVSAN   600
LGRRQAV                                                            607

SEQ ID NO: 3           moltype = DNA   length = 618
FEATURE                Location/Qualifiers
source                 1..618
                       mol_type = genomic DNA
                       organism = Bordetella spp
SEQUENCE: 3
catatgacca ttgatctcgg agtttcactc acgtcgcagg ccggcggcct gcaaggcatc    60
gacctcaaga gcatggatat ccagactctc atggtgtatg tgcagggtcg tcgcgccgaa   120
ctcctcacgg ctcaaatgca gacccaggcc gaagtggtgc agaaggccaa tgaacgcatg   180
gcgcagtca acgaggtcct gtccgcgctg tcccggcca ggccgagtt tccgcccaat      240
ccgaagccgg gcgacaccat cccgggctgg acaaccaga aggtcagccg gatcgaggtt   300
cctctcaatg atgcgctgcg cgctgccggc ctgacgggca tgttcgaagc gcgcgatggc   360
caagtgaccg ccccggcgg ccggggtacg caggtcgtga acggcacggg cgtcatggcc     420
ggttccacga cctataagga actcgaaagt gcctacacca gtcgtaaaggg gatgctggat   480
acggcgtcca atacgcaaca gatgacatg atcaggctgc aggccgccag caacaagcgc    540
aacgaggctt tcgaggtcat gaccaacacc gagaagcggc gcagcgacct gaacagttcc   600
atcaccaaca acatgcgc                                                 618

SEQ ID NO: 4           moltype = AA   length = 205
FEATURE                Location/Qualifiers
source                 1..205
                       mol_type = protein
                       organism = Bordetella spp
SEQUENCE: 4
MTIDLGVSLT SQAGGLQGID LKSMDIQTLM VYVQGRRAEL LTAQMQTQAE VVQKANERMA    60
QLNEVLSALS RAKAEFPPNP KPGDTIPGWD NQKVSRIEVP LNDALRAAGL TGMFEARDGQ   120
VTAPGGRGTQ VVNGTGVMAG STTYKELESA YTTVKGMLDT ASNTQQMDMI RLQAASNKRN   180
EAFEVMTNTE KRRSDLNSSI TNNMR                                        205

SEQ ID NO: 5           moltype = DNA   length = 1209
FEATURE                Location/Qualifiers
source                 1..1209
                       mol_type = genomic DNA
                       organism = Bordetella spp
SEQUENCE: 5
atgaccgtca tgagtacgac catatccaca gccccgagcg gcgccgcgct tgcgccgtct    60
cgcatagata tgcgggcacc ggagcccggg agtgccggcg aaggcgccgg catcctggcg   120
ccggtgacga cgctggctct ggcggcgggc cggccggctt ttccagcgtc accgtcgctg   180
cgcaccgcgc ccgtcctgga tccgccagtg cgcgatctca gcccccgcga cttggccgac   240
ctgctgcgcg tcttgcgatc caggcggtg gacgggcagt tggccacggc gcgcgagaac    300
ctgcaggacg cgcaagtcaa ggcgaagcag aacacccagg cccagctcga caagctggac   360
gcatggtttc ggaaggccga agaggccgag agcaagggat ggctgagcaa ggtgttcggc   420
tggatcggca aggtgctggc ggtcgtggca tcggccctgg cggtgggctt tgccgccgtc   480
gccagcgtgg ccaccggcgc ggcggccaca cccatgctgc tgctcagcgg catgcactg    540
gtcagcgccg tgacatcgct ggccgaccag atatcgcaag aggcgggagg cccgcctatc   600
agcctgggcg ggtttctctc cgggctggcc ggacgtctgc tgacagcgtt ggggggtggat   660
cagtcgcagg ccgaccaaat tgccaagatc gtcgccggcc tggccgtgcc cgtcgtcttg   720
ctgatcgaac cccagatgct gggcgaaatg gcgcaaggcg tggccaggct ggctggcgcc   780
agcgatgcca ccgcggggta catagcatg gcgatgtcca tcgtggcggc gatcgcggtc    840
gccgcgatca atgccgccgg tacagccggc gcgggtagcg cttcggcgat caaggggggcc   900
tgggatcggg ccgccgcggt agccaccca gtccttcaag ggggtacggc agtggcgcaa    960
ggcgggctcg gcgtgtcgat ggcagtcgat cgcaaacagg ccgatctcct ggtcgcgac    1020
aaggcggatc tggcggcgag cctgacaaaa ctgcgggcgg ccatgagcg tgaggcggac   1080
gatatcaaga gatcctggc tcaattcgac gaggcctatc acatgatcgc gaagatgatc   1140
agcgatatgg cgagtacgca cagccaggtc agcgccaacc tcgggcggcg ccaggcggtg   1200
tagctcgag                                                           1209

SEQ ID NO: 6           moltype = AA   length = 400
FEATURE                Location/Qualifiers
source                 1..400
                       mol_type = protein
                       organism = Bordetella spp
SEQUENCE: 6
MTVMSTTIST APSGAALAPS RIDMRAPEPG SAGEGAGILA PVTTLALAAG RPAFPASPSL    60
RTAPVLDPPV RDLSPADLAD LLRVLRSRAV DGQLATAREN LQDAQVKAKQ NTQAQLDKLD   120
AWFRKAEEEAE SKGWLSKVFG WIGKVLAVVA SALAVGFAAV ASVATGAAAT PMLLLSGMAL   180
VSAVTSLADQ ISQEAGGPPI SLGGFLSGLA GRLLTALGVD QSQADQIAKI VAGLAVPVVL   240
```

```
LIEPQMLGEM AQGVARLAGA SDATAGYIAM AMSIVAAIAV AAINAAGTAG AGSASAIKGA    300
WDRAAAVATQ VLQGGTAVAQ GGVGVSMAVD RKQADLLVAD KADLAASLTK LRAAMEREAD    360
DIKKILAQFD EAYHMIAKMI SDMASTHSQV SANLGRRQAV                          400

SEQ ID NO: 7              moltype = DNA   length = 534
FEATURE                   Location/Qualifiers
misc_feature              1..534
                          note = synthetic construct
source                    1..534
                          mol_type = other DNA
                          organism = synthetic construct
SEQUENCE: 7
atgggcagca gccatcacca tcatcaccac agccaggatc cgatgccaaa gtcagccgag     60
cagggcggct ccccggcgtc agcttcgcat gaggcgttgc gccatattct cgacgcaggc    120
gcttcgatgg gcagcttgca ggggttggac gaggtgcaac agcaggcgtt gtacgcgatc    180
gctcatggcg cctacgaaca gggccgctat gccgacgcgt tgaaaatgtt ctgcctgctg    240
gtcgcgtgcg atccgctgga agcccgttat ctgctggccc tggcgccgc ggcccaggag    300
ctggggctgt acgagcatgc cttgcagcaa tacgcggccg cggcgctttt gcagttggac    360
tcccccaggc ccctgttgca tggcgccgag tgcctgtatg cgttgggtcg tcgccgcgac    420
gccctggata cgctcgacat ggtgcttgag ttgtgcgggt cgccggagca tgcggccctg    480
cgcgaacggg ccgagtcgct gcgcaggagc tatgcacgtg ccgactgaaa gctt          534

SEQ ID NO: 8              moltype = AA   length = 175
FEATURE                   Location/Qualifiers
REGION                    1..175
                          note = synthetic construct
source                    1..175
                          mol_type = protein
                          organism = synthetic construct
SEQUENCE: 8
MGSSHHHHHH SQDPMPKSAE QGGSPASASH EALRHILDAG ASMGSLQGLD EVQQQALYAI     60
AHGAYEQGRY ADALKMFCLL VACDPLEARY LLALGAAAQE LGLYEHALQQ YAAAALQLD    120
SPRPLLHGAE CLYALGRRRD ALDTLDMVLE LCGSPEHAAL RERAESLRRS YARAD        175

SEQ ID NO: 9              moltype = AA   length = 161
FEATURE                   Location/Qualifiers
REGION                    1..161
                          note = synthetic construct
source                    1..161
                          mol_type = protein
                          organism = synthetic construct
SEQUENCE: 9
MPKSAEQGGS PASASHEALR HILDAGASMG SLQGLDEVQQ QALYAIAHGA YEQGRYADAL     60
KMFCLLVACD PLEARYLLAL GAAAQELGLY EHALQQYAAA AALQLDSPRP LLHGAECLYA    120
LGRRRDALDT LDMVLELCGS PEHAALRERA ESLRRSYARA D                       161

SEQ ID NO: 10             moltype = DNA   length = 544
FEATURE                   Location/Qualifiers
misc_feature              1..544
                          note = synthetic construct
source                    1..544
                          mol_type = other DNA
                          organism = synthetic construct
SEQUENCE: 10
ccatgggcag cagccatcat catcatcatc acagcagcgg cctggtgccg cgcggcagcc     60
atatgctcga gatgtcttta aatatcaccg aaaatgaaag catctctact gcagtaattg    120
atgcaattaa ctctggcgct acactgaaag atattaatgc aattcctgat gatatgatgg    180
atgcattta ttcatatgct tatgactttt acaacaaagg aagaatagag gaagctgaag    240
ttttcttcag gttttatgt atatacgact tttacaatat agactacatt atgggactcg    300
cagctattta tcagataaaa gaacagttcc aacaagcagc agacctttat gctgtcgctt    360
ttgcattagg aaaaaatgac tatacaccag tattccatac tggacaatgc cagcttcggt    420
tgaaagcccc cttaaaagct aaagagtgct cgaactcgt aattcaacac agcaatgatg    480
aaaaattaaa aataaaagca caatcatact tggacgcaat tcaggatatc aaggagtagg    540
atcc                                                                 544

SEQ ID NO: 11             moltype = AA   length = 155
FEATURE                   Location/Qualifiers
REGION                    1..155
                          note = synthetic construct
source                    1..155
                          mol_type = protein
                          organism = synthetic construct
SEQUENCE: 11
MSLNITENES ISTAVIDAIN SGATLKDINA IPDDMMDDIY SYAYDFYNKG RIEEAEVFFR     60
FLCIYDFYNV DYIMGLAAIY QIKEQFQQAA DLYAVAFALG KNDYTPVFHT GQCQLRLKAP    120
LKAKECFELV IQHSNDEKLK IKAQSYLDAI QDIKE                               155

SEQ ID NO: 12             moltype = DNA   length = 585
FEATURE                   Location/Qualifiers
```

| | | |
|---|---|---|
| source | 1..585<br>mol_type = genomic DNA<br>organism = Escherichia coli | |
| SEQUENCE: 12 | | |

```
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtattttta   240
tcaggctaca gcacatatta catttatgtg atcgccactg ccccaaacat gttcaatgtg   300
aacgatgtgt tggggggttta cagcccccat ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540
ccgtggatcc atcacgcccc tcaggggtgc gggaacagta gtcgc               585
```

| | | |
|---|---|---|
| SEQ ID NO: 13<br>FEATURE<br>source | moltype = AA  length = 194<br>Location/Qualifiers<br>1..194<br>mol_type = protein<br>organism = Escherichia coli | |
| SEQUENCE: 13 | | |

```
MDNGDRLYRA DSRPPDEIKR SGGLMPRGHN EYFDRGTQMN INLYDHARGT QTGFVRYDDG    60
YVSTSLSLRS AHLAGQSILS GYSTYYIYVI ATAPNMFNVN DVLGVYSPHP YEQEVSALGG   120
IPYSQIYGWY RVNFGVIDER LHRNREYRDR YYRNLNIAPA EDGYRLAGFP PDHQAWREEP   180
WIHHAPQGCG NSSR                                                    194
```

| | | |
|---|---|---|
| SEQ ID NO: 14<br>FEATURE<br>REGION | moltype = AA  length = 5<br>Location/Qualifiers<br>1..5<br>note = synthetic construct | |
| source | 1..5<br>mol_type = protein<br>organism = synthetic construct | |
| SEQUENCE: 14 | | |

```
GSAAS                                                                5
```

| | | |
|---|---|---|
| SEQ ID NO: 15<br>FEATURE<br>misc_feature | moltype = DNA  length = 3351<br>Location/Qualifiers<br>1..3351<br>note = synthetic construct | |
| source | 1..3351<br>mol_type = other DNA<br>organism = synthetic construct | |
| SEQUENCE: 15 | | |

```
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtattttta   240
tcaggctaca gcacatatta catttatgtg atcgccactg ccccaaacat gttcaatgtg   300
aacgatgtgt tggggggttta cagcccccat ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540
ccgtggatcc atcacgcccc tcaggggtgc gggaacagta gtcgcgggtc cgcggcatcc   600
atgaatataa caactctgac taatagtatt tccacctcat cattcagtcc aaacaataca   660
aacggttcat caaccgaaac agttaattct gatataaaaa caacgaccag ttctcatcct   720
gtaagttccc ttactatgct caacgacacc cttcataata tcagaacaac aaatcaggca   780
ttaaagaaag agctttcaca aaaaacgttg actaaaacat cgctagaaga aatagcatta   840
cattcatctc agattagcat ggatgtaaat aaatccgatc aactattgga tattctttcc   900
aggaacgaat atccaattaa taaagacgca agagaattat tacattcagc ccgaaagaa   960
gccgagcttg atggagatca aatgatatct catagagaac tgtgggctaa aattgcaaac  1020
tccatcaatg atattaatga acagtatctg aaagtatatg aacatgccgt tagttcatat  1080
actcaaaatgt atcaagattt tagcgctgtt cttttccagt ttgccggctg gatctctccc  1140
ggaggtaacg acggaaactc cgtgaaatta caagtcaact cgcttaaaaa ggcattggaa  1200
gaactcaagg aaaaatataa agatataaccc ctatatccag caaataatac tgttagtcag  1260
gaacaagcaa ataaatggct tacagaatta ggtggaacaa tcgcaaggt atctcaaaaa  1320
aacgggggat atgttgtcag tataaacatg accccaatag acaatatgtt aaaaagctta  1380
gataatctag gtggaaatgg cgaggttgtg ctagataata caaaatatca ggcatggaat  1440
gccggattct ctgccgaaga tgaaacaatg aaaaataatc ttcaaacttt agttcaaaaa  1500
tacagtaatg ccaatagtat ttttgataat ttagtaaagg ttttgagtag caataagc  1560
tcatgtacag atacagataa acttttttctc catttcctcg agatgcataa tgtaagcacc  1620
acaaccactg gttttcctct tgccaaaata ttgacttcca ctgagcttgg agacaatact  1680
atccaagctg caaatgatgc agctaacaaa ttatttttctc ttacaattgc tgatcttact  1740
gctaaccaaa atattaatac aactaatgca cactcaactt caatatatt aatccctaga  1800
cttaaagcac caaagtcatt aaatgcaagt tccaactaa cgcttttaat tggaaacctt  1860
attcaaatac tcggtgaaaa atctttaact gcattaacaa ataaaattac tgcttggaag  1920
tcccagcaac aggcaagaca gcaaaaaaac ctagaattct ccgataaaat taacactctt  1980
ctatctgaaa ctgaaggact aaccagagac tatgaaaaac aaattaataa actaaaaaac  2040
gcagattcta aaataaaaga cctagaaaat aaaattaacc aaattcaaac aagattatcg  2100
```

```
aacctcgatc cagagtcacc agaaaagaaa aaattaagcc gggaagaaat acaactcact    2160
atcaaaaaag acgcagcagt taaagacagg acattgattg agcagaaaac cctgtcaatt    2220
catagcaaac ttacagataa atcaatgcaa ctcgaaaaag aaatagactc tttttctgca    2280
ttttcaaaca cagcatctgc tgaacagcta tcaacccagc agaaatcatt aaccggactt    2340
gccagtgtta ctcaattgat ggcaacctt attcaactag ttggaaaaaa taatgaagaa    2400
tctttaaaaa atgatctggc tctattccag tctctccaag aatcaagaaa aactgaaatg    2460
gagagaaaat ctgatgagta tgctgctgaa gtacgtaaag cagaagaact caacagagta    2520
atgggttgtg ttgggaaaat acttggggca cttttaacta tcgttagtgt tgttgcagca    2580
gcttttttctg gaggagcctc tctagcactg gcagctgttg gtttagctct tatggttacg    2640
gatgctatag tacaagcagc gaccggcaat tccttcatgg aacaagccct gaatccgatc    2700
atgaaagcag tcattgaacc cttaatcaaa ctcctttcag atgcatttac aaaaatgctc    2760
gaaggcttgg gcgtcgactc gaaaaaagcc aaaatgattg gctctattct gggggcaatc    2820
gcaggcgctc ttgtcctagt tgcagcagtc gttctcgtag ccactgttgg taaacaggca    2880
gcagcaaaac ttgcagaaaa tattggcaaa ataataggta aaaccctcac agacttata    2940
ccaaagtttc tcaagaattt ttcttctcaa ctggacgatt taatcactaa tgctgttgcc    3000
agattaaata aatttcttgg tgcagcgggt gatgaagtaa tatccaaaca aattatttcc    3060
acccatttaa accaagcagt tttattagga gaaagtgtta actctgccac acaagcggga    3120
ggaagtgtcg cttctgctgt tttccagaac agcgcgtcga caaatctagc agacctgaca    3180
ttatcgaaat atcaagttga acaactgtca aaatatatca gtgaagcaat agaaaaattc    3240
ggccaattgc aggaagtaat tgcagatcta ttagcctcaa tgtccaactc tcaggctaat    3300
agaactgatg ttgcaaaagc aattttgcaa caaactactg cttgaggatc c              3351

SEQ ID NO: 16           moltype = AA   length = 1081
FEATURE                 Location/Qualifiers
REGION                  1..1081
                        note = synthetic construct
source                  1..1081
                        mol_type = protein
                        organism = synthetic construct
SEQUENCE: 16
MDNGDRLYRA DSRPPDEIKR SGGLMPRGHN EYFDRGTQMN INLYDHARGT QTGFVRYDDG    60
YVSTSLSLRS AHLAGQSILS GYSTYYIYVI ATAPNMFNVN DVLGVYSPHP YEQEVSALGG    120
IPYSQIYGWY RVNFGVIDER LHRNREYRDR YYRNLNIAPA EDGYRLAGFP PDHQAWREEP    180
WIHHAPQGCG NSSRGSAASM NITTLTNSIS TSSFSPNNTN GSSTETVNSD IKTTTSSHPS    240
SLTMLNDTLH NIRTTNQALK KELSQKTLRN EYPINKDARE LLHSAPKEAE LDGDQMISHR    300
ELWAKIANSI NDINEQYLKV YEHAVSSYTQ MYQDFSAVLS SLAGWISPGG NDGNSVKLQV    360
NSLKKALEEL KEKYKDKPLY PANNTVSQEQ ANKWLTELGG TIGKVSQKNG GYVVSINMTP    420
IDNMLKSLDN LGGNGEVVLD NAKYQAWNGF SAEDETMKNN LQTLVQKYSN ANSIFDNLVK    480
VLSSTISSCT DTDKLFLHPL EMHNVSTTTT GFPLAKILTS TELGDNTIQA ANDAANKLFS    540
LTIADLTANQ NINTTNAHST SNILIPELKA PKSLNASSQL TLLIGNLIQI LGEKSLTALT    600
NKITAWKSQQ QARQQKNLEF SDKINTLLSE TEGLTRDYEK QINKLKNADS KIKDLENKIN    660
QIQTLRSLND PESPEKKKLS REEIQLTIKK DAAVKDRTLI EQKTLSIHSK LTDKSMQLEK    720
EIDSFSAFSN TASAEQLSTQ QKSLTGLASV TQLMATFIQL VGKNNEESLK NDLALFQSLQ    780
ESRKTEMERK SDEYAAEVRK AEELNRVMGC VGKILGALLT IVSVVAAAFS GGASLALAAV    840
GLALMVTDAI VQAATGNSFM EQALNPIMKA VIEPLIKLLS DAFTKMLEGL GVDSKKAKMI    900
GSILGAIAGA LVLVAAVVLV ATVGKQAAAK LAENIGKIIG KTLTDLIPKF LKNFSSQLDD    960
LITNAVARLN KFLGAAGDEV ISKQIISTHL NQAVLLGESV NSATQAGGSV ASAVFQNSAS    1020
TNLADLTLSK YQVEQLSKYI SEAIEKFGQL QEVIADLLAS MSNSQANRTD VAKAILQQTT    1080
A                                                                    1081

SEQ ID NO: 17           moltype = DNA   length = 2415
FEATURE                 Location/Qualifiers
misc_feature            1..2415
                        note = synthetic construct
source                  1..2415
                        mol_type = other DNA
                        organism = synthetic construct
SEQUENCE: 17
catatggaca atggcgatcg tttataccgt gccgactcgc gtcccccaga tgagattaaa    60
cgtagcggtg ggttaatgcc acgtgggcac aatgagtatt ttgaccgtgg aacacagatg    120
aacattaacc tttacgatca tgcccgtggg acccagaccg gtttgtccg ttatgatgac    180
gggtatgtta gtacgagttt gtccttacgc tccgcacacc ttgcgggaca agtatttta    240
tcaggctaca gcacatatta catttatgtg atcgccactg ccccaaacat gttcaatgtg    300
aacgatgtgt tgggggttta cagccccat ccatatgaac aagaagtctc ggccctggg    360
gggatcccat atagccagat ttatggttgg taccgcgtaa attttggtgt gattgatgaa    420
cgtttgcatc gtaaccgtga ataccgcgat cgctactacc gtaacttgaa cattgcacct    480
gccgaggacg gctatcgttt agcgggattc ccacccgatc atcaggcgtg gcgtgaggaa    540
ccgtggatcc atcacgcccc tcaggggtgc gggaacagta gtcgcatgac cattgatctc    600
ggagtttcac tcacgtcgca ggccggcggc ctgcaaggca tcgacatgaa tcgccatgat    660
atccagactc tcatggtgta tgtgcagggt cgtcgcgccg aactcctcac ggctcaaatg    720
cagacccagg ccgaagtggt gcagaaggcc aatgaacgca tggcgcagct caacgaggtc    780
ctgtccgcgc tgtccggc caaggccgag tttccgccca tccgaagcc gggcgacacc    840
atccgggct gggacaacca gaaggtcagc cggatcgagg ttcctctcaa tgatgcgctg    900
cgcgcgtcg gctcgacggg catgttcgaa gcgcgcgagg gcaaagtgac gccccccgg    960
ggccggggta cgcaggtcgt gaacggcacg ggcgtcatgg ccggttccac gacctataag    1020
gaactcgaaa gtgcctacac caccgtaaag gggatgctgg atacggcgtc caatacgcaa    1080
cagatggaca tgatcaggct gcaggccgcc agcaacaagc gcaacgaggc tttcgaggtc    1140
atgaccaaca ccgagaagcg gcgcagcgac ctgaacagtt ccatccacca acacatgcgc    1200
aagcttatga ccgtcatgag tacgaccata tccacagccc gagcggcgc cgcgcttgcg    1260
```

```
ccgtctcgca tagatatgcg ggcaccggag cccgggagtg ccggcgaagg cgccggcatc    1320
ctggcgccgg tgacgacgct ggctctggcg gcgggccggc cggcttttcc agcgtcaccg    1380
tcgctgcgca ccgcgcccgt cctggatccg ccagtgcgcg atctcagccc cgccgacttg    1440
gccgacctgc tgcgcgtctt gcgatccagg cggtggacg gcagttggc cacggcgcgc     1500
gagaacctgc aggacgcgca agtcaaggcg aagcagaaca cccaggccca gctcgacaag    1560
ctggacgcat ggtttcggaa ggccgaagag gccgagagca agggatggct gagcaaggtg    1620
ttcggctgga tcggcaaggt gctggcggtc gtggcatcgg ccctggccgt gggcttttgcc   1680
gccgtcgcca gcgtggccac cggcgcgcg ccacacccca tgctgctgct cagcggcatg     1740
gcactggtca gcgccgtgac atcgctggcc gaccagatat cgcaagaggc gggaaggcccg   1800
cctatcagcc tgggcgggtt tctctccggg ctggccggac gtctgctgac agcgttgggg    1860
gtggatcagt cgcaggccga ccaaattgcc aagatcgtcg ccggcctggc cgtgcccgtc    1920
gtcttgctga tcgaaccca gatgctgggc gaaatgcgc aaggcgtggc caggctggct     1980
ggcgccagcg atgccaccgc ggggtacata gccatgcgca tgtccatcgt ggcggcgatc    2040
gcggtcgccg cgatcaatgc cgccggtaca gccggcgggg gtagcgcttc ggcgatcaag    2100
ggggcctggg atcgggccgc cgcggtagcc acccaggtcc ttcaaggggg tacggcagtg    2160
gcgcaaggcg gcgtcggcgt gtcgatggca gtcgatcgca aacaggccga tctcctggtc    2220
gccgacaagg cggatctggc ggcgagcctg acaaaactgc gggcggccat ggagcgtgag    2280
gcggacgata tcaagaagat cctggctcaa ttcgacgagg cctatcacat gatcgcgaag    2340
atgatcagcg atatggcgag tacgcacagc caggtcagcg ccaacctcgg gcggcgccag    2400
gcggtgtagc tcgag                                                    2415

SEQ ID NO: 18        moltype = AA   length = 801
FEATURE              Location/Qualifiers
REGION               1..801
                     note = synthetic construct
source               1..801
                     mol_type = protein
                     organism = synthetic construct
SEQUENCE: 18
MDNGDRLYRA DSRPPDEIKR SGGLMPRGHN EYFDRGTQMN INLYDHARGT QTGFVRYDDG     60
YVSTSLSLRS AHLAGQSILS GYSTYYIYVI ATAPNMFNVN DVLGVYSPHP YEQEVSALGG    120
IPYSQIYGWY RVNFGVIDER LHRNREYRDR YYRNLNIAPA EDGYRLAGFP PDHQAWREEP   180
WIHHAPQGCG NSSRMTIDLG VSLTSQAGGL QGIDLKSMDI QTLMVYVQGR RAELLTAQMQ   240
TQAEVVQKAN ERMAQLNEVL SALSRAKAEF PPNPKPGDTI PGWDNQKVSR IEVPLNDALR   300
AAGLTGMFEA RDGQVTAPGG RGTQVVNGTG VMAGSTTYKE LESAYTTVKG MLDTASNTQQ   360
MDMIRLQAAS NKRNEAFEVM TNTEKRRSDL NSSITNNMRK LMTVMSTTIS TAPSGAALAP   420
SRIDMRAPEP GSAGEGAGIL APVTTLALAA GRPAFPASPS LRTAPVLDPP VRDLSPADLA   480
DLLRVLRSRA VDGQLATARE NLQDAQVKAK QNTQAQLDKL DAWFRKAEEA ESKGWLSKVF   540
GWIGKVLAVV ASALAVGFAA VASVATGAAA TPMLLLSGMA LVSAVTSLAD QISQEAGGPP   600
ISLGGFLSGL AGRLLTALGV DQSQADQIAK IVAGLAVPVV LLIEPQMLGE MAQGVARLAG   660
ASDATAGYIA MAMSIVAAIA VAAINAAGTA GAGSASAIKG AWDRAAAVAT QVLQGGTAVA   720
QGGVGVSMAV DRKQADLLVA DKADLAASLT KLRAAMEREA DDIKKILAQF DEAYHMIAKM   780
ISDMASTHSQ VSANLGRRQA V                                              801

SEQ ID NO: 19        moltype = DNA  length = 566
FEATURE              Location/Qualifiers
misc_feature         1..566
                     note = synthetic construct
source               1..566
                     mol_type = other DNA
                     organism = synthetic construct
SEQUENCE: 19
atgggcagca gccatcacca tcatcaccac agccaggatc cgatgacgca acgcgacgtg     60
aacatagacg acatcgaggc gcaggaaatg gcggcggcgc tgctggacgc ggtccagaac    120
ggcgcgacgc tgaaggacct gcatcaggtg ccgcaggacc tgatggacgg catctatgcg    180
ttcgcgtacc gcttctacca gcaggggcgg ctcgacgacg cggaggtgtt cttccgcttt    240
ctgcgcatct acgacttcta caacgccgaa tacgacatgg ggctcgcggc ggtgtgccag    300
ttgaagaagg agtacgcgcg ggcgatcgat ctgtatgcac tcgcgtattc gctgtcgaag    360
gacgaccacc ggccgatgtt ccacaccggc caatgccatc tgctgatggg caaggcggcg    420
ctcgcgcggc gctgcttcgg catcgtcgtc gagcgctcgc gcgacgagcg cctcgcgcag    480
aaggcgcagt cctatctcga cgggctcgac gaagtgggcg ccgacgcggc gcccgcatcc    540
gccgggaacg accactgagc ggccgc                                         566

SEQ ID NO: 20        moltype = AA   length = 185
FEATURE              Location/Qualifiers
REGION               1..185
                     note = synthetic construct
source               1..185
                     mol_type = protein
                     organism = synthetic construct
SEQUENCE: 20
MGSSHHHHHH SQDPMTQRDV NIDDIEAQEM AAALLDAVQN GATLKDLHQV PQDLMDGIYA     60
FAYRFYQQGR LDDAEVFFRF LRIYDFYNAE YAMGLAAVCQ LKKEYARAID LYALAYSLSK   120
DDHRPMFHTG QCHLLMGKAA LARRCFGIVV ERSRDERLAQ KAQSYLDGLD EVGADAAPAS   180
AGNDH                                                                185

SEQ ID NO: 21        moltype = DNA  length = 930
FEATURE              Location/Qualifiers
source               1..930
```

```
                        mol_type = genomic DNA
                        organism = Burkholderia spp
SEQUENCE: 21
catatgaaca tgcacgtgga catgggtcgt gcgctgaccg ttcgtgattg gccggcgctg    60
gaggcgctgg cgaaaaccat gccggcggat gcgggtcgcg gtgcgatgac cgatgatgac   120
ctgcgtgcgg cgggtgtgga ccgtcgtgtt ccggagcaga agctgggtgc ggcgattgat   180
gaattcgcga gcctgcgtct gccggatcgt atcgacggtc gtttcgtgga tggccgtcgt   240
gcgaacctga ccgtttttga tgatgcgcgt gttgcggttc gtggtcatgc gcgtgcgcaa   300
cgtaacctgc tggagcgtct ggagaccgaa ctgctgggtg gcaccctgga taccgcgggt   360
gacgaaggtg gcattcagcc ggacccgatc ctgcaaggcg tggtggatgt tatcggtcag   420
ggcaaaagcg atattgacgc gtacgcgacc atcgtggaag gtctgaccaa gtattttcaa   480
agcgtggcga acgttatgag caaactgcag gattacatta gcgcgaagga tgacaaaaac   540
atgaagatcg acggtggcaa gatcaaagcg ctgattcagc aagtgatcga ccacctgccg   600
accatgcagc tgccgaaggg tgcggatatt gcgcgttggc gtaaagagct gggcgacgcg   660
gttagcatca gcgatagcgg tgtggttacc attaacccgg acaaactgat caagatgcgt   720
gatagcctgc cgccggatgg caccgtttgg gataccgcgc gttaccaagc gtggaacacc   780
gcgttcagcg gtcagaaagg ccagcatccg gaacgtcgtg cggatgcgcg tcgtaaatat   840
agccaccaga acagcaactt tgataacctg gtgaaggttc tgagcggtgc gattagcacc   900
ctgaccgaca cccagagcta tctgcaaatc                                    930

SEQ ID NO: 22           moltype = AA  length = 309
FEATURE                 Location/Qualifiers
source                  1..309
                        mol_type = protein
                        organism = Burkholderia spp
SEQUENCE: 22
MNMHVDMGRA LTVRDWPALE ALAKTMPADA GARAMTDDDL RAAGVDRRVP EQKLGAAIDE    60
FASLRLPDRI DGRFVDGRRA NLTVFDDARV AVRGHARAQR NLLERLETEL LGGTLDTAGD   120
EGGIQPDPIL QGLVDVIGQG KSDIDAYATI VEGLTKYFQS VADVMSKLQD YISAKDDKNM   180
KIDGGKIKAL IQQVIDHLPT MQLPKGADIA RWRKELGDAV SISDSGVVTI NPDKLIKMRD   240
SLPPDGTVWD TARYQAWNTA FSGQKGQHPE RRADARRKYS HQNSNFDNLV KVLSGAISTL   300
TDTQSYLQI                                                           309

SEQ ID NO: 23           moltype = DNA  length = 1869
FEATURE                 Location/Qualifiers
source                  1..1869
                        mol_type = genomic DNA
                        organism = Burkholderia spp
SEQUENCE: 23
atgagcagcg gtgttcaagg tggcccggcg gcgaacgcga acgcgtacca gacccacccg    60
ctgcgtgatg cggcgagcgc gctgggcacc ctgagcccgc aggcgtatgt ggatgtggtt   120
agcgcggcgc aacgtaactt cctggagcgt atgagccaac tggcgagcga acagtgcgat   180
gcgcaaccgg cggcgcatga tgcgcgtctg gatgatcgtc tgctgcgcag tgcgccgcag   240
gaacgtgacg cgccgccgct gggtgcgagc gataccggta gccgtgcgag cggtgcggcg   300
aaactgaccg agctgctggg tgtgctgatg agcgttatta gcgcgagcag cctgacgaa   360
ctgaagcaac gtagcgatat ctggaaccag atgagcaaag cggcgcaaga caacctgagc   420
cgtctgcagc atgcgtttca gcgtgcgacc gacgaggcga aagcgcgcgg ggatgcggcg   480
gaacaggcgc cggcggcggc gaagcaagcg ggtgcggacg cgaaagcggc ggatgcggcg   540
gtggatgcgg cgcaaaaacg ttacgatgac gcggttaagc agggcctgcc ggatgaccgt   600
ctgcaaagcc tgaaagcggc gctggagcag gcgcgtcagc aagcgggtga tgcgcatggt   660
cgtgcggatg cgctgcaggc ggatgcgacc aagaaactgg acgcgcgag cgcgctggcg   720
acccaagcgc gtgcgtgcga acagcaagtg gatgacgcgg ttaaccaggc gacccagcaa   780
tatggtgcga gcgcgagcct gcgtaccccg caaagcccgc gtctgagcgg tgcggcgag   840
ctgaccgcgg tgctgggcaa gctgcaggaa ctgattagca gcggcaacgt taagagctg   900
gaaagcaagc agaaactgtt caccgagatg caagcgcagc gtgaggcgaa actgcaaaag   960
aaaagcgacg aatatcaggc gcaagtgaag aaagcggagg aaatgcagaa acgcgatggt  1020
tgcatcggca agattgtggg ttgggttatt accgcggtta gctttgcggc ggcggcgttt  1080
accggtggcg cgagcctggc gctggcggcg gtgggcctgg cgctggcggt tggtgacgag  1140
attagccgtg cgaccaccgg cgtgagcttc atggacaagc tgatgcagcc ggttatggat  1200
gcgatcctga aaccgctgat ggagatgatt agcaccaagg cctggttgcg  1260
tgcggcgttg atcagcaaaa agcggaactg gcgggtgcga ttctgggtgc ggttgttacc  1320
ggtgtggcgc tggttgcggc ggcgtttgtt ggtgcgagcg cggtgaaagc ggttgcgagc  1380
aaggttatcg acgcgatggc gggtcagctg accaagctga tggatagcgc gattggcaaa  1440
atgctggtgc aactgatcga gaaattcagc gaaaagagcg gtctgcagcc gctgggtagc  1500
cgtaccgcga ccgcgatgac ccgtatgcgt cgtgcgattg cgttgaggc gaaggaagac  1560
ggtatgctgc tggcgaaccg tttttgaaaaa gcgggcaccg tgatgaacgt tggtaaccaa  1620
gtgagccaag cggcggtgg cattgtggtt ggcgttgagc gtgcgaaagc gatgggtctg  1680
ctggcggatg tgaagaagc gatgtatgac atcaagctgc tgggtgatct gctgaaacag  1740
gcggtggacg cgtttgcgga gcacaaccgt gttctggccg aactgatgca gcaaatgagc  1800
gatgcgggcg aaatgcagac cagcaccggc aagctgatcc tgcgtaacgc gcgtgcggtt  1860
taaggatcc                                                          1869

SEQ ID NO: 24           moltype = AA  length = 620
FEATURE                 Location/Qualifiers
source                  1..620
                        mol_type = protein
                        organism = Burkholderia spp
SEQUENCE: 24
MSSGVQGGPA ANANAYQTHP LRDAASALGT LSPQAYVDVV SAAQRNFLER MSQLASEQCD    60
```

```
AQPAAHDARL DDRPALRAPQ ERDAPPLGAS DTGSRASGAA KLTELLGVLM SVISASSLDE  120
LKQRSDIWNQ MSKAAQDNLS RLSDAFQRAT DEAKAAADAA EQAAAAAKQA GADAKAADAA  180
VDAAQKRYDD AVKQGLPDDR LQSLKAALEQ ARQQAGDAHG RADALQADAT KKLDAASALA  240
TQARACEQQV DDAVNQATQQ YGASASLRTP QSPRLSGAAE LTAVLGKLQE LISSGNVKEL  300
ESKQKLFTEM QAKREAELQK KSDEYQAQVK KAEEMQKTMG CIGKIVGWVI TAVSFAAAAF  360
TGGASLALAA VGLALAVGDE ISRATTGVSF MDKLMQPVMD AILKPLMEMI SSLITKALVA  420
CGVDQQKAEL AGAILGAVVT GVALVAAAFV GASAVKAVAS KVIDAMAGQL TKLMDSAIGK  480
MLVQLIEKFS EKSGLQALGS RTATAMTRMR RAIGVEAKED GMLLANRFEK AGTVMNVGNQ  540
VSQAAGGIVV GVERAKAMGL LADVKEAMYD IKLLGDLLKQ AVDAFAEHNR VLAQLMQQMS  600
DAGEMQTSTG KLILRNARAV                                              620

SEQ ID NO: 25           moltype = DNA  length = 2805
FEATURE                 Location/Qualifiers
misc_feature            1..2805
                        note = synthetic construct
source                  1..2805
                        mol_type = other DNA
                        organism = synthetic construct
SEQUENCE: 25
catatgaaca tgcacgtgga catgggtcgt gcgctgaccg ttcgtgattg gccggcgctg   60
gaggcgctgg cgaaaaccat gccggcggat gcgggtgcgc gtgcgatgac cgatgatgac  120
ctgcgtgcgg cgggtgtgga ccgtcgtgtt ccggagcaga agtcgggtgc ggcgattgat  180
gaattcgcga gcctgcgtct gccggatcgt atcgacgtc gtttcgtgga tggccgtcgt  240
gcgaacctga ccgtttttga tgatgcgcgt gttgcggttc gtggtcatgc gcgtgcgcaa  300
cgtaacctgc tggagcgtct ggagaccgaa ctgctgggtg gcaccctgga taccgcgggt  360
gacgaaggtg gcattcagcc ggaccccgatc ctgcaaggcc tggtggatgt tatcgatcag  420
ggcaaaagcg atattgacgc gtaccgcgacc atcgtggaag gtctgaccaa gtattttcaa  480
agcgtggcgg acgttatgag caaactgcag gattacatta gcgcgaagga tgacaaaaac  540
atgaagatcg acggtggcaa gatcaaagcg ctgattcagc aagtgatcga ccacctgccg  600
accatgcagc tgccgaaggg tgcggatatt cgcgttgtgc gtaaagagct gggcgacgcg  660
gttagcatca gcgatagcgg tgtggttacc attaacccgg acaaactgat caagatgcgt  720
gatagcctgc cgccggatgg caccgtttgg ataccgcgc gttaccaagc gtggaacacc  780
gcgttcagcg gtcagaaagg ccagcatccg aacgtcgtg cggatgcgcg tcgtaaatat  840
agccaccaga acagcaactt tgataacctg gtgaaggttc tgagcggtgc gattagcacc  900
ctgaccgaca cccagagcta tctgcaaatc aagcttatga gcagcggtgt tcaaggtcgg  960
ccggcggcga acgcgaacgc gtaccagacc caccgctgc gtgatgcggc gagcgcgctg  1020
ggcaccctga gcccgcaggc gtatgtggat gtggttagcg cggcgcaacg taacttcctg  1080
gagcgtatga gccaactggc gagcgaacag tgcgatgcgc aaccggcggc gcatgatgcg  1140
cgtctggatg atcgtccggc gctgctgcg ccgcaggaac gtgacgccgc gcgctggtg  1200
gcgagcgata ccggtagccg tgcgagcggt gcggcgaaac tgaccgagct gctgggtgtg  1260
ctgatgagcg ttattagcgc gagcagcctg acgaactga agcaacgtag cgatatctgg  1320
aaccagatga gcaaagcggc gcaagacaac ctgagccgtc tgagcgatgc gtttcagcgt  1380
gcgaccgacg aggcgaaagc ggcgcgcgat gcggcggcaa aggcggcgaag  1440
caagcgggtg cggacgcgaa agcggcggat gcggcggtgg atgcggcgca aaaacgttac  1500
gatgacgcgg ttaagcaggg cctgccggat gaccgtctgc aaagcctgaa agcggcgctg  1560
gagcaggcgc gtcagcaagc gggtgatgcg catggtcgtg cggatgcgct gcaggcggat  1620
gcgaccaaga aactgaccgc ctggcgacc aaagcgtgc gtgcgaacag  1680
caagtggatg acgcggttaa ccaggcgacc cagcaatatg gtgcgagcgc gagcctgcgt  1740
accccgcaaa gcccgcgtct gagcggtgcg cggagctga ccgcggtgct gggcaagctg  1800
caggaactga ttagcagcgg caacgttaaa gagctgaaa gcaagcagaa actgttcacc  1860
gagatgcaag cgaagcgtga ggcggaactg caaaagaaaa gcgacgaata tcaggcgcaa  1920
gtgaagaaag cggaggaaat gcagaaaacg atgggttgca tcggcaagat tgtgggttgg  1980
gttattaccg cggttagctt tgccgcggcg cgtttaccg gtggcgcgag cctggcgctg  2040
gcggcggtgg gcctggcgct ggcggttggt gacgagatta gccgtgcgac caccggtgtg  2100
agcttcatgg acaagctgat gcagccggtt atggatgcga tcctgaaacc gctgatggag  2160
atgattagca gcctgatcac caaggcgctg gttgcgtgcg gcgttgatca gcaaaaagcg  2220
gaactggcgg gtgcgattct gggtgcggtt gttaccggtg tggcgctggt tgcggcggcg  2280
tttgttggtg cgagcgcggt gaaagcggtt gcgagcaagg ttatcgacgc gatggcgggt  2340
cagctgacca agctgatgga tagcgcgatt ggcaaaatgc tggtgcaact gatcgagaaa  2400
ttcagcgaaa agagcggtct gcaggcgctg ggtagccgta ccgcgaccgc gatgaccgt  2460
atgcgtcgtg cgattggcgt tgaggcgaag gaagacggta tgctgctggc gaaccgtttt  2520
gaaaaagcgg gcaccgtgat gaacgttggt aaccaagtga gccaagcggc gggtggcatt  2580
gtggttggcg ttgagcgtgc gaaagcgatg ggtctgctgg cggatgtgaa agaagcgatg  2640
tatgacatca gctgctgggg tgatctgctg aacaggcgg tggcgcgtt tgcggagcac  2700
aaccgtgttc tggcgcaact gatgcagcaa atgagcgatg cgggcgaaat gcagaccagc  2760
accggcaagc tgatcctgcg taacgcgcgt gcggtttaag gatcc                  2805

SEQ ID NO: 26           moltype = AA  length = 931
FEATURE                 Location/Qualifiers
REGION                  1..931
                        note = synthetic construct
source                  1..931
                        mol_type = protein
                        organism = synthetic construct
SEQUENCE: 26
MNMHVDMGRA LTVRDWPALE ALAKTMPADA GARAMTDDDL RAAGVDRRVP EQKLGAAIDE   60
FASLRLPDRI DGRFVDGRRA NLTVFDDARV AVRGHARAQR NLLERLETEL LGGTLDTAGD  120
EGGIQPDPIL QGLVDVIGQG KSDIDAYATI VEGLTKYFQS VADVMSKLQD YISAKDDKNM  180
KIDGGKIKAL IQQVIDHLPT MQLPKGADIA RWRKELGDAV SISDSGVVTI NPDKLIKMRD  240
```

```
SLPPDGTVWD TARYQAWNTA FSGQKGQHPE RRADARRKYS HQNSNFDNLV KVLSGAISTL   300
TDTQSYLQIK LMSSGVQGGP AANANAYQTH PLRDAASALG TLSPQAYVDV VSAAQRNFLE   360
RMSQLASEQC DAQPAAHDAR LDDRPALRAP QERDAPPLGA SDTGSRASGA AKLTELLGVL   420
MSVISASSLD ELKQRSDIWN QMSKAAQDNL SRLSDAFQRA TDEAKAAADA AEQAAAAAKQ   480
AGADAKAADA AVDAAQKRYD DAVKQGLPDD RLQSLKAALE QARQQAGDAH GRADALQADA   540
TKKLDAASAL ATQARACEQQ VDDAVNQATQ QYGASASLRT PQSPRLSGAA ELTAVLGKLQ   600
ELISSGNVKE LESKQKLFTE MQAKREAELQ KKSDEYQAQV KKAEEMQKTM GCIGKIVGWV   660
ITAVSFAAAA FTGGASLALA AVGLALAVGD EISRATTGVS FMDKLMQPVM DAILKPLMEM   720
ISSLITKALV ACGVDQQKAE LAGAILGAVV TGVALVAAAF VGASAVKAVA SKVIDAMAGQ   780
LTKLMDSAIG KMLVQLIEKF SEKSGLQALG SRTATAMTRM RRAIGVEAKE DGMLLANRFE   840
KAGTVMNVGN QVSQAAGGIV VGVERAKAMG LLADVKEAMY DIKLLGDLLK QAVDAFAEHN   900
RVLAQLMQQM SDAGEMQTST GKLILRNARA V                                 931

SEQ ID NO: 27          moltype = DNA    length = 3390
FEATURE                Location/Qualifiers
misc_feature           1..3390
                       note = synthetic construct
source                 1..3390
                       mol_type = other DNA
                       organism = synthetic construct
SEQUENCE: 27
catatggaca atggcgatcg tttataccgt gccgactcgc gtcccccaga tgagattaaa   60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtatttta   240
tcaggctaca gcacatatta catttatgtg atcgccactg ccccaaacat gttcaatgtg   300
aacgatgtgt tggggggttta cagcccccat ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540
ccgtggatcc atcacgcccc tcaggggtgc gggaacagta gtcgccatat gaacatgcac   600
gtggacatgg gtcgtgcgct gaccgttcgt gattggccgg cgctggaggc gctggcgaaa   660
accatgccgg cggatgcggg tgcgcgtgcg atgaccgatg atgacctgcg tgcggcgggt   720
gtggaccgtc gtgttccgga gcagaagctg ggtgcggcga ttgaatcgc gcgagcctg    780
cgtctgccgg atcgtatcga cggtcgtttc gtggatgcgc gtcgtgcgaa cctgaccgtt   840
tttgatgatg cgcgtgttgc ggttcgtggt catgcgcgtg cgcaacgtaa cctgctggag   900
cgtctggaga ccgaactgct gggtggcacc ctggataccg cgggtgacga aggtggcatt   960
cagccggacc cgatcctgca aggcctggtg gatgttatcg gtcagggcaa aagcgatatt  1020
gacgcggtac cgaccatcgt ggaaggtctg accaagtatt ttcaaagcgt ggcggacgtt  1080
atgagcaaac tgcaggatta cattagcgcg aaggatgaca aaaacatgaa gatcgacggt  1140
ggcaagatca aagcgctgat tcagcaagtg atcgaccacc tgccgaccat gcagctgccg  1200
aagggtgcga atattgcgcg ttggcgtaaa gagctgggcg acgcggttag catcagcgat  1260
agcggtgtgg ttaccattaa cccggacaaa tgatcagca tgcgtgatag cctgccgccg  1320
gatggcaccg tttgggatac cgcgcgttac caagcgtgga acaccgcgtt cagcggtcag  1380
aaaggccagc atccggaacg tcgtgcggat gcgcgtcgta aatatagcca ccagaacagc  1440
aactttgata acctggtgaa ggttctgagc ggtgcgatta gcccctgac cgacacccag  1500
agctatctgc aaatcaagct tatgagcagc ggtgttcaag gtggccccggc ggcgaacgcg  1560
aacgcgtacc agaccacccc gctgcgtgat gcggcgagcg cgctgggcac cctgagcccg  1620
caggcgtatg tggatgtggt tagcgcggcg caacgtaact tcctggagcg tatgagccaa  1680
ctggcgagcg aacagtgcga tgcgcaaccg gcggcgcatg atgcgcgtct ggatgatcgt  1740
ccggcgctgc gtgcgccgca ggaacgtgac gcgccgccgc tgggtgcgag cgataccggt  1800
agccgtgcga gcggtgcggc gaaactgacc gagctgctgg gtgtgctgat gagcgttatt  1860
agcgcgagca gcctggacga actgaagcaa cgtagcgata tctggaacca gatgagcaaa  1920
gcggcgcaag acaacctgag ccgtctgagc gatgcgtttc agcgtgcgac cgacgaggcg  1980
aaagcgggcg cggatgcggc ggaacaggcg gcggcggcga cgaagcaagc gggtgcggcg  2040
gcgaaagcgg cggatgcggc ggtggatgcg gcgcaaaaac gttacgatga cgcggttaag  2100
cagggcctgc cggatgaccg tctgcaaagc ctgaaagcgg cgctggagca ggcgcgtcag  2160
caagcggcgt atgcgcatgg tcgtgcggat gcgctgcagg cggatgcgac caagaaactg  2220
gacgcggcga gcgcgctggc gacccaagcg cgtgcgtgcg aacagcaagt ggatgacgcg  2280
gttaaccagg cgacccagca atatggtgcg agcgcgagcc tgcgtacccc gcaaagcccg  2340
cgtctgagcg gtgcggcgga gctgaccgcg gtgctgggca agctgcagga actgattagc  2400
agcggcaacg ttaaagagct ggaaagcaag cagaaactgt tcaccgagat gcaagcgaag  2460
cgtgaggcgg aactgcaaaa agaaagcgac gaatatcagg cgcaagtgaa gaaagcggag  2520
gaaatgcaga aaacgatggg ttgcatcggt aagattgtgg gttgggttat taccgcggtt  2580
agctttgcgg cggcggcgtt taccggtggc gcgagcctgg cgctggcggc ggtgggcctg  2640
gcgctggcgg ttggtgacga gattagccgt gcgaccaccg gtgtgagctt catggacaag  2700
ctgatgcagc cggttatgga tgcgatcctg aaaccgctga tggagatgat tagcagcctg  2760
atcaccaagg cgctggttgc gtgcggcgtt gatcagcaaa aagcggaact ggcgggtgcg  2820
attctgggtg cggttgttac cggtgtggcg tggttgcgg cggcgtttgt tggtgcgggt  2880
gcggtgaaag cggttgcgag caaggttatc gacgcgatgg cgggtcagct gaccaagctg  2940
atggatagcg cgattggcaa aatgctggtg caactgatcg agaaattcag cgaaagagc   3000
ggtctgcagg cgctgggtag ccgtaccgcg accgcgatga cccgtatgcg tcgtgcgatt  3060
ggcgttgagg cgaaggaaga cggtatgctg ctggcgaacc gttttgaaaa agcgggcacc  3120
gtgatgaacg ttggtaacca agtgagccaa gcggcgggtg gcattgtggt tggcgttgag  3180
cgtgcgaaaa cgatgggtct gctggcggat gtgaaagaag cgatgtatga catcaagctg  3240
ctgggtgatc tgctgaaaca ggcggtggac gcgtttgcgg agcacaaccg tgttctggcg  3300
caactgatgc agcaaatgag cgatgcgggc gaaatgcaga ccagcaccgg caagctgatc  3360
ctgcgtaacg cgcgtgcggt ttaaggatcc                                   3390
```

```
SEQ ID NO: 28              moltype = AA   length = 1125
FEATURE                    Location/Qualifiers
REGION                     1..1125
                           note = synthetic construct
source                     1..1125
                           mol_type = protein
                           organism = synthetic construct
SEQUENCE: 28
MDNGDRLYRA DSRPPDEIKR SGGLMPRGHN EYFDRGTQMN INLYDHARGT QTGFVRYDDG    60
YVSTSLSLRS AHLAGQSILS GYSTYYIYVI ATAPNMFNVN DVLGVYSPHP YEQEVSALGG   120
IPYSQIYGWY RVNFGVIDER LHRNREYRDR YYRNLNIAPA EDGYRLAGFP PDHQAWREEP   180
WIHHAPQGCG NSSRMNMHVD MGRALTVRDW PALEALAKTM PADAGARAMT DDDLRAAGVD   240
RRVPEQKLGA AIDEFASLRL PDRIDGRFVD GRRANLTVFD DARVAVRGHA RAQRNLLERL   300
ETELLGGTLD TAGDEGGIQP DPILQGLVDV IGQGKSDIDA YATIVEGLTK YFQSVADVMS   360
KLQDYISAKD DKNMKIDGGK IKALIQQVID HLPTMQLPKG ADIARWRKEL GDAVSISDSG   420
VVTINPDKLI KMRDSLPPDG TVWDTARYQA WNTAFSGQKG QHPERRADAR RKYSHQNSNF   480
DNLVKVLSGA ISTLTDTQSY LQIKLMSSGV QGGPAANANA YQTHPLRDAA SALGTLSPQA   540
YVDVVSAAQR NFLERMSQLA SEQCDAQPAA HDARLDDRPA LRAPQERDAP PLGASDTGSR   600
ASGAAKLTEL LGVLMSVISA SSLDELKQRS DIWNQMSKAA QDNLSRLSDA FQRATDEAKA   660
AADAAEQAAA AAKQAGADAK AADAAVDAAQ KRYDDAVKQG LPDDRLQSLK AALEQARQQA   720
GDAHGRADAL QADATKKLDA ASALATQARA CEQQVDDAVN QATQQYGASA SLRTPQSPRL   780
SGAAELTAVL GKLQELISSG NVKELESKQK LFTEMQARKE AELQKKSDEY QAQVKKAEEM   840
QKTMGCIGKI VGWVITAVSF AAAAFTGGAS LALAAVGLAL AVGDEISRAT TGVSFMDKLM   900
QPVMDAILKP LMEMISSLIT KALVACGVDQ QKAELAGAIL GAVVTGVALV AAAFVGASAV   960
KAVASKVIDA MAGQLTKLMD SAIGKMLVQL IEKFSEKSGL QALGSRTATA MTRMRRAIGV  1020
EAKEDGMLLA NRFEKAGTVM NVGNQVSQAA GGIVVGVERA KAMGLLADVK EAMYDIKLLG  1080
DLLKQAVDAF AEHNRVLAQL MQQMSDAGEM QTSTGKLILR NARAV                  1125

SEQ ID NO: 29              moltype = DNA   length = 552
FEATURE                    Location/Qualifiers
misc_feature               1..552
                           note = synthetic construct
source                     1..552
                           mol_type = other DNA
                           organism = synthetic construct
SEQUENCE: 29
atgggcagca gccatcacca tcatcaccac agccaggatc cgatgaacca gccgaccct     60
tccgacaccg accagcaaca ggcgctggag gccttcctgc gcgacggcgg caccctggcg   120
atgcttcgcg gactcagcga ggacaccctg gagcagctct cttcaaccag cttcaaccag   180
taccaggcgg gcaagtggga cgacgcgcag aagatcttcc aggcactgtg catgctcgac   240
cactacgacg cccgctactt tctcggcctg ggcgcctgcc gccagtccct cggtctctat   300
gaacaggccc tgcagagcta cagctacggc gcgctgatgg acatcaacga gccgcgcttt   360
cccttccatg ccgccgagtg ccacttgcaa ctgggtgatc tcgacggagc cgagagtgga   420
ttctactcgg cccgggccct ggccgcggca cagccggcg acgaggccct ggccgcgcgt    480
gccggcgcca tgttggaagc cgtaaccgcg agaaaggatc gagcctatga atccgataac   540
gcttgaaagc tt                                                       552

SEQ ID NO: 30              moltype = AA   length = 181
FEATURE                    Location/Qualifiers
REGION                     1..181
                           note = synthetic construct
source                     1..181
                           mol_type = protein
                           organism = synthetic construct
SEQUENCE: 30
MGSSHHHHHH SQDPMNQPTP SDTDQQQALE AFLRDGGTLA MLRGLSEDTL EQLYALGFNQ    60
YQAGKWDDAQ KIFQALCMLD HYDARYFLGL GACRQSLGLY EQALQSYSYG ALMDINEPRF   120
PFHAAECHLQ LGDLDGAESG FYSARALAAA QPAHEALAAR AGAMLEAVTA RKDRAYESDN   180
A                                                                   181

SEQ ID NO: 31              moltype = DNA   length = 885
FEATURE                    Location/Qualifiers
source                     1..885
                           mol_type = genomic DNA
                           organism = Pseudomonas spp
SEQUENCE: 31
catatggaag tcagaaacct taatgccgct cgcgagctgt tcctggacga gctcctggcc    60
gcgtcggcgg cgcctgccag tgccgagcag gaggaactgc tggccctgtt gcgcagcgag   120
cggatcgtgc tggcccacgc cggccagccg ctgagcgcag cgcaagtgct caaggcgtcg   180
gcctggttgc tcgcgccaa tccgtccgcg cctccgggc agggcctcga ggtactccgc    240
gaagtcctgc aggcacgtcg gcagcccggt gcgcagtggg atctgcgtga gttcctggtg   300
tcggcctatt tcagcctgca cgggcgtctc gacgaggatg tcatcggtgt ctacaaggat   360
gtcctgcaga cccaggacgg caagcgcaag gcgctgctcg acgagctcaa ggcgctgacc   420
gcggagttga aggtctacag cgtgatccag tcgcagataa acgccggcgt gtcggccagg   480
cagggcatca ggatcgacgc tggcggtatc gatctggtcg accccacgct atatggctat   540
gccgtcggcg atcccaggtg gaaggacagc cccgagtatg cgctgctgag caatctggat   600
accttcagcg gcaagctgtc gatcaaggat tttctcagcg gctcgccgaa gcagagcggg   660
gaactcaagg gcctcagcga tgagtacccc ttcgagaagg acaacaaccc ggtcggcaat   720
ttcgccacca cggtgagcga ccgctcgcgt ccgctgaacg caaggtcaa cgagaagacc   780
```

```
acccctgctca acgacaccag ctcccgctac aactcggcgg tcgaggcgct caaccgcttc    840
atccagaaat acgacagcgt cctgagcgac attctcagcg cgatc                    885

SEQ ID NO: 32          moltype = AA  length = 294
FEATURE                Location/Qualifiers
source                 1..294
                       mol_type = protein
                       organism = Pseudomonas spp
SEQUENCE: 32
MEVRNLNAAR ELFLDELLAA SAAPASAEQE ELLALLRSER IVLAHAGQPL SEAQVLKALA     60
WLLAANPSAP PGQGLEVLRE VLQARRQPGA QWDLREFLVS AYFSLHGRLD EDVIGVYKDV    120
LQTQDGKRKA LLDELKALTA ELKVYSVIQS QINAALSARQ GIRIDAGGID LVDPTLYGYA    180
VGDPRWKDSP EYALLSNLDT FSGKLSIKDF LSGSPKQSGE LKGLSDEYPF EKDNNPVGNF    240
ATTVSDRSRP LNDKVNEKTT LLNDTSSRYN SAVEALNRFI QKYDSVLSDI LSAI          294

SEQ ID NO: 33          moltype = DNA  length = 1179
FEATURE                Location/Qualifiers
source                 1..1179
                       mol_type = genomic DNA
                       organism = Pseudomonas spp
SEQUENCE: 33
atgaaccega ttacgctgga acgtgctggt ctgccgtatg gtgttgccga tgctggtgac     60
atcccggctc tgggtcgccc ggtcgcacgt gatgtggaaa gtctgcgtgt tgaacgtctg    120
gcagcaccgg cagctgcaag cgcatctggc accggtgtcg ctctgacgcc gccgtctgca    180
gcaagtcagc aacgtctgga agttgctaac cgcgcggaaa ttgcctcact ggtccaggca    240
gtgggtgaag acgtgggtct ggcacgtcaa gtggttctgg caggtgcatc gaccctgctg    300
agcggcaggtc tgatgtcgcc gcaggcgttc gaaattgaac tggccaaaat caccggcgaa    360
gttgaaaatc agcagaaaaa actgaaactg acggaaatcg aacaggcccg taaacagaac    420
ctgcaaaaaa tggaagataa ccagcaaaaa atccgcgaat cggaagaagc tgcgaaagaa    480
gcgcagaaaa gcgggcctggc cgcaaaaatt tttggtttgga tttctgctat cgcgagtatt    540
atcgtgggtg caatcatggt tgcaaccggt gtcggtgctg cagcaggtgc actgatgatt    600
gctggcggtg tcatgggtgt cgtgagtcag tccgtgcagc aagcagctgc ggatggtctg    660
atctcaaaag aagtgatgga aaaactgggc ccggccctga tgggtattga atggccgtg     720
gcactgctgg ccgcagttgt ctcctttggt ggttcagcag ttggtggtct ggcacgtctg    780
ggtgcaaaaa tcggcggtaa agctgcggaa atgacggcat ccctggcttc aaaagtgctg    840
gacctgggcg gtaaattcgg ctctctggcg ggccagtcac tgtcgcatag cctgaaactg    900
ggtgtgcaag tttctgatct gaccctggac gttgcaaacg gcgccgcaca ggctacgcac    960
agtggttttc aagcgaaagc tgcgaatcgt caggccgatg ttcaagaatc ccgtgcagac   1020
ctgaccacgc tgcagggtgt cattgaacgt ctgaaagaag aactgagccg catgctggaa   1080
gcctttcagg aaattatgga acgcatcttc gcaatgctgc aagcgaaagg cgaaccctg    1140
cacaatctgt cttcccgtcc ggcggctatc tgaggatcc                          1179

SEQ ID NO: 34          moltype = AA  length = 390
FEATURE                Location/Qualifiers
source                 1..390
                       mol_type = protein
                       organism = Pseudomonas spp
SEQUENCE: 34
MNPITLERAG LPYGVADAGD IPALGRPVAR DVESLRVERL AAPAAASASG TGVALTPPSA     60
ASQQRLEVAN RAEIASLVQA VGEDVGLARQ VVLAGASTLL SAGLMSPQAF EIELAKITGE    120
VENQQKKLKL TEIEQARKQN LQKMEDNQQK IRESEEAAKE AQKSGLAAKI FGWISAIASI    180
IVGAIMVATG VGAAAGALMI AGGVMGVVSQ SVQQAAADGL ISKEVMEKLG PALMGIEMAV    240
ALLAAVVSFG GSAVGGLARL GAKIGGKAAE MTASLASKVA DLGGKFGSLA GQSLSHSLKL    300
GVQVSDLTLD VANGAAQATH SGFQAKAANR QADVQESRAD LTTLQGVIER LKEELSRMLE    360
AFQEIMERIF AMLQAKGETL HNLSSRPAAI                                     390

SEQ ID NO: 35          moltype = DNA  length = 2070
FEATURE                Location/Qualifiers
misc_feature           1..2070
                       note = synthetic construct
source                 1..2070
                       mol_type = other DNA
                       organism = synthetic construct
SEQUENCE: 35
catatggaag tcagaaacct taatgccgct cgcgagctgt tcctggacga gctcctggcc     60
gcgtcggcgg cgcctgccag tgccgagcag gaggaactgc tggcccctgtt gcgcagcgag    120
cggatcgtgc tggcccacgc cggccagccg ctgagcgagg cgcaagtgct caaggcgctc    180
gcctggttgc tcgcggccaa tccgtccgcg cctccggggc agggcctcga ggtactccgc    240
gaagtcctgc aggcacgtcg gcagcccggt gcgcagtgga tctgcgtga gttcctggtg    300
tcggcctatt tcagcctgca cgggcgtctc gacgaggatg tcatcggtgt ctacaaggat    360
gtcctgcaga cccaggacgg caagcgcaag gcgctgctcg acgagctcaa ggcgctgacc    420
gcggagttga aggtctacag cgtgatccag tcgcagatca acgccgcgct gtcggccagg    480
cagggcatca ggatcgacgc tggcggtatc gatctggtcg accccacgct atatggctat    540
gccgtcggcg atccccaggtg gaaggacagc cccgagtat cgctgctgag caatctggat    600
accttcagcg gcaagctgtc gatcaaggat tttctcagcg gctcgccgaa gcagagcggg    660
gaactcaagg gcctcagcga tgagtacccc ttcgagaagg acaacaaccc ggtcggcaat    720
ttcgccacca cggtgagcga ccgctcgcgt ccgctgaacg acaaggtcaa cgagaagacc    780
acccctgctca acgacaccag ctcccgctac aactcggcgg tcgaggcgct caaccgcttc    840
atccagaaat acgacagcgt cctgagcgac attctcagcg cgatcggatc catgaaccgg    900
```

```
attacgctgg aacgtgctgg tctgccgtat ggtgttgccg atgctggtga catcccggct    960
ctgggtcgcc cggtcgcacg tgatgtggaa agtctgcgtg ttgaacgtct ggcagcaccg   1020
gcagctgcaa gcgcatctgg caccggtgtc gctctgacgc cgccgtctgc agcaagtcag   1080
caacgtctgg aagttgctaa ccgcgcgaaa attgcctcac tggtccaggc agtgggtgaa   1140
gacgtgggtc tggcacgtca agtggttctg gcaggtgcat cgaccctgct gagcgcaggt   1200
ctgatgtcgc cgcaggcgtt cgaaattgaa ctggccaaaa tcaccggcga agttgaaaat   1260
cagcagaaaa aactgaaact gacggaaatc gaacaggccc gtaaacagaa cctgcaaaaa   1320
atggaagata ccagcaaaa  aatccgcgaa tcggaagaag ctgcgaaaga agcgcagaaa   1380
agcggcctgg ccgcaaaaat ttttggttgg atttctgcta tcgcgagtat tatcgtgggt   1440
gcaatcatgg ttgcaaccgg tgtcggttgc tgcagcaggtg cactgatgat tgctggcggt   1500
gtcatgggtg tcgtgagtca gtccgtgcag caagcagctg cggatggtct gatctcaaaa   1560
gaagtgatgg aaaaactggg cccggccctg atgggtattg aaatgccgt  ggcactgctg   1620
gccgcagttg tctcctttgg tggttcagca gttggtggtc tggcacgtct gggtgcaaaa   1680
atcgggcgta aagctgcgga aatgacggca tccctgcctt caaaagtggc agacctgggc   1740
ggtaaattcg gctctctggc gggccagtca ctgtcgcata gcctgaaact gggtgtgcaa   1800
gtttctgatc tgaccctgga cgttgcaaac ggcgccgcac aggctacgca cagtggtttt   1860
caagcgaaag ctgcgaatcg tcaggccgat gttcaagaat cccgtgcaga cctgaccacg   1920
ctgcagggtg tcattgaacg tctgaaagaa gaactgagcc gcatgctgga agcctttcag   1980
gaaattatgg aacgcatctt cgcaatgctg caagcgaaag gcgaaaccct gcacaatctg   2040
tcttcccgtc cggcggctat ctgaggatcc                                    2070

SEQ ID NO: 36         moltype = AA   length = 686
FEATURE               Location/Qualifiers
REGION                1..686
                      note = synthetic construct
source                1..686
                      mol_type = protein
                      organism = synthetic construct
SEQUENCE: 36
MEVRNLNAAR ELFLDELLAA SAAPASAEQE ELLALLRSER IVLAHAGQPL SEAQVLKALA    60
WLLAANPSAP PGQGLEVLRE VLQARRQPGA QWDLREFLVS AYFSLHGRLD EDVIGVYKDV   120
LQTQDGKRKA LLDELKALTA ELKVYSVIQS QINAALSARQ GIRIDAGGID LVDPTLYGYA   180
VGDPRWKDSP EYALLSNLDT FSGKLSIKDF LSGSPKQSGE LKGLSDEYPF EKDNNPVGNF   240
ATTVSDRSRP LNDKVNEKTT LLNDTSSRYN SAVEALNRFI QKYDSVLSDI LSAIGSMNPI   300
TLERAGLPYG VADAGDIPAL GRPVARDVES LRVERLAAPA AASASGTVA  LTPPSAASQQ   360
RLEVANRAEI ASLVQAVGED VGLARQVVLA GASTLLSAGL MSPQAFEIEL AKITGEVENQ   420
QKKLKLTEIE QARKQNLQKM EDNQQKIRES EEAAKEAQKS GLAAKIFGWI SAIASIIVGA   480
IMVATGVGAA AGALMIAGGV MGVVSQSVQQ AAADGLISKE VMEKLGPALM GIEMAVALLA   540
AVVSFGGSAV GGLARLGAKI GGKAAENMTAS LASKVADLGG KFGSLAGQSL SHSLKLGVQV   600
SDLTLDVANG AAQATHSGFQ AKAANRQADV QESRADLTTL QGVIERLKEE LSRMLEAFQE   660
IMERIFAMLQ AKGETLHNLS SRPAAI                                       686

SEQ ID NO: 37         moltype = DNA   length = 2655
FEATURE               Location/Qualifiers
misc_feature          1..2655
                      note = synthetic construct
source                1..2655
                      mol_type = other DNA
                      organism = synthetic construct
SEQUENCE: 37
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgccgtgggg acccagaccg ggtttgtccg ttatgatgac   180
gggtatgtta gtacgagttt gtccttacgc tccgcacacc ttgcgggaca agtatttta   240
tcaggctaca gcacatatta catttatgtg atcgccactg ccccaaacat gttcaatgtg   300
aacgatgtgt ggggggttta cagccccat  ccatatgaac aagaagtctc ggcccttggg   360
gggatcccat atagccagat ttatggttgg taccgcgtaa attttggtgt gattgatgaa   420
cgtttgcatc gtaaccgtga ataccgcgat cgctactacc gtaacttgaa cattgcacct   480
gccgaggacg gctatcgttt agcgggattc ccacccgatc atcaggcgtg gcgtgaggaa   540
ccgtggatcc atcacgcccc tcaggggtgc gggaacagta gtcgccatat ggaagtgcaga   600
aaccttaatg ccgctcgcga gctgttcctg gacgagctcc tggccgcgtc ggcggcgcct   660
gccagtgccg agcaggagga actgctggcc ctgttgcgca gcgagcggat cgtgctggcc   720
cacgccggcc agccgctgag cgaggcgcaa gtgctcaagg cgctcgcctg gttgctcgcg   780
gccaatccgt ccgcgcctcc ggggcagggc ctcgaggtcc tgcaggca   cctgcaggca   840
cgtcggcagc ccggtgcgca gtgggatctg cgtgagttcc tggtgtcggc ctatttcagc   900
ctgcacgggc gtctcgacga ggatgtcatc ggtgtctaca aggatgtcct gcagacccag   960
gacggcaagc gcaaggcgct gctcgacgag ctcaaggcgc tgaccgcgga gttgaaggtc  1020
tacagcgtga tccagtcgca gatcaacgcc gcgctgtcgg ccaggcaggg catcaggatc  1080
gacgctggcg gtatcgatct ggtcgacccc acgtatatgt gctatgccgt cggcgatccc  1140
aggtggaagg acagccccga gtatgcgctg ctgagcaatc tggataccct cagcggcaag  1200
ctgtcgatca aggatttct  cagcggctcg ccgaagcaga gcggggaact caagggcctc  1260
agcgatgagt accccttcga gaaggacaac aacccggtcg gcaatttcgc caccacggtg  1320
agcgaccgct cgcgtccgct gaacgacaag gtcaacgaga gaccacccct gctcaacgac  1380
accagctccc gctacaaact gcggttcagg gcgctcaacg cttcatcca  gaaatacgac  1440
agcgtcctga gcgacattct cagcgcgatc ggatccatga accgattac  gctgaacgt   1500
gctggtctgc cgtatggtgt tgccgatgct ggtgacatcc cggctctggg tcgcccggtc  1560
gcacgtgatg tggaaagtct gcgtgttgaa cgtctggcag caccggcagc tgcaagcgca  1620
tctggcaccg gtgtcgctct gacgccgccg tctgcagcaa gtcagcaacg tctggaagtt  1680
gctaaccgcg cggaaattgc ctcactggtc caggcagtgg gtgaagacgt gggtctggca  1740
```

```
cgtcaagtgg ttctggcagg tgcatcgacc ctgctgagcg caggtctgat gtcgccgcag  1800
gcgttcgaaa ttgaactggc caaaatcacc ggcgaagttg aaaatcagca gaaaaaactg  1860
aaactgacgg aaatcgaaca ggcccgtaaa cagaacctgc aaaaaatgga agataaccag  1920
caaaaaatcc gcgaatcgga agaagctgcg aaagaagcgc agaaaagcgg cctggccgca  1980
aaaattttg  gttggatttc tgctatcgcg agtattatgg ttgcaat    catggtttgca  2040
accggtgtcg gtgctgcagc aggtgcactg atgattgctg gcggtgtcat gggtgtcgtg  2100
agtcagtccg tgcagcaagc agctcgcgat ggtctgatct caaaagaagt gatggaaaaa  2160
ctgggcccgg ccctgatggg tattgaaatg gccgtggcac tgctggccgc agttgtctcc  2220
tttggtggtt cagcagttgg tggtctggca cgtctgggtg caaaaatcgg cggtaaagct  2280
gcggaaatga cggcatccct ggcttcaaaa gtggcagacc tgggcggtaa attcggctct  2340
ctggcgggcc agtcactgtc gcatagcctg aaactgggtg tgcaagtttc tgatctgacc  2400
ctggacgttg caaacggcgc cgcacaggct acgcacagtg ttttcaagc  gaaagctgcg  2460
aatcgtcagg ccgatgttca agaatcccgt gcagacctga ccacgctgca gggtgtcatt  2520
gaacgtctga agaagaact  gagccgcatg ctggaagcct tcaggaaat  tatggaacgc  2580
atcttcgcaa tgctgcaagc gaaaggcgaa accctgcaca atctgtcttc ccgtccggcg  2640
gctatctgag gatcc                                                    2655

SEQ ID NO: 38           moltype = AA  length = 880
FEATURE                 Location/Qualifiers
REGION                  1..880
                        note = synthetic construct
source                  1..880
                        mol_type = protein
                        organism = synthetic construct
SEQUENCE: 38
MDNGDRLYRA DSRPPDEIKR SGGLMPRGHN EYFDRGTQMN INLYDHARGT QTGFVRYDDG    60
YVSTSLSLRS AHLAGQSILS GYSTYYIYVI ATAPNMFNVN DVLGVYSPHP YEQEVSALGG   120
IPYSQIYGWY RVNFGVIDER LHRNREYRDR YYRNLNIAPA EDGYRLAGFP PDHQAWREEP   180
WIHHAPQGCG NSSRMEVRNL NAARELFLDE LLAASAAPAS AEQEELLALL RSERIVLAHA   240
GQPLSEAQVL KALAWLLAAN PSAPPGQGLE VLREVLQARR QPGAQWDLRE FLVSAYFSLH   300
GRLDEDVIGV YKDVLQTQDG KRKALLDELK ALTAELKVYS VIQSQINAAL SARQIRIDA    360
GGIDLVDPTL YGYAVGDPRW KDSPEYALLS NLDTFSGKLS IKDFLSGSPK QSGELKGLSD   420
EYPFEKDNNP VGNFATTVSD RSRPLNDKVN EKTTLLNDTS SRYNSAVEAL NRFIQKYDSV   480
LSDILSAIGS MNPITLERAG LPYGVADAGD IPALGRPVAR DVESLRVERL AAPAAASASG   540
TGVALTPPSA ASQQRLEVAN RAEIASLVQA VGEDVGLARQ VVLAGASTLL SAGLMSPQAF   600
EIELAKITGE VENQQKKLKL TEIEQARKQN LQKMEDNQQK IRESEEAAKE AQKSGLAAKI   660
FGWISAIASI IVGAIMVATG VGAAAGALMI AGGVMGVVSQ SVQQAAADGL ISKEVMEKLG   720
PALMGIEMAV ALLAVVSFG  GSAVGGLARL GAKIGGKAAE MTASLASKVA DLGGKFGSLA   780
GQSLSHSLKL GVQVSDLTLD VANGAAQATH SGFQAKAANR QADVQESRAD LTTLQGVIER   840
LKEELSRMLE AFQEIMERIF AMLQAKGETL HNLSSRPAAI                         880

SEQ ID NO: 39           moltype = DNA  length = 555
FEATURE                 Location/Qualifiers
misc_feature            1..555
                        note = synthetic construct
source                  1..555
                        mol_type = other DNA
                        organism = synthetic construct
SEQUENCE: 39
atgggcagca gccatcacca tcatcaccac agccaggatc cgatgcaaca agagacgaca    60
gacactcaag aataccagct ggcaatgaaa tccttcctaa aaggaggggg aactatcgca   120
atgctcaacg aaatttcaag tgacactta  gagcaactct actctcttgc gtttaaccaa   180
taccagtcag gaaaatacga ggatgctcac aaggtctttc aagctctctg tgtgctagac   240
cactatgatt cacgtttctt tttagggcta ggcgcttgtc gtcaagccat ggggcaatac   300
gacttagcga ttcatagcta cagctatggc gccataatgg atataaaaga acctcgtttt   360
ccgtttcatg ctgccgaatg tttactgcaa aagggagagc ttgctgaagc agaaagtggc   420
ttgttcttgg ctcaagagct tatcgcagac aaacctgagt taaggagct  tccacccga   480
gttagctcaa tgttagaagc aattaaattg aaaaaggaga tggaacatga gtgcgttgat   540
aacccatgaa agctt                                                    555

SEQ ID NO: 40           moltype = AA  length = 188
FEATURE                 Location/Qualifiers
REGION                  1..188
                        note = synthetic construct
source                  1..188
                        mol_type = protein
                        organism = synthetic construct
SEQUENCE: 40
MGSSHHHHHH SSGLVPRGSH MQQETTDTQE YQLAMESFLK GGGTIAMLNE ISSDTLEQLY    60
SLAFNQYQSG KYEDAHKVFQ ALCVLDHYDS RFFLGLGACR QAMGQYDLAI HSYSYGAIMD   120
IKEPRFPFHA AECLLQKGEL AEAESGLFLA QELIADKPEF KELSTRVSSM LEAIKLKKEM   180
EHECVDNP                                                            188

SEQ ID NO: 41           moltype = DNA  length = 981
FEATURE                 Location/Qualifiers
source                  1..981
                        mol_type = genomic DNA
                        organism = Yersinia spp
SEQUENCE: 41
```

```
catatgatta gagcctacga acaaaaccca caacatttta ttgaggatct agaaaaagtt    60
agggtggaac aacttactgg tcatggttct tcagttttag aagaattggt tcagttagtc   120
aaagataaaa atatagatat ttccattaaa tatgatccca gaaaagattc ggaggttttt   180
gccaatagag taattactga tgatatcgaa ttgctcaaga aaatcctagc ttatttcta   240
cccgaggatg ccattcttaa aggcggtcat tatgacaacc aactgcaaaa tggcatcaag   300
cgagtaaaag agttccttga atcatcgccg aatacacaat gggaattgcg ggcgttcatg   360
gcagtaatgc atttctcttt aaccgccgat cgtatcgatg atgatatttt gaaagtgatt   420
gttgattcaa tgaatcatca tggtgatgcc cgtagcaagt gcgtgaaga attagctgag    480
cttaccgccg aattaaagat ttattcagtt attcaagccg aaattaataa gcatctgtct   540
agtagtggca ccataaatat ccatgataaa tccattaatc tcatggataa aaatttatat   600
ggttatacag atgaagagat tttttaaagcc agcgcagagt acaaaattct cgagaaaatg  660
cctcaaacca ccattcaggt ggatgggagc gagaaaaaaa tagtctcgat aaaggacttt   720
cttggaagtg agaataaaag aaccggggcg ttgggtaatc tgaaaaactc atactcttat   780
aataaagata ataatgaatt atctcacttt gccaccacct gctcggataa gtccaggccg   840
ctcaacgact tggttagcca aaaaacaact cagctgctg atattacatc acgttttaat   900
tcagctattg aagcactgaa ccgtttcatt cagaaatatg attcagtgat gcaacgtctg   960
ctagatgaca cgtctggtaa a                                             981

SEQ ID NO: 42          moltype = AA   length = 326
FEATURE                Location/Qualifiers
source                 1..326
                       mol_type = protein
                       organism = Yersinia spp
SEQUENCE: 42
MIRAYEQNPQ HFIEDLEKVR VEQLTGHGSS VLEELVQLVK DKNIDISIKY DPRKDSEVFA    60
NRVITDDIEL LKKILAYFLP EDAILKGGHY DNQLQNGIKR VKEFLESSPN TQWELRAFMA   120
VMHFSLTADR IDDDILKVIV DSMNHHGDAR SKLREELAEL TAELKIYSVI QAEINKHLSS   180
SGTINIHDKS INLMDKNLYG YTDEEIFKAS AEYKILEKMP QTTIQVDGSE KKIVSIKDFL   240
GSENKRTGAL GNLKNSYSYN KDNNELSHFA TTCSDKSRPL NDLVSQKTTQ LSDITSRFNS   300
AIEALNRFIQ KYDSVMQRLL DDTSGK                                        326

SEQ ID NO: 43          moltype = DNA   length = 1212
FEATURE                Location/Qualifiers
source                 1..1212
                       mol_type = genomic DNA
                       organism = Yersinia spp
SEQUENCE: 43
atgagtgcgt tgataaccca tgatcgctca acgccagtaa ctggaagtct acttccctac    60
gtcgagacac cagcgcccgc cccccttcag actcaacaag tcgcgggaga actgaaggat   120
aaaaatggtg gggtgagttc tcagggcgta cagctccctg caccactagc agtggttgcc   180
agccaagtca ctgaaggaca cagcaagaa atcactaaat tattggagtc ggtcacccgc    240
ggcacggcag gatctcaact gatatcaaat tatgtttcag tgctaacgaa tttttacgtc   300
gcttcacctg atacatttga gattgagtta ggtaagctaa tttctaattt agaagaagta   360
cgcaaagaca taaaaatcgc tgatattcag cgtcttcatg aacaaaacat gaagaaaatt   420
gaagagaatc aagagaaaat caagaaaaca gaagagaatg ccaagcaagt caagaaatcc   480
ggcatggcat caaagatttt tggctggctc agcgccctag cctcagtggt tatccggtgcc  540
atcatggtgg cctcaggggt aggagccgtt gccggtgcaa tggctgattgc ctcaggcgta  600
attgggatgg cgaatatggc tgtgaaacaa gcgcggaag atggcctgat atcccaagag    660
gcaatgcaag tattagggcc gatactcact gcgattaag tcgcattgac tgtagtttca    720
accgtaatga ccttggcgg ttcggcacta aaatgcctgg ctgatattgg cgcaaaactc    780
ggtgctaaca ccgcaagtct tgctgctaaa ggagccgaat tttcggccaa agttgcccaa   840
atttcgacag gcatatcaaa cactgtcggg aatgcagtga ctaaattagg ggcagttttt   900
ggtagtttaa caatgagcca tgtaatccgt acaggatcac aggcaacaca agtcgccgtt   960
ggtgtgggca gcggaataac tcagaccatc aataataaaa aacaagctga tttacaacat  1020
aataacgctg atttggcctt gaacaaggca gacatgggca cgttacaaag tattattgac  1080
cgactcaaag aagagttatc ccatttgtca gagtcacatc aacaagtgat ggaactgatt  1140
ttccagatga ttaatgcaaa aggtgacatg ctgcataatt tggccggcag accccatact  1200
gtttaaggta cc                                                       1212

SEQ ID NO: 44          moltype = AA   length = 401
FEATURE                Location/Qualifiers
source                 1..401
                       mol_type = protein
                       organism = Yersinia spp
SEQUENCE: 44
MSALITHDRS TPVTGSLLPY VETPAPAPLQ TQQVAGELKD KNGGVSSQGV QLPAPLAVVA    60
SQVTEGQQQE ITKLLESVTR GTAGSQLISN YVSVLTNFTL ASPDTFEIEL GKLVSNLEEV   120
RKDIKIADIQ RLHEQNMKKI EENQEKIKET EENAKQVKKS GMASKIFGWL SAIASVVIGA   180
IMVASGVGAV AGAMMIASGV IGMANMAVKQ AAEDGLISQE AMQVLGPILT AIEVALTVVS   240
TVMTFGGSAL KCLADIGAKL GANTASLAAK GAEFSAKVAQ ISTGISNTVG NAVTKLGGSF   300
GSLTMSHVIR TGSQATQVAV GVGSGITQTI NNKKQADLQH NNADLALNKA DMAALQSIID   360
RLKEELSHLS ESHQQVMELI FQMINAKGDM LHNLAGRPHT V                       401

SEQ ID NO: 45          moltype = DNA   length = 2199
FEATURE                Location/Qualifiers
misc_feature           1..2199
                       note = synthetic construct
source                 1..2199
                       mol_type = other DNA
```

-continued

```
                        organism = synthetic construct
SEQUENCE: 45
catatgatta gagcctacga acaaaaccca caacatttta ttgaggatct agaaaaagtt   60
agggtggaac aacttactgg tcatggttct tcagttttag aagaattggt tcagttagtc  120
aaagataaaa atatagatat ttccattaaa tatgatccca gaaaagattc ggaggttttt  180
gccaatagag taattactga tgatatcgaa ttgctcaaga aaatcctagc ttattttcta  240
cccgaggatg ccattcttaa aggcggtcat tatgacaacc aactgcaaaa tggcatcaag  300
cgagtaaaag agttccttga atcatcgccg aatacacaat gggaattgcg ggcgttcatg  360
gcagtaatgc atttctcttt aaccgccgat cgtatcgatg atgatatttt gaaagtgatt  420
gttgattcaa tgaatcatca tggtgatgcc cgtagcaagt tgcgtgaaga attagctgag  480
cttaccgccg aattaaagat ttattcagtt attcaagccg aaattaataa gcatctgtct  540
agtagtggca cctaaaatat ccatgataaa tccattaatc tcatggataa aaatttatat  600
ggttatacag atgaagagat ttttaaagcc agcgcagagt acaaaattct cgagaaaatg  660
cctcaaacca ccattcaggt ggatgggagc gagaaaaaaa tagtctcgat aaaggacttt  720
cttggaagtg agaataaaag aaccggggcg ttgggtaatc tgaaaaactc atactcttat  780
aataaagata ataatgaatt atctcacttt gccaccacct gctcggataa gtccaggccg  840
ctcaacgact tggttagcca aaaaacaact cagctgtctg atattcatc acgttttaat  900
tcagctattg aagcactgaa ccgtttcatt cagaaatatt attcagtgat gcaacgtctg  960
ctagatgaca cgtctggtaa aggatccatg agtgcgttga taacccatga tcgctcaacg 1020
ccagtaactg gaagtctact tcctacgtc gagacaccag cgcccgcccc ccttcagact 1080
caacaagtcg cgggagaact gaaggataaa atggtgggg tgagttctca gggcgtacag 1140
ctcccctgcac cactagcagt ggttgccagc caagtcactg aaggacaaca gcaagaaatc 1200
actaaattat tggagtcggt cacccgcggc acggcaggat ctcaactgat atcaaattat 1260
gtttcagtgc taacgaattt tacgctcgct tcacctgata catttgagat tgagttaggt 1320
aagctagttt ctaatttaga agaagtacgc aaagacataa aaatcgctga tattcagcgt 1380
cttcatgaac aaaacatgaa gaaaattgaa gaaatcaag agaaacagaa 1440
gagaatgcca agcaagtcaa gaaatccggc atggcatcaa agattttgg ctggctcagc 1500
gccatagcct cagtggttat cggtgccatc atggtggcct caggggtagg agccgttgcc 1560
ggtgcaatga tgattgcctc aggcgtaatt gggatggcga atatgctgt gaaacaagcg 1620
gcggaagatg gcctgatatc ccaagaggca atgcaagtat tagggccgat actcactgcg 1680
attgaagtcg cattgactgt agtttcaacc gtaatgacct ttggcggttc ggcactaaaa 1740
tgcctggctg atattggcgc aaaactcggt gctaacaccg caagtcttgc tgctaaagga 1800
gccgagtttt cggccaaagt tgcccaaatt tcgacaggca tatcaaacac tgtcgggaat 1860
gcagtgacta aattagggg cagttttaac agtttaacaa tgagccatgt aatccgtaca 1920
ggatcacagg caacacaagt cgccgttggt gtgggcagcg gaataactca gaccatcaat 1980
aataaaaaac aagctgattt acaacataat aacgctgatt tggccttgaa caaggcagac 2040
atggcagcgt tacaaagtat tattgaccga ctcaaagaag agttatccca tttgtcagag 2100
tcacatcaac aagtgatgga actgatttc cagatgatta atgcaaaagg tgacatgctg 2160
cataatttgg ccggcagacc ccatactgtt aaggtacc                          2199

SEQ ID NO: 46            moltype = AA  length = 729
FEATURE                  Location/Qualifiers
REGION                   1..729
                         note = synthetic construct
source                   1..729
                         mol_type = protein
                         organism = synthetic construct
SEQUENCE: 46
MIRAYEQNPQ HFIEDLEKVR VEQLTGHGSS VLEELVQLVK DKNIDISIKY DPRKDSEVFA   60
NRVITDDIEL LKKILAYFLP EDAILKGGHY DNQLQNGIKR VKEFLESSPN TQWELRAFMA  120
VMHFSLTADR IDDDILKVIV DSMNHHGDAR SKLREELAEL TAELKIYSVI QAEINKHLSS  180
SGTINIHDKS INLMDKNLYG YTDEEIFKAS AEYKILEKMP QTTIQVDGSE KKIVSIKDFL  240
GSENKRTGAL GNLKNSYSYN KDNNELSHFA TTCSDKSRPL NDLVSQKTTQ LSDITSRFNS  300
AIEALNRFIQ KYDSVMQRLL DDTSGKGSMS ALITHDRSTP VTGSLLPYVE TPAPAPLQTQ  360
QVAGELKDKN GGVSSQGVQL PAPLAVVASQ VTEGQQQEIT KLLESVTRGT AGSQLISNYV  420
SVLTNFTLAS PDTFEIELGK LVSNLEEVRK DIKIADIQRL HEQNMKKIEE NQEKIKETEE  480
NAKQVKKSGM ASKIFGWLSA IASVVIGAIM VASGVGAVAG AMMIASGVIG MANMAVKQAA  540
EDGLISQEAM QVLGPILTAI EVALTVVSTV MTFGGSALKC LADIGAKLGA NTASLAAKGA  600
EFSAKVAQIS TGISNTVGNA VTKLGGSFGS LTMSHVIRTG SQATQVAVGV GSGITQTINN  660
KKQADLQHNN ADLALNKADM AALQSIIDRL KEELSHLSES HQQVMELIFQ MINAKGDMLH  720
NLAGRPHTV                                                          729

SEQ ID NO: 47            moltype = DNA  length = 2784
FEATURE                  Location/Qualifiers
misc_feature             1..2784
                         note = synthetic construct
source                   1..2784
                         mol_type = other DNA
                         organism = synthetic construct
SEQUENCE: 47
catatggaca atggcgatcg tttataccgt gccgactcgc gtcccccaga tgagattaaa   60
cgtagcggtt ggtaatgcc acgtgggcac aatgagtatt tgaccgtgg aacacagatg  120
aacattaacc tttacgatca tgcccgtggg acccagaccg ggtttgtccg ttatgatgac  180
gggttagtta gtcagtttt gtccttacgc tccgcacaa ttgcgggaca aagtattta  240
tcaggctaca gcacatatta catttatgtg atcgccactg ccccaaacat gttcaatgtg  300
aacgatgtgt ggggttta cagccccat ccatatgaac aagaagtctc ggcccttggg  360
gggatcccat atagccagat ttatggttgg taccgcgtaa attttggtgt gattgatgaa  420
cgtttgcatc gtaaccgtga ataccgcgat cgctactacc gtaacttgaa cattgcacct  480
gccgaggacg gctatcgttt agcgggattc ccacccgatc atcaggcgtg gcgtgaggaa  540
```

```
cgtggatcc atcacgcccc tcaggggtgc gggaacagta gtcgccatat gattagagcc    600
tacgaacaaa acccacaaca ttttattgag gatctagaaa aagttagggt ggaacaactt    660
actggtcatg gttcttcagt tttagaagaa ttggttcagt tagtcaaaga taaaaatata    720
gatatttcca ttaaatatga tcccagaaaa gattcggagg ttttttgccaa tagagtaatt    780
actgatgata tcgaattgct caagaaaatc ctagcttatt ttctacccga ggatgccatt    840
cttaaaggcg gtcattatga caaccaactg caaaatggga tcaagcgagt aaaagagttc    900
cttgaatcat cgccgaatac acaatgggaa ttgcgggcgt tcatggcagt aatgcatttc    960
tctttaaccg ccgatcgtat cgatgatgat attttgaaag tgattgttga ttcaatgaat   1020
catcatggtg atgcccgtag caagttgcgt gaagaattag ctgagcttac cgccgaatta   1080
aagatttatt cagttattca agccgaaatt aataagcatc tgtctagtag tggcaccata   1140
aatatccatg ataaatccat taatctcatg gataaaaatt tatatggtta tacagatgaa   1200
gagattttta aagccagcgc agagtacaaa attctcgaga aaatgcctca aaccaccatt   1260
caggtggatg ggagcgagaa aaaaatagtc tcgataaagg actttcttgg aagtgagaat   1320
aaaagaaccg gggcgttggg taatctgaaa aactcatact cttataataa agataataat   1380
gaattatctc actttgccac cacctgctcg gataagtcca ggccgctcaa cgacttggtt   1440
agccaaaaaa caactcagct gtctgatatt acatcacgtt ttaattcagc tattgaagca   1500
ctgaaccgtt tcattcagaa atatgattca gtgatgcaac gtctgctaga tgacacgtct   1560
ggtaaaggat ccatgagtgc gttgataacc catgatcgct caacgccagt aactggaagt   1620
ctacttccct acgtcgagac accagcgccc gccccccttc agactcaaca gtcgcggga    1680
gaactgaagg ataaaaatgg tgggggtgagt ctcagggcg tacagctccc tgcaccacta   1740
gcagtggttg ccagccaagt cactgaagga caacagcaag aaatcactaa attattggag   1800
tcggtcaccc gcggcacggc aggatctcaa ctgtatatca attatgtttc agtgctaacg   1860
aattttacgc tcgcttcacc tgatacattt gagattgagt taggtaagct agtttctaat   1920
ttagaagaag tacgcaaaga cataaaaatc gctgatattc agcgtcttca tgaacaaaac   1980
atgaagaaaa ttgaagagaa tcaagagaaa atcaaagaaa cagaagagaa tgccaagcaa   2040
gtcaaagaat ccggcatggc tcaaagattt tttggctgtg tcagcgccat agcctcagtg   2100
gttatcggtg ccatcatggt ggcctcaggg gtaggagccg ttgccggtgc aatgatgatt   2160
gcctcaggcg taattgggat ggcgaatatg gctgtgaaac aagcggcgga agatggcctg   2220
atatcccaag aggcaatgca agtattaggg ccgatactca ctgcgattga agtcgcattg   2280
actgtagttt caaccgtaat gaccttggcc ggttcggcac taaaatgcct ggctgatatt   2340
ggcgcaaaac tcggtgctaa caccgcaagt cttgctgcta aaggagccga gttttcggcc   2400
aaagttgccc aaatttcgac aggcatatca aacactgtcg gaatgcagt gactaaatta   2460
gggggcagtt ttggtagttt aacaatgagc catgtaatcc gtacaggatc acaggcaaca   2520
caagtcgccg ttggtgtggg cagcggaata actcagacca tcaataataa aaaacagatt   2580
gatttacaac ataataacgc tgatttggcc ttgaacaagg cagacatggc agcgttacaa   2640
agtattattg accgactcaa agaagagtta tcccatttgt cagagtcaca tcaacaagtg   2700
atggaactga ttttccagat gattaatgca aaggtgaca tgctgcataa tttggccggc   2760
agaccccata ctgtttaagg tacc                                           2784

SEQ ID NO: 48        moltype = AA  length = 923
FEATURE              Location/Qualifiers
REGION               1..923
                     note = synthetic construct
source               1..923
                     mol_type = protein
                     organism = synthetic construct
SEQUENCE: 48
MDNGDRLYRA DSRPPDEIKR SGGLMPRGHN EYFDRGTQMN INLYDHARGT QTGFVRYDDG    60
YVSTSLSLRS AHLAGQSILS GYSTYYIYVI ATAPNMFNVN DVLGVYSPHP YEQEVSALGG   120
IPYSQIYGWY RVNFGVIDER LHRNREYRDR YYRNLNIAPA EDGYRLAGFP PDHQAWREEP   180
WIHHAPQGCG NSSRMIRAYE QNPQHFIEDL EKVRVEQLTG HGSSVLEELV QLVKDKNIDI   240
SIKYDPRKDS EVFANRVITD DIELLKKILA YFLPEDAILK GGHYDNQLQN GIKRVKEFLE   300
SSPNTQWELR AFMAVMHFSL TADRIDDDIL KVIVDSMNHH GDARSKLREE LAELTAELKI   360
YSVIQAEINK HLSSSGTINI HDKSINLMDK NLYGYTDEEI FKASAEYKIL EKMPQTTIQV   420
DGSEKKIVSI KDFLGSENKR TGALGNLKNS YSYNKDNNEL SHFATTCSDK SRPLNDLVSQ   480
KTTQLSDITS RFNSAIEALN RFIQKYDSVM QRLLDDTSGK GSMSALITHD RSTPVTGSLL   540
PYVETPAPAP LQTQQVAGEL KDKNGGVSSQ GVQLPAPLAV VASQVTEGQQ QEITKLLESV   600
TRGTAGSQLI SNYVSVLTNF TLASPDTFEI ELGKLVSNLE EVRKDIKIAD IQRLHEQNMK   660
KIEENQEKIK ETEENAKQVK KSGMASKIFG WLSAIASVVI GAIMVASGVG AVAGAMMIAS   720
GVIGMANMAV KQAAEDGLIS QEAMQVLGPI LTAIEVALTV VSTVMTFGGS ALKCLADIGA   780
KLGANTASLA AKGAEFSAKV AQISTGISNT VGNAVTKLGG SFGSLTMSHV IRTGSQATQV   840
AVGVGSGITQ TINNKKQADL QHNNADLALN KADMAALQSI IDRLKEELSH LSESHQQVME   900
LIFQMINAKG DMLHNLAGRP HTV                                            923

SEQ ID NO: 49        moltype = DNA  length = 546
FEATURE              Location/Qualifiers
misc_feature         1..546
                     note = synthetic construct
source               1..546
                     mol_type = other DNA
                     organism = synthetic construct
SEQUENCE: 49
atgggcagca gccatcacca tcatcaccac agccaggatc cgatggacta ccagaacaac     60
gtcagcgaag aacgtgttgc ggaaatgatt gggatgccg ttagtgaagg cgccacgcta    120
aaagacgttc atggaatccc tcaagatatg atggacggtt tatatgctca tgcttatgag    180
ttttataacc agggacgact ggatgaagct gagacgttct tcgtttctt atgcatttat    240
gattttacca atcccgatta caccatggga ctggcggcag tatgccaact gaaaaaacaa    300
tttcagaaag catgtgacct ttatgcagta gcgtttacgt tacttaaaaa tgattatcgc    360
cccgtttttt ttaccgggca gtgtcaatta ttaatgcgta aggcagcaaa agccagacag    420
```

```
tgttttgaac ttgtcaatga acgtactgaa gatgagtctc tgcgggcaaa agcgttggtc    480
tatctggagg cgctaaaaac ggcggagaca gagcagcaca gcgagcagga gaaggagtaa    540
aagctt                                                               546

SEQ ID NO: 50           moltype = AA  length = 179
FEATURE                 Location/Qualifiers
REGION                  1..179
                        note = synthetic construct
source                  1..179
                        mol_type = protein
                        organism = synthetic construct
SEQUENCE: 50
MGSSHHHHHH SQDPMDYQNN VSEERVAEMI WDAVSEGATL KDVHGIPQDM MDGLYAHAYE     60
FYNQGRLDEA ETFFRFLCIY DFYNPDYTMG LAAVCQLKKQ FQKACDLYAV AFTLLKNDYR    120
PVFFTGQCQL LMRKAAKARQ CFELVNERTE DESLRAKALV YLEALKTAET EQHSEQEKE     179

SEQ ID NO: 51           moltype = DNA  length = 1029
FEATURE                 Location/Qualifiers
source                  1..1029
                        mol_type = genomic DNA
                        organism = Salmonella spp
SEQUENCE: 51
atgcttaata ttcaaaatta ttccgcttct cctcatccgg ggatcgttgc cgaacggccg     60
cagactccct cggcgagcga gcacgtcgag actgccgtgg taccgtctac cacagaacat    120
cgcggtacag atatcatttc attatcgcag gcggctacta aaatccacca ggcacagcag    180
acgctgcagt caacgccacc gatctctgaa gagaatagcg acgagcgaac gctggcgcgc    240
cagcagttga ccagcagcct gaatgcgctg gcgaagtccg gcgtgtcatt atccgcagaa    300
caaaatgaga acctgcggag cgcgttttct cgcgccgacg tcggccttat tagcgcttcg    360
cctatgcgcg agccgagaac aaccatttct gatgctgaga tttgggatat ggtttcccaa    420
aatatatcgg cgataggtga cagctatctg ggcgtttatg aaaacgttgt gcagtctat     480
accgattttt atcaggcctt cagtgatatt cttttccaaaa tgggaggctg gttattacca    540
ggtaaggacg gtaataccgt taagctagat gttacctcac tcaaaaatga tttaaacagt    600
ttagtcaata aatataatca aataaacagt aataccgttt tatttccagc gcagtcaggc    660
agcggcgtta aagtagccac tgaagcggaa gcgagacagt ggctcagtga attgaattta    720
ccgaatagct gcctgaaatc ttatggatcc ggttatgtcg tcaccgttga tctgacgcca    780
ttacaaaaaa tggttcagga tattgatggt ttaggcgcgc cgggaaaaga ctcaaaactc    840
gaaatggata acgccaaata tcaagcctgg cagtcgggtt ttaaagcgca ggaagaaaat    900
atgaaaacca cattacagac gctgacgcaa aaatatagca atgccaattc attgtacgac    960
aacctggtaa aagtgctgag cagtacgata agtagcagcc tggaaaccgc caaaagcttc   1020
ctgcaagga                                                           1029

SEQ ID NO: 52           moltype = AA  length = 343
FEATURE                 Location/Qualifiers
source                  1..343
                        mol_type = protein
                        organism = Salmonella spp
SEQUENCE: 52
MLNIQNYSAS PHPGIVAERP QTPSASEHVE TAVVPSTTEH RGTDIISLSQ AATKIHQAQQ     60
TLQSTPPISE ENNDERTLAR QQLTSSLNAL AKSGVSLSAE QNENLRSAFS APTSALFSAS    120
PMAQPRTTIS DAEIWDMVSQ NISAIGDSYL GVYENVVAVY TDFYQAFSDI LSKMGGWLLP    180
GKDGNTVKLD VTSLKNDLNS LVNKYNQINS NTVLFPAQSG SGVKVATEAE ARQWLSELNL    240
PNSCLKSYGS GYVVTVDLTP LQKMVQDIDG LGAPGKDSKL EMDNAKYQAW QSGFKAQEEN    300
MKTTLQTLTQ KYSNANSLYD NLVKVLSSTI SSSLETAKSF LQG                      343

SEQ ID NO: 53           moltype = DNA  length = 1782
FEATURE                 Location/Qualifiers
source                  1..1782
                        mol_type = genomic DNA
                        organism = Salmonella spp
SEQUENCE: 53
atggtaaatg acgcaagtag cattagccgt agcggatata cccaaaatcc gcgcctcgct     60
gaggcggctt ttgaaggcgt tcgtaagaac acggactttt taaaagcggc ggataaagct    120
tttaaagatg tggtggcaac gaaagcgggc gaccttaaag ccggaacaaa gtccggcgag    180
agcgctatta atacggacgg gtctaaagcc cctacggacg ccgcccggga aaactctcc     240
agcgaagggc aattgacatt actgcttggc aagttaatga ccctactggg cgatgtttcg    300
ctgtctcaac tggagtctcg tctgcggta tggcaggcga tgattgagtc acaaaaagag    360
atggggattc aggtatcgaa agaattccag acggctctgg gagaggctca ggaggcgacg    420
gatctctatg aagccagtat caaaaagacg gataccgcca agagtgttta tgacgctgcg    480
accaaaaaac tgacgcaggc gcaaaataaa ttgcaatcgc tggacccgtc tgaccccgag    540
tatgcacaag ctgaagccgc ggtagaacag gccggaaaag aagcgacaga ggcgaaagag    600
gcctagata aggccacgga tgcgacggtt aaagcaggca cagacgccaa agcgaaagcc    660
gagaaagcg ataacattct gaccaaattc caggaacgg ctaatgccgc ctctcagaat    720
caggtttccc agggtgagca ggataatctg tcaaatgtcg cccgcctcac tatgctcatg    780
gccatgttta ttgagattgt gggcaaaaat acggaagaaa gcctgcaaaa gatcttgcg    840
cttttcaacg ccttgcagga agggcgtcag gcgaagatgg aaaagaaatc gctgaattc    900
caggaagaga cgcgcaaagc cgaggaaacg aaccgcatta tgggatgtat cgggaaagtc    960
ctcggcgcgc tgctaaccat tgtcagcgtt gtggccgctg ttttaccgg tggggcgagt   1020
ctggcgctgg ctgcggtggg acttgcgta atggtgccgg atgaaattgt gaaggcgcg   1080
acgggagtgt cgtttattca gcaggcgcta aacccgatta tggagcatgt gctgaagccg   1140
```

```
ttaatggagc tgattggcaa ggcgattacc aaagcgctgg aaggattagg cgtcgataag   1200
aaaacggcag agatgccgg cagcattgtt ggtgcgattg tcgccgctat tgccatggtg    1260
gcggtcattg tggtggtcgc agttgtcggg aaaggcgcgg cggcgaaact gggtaacgcg   1320
ctgagcaaaa tgatgggcga aacgattaag aagttggtgc ctaacgtgct gaaacagttg   1380
gcgcaaaacg gcagcaaact cttttacccag gggatgcaac gtattactag cggtctgggt  1440
aatgtgggta gcaagatggg cctgcaaacg aatgccttaa gtaaagagct ggtaggtaat   1500
accctaaata aagtggcgtt gggcatggaa gtcacgaata ccgcagccca gtcagccggt   1560
ggtgttgccg agggcgtatt tattaaaaat gccagcgagg cgcttgctga ttttatgctc   1620
gcccgttttg ccatggatca gattcagcag tggcttaaac aatccgtaga aatatttggt   1680
gaaaaccaga aggtaacggc ggaactgcaa aaagccatgt cttctgcggt acagcaaaat   1740
gcggatgctt cgcgttttat tctgcgccag agtcgcgcat aa                     1782

SEQ ID NO: 54           moltype = AA   length = 593
FEATURE                 Location/Qualifiers
source                  1..593
                        mol_type = protein
                        organism = Salmonella spp
SEQUENCE: 54
MVNDASSISR SGYTQNPRLA EAAFEGVRKN TDFLKAADKA FKDVVATKAG DLKAGTKSGE    60
SAINTVGLKP PTDAAREKLS SEGQLTLLLG KLMTLLGDVS LSQLESRLAV WQAMIESQKE   120
MGIQVSKEFQ TALGEAQEAT DLYEASIKKT DTAKSVYDAA TKKLTQAQNK LQSLDPADPG   180
YAQAEAAVEQ AGKEATEAKE ALDKATDATV KAGTDAKAKA EKADNILTKF QGTANAASQN   240
QVSQGEQDNL SNVARLTMLM AMFIEIVGKN TEESLQNDLA LFNALQEGRQ AEMEKKSAEF   300
QEETRKAEET NRIMGCIGKV LGALLTIVSV VAAVFTGGAS LALAAVGLAV MVADEIVKAA   360
TGVSFIQQAL NPIMEHVLKP LMELIGKAIT KALEGLGVDK KTAEMAGSIV GAIVAAIAMV   420
AVIVVVAVVG KGAAAKLGNA LSKMMGETIK KLVPNVLKQL AQNGSKLFTQ GMQRITSGLG   480
NVGSKMGLQT NALSKELVGN TLNKVALGME VTNTAAQSAG GVAEGVFIKN ASEALADFML   540
ARFAMDQIQQ WLKQSVEIFG ENQKVTAELQ KAMSSAVQQN ADASRFILRQ SRA          593

SEQ ID NO: 55           moltype = DNA   length = 2817
FEATURE                 Location/Qualifiers
misc_feature            1..2817
                        note = synthetic construct
source                  1..2817
                        mol_type = other DNA
                        organism = synthetic construct
SEQUENCE: 55
atgcttaata ttcaaaatta ttccgcttct cctcatccgg ggatcgttgc cgaacggccg    60
cagactccct cggcgagcga gcacgtcgag actgccgtgg taccgtctac cacagaacat   120
cgcggtacag atatcatttc attatcgcag gcggctacta aaatccacca ggcacagcag   180
acgctgcagt caacgccacc gatctctgaa gagaataatg acgagcgcac gctggcgcgc   240
cagcagttga ccagcagcct gaatgcgctg gcgaagtccg gcgtgtcatt atccgcagaa   300
caaaatgaca acctgcggag cgcgttttct gcgccgacgt cggccttatt tagcgcttcg   360
cctatgcgcg agccgagaac aaccattttct gatgctgaga tttgggatat ggtttcccaa   420
aatatatcgg cgataggtga cagctatctg ggcgtttatg aaaacgttgt cgcagtctat   480
accgattttt atcaggcctt cagtgatatt cttttccaaa tgggaggctg gttattacca   540
ggtaaggacg gtaataccgt taagctagat gttacctcac tcaaaaatga tttaaacagt   600
ttagtcaata aatataatca aataaacagt aataccgttt tatttccagc gcagtcaggc   660
agcggcgtta aagtagccac tgaagcggaa gcgagacagt ggctcagtga attgaattta   720
ccgaatagct gcctgaaatc ttatggatcc ggttatgtcg tcaccgttga tctgacgcca   780
ttacaaaaaa tggttcagga tattgatggt ttaggcgcc cggaaaaga ctcaaaactc   840
gaaatggata acgccaaata tcaagcctgg cagtcgggtt ttaaagcgca ggaagaaaat   900
atgaaaacca cattcagac gctgacgcaa aaatatagca atgccaattc attgtacgac   960
aacctggtaa aagtgctgag cagtacgata agtagcagcc tggaaccgc aaaagcttc   1020
ctgcaaggag tcgacatggt aaatgacgca agtagcatta gccgtagcgg atataccgaa   1080
aatccgcgcc tcgctgaggc ggcttttgaa ggcgttcgta agaacacgga cttttttaaa   1140
gcggcggata agcttttaa agatgtggtg caacgaaag cgggcgacct taaagccgga   1200
acaaagtccg gcgagagcgc tattaatacg gtgggtctaa agccgcctac ggacgccgcc   1260
cgggaaaaac tctccagcga agggcaattg acattactga ttggcaagtt aatgaccgta   1320
ctgggcgatg tttcgctgtc tcaactggag tctcgtctgg cggtatggca ggcgatgatt   1380
gagtcacaaa aagagatggg gattcaggta tcgaaagaat tccagacggc tctgggagag   1440
gctcaggagg cgacggatct ctatgaagcc agtatcaaaa agacggatac cgccaagagt   1500
gtttatgacg ctgcgaccaa aaaactgacg caggcgcaaa ataaattgca atcgctggac   1560
ccggctgaca ccggctatgc acaagctgaa gccgcggtag aacagtccgga aaagaagcg   1620
acagaggcga aagaggcctt agataaggcc acggatgcga cggttaaagc aggcacagac   1680
gccaaagcga aagccgagaa agcggataac attctgacca aattcagggg aacggctaat   1740
gccgcctctc agaatcaggt ttcccagggt gagcaggata atctgtcaaa tgtcgcccgc   1800
ctcactatgc tcatggccat gtttattgag attgtgggca aaatacgga agaaagcctg   1860
caaaacgatc ttgcgctttt caacgccttg caggaaggc gtcaggcgga tgggaaaag   1920
aaatcggctg aattccagga agagacgcgc aaagccgagg aaacgaaccg cattatggga   1980
tgtatcggga agtcctcgg cgcgctgcta accattgtca gcgttgtggc cgctgttttt   2040
accggtgggg cgagtctggc gctggctgcg gtgggacttg cggtaatggt ggccgatgaa   2100
attgtgaagg cggcgacggg agtgtcgttt attcagcagg cgctaaaccc gattatggag   2160
catgtgctga gccgttaat ggagctgatt ggcaaggcga ttaccaaagc gctgaaggga   2220
ttaggcgtcg ataagaaaac ggcagagatg gccggcagca ttgttggtgc gattgtcgcc   2280
gctattgcca tggtggcggt cattgtggtg gtcgcagttg tcgggaaagg cgcggcggcg   2340
aaactgggta acgcgctgag caaaatgatg ggcgaaacga ttaagaagtt ggtgcctaac   2400
gtgctgaaac agttggcgca aaacggcagc aaactctttta cccaggggat gcaacgtatt   2460
actagcggtc tgggtaatgt gggtagcaag atgggcctgc aaacgaatgc cttaagtaaa   2520
```

```
gagctggtag gtaatacccct aaataaagtg gcgttgggca tggaagtcac gaataccgca  2580
gcccagtcag ccggtggtgt tgccgagggc gtatttatta aaaatgccag cgaggcgctt  2640
gctgatttta tgctcgcccg ttttgccatg gatcagattc agcagtggct taaacaatcc  2700
gtagaaatat ttggtgaaaa ccagaaggta acggcggaac tgcaaaaagc catgtcttct  2760
gcggtacagc aaaatgcgga tgcttcgcgt tttattctgc gccagagtcg cgcataa     2817

SEQ ID NO: 56          moltype = AA  length = 938
FEATURE                Location/Qualifiers
REGION                 1..938
                       note = synthetic construct
source                 1..938
                       mol_type = protein
                       organism = synthetic construct
SEQUENCE: 56
MLNIQNYSAS PHPGIVAERP QTPSASEHVE TAVVPSTTEH RGTDIISLSQ AATKIHQAQQ   60
TLQSTPPISE ENNDERTLAR QQLTSSLNAL AKSGVSLSAE QNENLRSAFS APTSALFSAS  120
PMAQPRTTIS DAEIWDMVSQ NISAIGDSYL GVYENVVAVY TDFYQAFSDI LSKMGGWLLP  180
GKDGNTVKLD VTSLKNDLNS LVNKYNQINS NTVLFPAQSG SGVKVATEAE ARQWLSELNL  240
PNSCLKSYGS GYVVTVDLTP LQKMVQDIDG LGAPGKDSKL EMDNAKYQAW QSGFKAQEEN  300
MKTTLQTLTQ KYSNANSLYD NLVKVLSSTI SSSLETAKSF LQGVDMVNDA SSISRSGYTQ  360
NPRLAEAAFE GVRKNTDFLK AADKAFKDVV ATKAGDLKAG TKSGESAINT VGLKPPTDAA  420
REKLSSEGQL TLLLGKLMTL LGDVSLSQLE SRLAVWQAMI ESQKEMGIQV SKEFQTALGE  480
AQEATDLYEA SIKKTDTAKS VYDAATKKLT QAQNKLQSLD PADPGYAQAE AAVEQAGKEA  540
TEAKEALDKA TDATVKAGTD AKAKAEKADN ILTKFQGTAN AASQNQVSQG EQDNLSNVAR  600
LTMLMAMFIE IVGKNTEESL QNDLALFNAL QEGRQAEMEK KSAEFQEETR KAEETNRIMG  660
CIGKVLGALL TIVSVVAAVF TGGASLALAA VGLAVMVADE IVKAATGVSF IQQALNPIME  720
HVLKPLMELI GKAITKALEG LGVDKKTAEM AGSIVGAIVA AIAMVAVIVV VAVVGKAAA   780
KLGNALSKMM GETIKKLVPN VLKQLAQNGS KLFTQGMQRI TSGLGNVGSK MGLQTNALSK  840
ELVGNTLNKV ALGMEVTNTA AQSAGGVAEG VFIKNASEAL ADFMLARFAM DQIQQWLKQS  900
VEIFGENQKV TAELQKAMSS AVQQNADASR FILRQSRA                         938

SEQ ID NO: 57          moltype = DNA  length = 3423
FEATURE                Location/Qualifiers
misc_feature           1..3423
                       note = synthetic construct
source                 1..3423
                       mol_type = other DNA
                       organism = synthetic construct
SEQUENCE: 57
catatggaca atggcgatcg tttataccgt gccgactcgc gtcccccaga tgagattaaa   60
cgtagcggtg ggttaatgcc acgtgggcac aatgagtatt ttgaccgtgg aacacagatg  120
aacattaacc tttacgatca tgcccgtggg acccagaccg gtttgtccg ttatgatgac   180
gggtatgtta gtacgagttt gtccttacgc tccgcacacg ttgcgggaca agtattta    240
tcaggctaca gcacatatta catttatgtg atcgccactg ccccaaacat gttcaatgtg  300
aacgatgtgt tggggtttta cagccccccat ccatatgaac aagaagtctc ggcccttggg  360
gggatcccat atagccagat ttatggttgg taccgcgtaa attttggtgt gattgatgaa  420
cgtttgcatc gtaaccgtga gtaaccgat cgctactacc gtaacttgaa cattgcacct    480
gccgaggacg gctatcgttt agcgggattc ccaccgatc atcaggcgtg gcgtgaggaa  540
ccgtggatcc atcacgcccc tcagggggtgc gggaacagta gtcgcgggtc cgcggcatcc  600
atgcttaata ttcaaaatta ttccgcttct cctcatccgg ggatcgttgc cgaacggccg  660
cagactccct cggcgagcga gcacgtcgag actgccgtgg taccgtctac cacagaaact  720
cgcggtacag atatcatttc attatcgcag gcgctactaa aaatccacca ggcacagcag  780
acgctgcagt caacgccacc gatctctgaa gagaataatg acgagcgcac gctggcgcgc  840
cagcagttga ccagcagcct gaatgcgctg gcgaagtccg gcgtgtcatt atccgcagaa  900
caaaatgcgg acctgcggag cgcgtttttc tgcgccgacgt cggccttatt tagcgcttcg  960
cctatggcgc agccgagaac aaccattct gatgctgcaga tttgggatat ggtttcccaa  1020
aatatatcgg cgataggtga cagctatctg ggcgtttatg aaaacgttgt cgcagtctat  1080
accgattttt atcaggcctt cagtgatatt ctttccaaaa tgggaggctg gttattacca  1140
ggtaaggacg gtaataccgt taagctagat gttacctcac tcaaaaatga tttaaacagt  1200
ttagtcaata aatataatca aataaacagt aataccgttt tatttccagc gcagtcaggc  1260
agcggcgtta agtagccac tgaagcggaa gcgagacagt ggctcagtga attgaattta  1320
ccgaatagct gcctgaaatc ttatggatcc ggttatgtcg tcaccgttga tctgacgcca  1380
ttacaaaaaa tggttcagga tattgatggt ttaggcgcgc cggaaaaga ctcaaaactc  1440
gaaatggata acgccaaata tcaagcctgg cagtcggtt ttaaagcgca aggaaaat    1500
atgaaaacca cattcagac gctgacgcaa aaatatagca atgccaattc attgtacgac  1560
aacctggtaa aagtgctgag cagtacgata gtagcagcc tggaaccgc caaaagcttc   1620
ctgcaaggag tcgacatggt aaatgacgca agtagcatta gccgtagcgg atatacccaa  1680
aatccgcgcc tcgctgaggc ggcttttgaa ggcgttcgta agaacacgga cttttttaaa  1740
gcggcggata aagcttttaa agatgtggtg caacgaaag cgggcgacct taagcggaa    1800
acaaagtccg gcgagagcgc tattaatacg gtgggtctaa agccgcctac ggacgccgcc  1860
cgggaaaaac tctccagcga agggcaattg acattactgc ttggcaagtt aatgaccct    1920
ctgggcgatg tttcgctgtc tcaactggag tctcgtctgg cggtatgcca ggcgatgatt  1980
gagtcacaaa aagagatggg gattcaggta tcgaaagaat tccagacggc tctgggagag  2040
gctcaggagg cgacggatct ctatgaagcc agtatcaaaa agacggatac cgccaagagt  2100
gtttatgacg ctgcgaccaa aaaactgacg caggcgcaaa ataaaattgca atcgctggac  2160
ccggctgacc ccggctatgc acaagctgaa gccgcggtag aacaggccgg aaaagaagcg  2220
acagaggcga aagaggcctt agataaggcc acggatgcga cggttaaagc aggcacagac  2280
gccaaagcga agccgagaa agcggataac attctgacca aattcagggg aacggctaat  2340
gccgcctctc agaatcaggt ttcccagggt gagcaggata atctgtcaaa tgtcgcccgc  2400
```

```
ctcactatgc tcatggccat gtttattgag attgtgggca aaaatacgga agaaagcctg  2460
caaaacgatc ttgcgctttt caacgccttg caggaagggc gtcaggcgga gatgaaaag   2520
aaatcggctg aattccagga agagacgcgc aaagccgagg aaacgaaccg cattatggga  2580
tgtatcggga aagtcctcgg cgcgctgcta accattgtca gcgttgtggc cgctgttttt  2640
accggtgggg cgagtctggc gctggtgcg gtgggacttg cggtaatgat ggccgatgaa   2700
attgtgaagg cggcgacggg agtgtcgttt attcagcagg cgctaaaccc gattatggag  2760
catgtgctga agccgttaat ggagctgatt ggcaaggcga ttaccaaagc gctgaagga   2820
ttaggcgtcg ataagaaaac ggcagagatg gccggcagca ttgttggtgc gattgtcgcc  2880
gctattgcca tggtggcggt cattgtggtg gtcgcagttg tcgggaaagg cgcggcggcg  2940
aaactgggta acgcgctgag caaaatgatg ggcaaacga ttaagaagtt ggtgcctaac   3000
gtgctgaaac agttggcgca aaacggcagc aaactcttta cccaggggat gcaacgtatt  3060
actagcggtc tgggtaatgt gggtagcaag atgggcctgc aaacgaatgc cttaagtaaa  3120
gagctggtag gtaatacccct aaataaagtg gcgttgggca tggaagtcac gaataccgca  3180
gcccagtcag ccggtggtgt tgccgagggc gtatttatta aaatgccag cgaggcgctt   3240
gctgattta tgctcgcccg ttttgccatg gatcagattc agcagtggct taaacaatcc    3300
gtagaaatat ttggtgaaaa ccagaaggta acggcgaaac tgcaaaaagc catgtcttct   3360
gcggtacagc aaaatgcgga tgcttcgcgt tttattctgc gccagagtcg cgcataactc   3420
gag                                                                3423

SEQ ID NO: 58           moltype = AA   length = 1137
FEATURE                 Location/Qualifiers
REGION                  1..1137
                        note = synthetic construct
source                  1..1137
                        mol_type = protein
                        organism = synthetic construct
SEQUENCE: 58
MDNGDRLYRA DSRPPDEIKR SGGLMPRGHN EYFDRGTQMN INLYDHARGT QTGFVRYDDG   60
YVSTSLSLRS AHLAGQSILS GYSTYYIYVI ATAPNMFNVN DVLGVYSPHP YEQEVSALGG  120
IPYSQIYGWY RVNFGVIDER LHRNREYRDR YYRNLNIAPA EDGYRLAGFP PDHQAWREEP  180
WIHHAPQGCG NSSRGSAASM LNIQNYSASP HPGIVAERPQ TPSASEHVET AVVPSTTEHR  240
GTDIISLSQA ATKIHQAQQT LQSTPPISEE NNDERTLARQ QLTSSLNALA KSGVSLSAEQ  300
NENLRSAFSA PTSALFSASP MAQPRTTISD AEIWDMVSQN ISAIGDSYLG VYENVVAVYT  360
DFYQAFSDIL SKMGGWLLPG KDGNTVKLDV TSLKNDLNSL VNKYNQINSN TVLFPAQSGS  420
GVKVATEAEA RQWLSELNLP NSCLKSYGSG YVVTVDLTPL QKMVQDIDGL GAPGKDSKLE  480
MDNAKYQAWQ SGFKAQEENM KTTLQTLTQK YSNANSLYDN LVKVLSSTIS SSLETAKSFL  540
QGVDMVNDAS SISRSGYTQN PRLAEAAFEG VRKNTDFLKA ADKAFKDVVA TKAGDLKAGT  600
KSGESAINTV GLKPPTDAAR EKLSSEGQLT LLLGKLMTLL GDVSLSQLES RLAVWQAMIE  660
SQKEMGIQVS KEFQTALGEA QEATDLYEAS IKKTDTAKSV YDAATKKLTQ AQNKLQSLDP  720
ADPGYAQAEA AVEQAGKEAT EAKEALDKAT DATVKAGTDA KAKAEKADNI LTKFQGTANA  780
ASQNQVSQGE QDNLSNVARL TMLMAMFIEI VGKNTEESLQ NDLALFNALQ EGRQAEMEKK  840
SAEFQEETRK AEETNRIMGC IGKVLGALLT IVSVVAAVFT GGASLALAAV GLAVMVDAEI  900
VKAATGVSFI QQALNPIMEH VLKPLMELIG KAITKALEGL GVDKKTAEMA GSIVGAIVAA  960
IAMVAVIVVV AVVGKGAAAK LGNALSKMMG ETIKKLVPNV LKQLAQNGSK LFTQGMQRIT 1020
SGLGNVGSKM GLQTNALSKE LVGNTLNKVA LGMEVTNTAA QSAGGVAEGV FIKNASEALA 1080
DFMLARFAMD QIQQWLKQSV EIFGENQKVT AELQKAMSSA VQQNADASRF ILRQSRA    1137

SEQ ID NO: 59           moltype = DNA   length = 522
FEATURE                 Location/Qualifiers
misc_feature            1..522
                        note = synthetic construct
source                  1..522
                        mol_type = other DNA
                        organism = synthetic construct
SEQUENCE: 59
atgggcagca gccatcacca tcatcaccac agccaggatc cgatgaaaaa agacccgacc   60
ctacaacagg cacatgacac gatgcggttt ttccggcgtg gcggctcgct gcgtatgttg  120
ttggatgacg atgttacaca gccgttaat actctgtatc gctatgccac gcagcttatg  180
gaggtaaaag aattcgccgg cgcagcgcga ctttttcaat tgcagctgct gacgatatat  240
tggtcatttg actactggtt tcggttaggg gaatgctgcc aggctcaaaa acattggggg  300
gaagcgatat acgcttatgg acgcgcggca caaattaaga ttgatgcgcc gcaggcgcca  360
tgggccgcag cggaatgcta tctcgcgtgt gataacgtct gttatgcaat caaagcgtta  420
aaggccgtgt gcgtatttg cggcgaggtc agtgaacatc aaattctccg acagcgtgca  480
gaaaagatgt tacagcaact ttctgacagg agctaaaagc tt                    522

SEQ ID NO: 60           moltype = AA   length = 171
FEATURE                 Location/Qualifiers
REGION                  1..171
                        note = synthetic construct
source                  1..171
                        mol_type = protein
                        organism = synthetic construct
SEQUENCE: 60
MGSSHHHHHH SQDPMKKDPT LQQAHDTMRF FRRGGSLRML LDDDVTQPLN TLYRYATQLM   60
EVKEFAGAAR LFQLLTIYDA WSFDYWFRLG ECCQAQKHWG EAIYAYGRAA QIKIDAPQAP  120
WAAAECYLAC DNVCYAIKAL KAVVRICGEV SEHQILRQRA EKMLQQLSDR S          171

SEQ ID NO: 61           moltype = DNA   length = 588
FEATURE                 Location/Qualifiers
```

| | | |
|---|---|---|
| source | 1..588 | |
| | mol_type = genomic DNA | |
| | organism = Salmonella spp | |

SEQUENCE: 61

```
atgtcttcag gaaacatctt atggggaagt caaaaccta ttgtgtttaa aaatagcttc    60
ggcgtcagca acgctgatac cgggagccag gatgacttat cccagcaaaa tccgtttgcc   120
gaagggtatg gtgttttgct tattctcctt atggttattc aggctatcgc aaataataaa   180
tttattgaag tccagaagaa cgctgaacgt gccagaaata cccaggaaaa gtcaaatgag   240
atggatgagg tgattgctaa agcagccaaa ggggatgcta aaaccaaaga ggaggtgcct   300
gaggatgtaa ttaaatacat gcgtgataat ggtattctca tcgatggtat gaccattgat   360
gattatatgg ctaaatatgg cgatcatggg aagctggata aagtggcct acaggcgatc   420
aaagcggctt tggataatga cgccaaccgg aataccgatc ttatgagtca ggggcagata   480
acaattcaaa aaatgtctca ggagcttaac gctgtcctta cccaactgac agggcttatc   540
agtaagtggg gggaaatttc cagtatgata gcgcagaaaa cgtactca                588
```

| | | |
|---|---|---|
| SEQ ID NO: 62 | moltype = AA length = 196 | |
| FEATURE | Location/Qualifiers | |
| source | 1..196 | |
| | mol_type = protein | |
| | organism = Salmonella spp | |

SEQUENCE: 62

```
MSSGNILWGS QNPIVFKNSF GVSNADTGSQ DDLSQQNPFA EGYGVLLILL MVIQAIANNK    60
FIEVQKNAER ARNTQEKSNE MDEVIAKAAK GDAKTKEEVP EDVIKYMRDN GILIDGMTID   120
DYMAKYGDHG KLDKGGLQAI KAALDNDANR NTDLMSQGQI TIQKMSQELN AVLTQLTGLI   180
SKWGEISSMI AQKTYS                                                  196
```

| | | |
|---|---|---|
| SEQ ID NO: 63 | moltype = DNA length = 1455 | |
| FEATURE | Location/Qualifiers | |
| source | 1..1455 | |
| | mol_type = genomic DNA | |
| | organism = Salmonella spp | |

SEQUENCE: 63

```
atgaatcgaa ttcacagtaa tagcgacagc gccgcaggag taaccgcctt aacacatcat    60
cacttaagca atgtcagttg cgtttcctcg ggttcgctgg aaagcgcca gcatcgtgtg   120
aattctactt ttggcgatgg caacgccgcg tgtctgctat ccgggaaaat tagtcttcag   180
gaggcaagca atgcgttgaa gcaactgctt gatgccgtac ccggaaatca taagcgtcca   240
tcattgcctg actttttgca gaccaatccc gcggttttat caatgatgat gacgtcatta   300
atactcaacg tctttggtaa taacgctcaa tcgttatgag aacagcttga gcgggcaact   360
gaggtgcaaa atgcattacg taataagcag gtaaaggagt atcaggagca gatccagaaa   420
gcgatagagc aggaggataa agcgcgtaaa gcgggtattt ttggcgctat ttttgactgg   480
attaccggca tatttgaaac cgtgattggc gccttaaaag ttgtgaagg ttttctgtcc   540
ggaaatcccg cagaaatggc tagcggcgta gcttatatgg ccgcaggttg tgcaggaatg   600
gttaaagccg gagccgaaac ggcaatgatg tgcggtgctg accacgatac ctgtcaggca   660
attattgacg tgacaagtaa gattcaattt ggttgtgaag ccgtcgcgct ggcactggat   720
gttttccaga ttggccgtgc ttttatggcg acgagaggtt tatctggcgc agctgcaaaa   780
gtgcttgact ccggtttggg cgaggaagtg gttgagcgta tggtaggtgc aggggaagca   840
gaaatagagg agttggctga aaagtttggc gaagaagtga gcgaaagttt ttccaaacaa   900
tttgagccgc ttgaacgtga aatggctatg gcgaatgaga tggcagagga ggctgccgag   960
ttttctcgta acgtagaaaa taatatgacg cgaagcgcgg gaaaaagctt tacgaaagag  1020
ggggtgaaaa caatggcaaa agaagcggca aagaagcccc tggaaaaatg tgtgcaagaa  1080
ggtggaaagt tcctgttaaa aaaattccgt aataaagttc tcttcaatat gttcaaaaaa  1140
atcctgtatg ccttactgag ggattgttca tttaaaggct acaggctat cagatgtgca  1200
accgagggcg ccagtcagat gaatactggc atggttaaca cagaaaaagc gaagatcgaa  1260
aagaaaaatag agcaattaat aactcagcaa cggtttctgg atttcataat gcaacaaaca  1320
gaaaaccaga aaaagataga acaaaaacgc ttagaggagc tttataaggg gagcggtgcc  1380
gcgcttagag atgtattaga taccattgat cactatagta gcgttcaggc gagaatagct  1440
ggctatcgcg cttaa                                                  1455
```

| | | |
|---|---|---|
| SEQ ID NO: 64 | moltype = AA length = 484 | |
| FEATURE | Location/Qualifiers | |
| source | 1..484 | |
| | mol_type = protein | |
| | organism = Salmonella spp | |

SEQUENCE: 64

```
MNRIHSNSDS AAGVTALTHH HLSNVSCVSS GSLGKRQHRV NSTFGDGNAA CLLSGKISLQ    60
EASNALKQLL DAVPGNHKRP SLPDFLQTNP AVLSMMMTSL ILNVFGNNAQ SLCQQLERAT   120
EVQNALRNKQ VKEYQEQIQK AIEQEDKARK AGIFGAIFDW ITGIFETVIG ALKVVEGFLS   180
GNPAEMASGV AYMAAGCAGM VKAGAETAMM CGADHDTCQA IIDVTSKIQF GCEAVALALD   240
VFQIGRAFMA TRGLSGAAAK VLDSGFGEEV VERMVGAGEA EIEELAEKFG EEVSESFSKQ   300
FEPLEREMAM ANEMAEEAAE FSRNVENNMT RSAGKSFTKE GVKAMAKEAA KEALEKCVQE   360
GGKFLLKKFR NKVLFNMFKK ILYALLRDCS FKGLQAIRCA TEGASQMNTG MVNTEKAKIE   420
KKIEQLITQQ RFLDFIMQQT ENQKKIEQKR LEELYKGSGA ALRDVLDTID HYSSVQARIA   480
GYRA                                                                484
```

| | | |
|---|---|---|
| SEQ ID NO: 65 | moltype = DNA length = 2049 | |
| FEATURE | Location/Qualifiers | |
| misc_feature | 1..2049 | |
| | note = synthetic construct | |
| source | 1..2049 | |

```
                        mol_type = other DNA
                        organism = synthetic construct
SEQUENCE: 65
atgtcttcag gaaacatctt atggggaagt caaaaccccta ttgtgtttaa aaatagcttc    60
ggcgtcagca acgctgatac cgggagccag gatgacttat cccagcaaaa tccgtttgcc   120
gaagggtatg gtgttttgct tattctcctt atggttattc aggctatcgc aaataataaa   180
tttattgaag tccagaagaa cgctgaacgt gccagaaata cccaggaaaa gtcaaatgag   240
atggatgagg tgattgctaa agcagccaaa ggggatgcta aaaccaaaga ggaggtgcct   300
gaggatgtaa ttaaatacat gcgtgataat ggtattctca tcgatggtat gaccattgat   360
gattatatgg ctaaatatgg cgatcatggg aagctggata aaggtggcct acaggcgatc   420
aaagcggctt tggataatga cgccaaccgg aataccgatc ttatgagtca ggggcagata   480
acaattcaaa aaatgtctca ggagcttaac gctgtcctta cccaactgac agggcttatc   540
agtaagtggg gggaaatttc cagtatgata gcgcagaaaa cgtactcaga gctcatgaat   600
cgaattcaca gtaatagcga cagcgccgca ggagtaaccg cctaacaca tcatcactta   660
agcaatgtca gttgcgtttc ctcgggttcg ctgggaaagc gccagcatcg tgtgaattct   720
acttttggcg atggcaacgc cgcgtgtctg ctatccggga aaattagtct tcaggaggca   780
agcaatgcgt tgaagcaact gcttgatgcc gtacccggaa atcataagcg tccatcattg   840
cctgactttt tgcagaccaa tcccgcggtt ttatcaatga tgactgtc attaatactc   900
aacgtctttg gtaataacgc tcaatcgtta tgccaacagc ttgagcgggc aactgaggtg   960
caaaatgcat acgtaataa gcaggtaaag gagtatcagg agcagatcca aaagcgata   1020
gagcaggagg ataaagcgcg taaagcgggt atttttggcg ctatttttga ctggattacc  1080
ggcatatttg aaaccgtgat tggcgcctta aaagttgtgg aaggttttc gtccggaaat  1140
cccgcagaaa tggctagcgg cgtagcttat atggccgcag gttgtgcagg aatggttaaa  1200
gccgagccga aaacgcaat gatgtgcggt gctgaccacg ataccgtca ggcaattatt  1260
gacgtgacaa gtaagattca atttggttgt gaagccgtcg cgctggcact ggatgttttc  1320
cagattggcc gtgcttttat ggcgacgaga ggtttatctg gcgcagctgc aaaagtgctt  1380
gactccggtt ttggcgagga agtggttgag cgtatggtag gtcagggga agcagaaata  1440
gaggagttgg ctgaaaagtt tggcgaagaa gtgagcgaaa gttttccaa acaatttgag  1500
ccgcttgaac gtgaaatggc tatggcgaat gagatgcag aggaggctgc cgagttttct  1560
cgtaacgtag aaaataatat gacgcgaagc gcgggaaaa gctttacgaa agagggggtg  1620
aaagcaatgg caaaagaagc ggcaaaagaa gccctgaaa atgtgtgca agaaggtgga  1680
aagttcctgt taaaaaaatt ccgtaataaa gttctcttca atatgttcaa aaaaatcctg  1740
tatgccttac tgagggattg ttcatttaaa ggcttacagg ctatcagatg tgcaaccgag  1800
ggcgccagtc agatgaatac tggcatggtt aacacagaaa aagcgaagat cgaaaagaat  1860
atagagcaat taataactca gcaacggttt ctggatttca taatgcaaca aacagaaaac  1920
cagaaaaaga tagaacaaaa acgcttgag gagctttata aggggagcgg tgccgcgctt  1980
agagatgtat tagataccat tgatcactat agtagcgttc aggcgagaat agctggctat  2040
cgcgcttaa                                                          2049

SEQ ID NO: 66           moltype = AA  length = 682
FEATURE                 Location/Qualifiers
REGION                  1..682
                        note = synthetic construct
source                  1..682
                        mol_type = protein
                        organism = synthetic construct
SEQUENCE: 66
MSSGNILWGS QNPIVFKNSF GVSNADTGSQ DDLSQQNPFA EGYGVLLILL MVIQAIANNK    60
FIEVQKNAER ARNTQEKSNE MDEVIAKAAK GDAKTKEEVP EDVIKYMRDN GILIDGMTID   120
DYMAKYGDHG KLDKGGLQAI KAALDNDANR NTDLMSQGQI TIQKMSQELN AVLTQLTGLI   180
SKWGEISSMI AQKTYSELMN RIHSNSDSAA GVTALTHHHL SNVSCVSSGS LGKRQHRVNS   240
TFGDGNAACL LSGKISLQEA SNALKQLLDA VPGNHKRPSL PDFLQTNPAV LSMMMTSLIL   300
NVFGNNAQSL CQQLERATEV QNALRNKQVK EYQEQIQKAI EQEDKARKAG IFGAIFDWIT   360
GIFETVIGAL KVVEGFLSGN PAEMASGVAY MAAGCAGMVK AGAETAMMCG ADHDTCQAII   420
DVTSKIQFGC EAVALALDVF QIGRAFMATR GLSGAAAKVL DSGFGEEVVE RMVGAGEAEI   480
EELAEKFGEE VSESFSKQFE PLEREMAMAN EMAEEAAEFS RNVENNMTRS AGKSFTKEGV   540
KAMAKEEAKE ALEKCVQEGG KFLLKKFRNK VLFNMFKKIL YALLRDCSFK GLQAIRCATE   600
GASQMNTGMV NTEKAKIEKK IEQLITQQRF LDFIMQQTEN QKKIEQKRLE ELYKGSGAAL   660
RDVLDTIDHY SSVQARIAGY RA                                             682

SEQ ID NO: 67           moltype = DNA  length = 2655
FEATURE                 Location/Qualifiers
misc_feature            1..2655
                        note = synthetic construct
source                  1..2655
                        mol_type = other DNA
                        organism = synthetic construct
SEQUENCE: 67
catatggaca atggcgatcg tttataccgt gccgactcgc gtcccccaga tgagattaaa    60
cgtagcggtg ggtaatgcc acgtgggcac aatgagtatt tgaccgtgg aacacagatg   120
aacattaacc tttacgatca tgcccgtggg acccagaccg gtttgtccg ttatgatgac   180
gggtatgtta gtacgagttt gtccttacgc tccgcacacc ttgcgggaca agtatttta   240
tcaggctaca gcacatatta catttatgtg atcgccactg ccccaaacat gttcaatgtg   300
aacgctgtg tgggggttta cagccccca ccatatgaac aagaagttc ggcccttggg   360
gggatcccat atagccagat ttatggttgg taccgcgtaa attttggtgt gattgatgag   420
cgtttgcatc gtaaccgtga ataccgcgat cgctactacc gtaacttgaa cattgcacct   480
gccgaggacg ctatcgtttt agcgggattc ccacccgatc atcaggcgtg gcgtgaggaa   540
ccgtggatcc atcacgcccc tcagggtgc gggaacagta gtcgcgggtc gcggcatcc   600
atgtcttcag gaaacatctt atggggaagt caaaaccccta ttgtgtttaa aaatagcttc   660
```

```
ggcgtcagca acgctgatac cgggagccag gatgacttat cccagcaaaa tccgtttgcc    720
gaagggtatg gtgttttgct tattctcctt atggttattc aggctatcgc aaataataaa    780
tttattgaag tccagaagaa cgctgaacgt gccagaaata cccaggaaaa gtcaaatgag    840
atggatgagg tgattgctaa agcagccaaa ggggatgcta aaaccaaaga ggaggtgcct    900
gaggatgtaa ttaaatacat gcgtgataat ggtattctca tcgatggtat gaccattgat    960
gattatatgg ctaaatatgg cgatcatggg aagctggata aaggtggcct acaggcgatc   1020
aaagcggctt tggataatga cgccaaccgg aataccgatc ttatgagtca ggggcagata   1080
acaattcaaa aaatgtctca ggagcttaac gctgtcctta cccaactgac agggcttatc   1140
agtaagtggg gggaaatttc cagtatgata gcgcagaaaa cgtactcaga gctcatgaat   1200
cgaattcaca gtaatagcga cagcgccgca ggagtaaccg ccttaacaca tcatcactta   1260
agcaatgtca gttgcgtttc ctcggggtcg ctgggaaagc gccagcatcg tgtgaattct   1320
acttttggcg atggcaacgc cgcgtgtctg ctatccggga aaattagtct tcaggaggca   1380
agcaatgcgt tgaagcaact gcttgatgcc gtacccggaa atcataagcg tccatcattg   1440
cctgactttt tgcagaccaa tcccgcggtt ttatcaatga tgatgacgtc attaatactc   1500
aacgtctttg gtaataacgc tcaatcgtta tgccaacagc ttgagcgggc aactgaggtg   1560
caaaatgcat tacgtaataa gcaggtaaag gagtatcagg agcagatcca aaagcgata    1620
gagcaggagg ataaagcgcg taaagcgggt atttttggcg ctatttttga ctggattacc   1680
ggcatatttg aaaccgtgat tggcgcctta aaagttgtgg aaggttttct gtccggaaat   1740
cccgcagaaa tggctagcgg cgtagcttat atggccgcag gttgtgcagg aatggttaaa   1800
gccggagccg aaacgcgcaat gatgtgcggt gctgaccacg atacctgtca ggcaattatt   1860
gacgtgacaa gtaagattca atttggttgt gaagccgtcg cgctggcact ggatgttttc   1920
cagattggcc gtgcttttat ggcgacgaga ggtttatctg gcagctgc aaaagtgctt     1980
gactccggtt ttggcgagga agtggttgag cgtatggtag gtgcagggga agcagaaata   2040
gaggagttgg ctgaaaagtt tggcgaagaa gtgagcgaaa gtttttccaa acaatttgag   2100
ccgcttgaac gtgaaatggc tatggcgaat gagatgcag aggaggctgc cgagtttct     2160
cgtaacgtag aaaataatat gacgcgaagc gcgggaaaca gctttacgaa gggggtg      2220
aaagcaatgg caaaagaagc ggcaaaagaa gccctgaaa aatgtgtgca agaaggtgga    2280
aagttcctgt taaaaaaatt ccgtaataaa gttctcttca atatgttcaa aaaaatcctg   2340
tatgccttac tgagggattg ttcatttaaa ggcttacagg ctatcagatg tgcaaccgag   2400
ggcgccagtc agatgaatac tggcatggtt aacacagaaa aagtcgaagat cgaaaagaaa  2460
atagagcaat taataactca gcaacggttt ctggatttca taatgcaaca aacagaaaac   2520
cagaaaaaga tagaacaaaa acgcttagag gagctttata aggggagcgg tgccgcgctt   2580
agagatgtat tagataccat tgatcactat agtagcgttc aggcgagaat agctggctat   2640
cgcgcttaac tcgag                                                    2655

SEQ ID NO: 68           moltype = AA  length = 881
FEATURE                 Location/Qualifiers
REGION                  1..881
                        note = synthetic construct
source                  1..881
                        mol_type = protein
                        organism = synthetic construct
SEQUENCE: 68
MDNGDRLYRA DSRPPDEIKR SGGLMPRGHN EYFDRGTQMN INLYDHARGT QTGFVRYDDG     60
YVSTSLSLRS AHLAGQSILS GYSTYYIYVI ATAPNMFNVN DVLGVYSPHP YEQEVSALGG    120
IPYSQIYGWY RVNFGVIDER LHRNREYRDR YYRNLNIAPA EDGYRLAGFP PDHQAWREEP   180
WIHHAPQGCG NSSRGSAASM SSGNILWGSQ NPIVFKNSFG VSNADTGSQD DLSQQNPFAE   240
GYGVLLILLM VIQAIANNKF IEVQKNAERA RNTQEKSNEM DEVIAKAAKG DAKTKEEVPE   300
DVIKYMRDNG ILIDGMTIDD YMAKYGDHGK LDKGGLQAIK AALDNDANRN TDLMSQGQIT   360
IQKMSQELNA VLTQLTGLIS KWGEISSMIA QKTYSELMNR IHSNSDSAAG VTALTHHHLS   420
NVSCVSSGSL GKRQHRVNST FGDGNAACLL SGKISLQEAS NALKQLLDAV PGNHKRPSLP   480
DFLQTNPAVL SMMMTSLILN VFGNNAQSLC QQLERATEVQ NALRNKQVKE YQEQIQKAIE   540
QEDKARKAGI FGAIFDWITG IFETVIGALK VVEGFLSGNP AEMASGVAYM AAGCAGMVKA   600
GAETAMMCGA DHDTCQAIID VTSKIQFGCE AVALALDVFQ IGRAFMATRG LSGAAAKVLD   660
SGFGEEVVER MVGAGEAEIE ELAEKFGEEV SESFSKQFEP LEREMAMANE MAEEAAEFSR   720
NVENNMTRSA GKSFTKEGVK AMAKEAAKEA LEKCVQEGGK FLLKKFRNKV LFNMFKKILY   780
ALLRDCSFKG LQAIRCATEG ASQMNTGMVN TEKAKIEKKI EQLITQQRFL DFIMQQTENQ   840
KKIEQKRLEE LYKGSGAALR DVLDTIDHYS SVQARIAGYR A                       881

SEQ ID NO: 69           moltype = DNA  length = 1254
FEATURE                 Location/Qualifiers
misc_feature            1..1254
                        note = synthetic construct
source                  1..1254
                        mol_type = other DNA
                        organism = synthetic construct
SEQUENCE: 69
atgggcagca gccatcatca tcatcatcac agcagcggcc tggtgccgcg cggcagccat     60
atggacaatg gcgatcgttt ataccgtgcc gactcgcgtc ccccagatga gattaaacgt    120
agcggtgggt taatgccacg tgggcacaat gagtattttg accgtggaac acagatgaac    180
attaaccttt acgatcatgc ccgtgggacc cagacccggg ttgtccgtta tgatgacggg    240
tatgttagta cgagtttgtc cttacgctcc gcacaccttg cgggacaaag tatttttatca   300
ggctacagca catattacat ttatgtgatc gccactgccc caaacatgtt caatgtgaac    360
gatgtgttgg gggtttacag cccccatcca tatgaacaag aagtctcgac ccttgggggg   420
atcccatata gccagattta tggttggtac cgcgtaaatt ttggtgtgat tgatgaacgt    480
ttgcatcgta accgtgaata ccgcgatcgc tactaccgta acttgaacat tgcacctgcc    540
gaggacggct atcgtttagc gggattccca cccgatcatc aggcgtggcg tgaggaaccg    600
tggatccatc acgcccctca ggggtgcggg aacagtagtc gcgggtccgc ggcatccatg    660
tcttcaggaa acatcttatg gggaagtcaa aaccctattg tgtttaaaaa tagcttcggc    720
```

```
gtcagcaacg ctgataccgg gagccaggat gacttatccc agcaaaatcc gtttgccgaa    780
gggtatggtg ttttgcttat tctccttatg gttattcagg ctatcgcaaa taataaattt    840
attgaagtcc agaagaacgc tgaacgtgcc agaaataccc aggaaaagtc aaatgagatg    900
gatgaggtga ttgctaaagc agccaaaggg gatgctaaaa ccaagagga ggtgcctgag     960
gatgtaatta aatacatgcg tgataatggt attctcatcg atggtatgac cattgatgat   1020
tatatggcta aatatggcga tcatgggaag ctggataaag gtggcctaca ggcgatcaaa   1080
gcggctttgg ataatgacgc caaccggaat accgatctta tgagtcaggg gcagataaca   1140
attcaaaaaa tgtctcagga gcttaacgct gtccttaccc aactgacagg cttatcagt    1200
aagtggggggg aaatttccag tatgatagcg cagaaaacgt actcataagg atcc          1254
```

SEQ ID NO: 70        moltype = AA   length = 415
FEATURE              Location/Qualifiers
REGION               1..415
                     note = synthetic construct
source               1..415
                     mol_type = protein
                     organism = synthetic construct
SEQUENCE: 70
MGSSHHHHHH SSGLVPRGSH MDNGDRLYRA DSRPPDEIKR SGGLMPRGHN EYFDRGTQMN     60
INLYDHARGT QTGFVRYDDG YVSTSLSLRS AHLAGQSILS GYSTYYIYVI ATAPNMFNVN    120
DVLGVYSPHP YEQEVSALGG IPYSQIYGWY RVNFGVIDER LHRNREYRDR YYRNLNIAPA    180
EDGYRLAGFP PDHQAWREEP WIHHAPQGCG NSSRGSAASM SSGNILWGSQ NPIVFKNSFG    240
VSNADTGSQD DLSQQNPFAE GYGVLLILLM VIQAIANNKF IEVQKNAERA RNTQEKSNEM    300
DEVIAKAAKG DAKTKEEVPE DVIKYMRDNG ILIDGMTIDD YMAKYGDHGK LDKGGLQAIK    360
AALDNDANRN TDLMSQGQIT IQKMSQELNA VLTQLTGLIS KWGEISSMIA QKTYS         415

SEQ ID NO: 71        moltype = DNA   length = 749
FEATURE              Location/Qualifiers
misc_feature         1..749
                     note = synthetic construct
source               1..749
                     mol_type = other DNA
                     organism = synthetic construct
SEQUENCE: 71
atgggcagca gccatcacca tcatcaccac agccaggatc cgatgagcac tccatcttct     60
aataattcta aaaaaccttc ggcctctttt aataaaaaat cacgtagccg cttggccgag    120
attgctgcac aaaaaaaagc aaaagctgag gatttggaac aaaaatatcc tgttcctacg    180
gaagaggaga caaaacaagt tctcatggac atcctcaggg ggttaagcaa cggattaact    240
cttcagcaaa ttttaggtct ctccgacgtc ctccttgaag agatctacac cgtagcatat    300
accttctact cccaagggaa atatcgggaa gctatcggtc ttttccaaat cttaacagcc    360
tccaaacctc aatgctacaa atacatctta ggtcttagct cttgctatca ccagctaaaa    420
atgtatgatg aagccgcttt tggtttcttc ctagctttcg atgctcaacc cgaaaacccc    480
atccctcctt actacatcgc cgatagcttg gataagctaa accaaccga agaatctcaa    540
gacttcctcg atattacgat cgatatgtgt aagaacaagc cggaatataa agttcttaaa    600
gatcgctgca gcattatgaa gcaatcttta gatgccgtgc tgaaaaaaga gaatctgca    660
aaaggctctg aaacacaagc ctcctctcct aaaaacacaa aagctaaaaa agctgcttct    720
aacaagaaaa agcaaagta agcggccgc                                        749

SEQ ID NO: 72        moltype = AA   length = 246
FEATURE              Location/Qualifiers
REGION               1..246
                     note = synthetic construct
source               1..246
                     mol_type = protein
                     organism = synthetic construct
SEQUENCE: 72
MGSSHHHHHH SQDPMSTPSS NNSKKPSASF NKKSRSRLAE IAAQKKAKAE DLEQKYPVPT     60
EEETKQVLMD ILQGLSNGLT LQQILGLSDV LLEEIYTVAY TFYSQGKYRE AIGLFQILTA    120
SKPQCYKYIL GLSSCYHQLK MYDEAAFGFF LAFDAQPENP IPPYYIADSL MKLNQPEESQ    180
DFLDITIDMC KNKPEYKVLK DRCSIMKQSL DAVLKKEKSA KGSETQASSP KNTKAKKAAS    240
NKKKAK                                                                246

SEQ ID NO: 73        moltype = DNA   length = 441
FEATURE              Location/Qualifiers
source               1..441
                     mol_type = genomic DNA
                     organism = Chlamydia spp
SEQUENCE: 73
aaaagtgagc gtttaaaaaa attagaatca gagcttcatg atcttaccca gtggatgcaa     60
cttggccttg ttcctaaaaa agaaatcgag agacaccagg aagaaatccg tctgctagaa    120
agcaaaatcc ttgaagagaa agaacgtcta caacttctca agaaaagcgg tgagatcaaa    180
gagtacgtaa cccctcgaag aactccagct aaaaccattt acccagatgg ccccagcgtt    240
tcagacgttg agtttgtaga atcctcggat acagaagtgg atctcgatgc cggtgacaca    300
attgagattg acctaggtga tgaggcaaga aagaaagcg gaaacgaact cgactactct    360
agtgaagacg atgaggatcc tttcagcgat cgcaatcgtt ggcgccgagg aggcatcata    420
gatcctgacg cgaatgaatg g                                               441

SEQ ID NO: 74        moltype = AA   length = 148
FEATURE              Location/Qualifiers

```
source                    1..148
                          mol_type = protein
                          organism = Chlamydia spp
SEQUENCE: 74
MKSERLKKLE SELHDLTQWM QLGLVPKKEI ERHQEEIRLL ESKILEEKER LQLLKESGEI    60
KEYVTPRRTP AKTIYPDGPS VSDVEFVESS DTEVDLDAGD TIEIDLGDEA REESGNELDY   120
SSEDDEDPFS DRNRWRRGGI IDPDANEW                                     148

SEQ ID NO: 75             moltype = DNA  length = 1464
FEATURE                   Location/Qualifiers
source                    1..1464
                          mol_type = genomic DNA
                          organism = Chlamydia spp
SEQUENCE: 75
atgagcttgt catccagcag cagctcggat agttcgaatc tgaaaaatgt gttatctcag    60
gtcatcgcgt ctacaccaca gggggttcct aatgctgaca aattaaccga caatcaggta   120
aaacaagtcc agcagaccg tcaaaaccgt gatgatctgt ccatggagag cgacgtcgcg   180
gtggcgggaa cagccggaaa agatcgtgct gcgtcgcaga cccagatcga gggacaagag   240
ctgattgagc aacagggact tgcggctggg aaagagacgg cttctgctga tgctacatca   300
ttgacccagt cggcatccaa aggcgcttcc agtcagcagt gtattgagga taccagtaag   360
tccctggagc tttcttcgct ttcgagcctg tcaagcgtag atgcgacaca tttgcaggaa   420
atccaatcga tcgtgtcttc agcaatgggc gccaccaacg aattgtcatt gacgaactta   480
gagacaccgg gattaccaaa gccgagtacc actccacgcc aggaagttat ggagatcagc   540
cttgccttag cgaaggccat cactgcattg ggtgagagca ctcaggctgc cttggaaaat   600
tttcagtcca ctcagagtca gtccgcgaac atgaataaga tgagtttgga atcccaaggc   660
ttgaaaatcg acaaggagcg tgaagaattt aagaaaatgc aggagattca gcaaaagagc   720
ggcacaaatt caaccatgga tactgtgaat aaagttatga ttggcgtgac agtggcaatt   780
acagtaatct ctgttgtttc agcattgttt acctgcggtt tgggcttgat ggcacagcc   840
gctgcgggtg ccacagccgc caccgctggg gcaacggccg ccgccacgac cgctacctct   900
gtgacgacca cagtcgctac ccaggtgacg atgcaagcgg tggtccaagt cgttaagcag   960
gctattatcc aagcagtaaa acgcgccatc gtccaagcga ttaaacaggg gattaagcaa  1020
ggcattaaac aagcgatcaa acaggcagtc aaggcaagcg tgaagacact tgccaaaaat  1080
gtaggcaaga ttttcagcgc aggcaagaac gctgtgagta agtccttccc aaaattgtct  1140
aaggtgatta atacacttgg ttccaaatgg gttactcttg gcgtggggc ccttacagcg  1200
gtgccgcagt tagtcagtgg cattacctcc cttcaattgt ctgatatgca aaaagaactt  1260
gcacaaatcc aaaaggaagt gggtgcactt acgcgcaga gtgagatgat gaaagcgttt  1320
acactgttct ggcagcaagc ttcgaaaatc gcggccaaac aaacggaatc accttcagag  1380
acgcaacaac aggcagctaa gaccggcgcc cagatcgcta aagcgttgtc cgccatttcg  1440
ggtgcttag ctgctgctgc ttag                                         1464

SEQ ID NO: 76             moltype = AA  length = 487
FEATURE                   Location/Qualifiers
source                    1..487
                          mol_type = protein
                          organism = Chlamydia spp
SEQUENCE: 76
MSLSSSSSD SSNLKNVLSQ VIASTPQGVP NADKLTDNQV KQVQQTRQNR DDLSMESDVA    60
VAGTAGKDRA ASASQIEGQE LIEQQGLAAG KETASADATS LTQSASKGAS SQQCIEDTSK   120
SLELSSLSSL SSVDATHLQE IQSIVSSAMG ATNELSLTNL ETPGLPKPST TPRQEVMEIS   180
LALAKAITAL GESTQAALEN FQSTQSQSAN MNKMSLESQG LKIDKEREEF KKMQEIQQKS   240
GTNSTMDTVN KVMIGVTVAI TVISVVSALF TCGLGLIGTA AAGDATAATAG ATAAATTATS  300
VTTTVATQVT MQAVVQVVKQ AIIQAVKRAI VQAIKQGIKQ GIKQAIKQAV KASVKTLAKN   360
VGKIFSAGKN AVSKSFPKLS KVINTLGSKW VTLGVGALTA VPQLVSGITS LQLSDMQKEL   420
AQIQKEVGAL TAQSEMMKAF TLFWQQASKI AAKQTESPSE TQQQAAKTGA QIAKALSAIS   480
GALAAAA                                                            487

SEQ ID NO: 77             moltype = DNA  length = 1920
FEATURE                   Location/Qualifiers
misc_feature              1..1920
                          note = synthetic construct
source                    1..1920
                          mol_type = other DNA
                          organism = synthetic construct
SEQUENCE: 77
aaaagtgagc gtttaaaaaa attagaatca gagcttcatg atcttaccca gtggatgcaa    60
cttggccttg ttcctaaaaa agaaatcgag agacaccagg aagaaatccg tctgctagaa   120
agcaaaatcc ttgaagagaa agaacgtcta caacttctca agaaagcgg tgagatcaaa   180
gagtacgtaa cccctcgaag aactccagct aaaaccattt acccagatgg ccccagcgtt   240
tcagacgttg agtttgtaga atcctcggat acagaagttg atctcgatgc cggtgacaca   300
attgagattg acctaggtga tgaggcaaga gaagaaagcg gaaacgaact cgactactct   360
agtgaagacg atgaggatcc tttcagcgat cgcaatcgtt ggcgccgagg aggcatcata   420
gatcctgacg cgaatgaatg gggttcagct gcttcaatga gcttgtcatc cagcagcagc   480
tcggatagtt cgaatctgaa aaatgtgtta tctcaggtca tcgcgtctac accaggggg   540
gttcctaatg ctgacaaatt aaccgacaat caggtaaaac aagtccagca gaccagacag   600
aaccgtgatg atctgtccat ggagagcgac gtcgcggtgg cgggaacagc cggaaaagat   660
cgtgctgcgt cggcgtccca gatcgaggga caagagctga ttgagcaaca gggacttgcg   720
gctgggaaag acgcttc tgctgatgct acatcatga cccagtcggc atccaaaggc   780
gcttccagtc agcagtgtat tgaggatacc agtaagtccc tggagctttc ttcgctttcg   840
agcctgtcaa gcgtagatgc gacacatttg caggaaatcc aatcgatcgt gtcttcagca   900
```

-continued

```
atgggcgcca ccaacgaatt gtcattgacg aacttagaga caccgggatt accaaagccg   960
agtaccactc cacgccagga agttatggag atcagccttg ccttagcgaa ggccatcact  1020
gcattgggtg agagcactca ggctgccttg gaaaattttc agtccactca gagtcagtcc  1080
gcgaacatga ataagatgag tttggaatcc caaggcttga aaatcgacaa ggagcgtgaa  1140
gaatttaaga aaatgcagga gattcagcaa aagagcggca caaattcaac catggatact  1200
gtgaataaag ttatgattgg cgtgacagtg gcaattacag taatctctgt tgtttcagca  1260
ttgtttacct gcggtttggg cttgattggc acagccgctg cgggtgccac agccgccacc  1320
gctgggcaa cggccgccgc cacgaccgct acctctgtga cgaccacagt cgctacccag  1380
gtgacgatgc aagcggtggt ccaagtcgtt aagcaggcta ttatccaagc agtaaaacgc  1440
gccatcgtcc aagcgattaa acaggggatt aagcaaggca ttaaacaagc gatcaaacag  1500
gcagtcaagg caagcgtgaa gacacttgcc aaaaatgtag gcaagatttt cagcgcaggc  1560
aagaacgctg tgagtaagtc cttcccaaaa ttgtctaagg tgattaatac acttggttcc  1620
aaatgggtta ctcttggcgt gggggcccctt acagcggtgc cgcagttagt cagtggcatt  1680
acctcccttc aattgtctga tatgcaaaaa gaacttgcac aaatccaaaa ggaagtgggt  1740
gcacttacgg cgcagagtga gatgatgaaa gcgtttacac tgttctggca gcaagctcg  1800
aaaatcgcgg ccaaacaaac ggaatcacct tcagagacgc aacaacaggc agctaagacc  1860
ggcgcccaga tcgctaaagc gttgtccgcc atttcgggtg cttttagctgc tgctgcttag  1920
```

```
SEQ ID NO: 78           moltype = AA  length = 640
FEATURE                 Location/Qualifiers
REGION                  1..640
                        note = synthetic construct
source                  1..640
                        mol_type = protein
                        organism = synthetic construct
SEQUENCE: 78
MKSERLKKLE SELHDLTQWM QLGLVPKKEI ERHQEEIRLL ESKILEEKER LQLLKESGEI   60
KEYVTPRRTP AKTIYPDGPS VSDVEFVESS DTEVDLDAGD TIEIDLGDEA REESGNELDY  120
SSEDDEDPFS DRNRWRRGGI IDPDANEWGS AASMSLSSSS SSDSSNLKNV LSQVIASTPQ  180
GVPNADKLTD NQVKQVQQTR QNRDDLSMES DVAVAGTAGK DRAASASQIE GQELIEQQGL  240
AAGKETASAD ATSLTQSASK GASSQQCIED TSKSLELSSL SSLSSVDATH LQEIQSIVSS  300
AMGATNELSL TNLETPGLPK PSTTPRQEVM EISLALAKAI TALGESTQAA LENFQSTQSQ  360
SANMNKMSLE SQGLKIDKER EEFKKMQEIQ QKSGTNSTMD TVNKVMIGVT VAITVISVVS  420
ALFTCGLGLI GTAAAGATAA TAGATAAATT ATSVTTTVAT QVTMQAVVQV VKQAIIQAVK  480
RAIVQAIKQG IKQGIKQAIK QAVKASVKTL AKNVGKIFSA GKNAVSKSFP KLSKVINTLG  540
SKWVTLGVGA LTAVPQLVSG ITSLQLSDMQ KELAQIQKEV GALTAQSEMM KAFTLFWQQA  600
SKIAAKQTES PSETQQQAAK TGAQIAKALS AISGALAAAA                        640
```

```
SEQ ID NO: 79           moltype = DNA  length = 2517
FEATURE                 Location/Qualifiers
misc_feature            1..2517
                        note = synthetic construct
source                  1..2517
                        mol_type = other DNA
                        organism = synthetic construct
SEQUENCE: 79
catatggaca atggcgatcg tttataccgt gccgactcgc gtcccccaga tgagattaaa   60
cgtagcggtg ggttaatgcc acgtgggcac aatgagtatt ttgaccgtgg aacacagatg  120
aacattaacc tttacgatca tgcccgtggg acccagaccg ggtttgtccg ttatgatgac  180
gggtatgtta gtacgagttt gtccttacgc tccgcacacc ttgcgggaca agtattta    240
tcaggctaca gcacatatta catttatgtg atcgccactg cccaaaacat gttcaatgtg  300
aacgatgtgt gggggttta cagccccat ccatatgaac aagaagtctc ggcccttggg  360
gggatcccat atagccagat ttatggttgg taccgtgtaa attttggtgt gattgatgaa  420
cgtttgcatc gtaaccgtga ataccgcgat cgctactacc gtaacttgaa cattgcacct  480
gccgaggacg gctatcgttt agcgggattc ccacccgatc atcaggcgtg gcgtgaggaa  540
ccgtggatcc atcacgcccc tcaggggtgc gggaacagta gtcgccatat gaaaagtgag  600
cgtttaaaaa aattagaatc agagcttcat gatcttaccc agtggatgca acttggcctt  660
gttcctaaaa agaaaatcga gagacaccag gaagaaatcc gtctgctaga aagcaaaatc  720
cttgaagaga aagaacgtct acaacttctc aaagaaagcg gtgagatcaa agagtacgta  780
accccctcgaa gaactccagc taaaaccatt tacccagatg gccccagcgt ttcagacgtt  840
gagtttgtag aatcctcgga tacagaagtg gatctcgatg ccggtgacac aattgagatt  900
gacctaggtg atgaggcaag agaagaaagc ggaaacgaac tcgactactc tagtgaagac  960
gatgaggatc ctttcagcga tcgcaatcgt tggcgccgag gaggcatcat agatcctgac 1020
gcgaatgaat ggggttcagc tgcttcaatg agcttgtcat ccagcagcag ctcggatagt 1080
tcgaatctga aaaatgtgtt atctcaggtc atcgcgtcta caccacaggg ggttcctaat 1140
gctgacaaat taaccgacaa tcaggtaaaa caagtccagc agaccccgtca aaaccgtgat 1200
gatctgtcca tggagagcga cgtcgcggtg gcgggaacag ccggaaaaga tcgtgctgcg 1260
tcggcgtccc agatcgaggg acaagagctg attgagcaac agggactttgc ggctgggaaa 1320
gagacggctt ctgctgatgc tacatcattg acccagtcgg catccaaagg cgcttccagt 1380
cagcagtgta ttgaggatac cagtaagtcc ctgagctttt cttcgctttc gagcctgtca 1440
agcgtagatg cgacacattt gcaggaaatc caatcgatcg tgtcttcagc aatgggcgcc 1500
accaacgaat tgtcattgac gaactagag acaccgggat taccaaagcc gagtaccact 1560
ccacgccagg aagttatgga tcagccttg ccttagcga aggccatcac tgcattgggt 1620
gagagcactc aggctgcctt ggaaaattttc agtccactca gagtcagtcc gcgaacatg 1680
aataagatga gtttggaatc caaggcttga aaatcgaca aggagcgtga agaatttaag 1740
aaaatgcagg agattcagca aaagagcggc acaaattcaa ccatggatac tgtgaataaa 1800
gttatgattg gcgtgacagt ggcaattaca gtaatctctg ttgtttcagc attgtttacc 1860
tgcggtttgg gcttgattgg cacagccgct gcgggtgcca cagccgccac cgctgggca 1920
acggccgccg ccacgaccgc tacctctgtg acgaccacag tcgctaccca ggtgacgatg 1980
```

```
caagcggtgg tccaagtcgt taagcaggct attatccaag cagtaaaacg cgccatcgtc  2040
caagcgatta aacaggggat taagcaaggc attaaacaag cgatcaaaca ggcagtcaag  2100
gcaagcgtga agacacttgc caaaaatgta ggcaagattt tcagcgcagg caagaacgct  2160
gtgagtaagt ccttcccaaa attgtctaag gtgattaata cacttggttc caaatggggtt 2220
actcttggcg tgggggccct tacagcggtg ccgcagttag tcagtggcat tacctccctt  2280
caattgtctg atatgcaaaa agaacttgca caaatccaaa aggaagtggg tgcacttacg  2340
gcgcagagtg agatgatgaa agcgtttaca ctgttctggc agcaagcttc gaaaatcgcg  2400
gccaaacaaa cggaatcacc ttcagagacg caacaacagg cagctaagac cggcgcccag  2460
atcgctaaag cgttgtccgc catttcgggt gctttagctg ctgctgctta gctcgag     2517
```

SEQ ID NO: 80          moltype = AA   length = 834
FEATURE                Location/Qualifiers
REGION                 1..834
                       note = synthetic construct
source                 1..834
                       mol_type = protein
                       organism = synthetic construct
SEQUENCE: 80
```
MDNGDRLYRA DSRPPDEIKR SGGLMPRGHN EYFDRGTQMN INLYDHARGT QTGFVRYDDG   60
YVSTSLSLRS AHLAGQSILS GYSTYYIYVI ATAPNMFNVN DVLGVYSPHP YEQEVSALGG  120
IPYSQIYGWY RVNFGVIDER LHRNREYRDR YYRNLNIAPA EDGYRLAGFP PDHQAWREEP  180
WIHHAPQGCG NSSRMKSERL KKLESELHDL TQWMQLGLVP KKEIERHQEE IRLLESKILE  240
EKERLQLLKE SGEIKEYVTP RRTPAKTIYP DGPSVSDVEF VESSDTEVDL DAGDTIEIDL  300
GDEAREESGN ELDYSSEDDE DPFSDRNRWR RGGIIDPDAN EWGSAASMSL SSSSSSDSSN  360
LKNVLSQVIA STPQGVPNAD KLTDNQVKQV QQTRQNRDDL SMESDVAVAG TAGKDRAASA  420
SQIEGQELIE QQGLAAGKET ASADATSLTQ SASKGASSQQ CIEDTSKSLE LSSLSSLSSV  480
DATHLQEIQS IVSSAMGATN ELSLTNLETP GLPKPSTTPR QEVMEISLAL AKAITALGES  540
TQAALENFQS TQSQSANMNK MSLESQGLKI DKEREEFKKM QEIQQKSGTN STMDTVNKVM  600
IGVTVAITVI SVVSALFTCG LGLIGTAAAG ATAATAGATA AATTATSVTT TVATQVTMQA  660
VVQVVKQAII QAVKRAIVQA IKQGIKQGIK QAIKQAVKAS VKTLAKNVGK IFSAGKNAVS  720
KSFPKLSKVI NTLGSKWVTL GVGALTAVPQ LVSGITSLQL SDMQKELAQI QKEVGALTAQ  780
SEMMKAFTLF WQQASKIAAK QTESPSETQQ QAAKTGAQIA KALSAISGAL AAAA         834
```

SEQ ID NO: 81          moltype = DNA   length = 749
FEATURE                Location/Qualifiers
misc_feature           1..749
                       note = synthetic construct
source                 1..749
                       mol_type = other DNA
                       organism = synthetic construct
SEQUENCE: 81
```
atgggcagca gccatcacca tcatcaccac agccaggatc cgatgagcac tccatcttct   60
aataattcta aaaaccttcc ggcctctttt aataaaaaat cacgtagccg cttggccgag  120
attgctgcac aaaaaaagc aaaagctgag gatttggaac aaaaatatcc tgttcctacg  180
gaagaggaga caaaacaagt tctcatggac atcctacagg ggttaagcaa cggattaact  240
cttcagcaaa ttttaggtct ctccgacgtc ctccttgaag gatctacac cgtagcatat  300
accttctact cccaagggaa atatcgggaa gctatcggtt ttttccaaat cttaacagcc  360
tccaaacctc aatgctacaa atacatctta ggtcttagct cttgctatca ccagctaaaa  420
atgtatgatg aagccgcttt tggtttcttc ctagctttcg atgctcaacc cgaaaacccc  480
atccctcctc actacatcgc cgatagcttg atgaagctaa accaacccga gaatctcaa   540
gacttcctcg atattacgat cgatatgtgt aagaacgacc tggaatataa agttcttaaa  600
gatcgctgca gcattatgaa gcaatctta tgatgccgtgc tgaaaaaga gaaatctgca  660
aaaggctctg aaacacaagc ctcctctcct aaaaacacaa agctaaaaa agctgcttct  720
aacaagaaaa aagcaaagta agcggccgc                                    749
```

SEQ ID NO: 82          moltype = AA   length = 246
FEATURE                Location/Qualifiers
REGION                 1..246
                       note = synthetic construct
source                 1..246
                       mol_type = protein
                       organism = synthetic construct
SEQUENCE: 82
```
MGSSHHHHHH SQDPMSTPSS NNSKKPSASF NKKSRSRLAE IAAQKKAKAE DLEQKYPVPT   60
EEETKQVLMD ILQGLSNGLT LQQILGLSDV LLEEIYTVAY TFYSQGKYRE AIGLFQILTA  120
SKPQCYKYIL GLSSCYHQLK MYDEAAFGFF LAFDAQPENP IPPYYIADSL MKLNQPEESQ  180
DFLDITIDMC KNKPEYKVLK DRCSIMKQSL DAVLKKEKSA KGSETQASSP KNTKAKKAAS  240
NKKKAK                                                              246
```

SEQ ID NO: 83          moltype = DNA   length = 666
FEATURE                Location/Qualifiers
source                 1..666
                       mol_type = genomic DNA
                       organism = Chlamydia spp
SEQUENCE: 83
```
atagatcctc ttaagctttt tccaaatttt gatgggggata aggagagtgc tgcggtgaat   60
aaaccttcag catctcctat gcccagcgaa ttaagtaaaa atgttgcctc attctcttta  120
gggggtggag tgctgcgtt ggattcgaca gtgtccacag aaaagctatc gttgatggct  180
atgatgcagg ataaaaattc gcagttgatc gatcctgagt ggaggaagc tctgaactct  240
```

```
gaagagttac aagagcagat ccatttgtta aaaagtcgtt tgtgggatgc acaaacgcag  300
atgcaaatgc aagatcccga caagttggcc tctgagcatg tagatgcttt aggagtcatt  360
gttgatttaa tcaatgggga ttttcaagcg atagctgaac atacacaaca gacggtcaag  420
cagggtaatg gtgacgaaga aaaatctgtt acacgcaaga tagtcgattg ggtctcttca  480
ggagaagaaa ttttgaatcg tgctttgttg tatttctccg atcgtaatgg agaaagagaa  540
acattagccg atttcttaaa agttcagtat gccgttcaaa gagctacaca acgcgccgag  600
ttatttgcca gtattctagg tgccacggtg agtagtgtaa aaacgattat gacaacccag  660
ttaggt                                                              666

SEQ ID NO: 84           moltype = AA  length = 222
FEATURE                 Location/Qualifiers
source                  1..222
                        mol_type = protein
                        organism = Chlamydia spp
SEQUENCE: 84
MIDPLKLFPN FDGDKESAAV NKPSASPMPS ELSKNVASFS LGGGGAALDS TVSTEKLSLM   60
AMMQDKNSQL IDPELEEALN SEELQEQIHL LKSRLWDAQT QMQMQDPDKL ASEHVDALGV  120
IVDLINGDFQ AIAEHTQQTV KQGNGDEEKS VTRKIVDWVS SGEEILNRAL LYFSDRNGER  180
ETLADFLKVQ YAVQRATQRA ELFASILGAT VSSVKTIMTT QL                     222

SEQ ID NO: 85           moltype = DNA  length = 2145
FEATURE                 Location/Qualifiers
misc_feature            1..2145
                        note = synthetic construct
source                  1..2145
                        mol_type = other DNA
                        organism = synthetic construct
SEQUENCE: 85
atagatcctc ttaagctttt tccaaatttt gatggggata aggagagtgc tgcggtgaat   60
aaaccttcag catctcctat gcccagcgaa ttaagtaaaa atgttgcctc attctctta  120
gggggtggag gtgctgcgtt ggattcgaca gtgtccacag aaaagctatc gttgatggct  180
atgatgcagg ataaaaattc gcagttgatc gatcctgagt tggaggaagc tctgaactct  240
gaagagttac aagagcagat ccatttgtta aaaagtcgtt tgtgggatgc acaaacgcag  300
atgcaaatgc aagatcccga caagttggcc tctgagcatg tagatgcttt aggagtcatt  360
gttgatttaa tcaatgggga ttttcaagcg atagctgaac atacacaaca gacggtcaag  420
cagggtaatg gtgacgaaga aaaatctgtt acacgcaaga tagtcgattg ggtctcttca  480
ggagaagaaa ttttgaatcg tgctttgttg tatttctccg atcgtaatgg agaaagagaa  540
acattagccg atttcttaaa agttcagtat gccgttcaaa gagctacaca acgcgccgag  600
ttatttgcca gtattctagg tgccacggtg agtagtgtaa aaacgattat gacaacccag  660
ttaggtggtt cagctgcttc aatgagcttg tcatccagca gcagctcgga tagttcgaat  720
ctgaaaaatg tgttatctca ggtcatcgcg tctacaccac aggggttcc taatgctgac  780
aaattaaccg acaatcaggt aaaacaagtc cagcagaccc gtcaaaaccg tgatgatctg  840
tccatggaga gcgacgtcgc ggtgcggga acagccggaa aagatcgtgc tgcgtcggcg  900
tcccagatcg agggacaaga gctgattgag caacagggac ttgcggctgg aaagagacg  960
gcttctgctg atgctacatc attgacccag tcggcatcca aaggcgcttc cagtcagcag 1020
tgtattgagg ataccagtaa gtccctggag ctttcttcgc tttcgagcct gtcaagcgta 1080
gatgcgcacac atttgcagga aatccaatcg atcgtgtctt cagcaatggg cgccaccaac 1140
gaattgtcat tgacgaactt agagacaccg ggattaccaa agccgagtac cactccacgg 1200
caggaagtta tggagatcag ccttgcctta gcgaaggcca tcactgcatt gggtgagagc 1260
actcaggctg ccttggaaaa ttttcagtcc actcagagtc agtccgcgaa catgaataag 1320
atgagtttgg aatcccaagg cttgaaaatc gacaaggagc gtgaagaatt taagaaaatg 1380
caggagattc agcaaaagag cggcacaaat tcaaccatgg atactgtgaa taagttatg 1440
attggcgtga cagtggcaat tacagtaatc tctgttgttt cagcattgtt tacctgcggt 1500
ttgggcttga ttggcacagc cgctgcgggt gccacagccg ccaccgctgg ggcaacggcc 1560
gccgccacga ccgctacctc tgtgacgacc acagtcgtca cccaggtgac gatgcaagcg 1620
gtggtccaag tcgttaagca ggctattatc caagcagtaa aacgcgccat cgtccaagcg 1680
attaaacagg gattaagcaa aggcattaaa caagcgatca aacaggcagt caaggcaagc 1740
gtgaagacac ttgccaaaaa tgtaggcaag attttcagcg caggcaagaa cgctgtgagt 1800
aagtccttcc caaaattgtc taaggtgatt aatacacttg gttccaaatg ggttactctt 1860
ggcgtggggg cccttacagc ggtgccgcag ttagtcagtg gcattacctc ccttcaattg 1920
tctgatatgc aaaaagaact tgcacaaatc caaaaggaag tgggtgcact acggcgcag 1980
agtgagatga tgaaagcgtt tacactgttc tggcagcaag cttcgaaaat cgcggccaaa 2040
caaacggaat caccttcaga gacgcaacaa caggcagcta gaccggcgc ccagatcgct 2100
aaagcgttgt ccgccatttc gggtgcttta gctgctgctg cttag                 2145

SEQ ID NO: 86           moltype = AA  length = 715
FEATURE                 Location/Qualifiers
REGION                  1..715
                        note = synthetic construct
source                  1..715
                        mol_type = protein
                        organism = synthetic construct
SEQUENCE: 86
MIDPLKLFPN FDGDKESAAV NKPSASPMPS ELSKNVASFS LGGGGAALDS TVSTEKLSLM   60
AMMQDKNSQL IDPELEEALN SEELQEQIHL LKSRLWDAQT QMQMQDPDKL ASEHVDALGV  120
IVDLINGDFQ AIAEHTQQTV KQGNGDEEKS VTRKIVDWVS SGEEILNRAL LYFSDRNGER  180
ETLADFLKVQ YAVQRATQRA ELFASILGAT VSSVKTIMTT QLGGSAASMS LSSSSSSDSS  240
NLKNVLSQVI ASTPQGVPNA DKLTDNQVKQ VQQTRQNRDD LSMESDVAVA GTAGKDRAAS  300
ASQIEGQELI EQQGLAAGKE TASADATSLT QSASKGASSQ QCIEDTSKSL ELSSLSSLSS  360
```

```
VDATHLQEIQ SIVSSAMGAT NELSLTNLET PGLPKPSTTP RQEVMEISLA LAKAITALGE  420
STQAALENFQ STQSQSANMN KMSLESQGLK IDKEREEFKK MQEIQQKSGT NSTMDTVNKV  480
MIGVTVAITV ISVVSALFTC GLGLIGTAAA GATAATAGAT AAATTATSVT TTVATQVTMQ  540
AVVQVVKQAI IQAVKRAIVQ AIKQGIKQGI KQAIKQAVKA SVKTLAKNVG KIFSAGKNAV  600
SKSFPKLSKV INTLGSKWVT LGVGALTAVP QLVSGITSLQ LSDMQKELAQ IQKEVGALTA  660
QSEMMKAFTL FWQQASKIAA KQTESPSETQ QQAAKTGAQI AKALSAISGA LAAAA       715

SEQ ID NO: 87           moltype = DNA   length = 2742
FEATURE                 Location/Qualifiers
misc_feature            1..2742
                        note = synthetic construct
source                  1..2742
                        mol_type = other DNA
                        organism = synthetic construct
SEQUENCE: 87
catatggaca atggcgatcg tttataccgt gccgactcgc gtcccccaga tgagattaaa    60
cgtagcggtg ggttaatgcc acgtgggcac aatgagtatt ttgaccgtgg aacacagatg   120
aacattaacc tttacgatca tgcccgtggg acccagaccg ggtttgtccg ttatgatgac   180
gggtatgtta gtacgagttt gtccttacgc tccgcacacc ttgcgggaca agtattttta   240
tcaggctaca gcacatatta catttatgtg atcgccactg ccccaaacat gttcaatgtg   300
aacgatgtgt tgggggttta cagcccccat ccatatgaac aagaagtctc ggcccttggg   360
gggatcccat atagccagat ttatggttgg taccgcgtaa atttggtgt gattgatgaa    420
cgtttgcatc gtaacgtga ataccgcgat cgctactacc gtaacttgaa cattgcacct    480
gccgaggacg gctatcgttt agcgggattc ccacccgatc atcaggcgtg gcgtgaggaa   540
ccgtggatcc atcacgcccc tcaggggtgc gggaacagta gtcgccatat gatagatcct   600
cttaagcttt ttccaaattt tgatggggat aaggagagtg ctgcggtgaa taaccttca    660
gcatctccta tgcccagcga attaagtaaa aatgttgcct cattctcttt agggggtgga   720
ggtgctgcgt tggattcgac agtgtccaca gaaaagctat cgttgatggc tatgatgcag   780
gataaaaatt cgcagttgat cgatcctgag ttggaggaag ctctgaactc tgaagagtta   840
caagagcaga tccatttgtt aaaaagtcgt ttgtgggata cacaaacgca gatgcaaatg   900
caagatcccg acaagttggc ctctgagcat gtagatgctt taggagtcat tgttgattta   960
atcaatgggg attttcaagc gatagctgaa catacacaac agacggtcaa gcagggtaat  1020
ggtgacgaag aaaaatctgt tacacgcaag atagtcgatt gggtctcttc aggagaagaa  1080
attttgaatc gtgctttgtt gtatttctcc gatcgtaatg gagaaagaga aacattagac  1140
gatttcttaa aagttcagta tgccgttcaa agagctacac aacgcgccga gttatttgcc  1200
agtattctag gtgccacggt gagtagtgta aaaacgatta tgacaaccca gttaggtggt  1260
tcagctgctt caatgagctt gtcatccagc agcagctcgg atagttcgaa tctgaaaaat  1320
gtgttatctc aggtcatcgc gtctacacca caggggttc ctaatgctga caaattaacc   1380
gacaatcagg taaaacaagt ccagcagacc cgtcaaaacc gtgatgatct gtccatggag  1440
agcgacgtcg cggtggcggg aacagccgga aaagatcgtg ctgcgtcggc gtcccagatc  1500
gagggacaag agctgattga gcaacaggga cttgcggctg ggaaagagac ggcttctgct  1560
gatgctacat cattgaccca gtcggcatcc aaaggcgctt ccagtcagca gtgtattgag  1620
gataccagta agtccctgga gctttcttcg ctttcgagcc tgtcaagcgt agatgcgaca  1680
catttgcagg aaatccaatc gatcgtgtct tcagcaatgg gcgccaccaa cgaattgtca  1740
ttgacgaact tagagacacc gggattacca agccgagta ccactccacg ccaggaagtt   1800
atggagatca gccttgcctt agcgaaggcc atcactgcat gggtgagag cactcaggct   1860
gccttggaaa attttcagtc cactcagagt cagtccgcga acatgaataa gatgagtttg  1920
gaatcccaag gcttgaaaat cgacaaggag cgtgaagaat ttaagaaaat gcaggagatt  1980
cagcaaaaga gcggcacaaa ttcaaccatg gatactgtga ataaagttat gattggcgtg  2040
acagtggcaa ttacagtaat ctctgttgtt tcagcattgt ttacctgcgg tttgggcttg  2100
attggcacag ccgctgcggg tgccacagcc gccaccgttg gggcaacggc cgccgccaag  2160
accgctacct ctgtgacgac cacagtcgct acccaggtga cgatgcaagc ggtggtccaa  2220
gtcgttaagc aggctattat ccaagcagta aaacgcgcca tcgtccaagc gattaaacag  2280
gggattaagc aaggcattaa acaagcgatc aaacaggcag tcaaggcaag cgtgaagaca  2340
cttgccaaaa atgtaggcaa gatttttcagc gcaggcaaga acgctgtgag taagtcctc   2400
ccaaaattgt ctaaggtgat taatacactt ggttccaaat gggttactct tggcgtgggg  2460
gcccttacag cggtgccgca gttagtcagt ggcattacct cccttcaatt gtctgatatg  2520
caaaaagaac ttgcacaaat ccaaaaggaa gtgggtgcac ttacggcgca gagtgagatg  2580
atgaaagcgt ttacactgtt ctggcagcaa gcttcgaaaa tcgcggccaa acaaacggaa  2640
tcaccttcag agacgcaaca acaggcagct aagaccggcg cccagatcgc taaagcgttg  2700
tccgccattt cgggtgcttt agctgctgct gcttagctcg ag                    2742

SEQ ID NO: 88           moltype = AA   length = 909
FEATURE                 Location/Qualifiers
REGION                  1..909
                        note = synthetic construct
source                  1..909
                        mol_type = protein
                        organism = synthetic construct
SEQUENCE: 88
MDNGDRLYRA DSRPPDEIKR SGGLMPRGHN EYFDRGTQMN INLYDHARGT QTGFVRYDDG   60
YVSTSLSLRS AHLAGQSILS GYSTYYIYVI ATAPNMFNVN DVLGVYSPHP YEQEVSALGG  120
IPYSQIYGWY RVNFGVIDER LHRNREYRDR YYRNLNIAPA EDGYRLAGFP PDHQAWREEP  180
WIHHAPQGCG NSSRMIDPLK LFPNFDGDKE SAAVNKPSAS PMPSELSKNV ASFSLGGGGA  240
ALDSTVSTEK LSLMAMMQDK NSQLIDPELE EALNSEELQE QIHLLKSRLW DAQTQMQMQD  300
PDKLASEHVD ALGIVVDLIN GDFQAIAEHT QQTVKQGNGD EEKSVTRKIV DWVSSGEEIL  360
NRALLYFSDR NGERETLADF LKVQYAVQRA TQRAELFASI LGATVSSVKT IMTTQLGGSA  420
ASMSLSSSSS SDSSNLKNVL SQVIASTPQG VPNADKLTDN QVKQVQQTRQ NRDDLSMESD  480
VAVAGTAGKD RAASASQIEG QELIEQQGLA AGKETASADA TSLTQSASKG ASSQQCIEDT  540
```

```
SKSLELSSLS SLSSVDATHL QEIQSIVSSA MGATNELSLT NLETPGLPKP STTPRQEVME    600
ISLALAKAIT ALGESTQAAL ENFQSTQSQS ANMNKMSLES QGLKIDKERE EFKKMQEIQQ    660
KSGTNSTMDT VNKVMIGVTV AITVISVVSA LFTCGLGLIG TAAAGATAAT AGATAAATTA    720
TSVTTTVATQ VTMQAVVQVV KQAIIQAVKR AIVQAIKQGI KQGIKQAIKQ AVKASVKTLA    780
KNVGKIFSAG KNAVSKSFPK LSKVINTLGS KWVTLGVGAL TAVPQLVSGI TSLQLSDMQK    840
ELAQIQKEVG ALTAQSEMMK AFTLFWQQAS KIAAKQTESP SETQQQAAKT GAQIAKALSA    900
ISGALAAAA                                                           909

SEQ ID NO: 89              moltype = DNA   length = 647
FEATURE                    Location/Qualifiers
misc_feature               1..647
                           note = synthetic construct
source                     1..647
                           mol_type = other DNA
                           organism = synthetic construct
SEQUENCE: 89
atgggcagca gccatcacca tcatcaccac agccaggatc cgatgccacc aagcaagatc     60
caatgtcttg aaactttga aagaacttat ggacacctat atctacaaca tgcctcccta    120
atgcgtcatt tagcctatct actcgataaa attgctcgct cttaccctca tatgtgtccg    180
cttcccgata atatggaagc gtactttgag aattatatcc ccaataaaga tatccctctg    240
gacacctatc aaaaaatttt caaactgtcc tcagaagatc ttgaacaagt ctacaaggaa    300
ggatacaacg cctatttaca aggagactat gaggaaagtt ctaccgcttt ttactggtta    360
attttcttta acccatttgt gtctaaattt tggttttcat taggagcttc gctccatatg    420
cgccaaaaat atcaacaagc tcttcatgct tatggtgtag ctgctttgct aagagaaaaa    480
gacccttatc ctcattacta tgcctacatc tgctacaccc tgctcaataa tcctgaagaa    540
gctgaaaaag ctcttgatct tgcttggcaa aaagtaaaaa caagctctgc ctatagctct    600
ttaaaagaag aaatttagc gatcaaatcg tacgcctaag cggccgc                   647

SEQ ID NO: 90              moltype = AA   length = 212
FEATURE                    Location/Qualifiers
REGION                     1..212
                           note = synthetic construct
source                     1..212
                           mol_type = protein
                           organism = synthetic construct
SEQUENCE: 90
MGSSHHHHHH SQDPMPPSKI QCLETFERTY GHLYLQHASL MRHLAYLLDK IARSYPHMCP     60
LPDNMEAYFE NYIPNKDIPL DTYQKIFKLS SEDLEQVYKE GYNAYLQGDY EESSTAFYWL    120
IFFNPFVSKF WFSLGASLHM RQKYQQALHA YGVAALLREK DPYPHYYAYI CYTLLNNPEE    180
AEKALDLAWQ KVKTSSAYSS LKEEILAIKS YA                                  212

SEQ ID NO: 91              moltype = DNA   length = 1521
FEATURE                    Location/Qualifiers
source                     1..1521
                           mol_type = genomic DNA
                           organism = Chlamydia spp
SEQUENCE: 91
atgagctctt ggtttgcaca ggcgacggac gtcgctttga ccagaccct tgatctgcct      60
gacgcttcat tggcggttca aaccgaaaaa tttccataca gctgttcaat ctctaaggaa    120
tccgccccat catgtattcg taaaatcttc gcccatttag catctcagaa ggaaagtgct    180
ccgctgtctt tttctcgttt acaaccgact actccgacaa aacgcatcct gtttttccgg    240
tcatcgcctt cctcccaatt gtcctcgact gtccgcacca caacctcttc tccatggaat    300
ctttttagca actcccaggc acgcaactcg acccgtaaat tgtcggagaa gcttcatttg    360
agctcagagt tatccgcccg tgactccact aagccttcgt cgagcgaacc ggttaaacca    420
tcggaaaatc ttttgcacac ccctgagcat cataaggaat ccttctcaag tttgaaaaag    480
gataacttat ctcctatcat ggaggagatc gactcattct ctgcagagac agagtccctt    540
gaagagcgtt tggtcaccca gaaaaaggag gagacggtgg cccaggagca aaagcaccca    600
ttgctgcgta catctactcc gccatcaaag gccagcgggg aatcacaaga ttctagcgaa    660
cacagctcaa aggaagatcc ttatagtcaa caaccgagcc ataaaatcca acgccgtaaa    720
gagcgtgcta agcgcgtcgt cccaattatt actccgccaa cggtgggtat ctttagtttg    780
agctaccttc ttacaaaaca ggggatctta gcggatttca gcgccattc ggcatacaag    840
gataatttag aaacaactca gcaagagctg accatgttgc atcaagaacg tatcgagcaa    900
gtccaaaaga tcgtggataa agtaagaca atgcgctttt gggattcatt agcatccatt    960
gtggccacaa tcattccatg gatcgaaatg ggtgttgcaa taaccatcat cgcactggga   1020
ggtggaatcc tttcctggtg ctctcttttt gctgcgctta tcatgattgt aatttcatta   1080
ttggaagcat cgacgggtg gcgtgcaatc gctaagcatt taccaggtaa cgatcttgaa   1140
aagaagatgc gttatttagg ttacgtaaag ttggccttaa ctgtgttctc gtgcttactg   1200
agtttaagcg cccttgtatgt agcaaaatta ggaatgagtc cgcttttgga ggggttgtg   1260
aagagtatcg caccagcatt aagtggtatg ctgggtttga ctcaaggcgt agcactgtat   1320
ttacaatctt catcgcaaaa gattcgtgcc cgctgcactc agatcgacgc acgcattgaa   1380
ttgattaact gggaacgcga tgagtatttc ttgcgtgctg aacaacttct tgattcaatg   1440
caaacgtcct tcgaacaact tactgaaaca ttacagttac aacgtgaaat tgatcagaca   1500
tttacagacg ctttgcgcta g                                              1521

SEQ ID NO: 92              moltype = AA   length = 506
FEATURE                    Location/Qualifiers
source                     1..506
                           mol_type = protein
                           organism = Chlamydia spp
```

```
SEQUENCE: 92
MSSWFAQATD VALSQTLDLP DASLAVQTEK FPYSCSISKE SAPSCIRKIF AHLASQKESA    60
PLSFSRLQPT TPKERILFFG SSPSSQLSST VRTTTSSPWN LFSNSQARNS TRKLSEKLHL   120
SSELSARDST KPSSSEPVKP SENLLHTPEH HKESFSSLKK DNLSPIMEEI DSFSAETESL   180
EERLVTQKKE ETVAQEQKHP LLRTSTPPSK ASGESQDSSE HSSKEDPYSQ QPSHKIQRRK   240
ERAKRVVPII TPPTVGIFSL SYLLTKQGIL ADFSAYSAYK DNLETTQQEL TMLHQERIEQ   300
VQKIVDKSKT MRFWDSLASI VATIIPWIEM GVAVTIIALG GGILSWCSLF AALIMIVISL   360
LEAFDGWRAI AKHLPGNDLE KKMRYLGYVK LALTVFSCLL SLSALYVAKL GMSPLLEGVV   420
KSIAPALSGM LGLTQGVALY LQSSSQKIRA RCTQIDARIE LINWERDEYF LRAEQLLDSM   480
QTSFEQLTET LQLQREIDQT FTDALR                                       506

SEQ ID NO: 93              moltype = DNA   length = 1977
FEATURE                    Location/Qualifiers
misc_feature               1..1977
                           note = synthetic construct
source                     1..1977
                           mol_type = other DNA
                           organism = synthetic construct
SEQUENCE: 93
aaaagtgagc gtttaaaaaa attagaatca gagcttcatg atcttaccca gtggatgcaa    60
cttggccttg ttcctaaaaa agaaatcgag agacaccagg aagaaatccg tctgctagaa   120
agcaaaatcc ttgaagagaa agaacgtcta caacttctca aagaaagcgg tgagatcaaa   180
gagtacgtaa cccctcgaag aactccagct aaaaccattt acccagatgg ccccagcgtt   240
tcagacgttg agtttgtaga atcctcggat acagaagtgg atctcgatgc cggtgacaca   300
attgagattg acctaggtga tgaggcaaga gaagaaagcg gaaacgaact cgactactct   360
agtgaagacg atgaggatcc tttcagcgat cgcaatcgtt ggcgccgagg aggcatcata   420
gatcctgacg cgaatgaatg gggttcagct gcttcaatga gctcttggtt tgcacaggcg   480
acggacgtcg ctttgagcca gacccttgat ctgcctgacg cttcattggc ggttcaaacc   540
gaaaaatttc catacagctg ttcaatctct aaggaatccg cccatcatg tattcgtaaa   600
atcttcgccc atttagcatc tcagaaggaa agtgctccgc tgtcttttc tcgtttacaa   660
ccgactactc cgaaagaacg catcctgttt ttcgggtcat cgccttcctc ccaattgtcc   720
tcgactgtcc gcaccacaac ctcttctcca tggaatcttt ttagcaactc ccaggcacgc   780
aactcgaccc gtaaattgtc ggagaagctt catttgagct cagagttatc cgcccgtgac   840
tccactaaag cttcgtcgag cgaaccggtt aaaccatcgg aaaatcttt gcacacccct   900
gagcatcata aggaatcctt ctcaagtttg aaaaaggata acttatctcc tatcatggag   960
gagatcgact cattctctgc agagacagag tcccttgaag agcgtttggt cacccagaaa  1020
aaggaggaga cggtggccca ggagcaaaag cacccattgc tgcgtacatc tactccgcca  1080
tcaaaggcca gcggggaatc acaagattct agcgaacaca gctcaaagga agatcctta   1140
agtcaacaac cgagccataa aatccaacgc cgtaaagagc gtgctaagcg cgtcgtccca  1200
attattactc cgccaacggt gggtatcttt agtttgagct accttcttac aaaacagggg  1260
atcttagcgg atttcagcgc ctattcggca tacaaggata atttagaaac aactcagcaa  1320
gagctgacca tgttgcatca agaacgtatc gagcaagtcc aaaagatcgt ggataaaagt  1380
aagacaatgc gcttttggga ttcattagca tccattgtgg ccacaatcat tccatggatt  1440
gaaatgggtg ttgcagtaac catcatcgca ctggggaggtg aatcctttc ctggtgctct  1500
cttttttgctg cgcttatcat gattgtaatt tcattattgg aagcattcga cgggtggcgt  1560
gcaatcgcta agcatttacc aggtaacgat cttgaaagaa agatgcgtta tttaggttac  1620
gtaaagttgg ccttaactgt gttctcgtgt ctactagttt caagcgcctt gtatgtagca  1680
aaattaggaa tgagtccgct tttggagggg gttgtgaaga gtatcgcacc agcattaagt  1740
ggtatgctgg gtttgactca aggcgtagca ctgtatttac aatcttcatc gcaaaagatt  1800
cgtgcccgct gcactcagat cgacgcacgc attgaattga ttaactggga acgcgatgag  1860
tatttcttgc gtgctgaaca acttcttgat tcaatgcaaa cgtccttcga acaacttact  1920
gaaacattac agttacaacg tgaaattgat cagacattta cagacgcttt gcgctag     1977

SEQ ID NO: 94              moltype = AA   length = 659
FEATURE                    Location/Qualifiers
REGION                     1..659
                           note = synthetic construct
source                     1..659
                           mol_type = protein
                           organism = synthetic construct
SEQUENCE: 94
MKSERLKKLE SELHDLTQWM QLGLVPKKEI ERHQEEIRLL ESKILEEKER LQLLKESGEI    60
KEYVTPRRTP AKTIYPDGPS VSDVEFVESS DTEVDLDAGD TIEIDLGDEA REESGNELDY   120
SSEDDEDPFS DRNRWRRGGI IDPDANEWGS AASMSSWFAQ ATDVALSQTL DLPDASLAVQ   180
TEKFPYSCSI SKESAPSCIR KIFAHLASQK ESAPLSFSRL QPTTPKERIL FFGSSPSSQL   240
SSTVRTTTSS PWNLFSNSQA RNSTRKLSEK LHLSSELSAR DSTKPSSSEP VKPSENLLHT   300
PEHHKESFSS LKKDNLSPIM EEIDSFSAET ESLEERLVTQ KKEETVAQEQ KHPLLRTSTP   360
PSKASGESQD SSEHSSKEDP YSQQPSHKIQ RRKERAKRVV PIITPPTVGI FSLSYLLTKQ   420
GILADFSAYS AYKDNLETTQ QELTMLHQER IEQVQKIVDK SKTMRFWDSL ASIVATIIPW   480
IEMGVAVTII ALGGGILSWC SLFAALIMIV ISLLEAFDGW RAIAKHLPGN DLEKKMRYLG   540
YVKLALTVFS CLLSLSALYV AKLGMSPLLE GVVKSIAPAL SGMLGLTQGV ALYLQSSSQK   600
IRARCTQIDA RIELINWERD EYFLRAEQLL DSMQTSFEQL TETLQLQREI DQTFTDALR    659

SEQ ID NO: 95              moltype = DNA   length = 2574
FEATURE                    Location/Qualifiers
misc_feature               1..2574
                           note = synthetic construct
source                     1..2574
                           mol_type = other DNA
```

```
                        organism = synthetic construct
SEQUENCE: 95
catatggaca   atggcgatcg   tttataccgt   gccgactcgc   gtcccccaga   tgagattaaa     60
cgtagcggtg   ggtaatgcc    acgtgggcac   aatgagtatt   ttgaccgtgg   aacacagatg    120
aacattaacc   tttacgatca   tgcccgtggg   acccagaccg   ggtttgtccg   ttatgatgac   180
gggtatgtta   gtacgagttt   gtccttacgc   tccgcacacc   ttgcgggaca   aagtattta    240
tcaggctaca   gcacatatta   catttatgtg   atcgccactg   ccccaaacat   gttcaatgtg   300
aacgatgtgt   tggggttta    cagccccat    ccatatgaac   aagaagtctc   ggcccttggg   360
gggatcccat   atagccagat   ttatggttgg   taccgcgtaa   attttggtgt   gattgatgaa   420
cgtttgcatc   gtaaccgtga   ataccgcgat   cgctactacc   gtaacttgaa   cattgcacct   480
gccgaggacg   gctatcgttt   agcgggattc   ccacccgatc   atcaggcgtg   gcgtgaggaa   540
ccgtggatcc   atcacgcccc   tcaggggtgc   gggaacagta   gtcgccatat   gaaaagtgag   600
cgtttaaaaa   aattagaatc   agagcttcat   gatcttaccc   agtggatgca   acttggcctt   660
gttcctaaaa   aagaaatcga   gagaccaccag  gaagaaatcc   gtctgctaga   aagcaaaatc   720
cttgaagaga   aagaacgtct   acaacttctc   aaagaaagcg   gtgagatcaa   agagtacgta   780
acccctcgaa   gaactccagc   taaaaccatt   tacccagatg   gccccagcgt   ttcgagacgt   840
gagtttgtag   aatcctcgga   tacagaagtg   gatctcgatg   ccggtgacac   aattgagatt   900
gacctaggtg   atgaggcaag   agaagaaagc   ggaaacgaac   tcgactactc   tagtgaagac   960
gatgaggatc   ctttcagcga   tcgcaatcgt   tggcgccgag   gaggcatcat   agatcctgac  1020
gcgaatgaat   ggggttcagc   tgcttcaatg   agctcttggt   ttgcacaggc   gacggacgtc  1080
gctttgagcc   agaccttga    tctgcctgac   gcttcattgg   cggttcaaac   cgaaaaattt  1140
ccatacagct   gttcaatctc   taaggaatcc   gccccatcat   gtattcgtaa   aatcttcgcc  1200
catttagcat   ctcagaagga   aagtgctccg   ctgtcttttt   ctcgtttaca   accgactact  1260
ccgaaagaac   gcatcctgtt   tttcgggtca   tcgccttcct   cccaattgtc   ctcgactgtc  1320
cgcaccacaa   cctcttctcc   atggaatctt   tttagcaact   cccaggcacg   caactcgacc  1380
cgtaaattgt   cggagaagct   tcatttgagc   tcagagttat   ccgcccgtga   ctccactaag  1440
ccttcgtcga   gcgaaccggt   taaccatcg    gaaatctctt   tgcacacccc   tgagcatcat  1500
aaggaatcct   tctcaagttt   gaaaaaggat   aacttatctc   ctatcatgga   ggagatcgac  1560
tcattctctg   cagagacaga   gtcccttgaa   gagcgtttgg   tcacccagaa   aaaggaggag  1620
acggtggccc   aggagcaaaa   gcacccattg   ctgcgtacat   ctactccgcc   atcaaaggcc  1680
agcggggaat   cacaagattc   tagcgaacac   agctcaaagg   aagatcctta   tagtcaacaa  1740
ccgagccata   aaatccaacg   ccgtaaagag   cgtgctaagc   gcgtcgtccc   aattattact  1800
ccgccaacgt   gggtatctt    tagtttgagc   taccttctta   caaacaggg    gatcttagcg  1860
gatttcagcg   cctattcggc   atacaaggat   aatttagaaa   caactcagca   agagctgaca  1920
atgttgcatc   aagaacgtat   cgagcaagtc   caaaagatcg   tggataaaag   taagacaatg  1980
cgcttttggg   attcattagc   atccattgtg   gccacaatca   ttccatggat   cgaaatgggt  2040
gttgcagtaa   ccatcatcgc   actgggaggt   ggaatccttt   cctggtgctc   tcttttgct   2100
gcgcttatca   tgattgtaat   ttcattattg   gaagcattcg   acgggtggcg   tgcaatcgct  2160
aagcatttac   caggtaacga   tcttgaaaag   aagtgcgtt    atttaggtta   cgtaaagttg  2220
gccttaactg   tgttctcgtg   cttactgagt   ttaagcgcct   tgtatgtagc   aaaattagga  2280
atgagtccgc   ttttggaggg   ggtgtgaag   agtatcgcac   cagcattaag   tggtatgctg  2340
ggtttgactc   aaggcgtagc   actgtattta   caatcttcat   cgcaaaagat   tcgtgcccgc  2400
tgcactcaga   tcgacgcacg   cattgaattg   attaactggg   aacgcgatga   gtatttcttg  2460
cgtgctgaac   aacttcttga   ttcaatgcaa   acgtccttcg   aacaacttac   tgaaacatta  2520
cagttacaac   gtgaaattga   tcagacattt   acagacgctt   tgcgctagct   cgag        2574

SEQ ID NO: 96          moltype = AA   length = 853
FEATURE                Location/Qualifiers
REGION                 1..853
                       note = synthetic construct
source                 1..853
                       mol_type = protein
                       organism = synthetic construct
SEQUENCE: 96
MDNGDRLYRA DSRPPDEIKR SGGLMPRGHN EYFDRGTQMN INLYDHARGT QTGFVRYDDG    60
YVSTSLSLRS AHLAGQSILS GYSTYYIYVI ATAPNMFNVN DVLGVYSPHP YEQEVSALGG   120
IPYSQIYGWY RVNFGVIDER LHRNREYRDR YYRNLNIAPA EDGYRLAGFP PDHQAWREEP   180
WIHHAPQGCG NSSRMKSERL KKLESELHDL TQWMQLGLVP KKEIERHQEE IRLLESKILE   240
EKERLQLLKE SGEIKEYVTP RRTPAKTIYP DGPSVSDVEF VESSDTEVDL DAGDTIEIDL   300
GDEAREESGN ELDYSSEDDE DPFSDRNRWR RGGIIDPDAN EWGSAASMSS WFAQATDVAL   360
SQTLDLPDAS LAVQTEKFPY SCSISKESAP SCIRKIFAHL ASQKESAPLS FSRLQPTTPK   420
ERILFFGSSP SSQLSSTVRT TTSSPWNLFS NSQARNSTRK LSEKLHLSSE LSARDSTKPS   480
SSEPVKPSEN LLHTPEHHKE SFSSLKKDNL SPIMEEIDSF SAETESLEER LVTQKKEETV   540
AQEQKHPLLR TSTPPSKASG ESQDSSEHSS KEDPYSQQPS HKIQRRKERA KRVVPIITPP   600
TVGIFSLSYL LTKQGILADF SAYSAYKDNL ETTQQELTML HQERIEQVQK IVDKSKTMRF   660
WDSLASIVAT IIPWIEMGVA VTIIALGGGI LSWCSLFAAL IMIVISLLEA FDGWRAIAKH   720
LPGNDLEKKM RYLGYVKLAL TVFSCLLSLS ALYVAKLGMS PLLEGVVKSI APALSGMLGL   780
TQGVALYLQS SSQKIRARCT QIDARIELIN WERDEYFLRA EQLLDSMQTS FEQLTETLQL   840
QREIDQTFTD ALR                                                     853

SEQ ID NO: 97          moltype = DNA   length = 647
FEATURE                Location/Qualifiers
misc_feature           1..647
                       note = synthetic construct
source                 1..647
                       mol_type = other DNA
                       organism = synthetic construct
SEQUENCE: 97
atgggcagca gccatcacca tcatcaccac agccaggatc cgatgccacc aagcaagatc    60
```

```
caatgtcttg aaactttga aagaacttat ggacaccttt atctacaaca tgcgtccta    120
atgcgtcatt tagcctatct actcgataaa attgctcgct cttaccctca tatgtgtccg    180
cttcccgata atatggaagc gtactttgag aattatatcc ccaataaaga tatccctctg    240
gacacctatc aaaaaatttt caaactgtcc tcagaagatc ttgaacaagt ctacaaggaa    300
ggatacaacg cctatttaca aggagactat gaggaaagct ctaccgcttt ttactggttg    360
attttcttta acccatttgt gtctaaattt tggttttcat taggagcttc gctccatatg    420
cgccaaaaat atcaacaagc tcttcatgct tatggtgtag ctgctttgct aagagaaaaa    480
gacccttatc ctcattacta tgcctacatc tgctacaccc tgctcaataa tcctgaagaa    540
gctgaaaaag ctcttgatct tgcttggcaa aaagtaaaaa caagtctgc ctatagctct    600
ttaaaagaag aaatttagc gatcaaatcg tacgcctaag cggccgc                  647

SEQ ID NO: 98              moltype = AA  length = 212
FEATURE                    Location/Qualifiers
REGION                     1..212
                           note = synthetic construct
source                     1..212
                           mol_type = protein
                           organism = synthetic construct
SEQUENCE: 98
MGSSHHHHHH SQDPMPPSKI QCLETFERTY GHLYLQHASL MRHLAYLLDK IARSYPHMCP    60
LPDNMEAYFE NYIPNKDIPL DTYQKIFKLS SEDLEQVYKE GYNAYLQGDY EESSTAFYWL   120
IFFNPFVSKF WFSLGASLHM RQKYQQALHA YGVAALLREK DPYPHYYAYI CYTLLNNPEE   180
AEKALDLAWQ KVKTSSAYSS LKEEILAIKS YA                                 212

SEQ ID NO: 99              moltype = DNA  length = 1977
FEATURE                    Location/Qualifiers
misc_feature               1..1977
                           note = synthetic construct
source                     1..1977
                           mol_type = other DNA
                           organism = synthetic construct
SEQUENCE: 99
aaaagtgagc gttaaaaaa attagaatca gagcttcatg atcttaccca gtggatgcaa     60
cttggccttg ttcctaaaaa agaaatcgag agacaccagg aagaaatccg tctgctagaa   120
agcaaaatcc ttgaagagaa gaacgtgtca caacttctca aagaaagcgg tgagatcaaa   180
gagtacgtaa cccctcgaag aactccagct aaaaccattt acccagatgg ccccagcgtt   240
tcagacgttg agtttgtaga atcctcggat acagaagtgg atctcgatgc cggtgacaca   300
attgagattg aactaggtga tgaggcaaga aagaaagcg gaaacgaact cgactactct   360
agtgaagacg atgaggatcc tttcagcgat cgcaatcgtt ggcgccgagg aggcatcata   420
gatcctgacg cgaatgaatg gggttcagct gcttcaatga gctcttggtt tgcacaggcg   480
acggacgtcg ctttgagcca gacccttgat ctgcctgacg cttcattggc ggttcaaacc   540
gaaaaatttc catacagctg ttcaatctct aaggaatccg cccatcatg tattcgtaaa   600
atcttcgccc atttagcatc tcagaaggaa agtgctccgc tctcttttc tcgtttacaa   660
ccgactactc cgaaagaacg catcctgttt ttcgggtcat cgccttcctc ccaattgtcc   720
tcgactgtcc gcaccacaac ctcttctcca tggaatcttt ttagcaactc ccaggcacgc   780
aactcgaccc gtaaattgtc ggagaagctt catttgagct cagagttatc cgcccgtgac   840
tccactaagc cttcgtcgag cgaaccggtt aaaccatcttt gcacaccct                900
gagcatcata aggaatcctt ctcaagtttg aaaaaggata acttatctcc tatcatggag   960
gagatcgact cattctctgc agagacagag tcccttgaag agcgtttggt cacccagaaa   1020
aaggaggaga cggtggccca ggagcaaaag cacccattgc tgcgtacatc tactccgcca   1080
tcaaaggcca gcggggaatc acaagattct agcgaacaca gctcaaagga agatccttat   1140
agtcaacaac cgagccataa aatccaacgc cgtaaagagc gtgctaagcg cgtcgtccca   1200
attattactc cgccaacggt gggtatcttt agtttgagct accttcttac aaaacagggg   1260
atcttagcgg atttcagcgc ctattcggca tacaaggata atttagaaac aactcagcaa   1320
gagctgacca tgttgcatca gaaacgtatc gagcaagtcc aaaagatcgt ggataaaagt   1380
aagacaatgc gctttgggga ttcattagca tccattgtgg ccacaatcat tccatggatc   1440
gaaatggggt tgcagtaac catcatcgca ctggggaggtg gaatcctttc ctggtgctct   1500
cttttttgctg cgcttatcat gattgtaatt tcattattgg aagcattcga cgggtggcgt   1560
gcaatcgcta agcatttacc aggtaacgat cttgaaaaga agatgcgtta tttaggtttac   1620
gtaaagttgg ccttaactgt gttctcgtgc ttactgagtt taagcgcctt gtatgtagca   1680
aaattaggaa tgagtccgct tttggagggg gttgtgaaga gtatcgcacc agcattaagt   1740
ggtatgctgg gtttgactca aggcgtagca ctgtatttac aatcttcatc gcaaaagatt   1800
cgtgcccgct gcactcagat cgacgcacgc attgaattga ttaactggga acgcgatgag   1860
tatttcttgc gtgctgaaca acttcttgat tcaatgcaaa cgtccttcga caacttact   1920
gaaacattac agttacaacg tgaaattgat cagacattta cagacgcttt gcgctag     1977

SEQ ID NO: 100             moltype = AA  length = 659
FEATURE                    Location/Qualifiers
REGION                     1..659
                           note = synthetic construct
source                     1..659
                           mol_type = protein
                           organism = synthetic construct
SEQUENCE: 100
MKSERLKKLE SELHDLTQWM QLGLVPKKEI ERHQEEIRLL ESKILEEKER LQLLKESGEI    60
KEYVTPRRTP AKTIYPDGPS VSDVEFVESS DTEVDLDAGD TIEIDLGDEA REESGNELDY   120
SSEDDEDPFS DRNRWRRGGI IDPDANEWGS AASMSSWFAQ ATDVALSQTL DLPDASLAVQ   180
TEKFPYSCSI SKESAPSCIR KIFAHLASQK ESAPLSFSRL QPTTPKERIL FFGSSPSSQL   240
SSTVRTTTSS PWNLFSNSQA RNSTRKLSEK LHLSSELSAR DSTKPSSSEP VKPSENLLHT   300
```

```
PEHHKESFSS LKKDNLSPIM EEIDSFSAET ESLEERLVTQ KKEETVAQEQ KHPLLRTSTP    360
PSKASGESQD SSEHSSKEDP YSQQPSHKIQ RRKERAKRVV PIITPPTVGI FSLSYLLTKQ    420
GILADFSAYS AYKDNLETTQ QELTMLHQER IEQVQKIVDK SKTMRFWDSL ASIVATIIPW    480
IEMGVAVTII ALGGGILSWC SLFAALIMIV ISLLEAFDGW RAIAKHLPGN DLEKKMRYLG    540
YVKLALTVFS CLLSLSALYV AKLGMSPLLE GVVKSIAPAL SGMLGLTQGV ALYLQSSSQK    600
IRARCTQIDA RIELINWERD EYFLRAEQLL DSMQTSFEQL TETLQLQREI DQTFTDALR     659

SEQ ID NO: 101          moltype = DNA   length = 2574
FEATURE                 Location/Qualifiers
misc_feature            1..2574
                        note = synthetic construct
source                  1..2574
                        mol_type = other DNA
                        organism = synthetic construct
SEQUENCE: 101
catatggaca atggcgatcg tttataccgt gccgactcgc gtcccccaga tgagattaaa     60
cgtagcggtg ggtaatgcc acgtgggcac aatgagtatt tgaccgtgg aacacagatg    120
aacattaacc tttacgatca tgcccgtggg acccagaccg ggtttgtcg ttatgatgac    180
gggtatgtta gtacgagttt gtccttacgc tccgcacacc ttgcgggaca agtattta    240
tcaggctaca gcacatatta catttatgtg atcgccactg ccccaaacat gttcaatgtg    300
aacgatgtgt tggggggttta cagccccat ccatatgaac aagaagtctc ggcccttggg    360
gggatcccat atagccagat ttatggttgg taccgcgtaa atttggtgt gattgatgaa    420
cgtttgcatc gtaaccgtga ataccgcgat cgctactacc gtaacttgaa cattgcacct    480
gccgaggacg gctatcgttt agcgggattc cacccgatcc atcaggcgtg gcgtgaggaa    540
ccgtggatcc atcacgcccc tcaggggtgc gggaacagta gtcgccatat gaaaagtgag    600
cgtttaaaaa aattagaatc agagcttcat gatcttaccc agtggatgca acttggcctt    660
gttcctaaaa aagaaatcga gagacaccag gaagaaatcc gtctgctaga agcaaaatc    720
cttgaagaga aagaacgtct acaacttctc aaagaaagcg gtgagatcaa agagtacgta    780
accctcgaa gaactccagc taaaaccatt acccagatg gccccagcgt ttcagacgtt    840
gagtttgtag aatcctcgga tacagaagtg gatctcgata ccggtgacac aattgagatt    900
gacctaggtg atgaggcaag agaagaaagc ggaaacgaac tcgactactc tagtgaagac    960
gatgaggatc ctttcagcga tcgcaatcgt tggcgccgag gaggcatcat agatcctgac   1020
gcgaatgaat ggggttcagc tgcttcaatg agctcttggt ttgcacaggc gacggacgtc   1080
gctttgagcc agacccttga tctgcctgac gcttcattgg cggttcaaac cgaaaaattt   1140
ccatacagct gttcaatctc taaggaatcc gccccatcag gtattcgtaa aatcttcgcc   1200
catttagcat ctcagaagga aagtgctccg ctgtctttt ctcgtttaca accgactact   1260
ccgaaagaac gcatcctgtt tttcgggtca tcgccttcct cccaattgtc ctcgactgtc   1320
cgcaccacaa cctcttctcc atggaatctt tttagcaact cccaggcacg caactcgacc   1380
cgtaaattgt cggagaagct tcatttgagc tcagagttat ccgccccgtga tccactaag   1440
ccttcgtcga gcgaaccggt taaaccatcg gaaaatcttt tgcacacccc tgagcatcat   1500
aaggaatcct tctcaagttt gaaaaaggat aacttatctc ctatcatgga ggagatcgac   1560
tcattctctg cagagacaga gtcccttgaa gagcgtttgg tcacccagaa aaaggaggag   1620
acggtggccc aggagcaaaa gcacccattg tcgtacat ctactccgcc atcaaaggcc   1680
agcggggaat cacaagattc tagcgaacac agctcaaagg aagatccta tagtcaacaa   1740
ccgagccata aaatccaacg ccgtaaagag cgtgctaagc gcgtcgtccc aattattact   1800
ccgccaacgg tgggtatctt tagtttgagc taccttctta caaaacaggg gatcttagcg   1860
gatttcagcg cctattcggc atacaaggat aatttagaaa caactcagca agagctgacc   1920
atgttgcatc aagaacgtat cgagcaagtc caaaagatcg tggataaaag taagacaatg   1980
cgcttttggg attcattagc atccattgtg ccacaatca ttccatggat cgaaatgggt   2040
gttgcagtaa ccatcatcgc actggaggt ggaatccttt cctggtgtc tcttttgct   2100
gcgcttatca tgattgtaat ttcattattg gaagcattcg acgggtggcg tgcaatcgat   2160
aagcatttac caggtaacga tcttgaaaag aagatgcgtt atttaggtta cgtaaagttg   2220
gccttaactg tgttctcgtg cttactgagt ttaagcgcct tgtatgtagc aaaattagga   2280
atgagtccgc ttttggaggg ggttgtgaag agtatcgcac cagcattaag tggtatgctg   2340
ggtttgactc aaggcgtagc actgtattta caatcttcat cgcaaaagat tcgtgcccgc   2400
tgcactcaga tcgacgcacg cattgaattg attaactggg aacgcgatga gtatttcttg   2460
cgtgctgaac aacttcttga ttcaatgcaa acgtccttcg aacaacttac tgaaacatta   2520
cagttacaac gtgaaattga tcagactttt acagacgctt tgcgctagct cgag          2574

SEQ ID NO: 102          moltype = AA    length = 853
FEATURE                 Location/Qualifiers
REGION                  1..853
                        note = synthetic construct
source                  1..853
                        mol_type = protein
                        organism = synthetic construct
SEQUENCE: 102
MDNGDRLYRA DSRPPDEIKR SGGLMPRGHN EYFDRGTQMN INLYDHARGT QTGFVRYDDG     60
YVSTSLSLRS AHLAGQSILS GYSTYYIYVI ATAPNMFNVN DVLGVYSPHP YEQEVSALGG    120
IPYSQIYGWY RVNFGVIDER LHRNREYRDR YYRNLNIAPA EDGYRLAGFP PDHQAWREEP    180
WIHHAPQGCG NSSRMKSERL KKLESELHDL TQWMQLGLVP KKEIERHQEE IRLLESKILE    240
EKERLQLLKE SGEIKEYVTP RRTPAKTIYP DGPSVSDVEF VESSDTEVDL DAGDTIEIDL    300
GDEAREESGN ELDYSSEDDE DPFSDRNRWR RGGIIDPDAN EWGSAASMSS WFAQATDVAL    360
SQTLDLPDAS LAVQTEKFPY SCSISKESAP SCIRKIFAHL ASQKESAPLS FSRLQPTTPK    420
ERILFFGSSP SSQLSSTVRT TTSSPWNLFS NSQARNSTRK LSEKLHLSSE LSARDSTKPS    480
SSEPVKPSEN LLHTPEHHKE SFSSLKKDNL SPIMEEIDSF SAETESLEER LVTQKKEETV    540
AQEQKHPLLR TSTPPSKASG ESQDSSEHSS KEDPYSQQPS HKIQRRKERA KRVVPIITPP    600
TVGIFSLSYL LTKQGILADF SAYSAYKDNL ETTQQELTML HQERIEQVQK IVDKSKTMRF    660
WDSLASIVAT IIPWIEMGVA VTIIALGGGI LSWCSLFAAL IMIVISLLEA FDGWRAIAKH    720
```

```
LPGNDLEKKM RYLGYVKLAL TVFSCLLSLS ALYVAKLGMS PLLEGVVKSI APALSGMLGL    780
TQGVALYLQS SSQKIRARCT QIDARIELIN WERDEYFLRA EQLLDSMQTS FEQLTETLQL    840
QREIDQTFTD ALR                                                       853

SEQ ID NO: 103            moltype = DNA  length = 810
FEATURE                   Location/Qualifiers
misc_feature              1..810
                          note = synthetic construct
source                    1..810
                          mol_type = other DNA
                          organism = synthetic construct
SEQUENCE: 103
atgcgttgca ctcgggcaat tcgccaaacc gcaagaacag gctggctgac gtggctggcg    60
attcttgccg tcacggcgcc cgtgacttcg ccggcatgag ccgacgatcc tcccgccacc   120
gtataccgct atgactcccg cccgccgagg acgttttcc agaacggatt cacggcgtgg    180
ggaaacaacg acaatgtgct cgaccatctg accggacgtt cctgccaggt cggcagcagc   240
aacagcgctt tcgtctccac cagcagcagc cggcgctata ccgaggtcta tctcgaacat   300
cgcatgcagg aagcggtcga ggccgaacgc gccggcaggg gcaccggcca cttcatcgga   360
tacatctacg aagtccgcgc cgacaacaat ttctacggcg ccgccagctc gtacttcgaa   420
tacgtcgaca cttatggcga caatgccggc cgtatcctcg ccggcgcgct ggccacctac   480
cagagcgaat atctggcaca ccggcgcatt ccgcccgaaa acatccgcag ggtaacgcgg   540
gtctatcaca acggcatcac cggcgagacc acgaccacga agtattccaa cgctcgctac   600
gtcagccagc agactcgcgc caatcccaac ccctacacat cgcgaaggtc cgtagcgtcg   660
atcgtcggca cattggtgcg catggcgccg gtgataggcg cttgcatggc gcggcaggcc   720
gaaagctccg aggccatggc agcctggtcc gaacgcgccg gcgaggcgat ggttctcgtg   780
tactacgaaa gcatcgcgta ttcgttctag                                    810

SEQ ID NO: 104            moltype = AA  length = 269
FEATURE                   Location/Qualifiers
REGION                    1..269
                          note = synthetic construct
source                    1..269
                          mol_type = protein
                          organism = synthetic construct
SEQUENCE: 104
MRCTRAIRQT ARTGWLTWLA ILAVTAPVTS PAWADDPPAT VYRYDSRPPE DVFQNGFTAW     60
GNNDNVLDHL TGRSCQVGSS NSAFVSTSSS RRYTEVYLEH RMQEAVEAER AGRGTGHFIG   120
YIYEVRADNN FYGAASSYFE YVDTYGDNAG RILAGALATY QSEYLAHRRI PPENIRRVTR   180
VYHNGITGET TTTEYSNARY VSQQTRANPN PYTSRRSVAS IVGTLVRMAP VIGACMARQA   240
ESSEAMAAWS ERAGEAMVLV YYESIAYSF                                     269

SEQ ID NO: 105            moltype = DNA  length = 681
FEATURE                   Location/Qualifiers
misc_feature              1..681
                          note = synthetic construct
source                    1..681
                          mol_type = other DNA
                          organism = synthetic construct
SEQUENCE: 105
atgccgatcg accgcaagac gctctgccat ctcctgtccg ttctgccgtt ggccctcctc    60
ggatctcacg tggcgcgggc ctccacgcca ggcatcgtca ttccgccgca ggaacagatt   120
acccagcatg gcagccccta tggacgctgc gcgaacaaga cccgtgccct gaccgtggcc   180
gaattgcgcg gcagcggcga tctgcaggag tacctgcgtc atgtgacgcg cggctggtca   240
atatttgcgc tctacgatgg cacctatctc ggcggcgaat atggcggcgt gatcaaggac   300
ggaacacccg gcgggcgcatt cgacctgaaa acgacgttct gcatcatgac cacgcgcaat   360
acgggtcaac ccgcaacgga tcactactac agcaacgtca ccgccactcg cctgctctcc   420
agcaccaaca gcaggctatg cgcggtcttc gtcagaagcg ggcaaccggt cattggcgcc   480
tgcaccagcc cgtatgacgg caagtactgg agcatgtaca gccggctgcg gaaaatgctt   540
tacctgatct acgtggccgg catctccgta cgcgtccatg tcagcaagga gaacagtat    600
tacgactatg aggacgcaac gttcgagact tacgcccta ccggcatctc catctgcaat    660
cctggatcat ccttatgctg a                                             681

SEQ ID NO: 106            moltype = AA  length = 226
FEATURE                   Location/Qualifiers
REGION                    1..226
                          note = synthetic construct
source                    1..226
                          mol_type = protein
                          organism = synthetic construct
SEQUENCE: 106
MPIDRKTLCH LLSVLPLALL GSHVARASTP GIVIPPQEQI TQHGGPYGRC ANKTRALTVA    60
ELRGSGDLQE YLRHVTRGWS IFALYDGTYL GGEYGGVIKD GTPGGAFDLK TTFCIMTTRN   120
TGQPATDHYY SNVTATRLLS STNSRLCAVF VRSGQPVIGA CTSPYDGKYW SMYSRLRKML   180
YLIYVAGISV RVHVSKEEQY YDYEDATFET YALTGISICN PGSSLC                  226

SEQ ID NO: 107            moltype = DNA  length = 684
FEATURE                   Location/Qualifiers
misc_feature              1..684
                          note = synthetic construct
```

```
source                  1..684
                        mol_type = other DNA
                        organism = synthetic construct
SEQUENCE: 107
atgctgatca acaacaagaa gctgcttcat cacattctgc ccatcctggt gctcgccctg   60
ctgggcatgc gcacggccca ggccgttgcg ccaggcatcg tcatcccgcc gaaggcactg  120
ttcacccaac agggcggcgc ctatggacgc tgcccgaacg gaacccgcgc cttgaccgtg  180
gccgaactgc gcggcaacgc cgaattgcag acgtatttgc ccagataacg cccggctgg   240
tccatatacg gtctctatga cggtacgtac ctgggccagg cgtacggcgg catcatcaag  300
gacgcgccgc caggcgcggg gttcatttat cgcgaaactt tctgcatcac gaccatatac  360
aagaccgggc aaccggctgc ggatcactac tacagcaagg tcacggccac cgcctgctc   420
gccagcacca acagcaggct gtgcgcggta ttcgtcaggg acgggcaatc ggtcatcgga  480
gcctgcgcca gcccgtatga aggcaggtac agagacatgt acgacgcgct gcggcgcctg  540
ctgtacatga tctatatgtc cggccttgcc gtacgcgtcc acgtcagcaa ggaagagcag  600
tattacgact acgaggacgc cacattccag acctatgccc tcaccggcat ttccctctgc  660
aacccggcag cgtcgatatg ctga                                        684

SEQ ID NO: 108          moltype = AA length = 227
FEATURE                 Location/Qualifiers
REGION                  1..227
                        note = synthetic construct
source                  1..227
                        mol_type = protein
                        organism = synthetic construct
SEQUENCE: 108
MLINNKKLLH HILPILVLAL LGMRTAQAVA PGIVIPPKAL FTQQGGAYGR CPNGTRALTV   60
AELRGNAELQ TYLRQITPGW SIYGLYDGTY LGQAYGGIIK DAPPGAGFIY RETFCITTIY  120
KTGQPAADHY YSKVTATRLL ASTNSRLCAV FVRDGQSVIG ACASPYEGRY RDMYDALRRL  180
LYMIYMSGLA VRVHVSKEEQ YYDYEDATFQ TYALTGISLC NPAASIC               227

SEQ ID NO: 109          moltype = DNA length = 459
FEATURE                 Location/Qualifiers
misc_feature            1..459
                        note = synthetic construct
source                  1..459
                        mol_type = other DNA
                        organism = synthetic construct
SEQUENCE: 109
atgctgagac gcttccccac tcgaaccacc gccccgggac agggcggcgc ccggcggtcg   60
cgcgtgcgcg ccctggcgtg gttgctggca tccggcgcga tgacgcatct ttccccccgcc 120
ctggccgact tccttatgt gctggtgaag accaatatgg tggtcaccag cgtagccatg  180
aagccgtatg aagtcacccc gacgcgcatg ctggtctgcg gcatcgccgc caaactgggc  240
gccggccgca gcagcccgga cgcgcacgtg ccgttctgcg tcggcaagga tctcaagcgt  300
cccggcagca gtcccatgga agtcatgttg cgcgccgtct tcatgcaaca acggccgctg  360
cgcatgtttc tgggtcccaa gcaactcact ttcgaaggca gcccgcgct cgaactgatc   420
cggatggtcg aatgcagcgg caagcaggat tgcccctga                         459

SEQ ID NO: 110          moltype = AA length = 152
FEATURE                 Location/Qualifiers
REGION                  1..152
                        note = synthetic construct
source                  1..152
                        mol_type = protein
                        organism = synthetic construct
SEQUENCE: 110
MLRRFPTRTT APGQGGARRS RVRALAWLLA SGAMTHLSPA LADVPYVLVK TNMVVTSVAM   60
KPYEVTPTRM LVCGIAAKLG AAASSPDAHV PFCFGKDLKR PGSSPMEVML RAVFMQQRPL  120
RMFLGPKQLT FEGKPALELI RMVECSGKQD CP                               152

SEQ ID NO: 111          moltype = DNA length = 402
FEATURE                 Location/Qualifiers
misc_feature            1..402
                        note = synthetic construct
source                  1..402
                        mol_type = other DNA
                        organism = synthetic construct
SEQUENCE: 111
atgcagcggc aagcaggatt gcccctgaag gcgaacccca tgcataccat cgcatccatc   60
ctgttgtccg tgctcggcat atacagcccg gctgacgtcg ccggcttgcc gacccatctg  120
tacaagaact tcactgtcca ggagctggcc ttgaaactga aggcaagaa tcaggagttc   180
tgcctgaccg ccttcatgtc gggcagaagc ctggtccggg cgtgcctgtc cgacgcggga  240
cacgagcacg acacgtggtt cgacaccatg cttggctttg ccatatccgc gtatgcgctc  300
aagagccgga tcgcgctgac ggtggaagac tcgccgtatc cggcactcc cggcgatctg   360
ctcgaactgc agatctgccc gctcaacgga tattgcgaat ga                    402

SEQ ID NO: 112          moltype = AA length = 133
FEATURE                 Location/Qualifiers
REGION                  1..133
                        note = synthetic construct
```

```
source                    1..133
                          mol_type = protein
                          organism = synthetic construct
SEQUENCE: 112
MQRQAGLPLK ANPMHTIASI LLSVLGIYSP ADVAGLPTHL YKNFTVQELA LKLKGKNQEF    60
CLTAFMSGRS LVRACLSDAG HEHDTWFDTM LGFAISAYAL KSRIALTVED SPYPGTPGDL   120
LELQICPLNG YCE                                                     133

SEQ ID NO: 113            moltype = DNA  length = 868
FEATURE                   Location/Qualifiers
misc_feature              1..868
                          note = synthetic construct
source                    1..868
                          mol_type = other DNA
                          organism = synthetic construct
SEQUENCE: 113
atgattgaca tcatgttgca tataggttag ataaaacaag tggttatctt tccggattgt    60
cttcttgtat gatatataag ttttcctcga tgaaaaatat aactttcatt tttttattt   120
tattagcatc gccattatat gcaaatggcg acagattata ccgtgctgac tctagacccc   180
cagatgaaat aaaacgtttc cggagtctta tgcccagagg taatgagtac ttcgatagag   240
gaactcaaat gaatattaat ctttatgatc acgcgagagg aacacaaacc ggctttgtca   300
gatatgatga cggatatgtt tccacttctc ttagtttgag aagtgctcac ttagcaggac   360
agtatatatt atcaggatat tcacttacta tatatatcgt tatagcaaat atgtttaatg   420
ttaatgatgt aattagcgta tacagccctc acccatatga acaggaggtt tctgcgttag   480
gtggaatacc atattctcag atatatggat ggtatcgtgt taattttggt gtgattgatg   540
aacgattaca tcgtaacagg gaatatagag accggtatta cagaaatctg aatatagctc   600
cggcagagga tggttacaga ttagcaggtt tcccaccgga tcaccaagct tggagagaag   660
aacccctgga tcatcatgca ccacaaggtt gtggagattc atcaggaaca atcacaggtg   720
atacttgtaa tgaggagacc cagaatctga gcacaatata tgccagggaa tatcaatcaa   780
aagttaagag gcagatattt tcagactatc agtcagaggt tgacatatat aacagaattc   840
gggatgaatt atgaataaag taaaatgt                                     868

SEQ ID NO: 114            moltype = DNA  length = 604
FEATURE                   Location/Qualifiers
misc_feature              1..604
                          note = synthetic construct
source                    1..604
                          mol_type = other DNA
                          organism = synthetic construct
SEQUENCE: 114
gttgacatat ataacagaat tcgggatgaa ttatgaataa agtaaaatgt tatgttttat    60
ttacggcgtt actatcctct ctatatgcac acggagctcc ccagactatt acagaactat   120
gttcggaata tcgcaacaca caaatatata cgataaatga caagtacta tcatataggg   180
aatcgatggc aggcaaaaga gaaatggtta tcattacatt taagagcggc gaaacatttc   240
aggtcgaagt ccccgggcagt caacatatag actcccagaa aaaagccatt gaaaggatga   300
aggacacatt aagaatcaca tatctgaccg agaccaaaat tgataaatta tgtgtatgga   360
ataataaaac ccccaattca attgcggcaa tcagtatgaa aaactagttt gcttttaaaag   420
catgtctaat gctaggaacc tatataacaa ctactgtact tatactaatg agccttatgc   480
tgcatttgaa aaggcggtag aggaggcaat accgatcctt aaactgtaac actataacag   540
cttccactac agggagctgt tatagcacac agaaaaaact aagctaggct ggaggggcaa   600
gctt                                                               604

SEQ ID NO: 115            moltype = DNA  length = 777
FEATURE                   Location/Qualifiers
source                    1..777
                          mol_type = genomic DNA
                          organism = Vibrio cholerae
SEQUENCE: 115
atggtaaaga taatatttgt gttttttatt ttcttatcat cattttcata tgcaaatgat    60
gataagttat atcgggcaga ttctagacct cctgatgaaa taaagcagtc aggtggtctt   120
atgccaagag gacagagtga gtactttgac cgaggtactc aaatgaatat caacctttat   180
gatcatgcaa gaggaactca gacgggattt gttaggcacg atgatggata tgtttccacc   240
tcaattagtt tgagaagtgc ccacttagtg ggtcaaacta tattgtctgg tcattctact   300
tattatatat atgttatagc cactgcaccc aacatgttaa tgtattaggg   360
gcatacagtc ctcatccaga tgaacaagaa gtttctgctt taggtgggat tccatactcc   420
caaatatatg gatggtatcg agttcatttt ggggtgcttg atgaacaatt acatcgtaat   480
aggggctaca gagatagata ttacagtaac ttagatattg ctccagcagc agatggttat   540
ggattggcag gttttccctcc ggagcataga gcttggaggg aagaccgtg gattcatcat   600
gcaccgccgg gttgtgggaa tgctccaaga tcatcgatca gtaatacttg cgatagaaaa   660
acccaaagtc taggtgtaaa attccttgac gaataccaat ctaaagttaa aagacaaata   720
ttttcaggct atcaatctga tattgataca cataatagaa ttaaggatga attatga     777

SEQ ID NO: 116            moltype = AA  length = 70
FEATURE                   Location/Qualifiers
source                    1..70
                          mol_type = protein
                          organism = Vibrio cholerae
SEQUENCE: 116
HRAWREEPWI HHAPPGCGNA PRSSMSNTCD EKTQSLGVKF LDEYQSKVKR QIFSGYQSDI    60
```

```
DTHNRIKDEL                                                                         70

SEQ ID NO: 117         moltype = DNA  length = 375
FEATURE                Location/Qualifiers
source                 1..375
                       mol_type = genomic DNA
                       organism = Vibrio cholerae
SEQUENCE: 117
atgattaaat taaaatttgg tgtttttttt acagttttac tatcttcagc atatgcacat   60
ggaacacctc aaaatattac tgatttgtgt gcagaatacc acaacacaca aatatatacg  120
ctaaatgata agatattttc gtatacagaa tctctagctg gaaaaagaga gatggctatc  180
attactttta agaatggtgc aattttttcaa gtagaagtac caggtagtca acatatagat  240
tcacaaaaaa aagcgattga aaggatgaag gataccctga ggattgcata tcttactgaa  300
gctaaagtcg aaaagttatg tgtatggaat aataaaacgc ctcatgcgat tgccgcaatt  360
agtatggcaa attaa                                                   375

SEQ ID NO: 118         moltype = AA  length = 124
FEATURE                Location/Qualifiers
source                 1..124
                       mol_type = protein
                       organism = Vibrio cholerae
SEQUENCE: 118
MIKLKFGVFF TVLLSSAYAH GTPQNITDLC AEYHNTQIYT LNDKIFSYTE SLAGKREMAI   60
ITFKNGAIFQ VEVPGSQHID SQKKAIERMK DTLRIAYLTE AKVEKLCVWN NKTPHAIAAI  120
SMAN                                                               124
```

What is claimed is:

1. A fusion polypeptide comprising (i) a fusion of PcrV needle tip protein of *Pseudomonas* spp. and PopB translating protein of *Pseudomonas* spp., wherein the fusion comprises the amino acid sequence set forth in SEQ ID NO: 36; and ii) a double mutant labile toxin (dmLT) of *Escherichia coli* or an antigenic fragment thereof, or cholera toxin or an antigenic fragment thereof.

2. The fusion polypeptide of claim 1, wherein the fusion polypeptide is arranged so that the PcrV needle tip protein is 5' of the PopB translocator protein.

3. The fusion polypeptide of claim 1, wherein the dmLT retains its ADP ribosylation activity.

4. The fusion polypeptide of claim 1, wherein the dmLT is 5' of the needle tip protein and the translocator protein fusion.

5. A vaccine comprising an effective amount of the fusion polypeptide of claim 1.

6. The vaccine of claim 5, further comprising one or more components of an acellular pertussis vaccine.

7. The vaccine of claim 5, further comprising pertussis toxoid (PTd).

8. The fusion polypeptide of claim 4; wherein the fusion polypeptide comprises the amino acid sequence as set forth in SEQ ID NO: 38.

9. The fusion polypeptide of claim 4; wherein the cholera toxin comprises the amino acid sequence as set forth in SEQ ID NO: 116 and SEQ ID NO: 118.

10. A method of eliciting an immune response in a subject in need thereof against *Pseudomonas* spp. comprising administering to the subject the vaccine of claim 5 in an amount sufficient to elicit the immune response.

11. A method of inhibiting a pulmonary infection due to *Pseudomonas* spp. in a subject in need thereof comprising administering to the subject an effective dosage of the vaccine of claim 5.

* * * * *

UNITED STATES PATENT AND TRADEMARK OFFICE
CERTIFICATE OF CORRECTION

| | | |
|---|---|---|
| PATENT NO. | : 12,331,085 B2 | Page 1 of 1 |
| APPLICATION NO. | : 17/931356 | |
| DATED | : June 17, 2025 | |
| INVENTOR(S) | : Wendy L. Picking and William D. Picking | |

It is certified that error appears in the above-identified patent and that said Letters Patent is hereby corrected as shown below:

On the Title Page

Under the Applicant item (71):

Please delete:
"University of Kansas, Lawrence, KS (US)"

Please insert:
--University of Kansas, Lawrence, KY (US)--

Under the Inventors item (72):

Please delete:
"Wendy L. Picking, Lawrence, KS (US); William D. Picking, Lawrence, KS (US)"

Please insert:
--Wendy L. Picking, Lawrence, KY (US); William D. Picking, Lawrence, KY (US)--

Signed and Sealed this
Twelfth Day of August, 2025

Coke Morgan Stewart
*Acting Director of the United States Patent and Trademark Office*